United States Patent
Taniguchi et al.

(10) Patent No.: US 6,432,041 B1
(45) Date of Patent: Aug. 13, 2002

(54) ENDOSCOPE SHAPE DETECTING APPARATUS WHEREIN FORM DETECTING PROCESSING IS CONTROLLED ACCORDING TO CONNECTION STATE OF MAGNETIC FIELD GENERATING MEANS

(75) Inventors: Akira Taniguchi; Chieko Aizawa; Yasuhiro Yoshizawa, all of Hachioji; Fumiyuki Onoda, Tama; Seiki Toriyama, Hino; Takeshi Kawabata, Sagamihara; Katsuyoshi Sasagawa, Hino; Sumihiro Uchimura, Sagamihara; Masanao Hara, Hino; Kazutaka Tsuji; Takayasu Miyagi, both of Hachioji; Hiroki Moriyama, Akishima; Hiroshi Ishii; Yoshinao Oaki, both of Hino; Tsugio Okazaki, Aizuwakamatsu; Jun Hasegawa, Hino; Yasuo Hirata, Hachioji, all of (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/392,581

(22) Filed: Sep. 9, 1999

(30) Foreign Application Priority Data

| Sep. 9, 1998 | (JP) | 10-255749 |
| Sep. 21, 1998 | (JP) | 10-266754 |
| Sep. 25, 1998 | (JP) | 10-272038 |
| Nov. 27, 1998 | (JP) | 10-338031 |
| Dec. 2, 1998 | (JP) | 10-343159 |
| Dec. 8, 1998 | (JP) | 10-348890 |
| Dec. 17, 1998 | (JP) | 10-359670 |
| Dec. 18, 1998 | (JP) | 10-361340 |
| Dec. 28, 1998 | (JP) | 10-374010 |

(51) Int. Cl.[7] .............................................. A61B 1/00
(52) U.S. Cl. ...................... 600/118; 600/117; 600/132; 600/424
(58) Field of Search ................................. 600/117, 118, 600/160, 132, 109, 407, 424

(56) References Cited

U.S. PATENT DOCUMENTS

5,997,473 A * 12/1999 Tasniguchi et al. .......... 600/117
6,110,107 A * 8/2000 Bellahsene et al. .......... 385/101

FOREIGN PATENT DOCUMENTS

| JP | 62-7846 | 2/1987 |
| JP | 8-107875 | 4/1996 |

* cited by examiner

Primary Examiner—John P. Leubecker
(74) Attorney, Agent, or Firm—Ostrolenk, Faber, Gerb & Soffen, LLP

(57) ABSTRACT

A source coil line-break/short-circuit detecting circuit and a probe connection detecting circuit are provided to the source coil driving circuit unit of an endoscope shape detecting apparatus. The source coil line-break/short-circuit detecting circuit detects line-breaks and short-circuits of the source coils. The probe connection detecting circuit detects whether a connection exists with a probe. A marker coil line-break/short-circuit detecting circuit detects line-breaks and short-circuits of the marker coils. A marker connection detecting circuit detects whether a connection exists with a marker. Accordingly, using the apparatus without being connected to a probe or markers can be avoided by detecting the connection of the probe and markers by the probe connection detecting circuit and marker connection detecting circuit, respectively, when the system is energized, thereby avoiding detecting noise and consequently displaying a random image on the monitor.

42 Claims, 70 Drawing Sheets

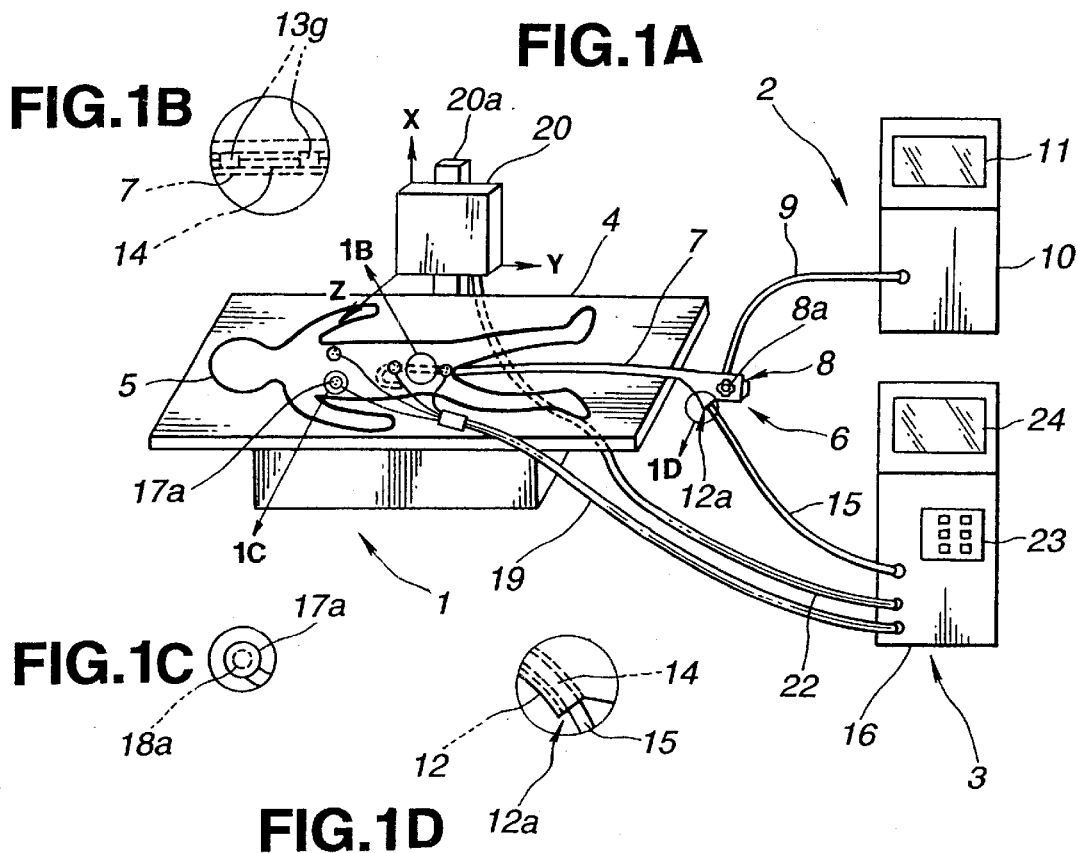
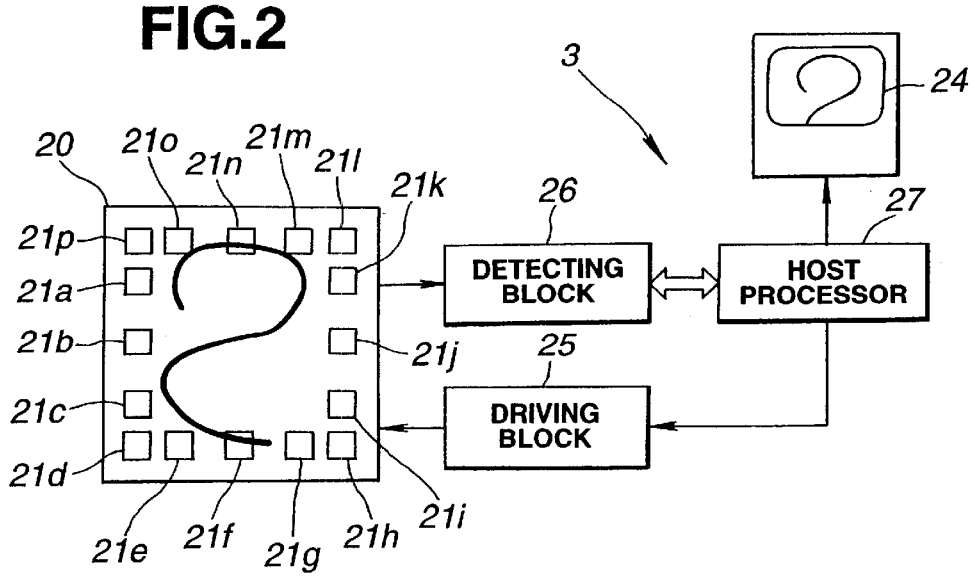

FIG.8
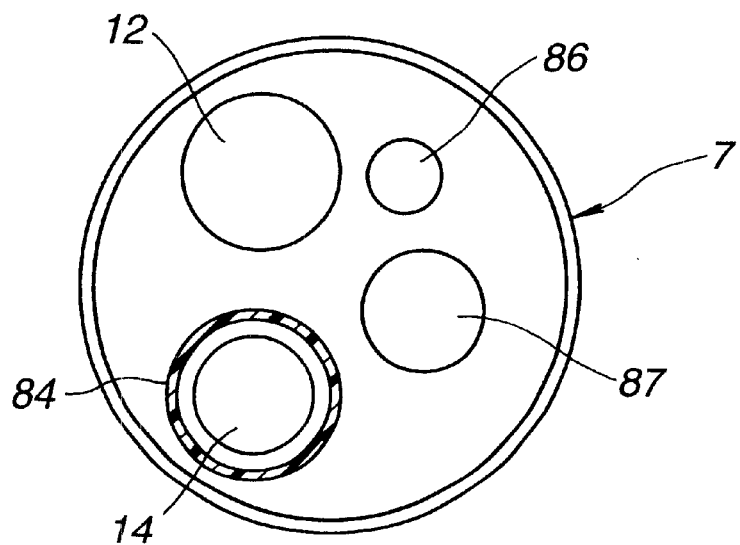
FIG.9 FIG.10
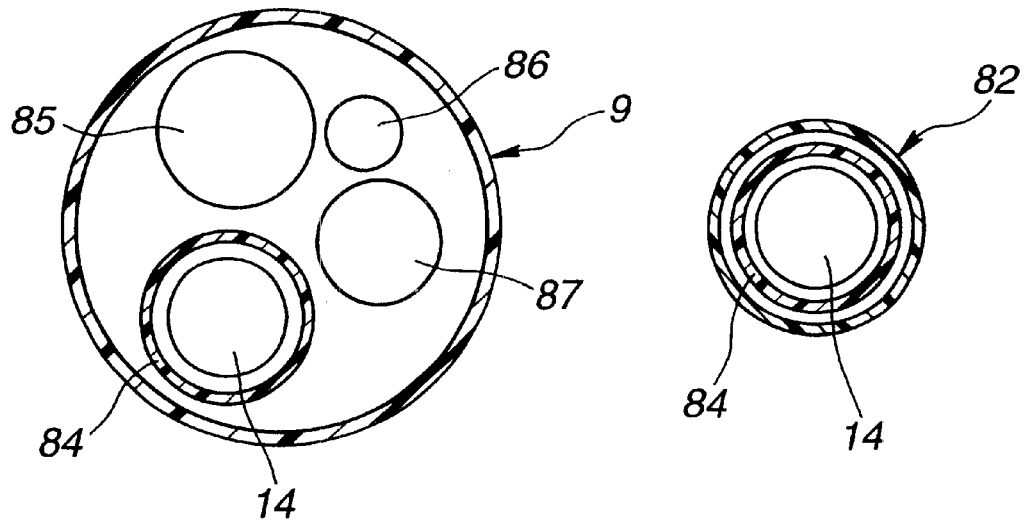

ENDOSCOPE SHAPE

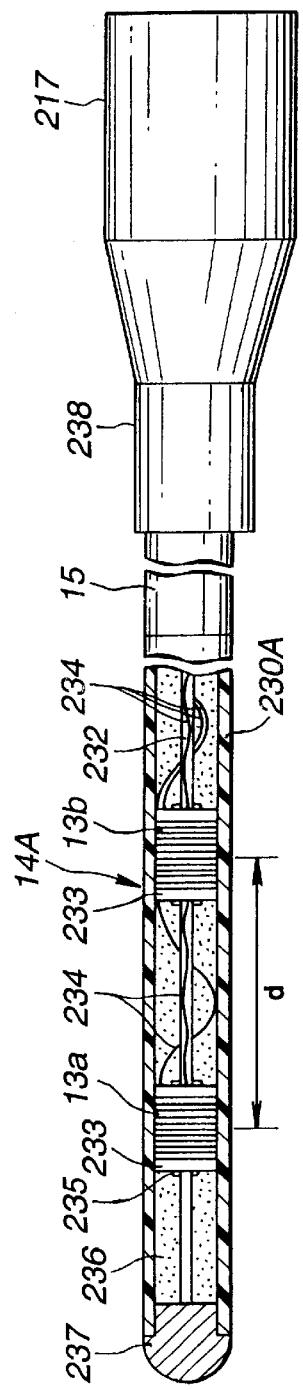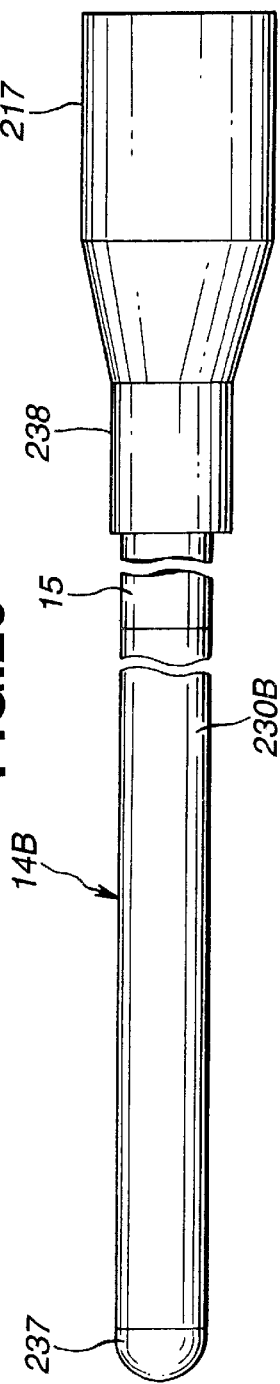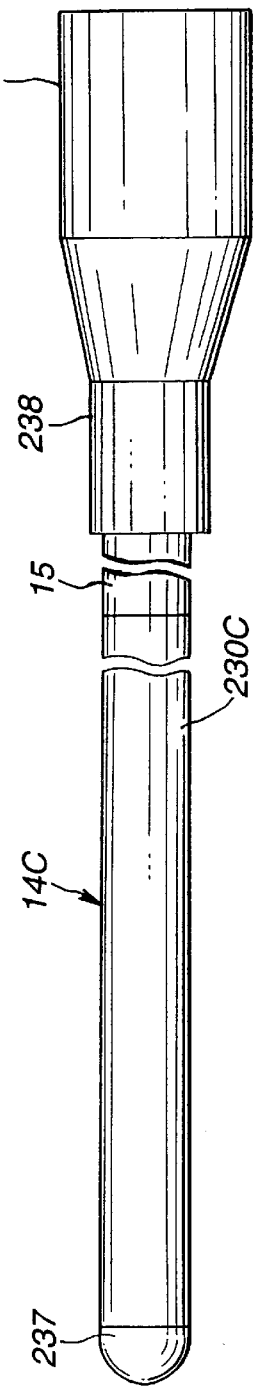

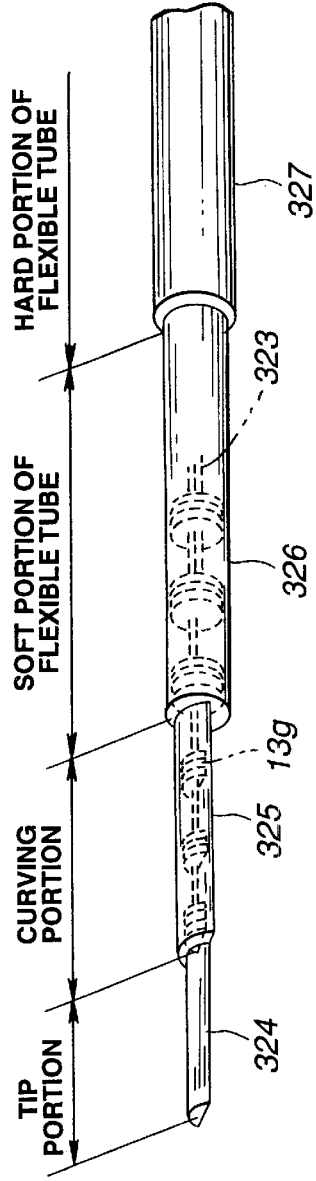
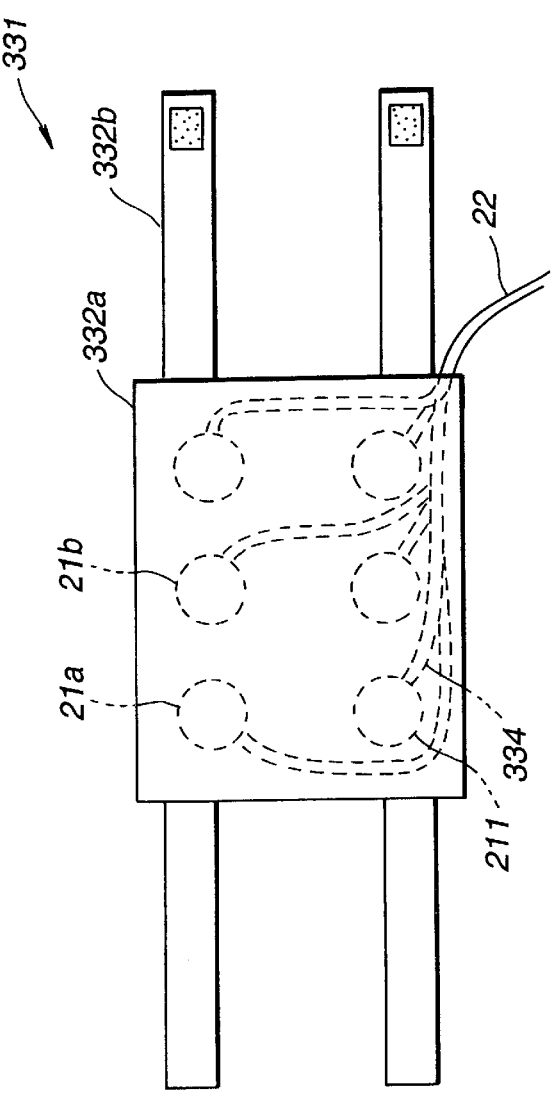
FIG.42
FIG.43

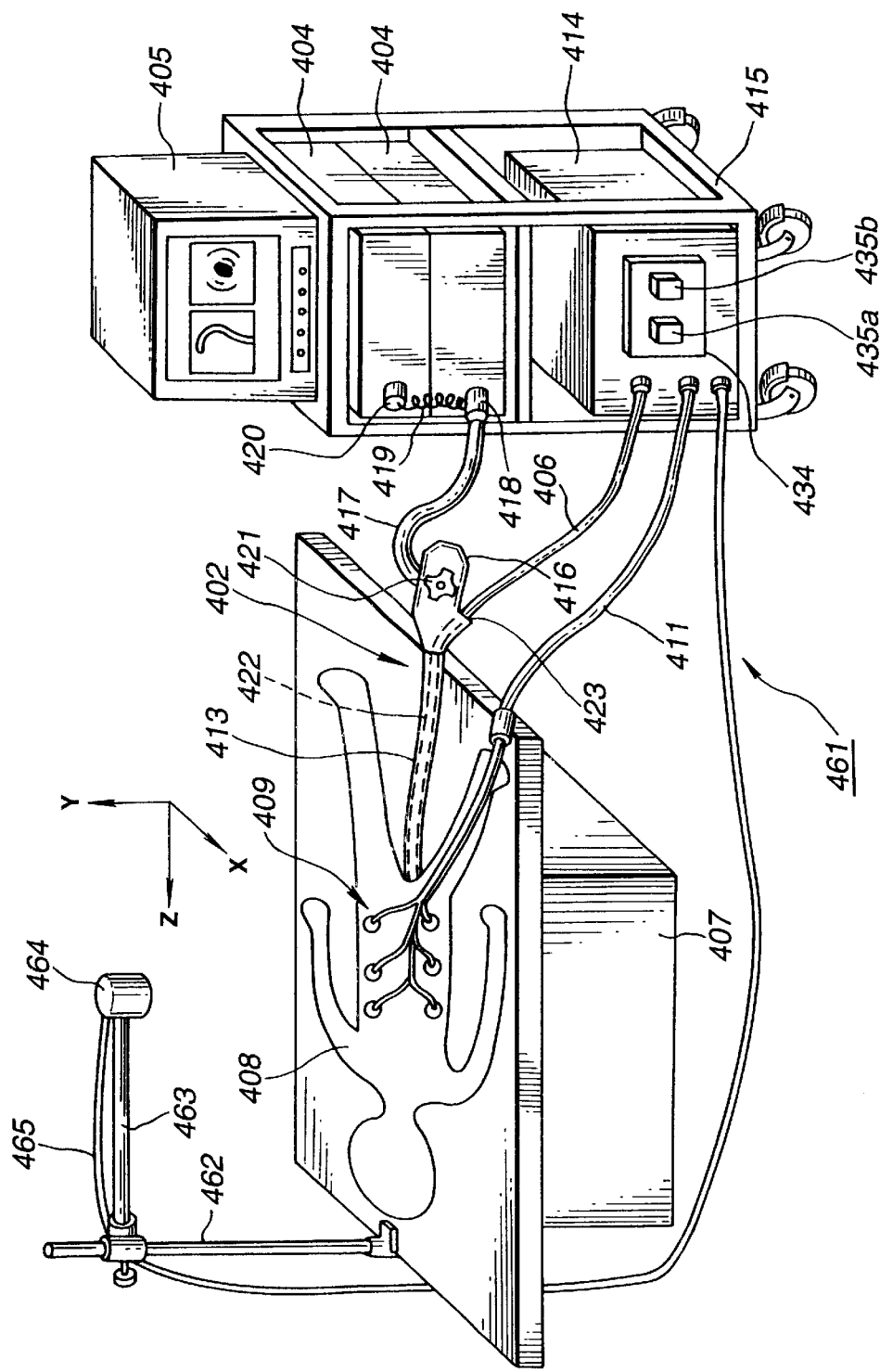

FIG.67
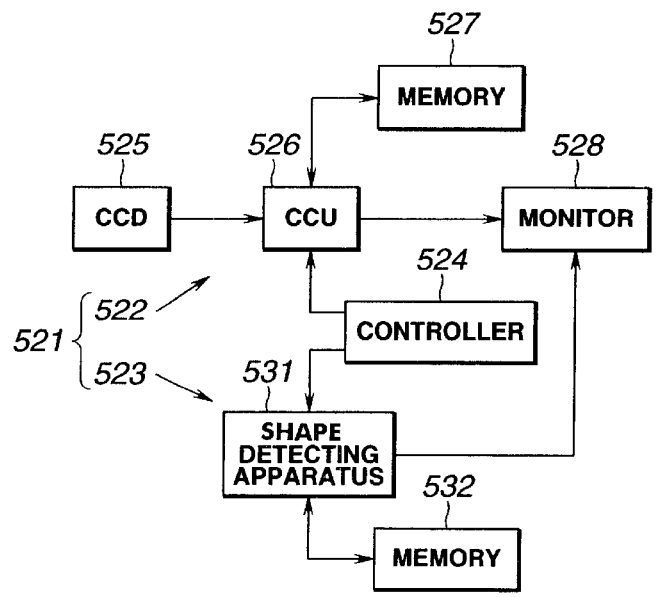
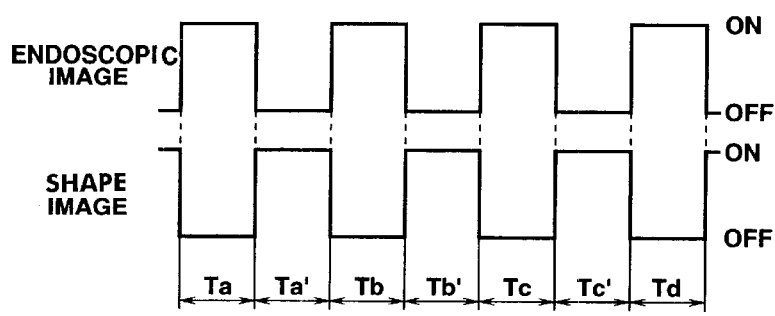
FIG.68A ENDOSCOPIC IMAGE
FIG.68B SHAPE IMAGE

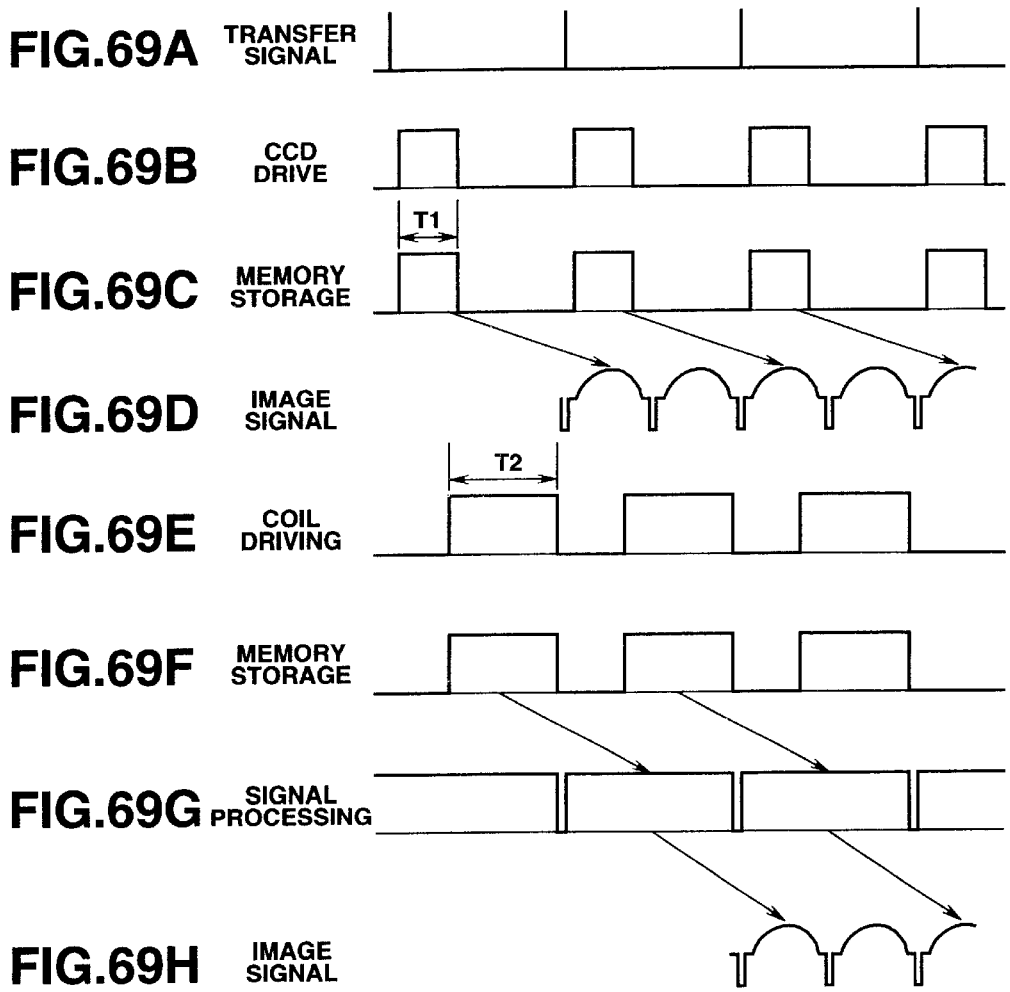

FIG.79
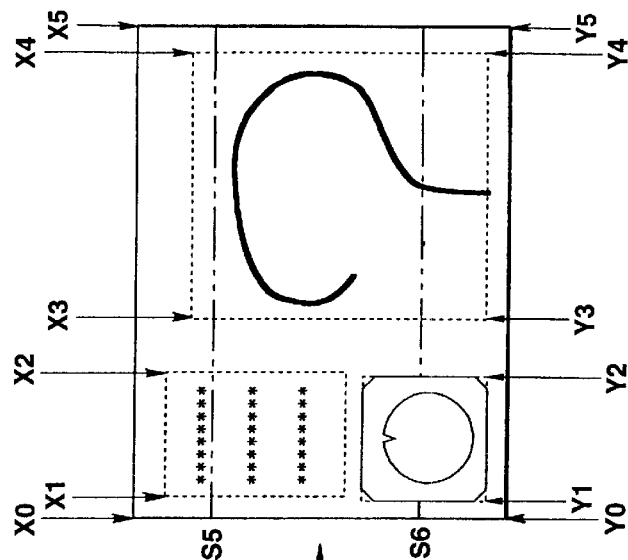
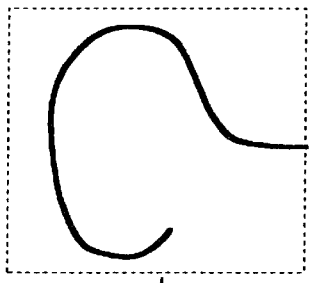
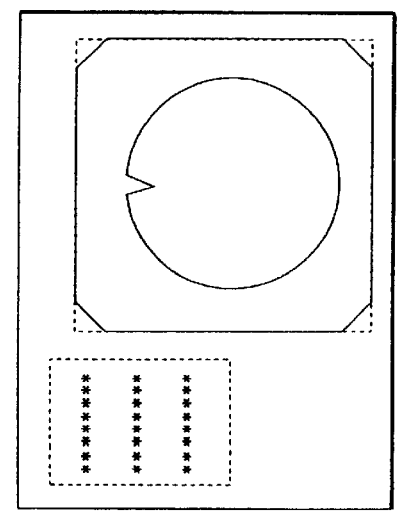
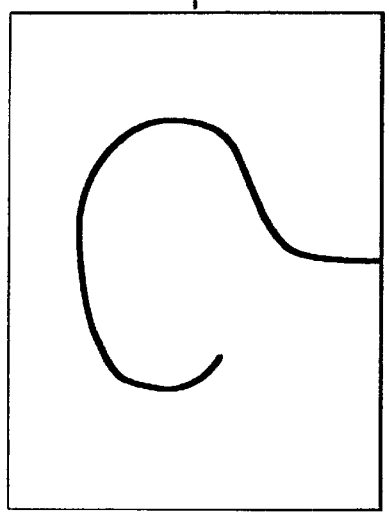
REDUCTION

ENDOSCOPE SHAPE DETECTING APPARATUS WHEREIN FORM DETECTING PROCESSING IS CONTROLLED ACCORDING TO CONNECTION STATE OF MAGNETIC FIELD GENERATING MEANS

BACKGROUND OF THE INVENTION

1. Field of the Invention

The present invention relates to an endoscope shape detecting apparatus for detecting the insertion shape of the insertion portion of an endoscope inserted into a body cavity.

2. Description of the Related Art

Generally, endoscopes are arranged such that a flexible insertion portion is externally inserted into a subject area, i.e., the lumen of the body cavity, thereby allowing the subject area to be observed and necessary treatment to be performed.

However, the lumen of the body cavity is not straight but has many bends, as with the large and small intestines, so a technician cannot readily tell how far the endoscope insertion portion has been inserted, nor what sort of shape the endoscope has.

Accordingly, conventional methods have involved externally irradiating x-rays to the subject area wherein the endoscope insertion portion has been inserted, thereby detecting the insertion position in the lumen in the body cavity, and the shape thereof. However, such x-rays are by no means harmless to the human body. Additionally, the areas where such irradiation can be performed are limited, so such an arrangement is not necessarily preferable as a means for detecting the insertion shape of the endoscope insertion portion.

Accordingly, an apparatus for detecting the insertion shape of endoscopes and catheters using a magnetic field with magnetic field generating means and magnetic field detecting means so as to detect the endoscope insertion shape into the lumen without any negative physiological effects has been proposed, e.g., Japanese Patent Application No. 10-69075 filed by the present Assignee.

However, the above does not provide for detecting the connection state of the magnetic field generating means to the driving means. In the event that the magnetic field generating means is not connected, the magnetic field detecting means picks up background environment noise, at times resulting in an unintended random shape being displayed on the monitor.

In the event that the magnetic field generating means is malfunctioning, the portion corresponding with the malfunctioning portion may be displayed in a deformed manner. In the event that the malfunction involves a short-circuit, excessive current may damage the endoscope shape detecting apparatus itself.

An endoscope shape detecting apparatus or endoscope shape detecting system, wherein an endoscope shape detecting probe comprised of magnetic field generating elements built into the endoscope for detecting the insertion shape is provided within the insertion portion, thereby displaying a three-dimensional image of the insertion shape by a magnetic field detecting device has been proposed in Japanese Unexamined Patent Publication No. 8-107875, etc., for example.

Typically, the entire insertion portion of an endoscope is freely bendable. However, a curving portion is provided on the tip thereof, so repeated usage of the endoscope insertion shape detecting probe in the endoscope necessitates periodic replacement, due to mechanical fatigue. Unfortunately, endoscope shape detecting probes built into the endoscope have not been of an easily-replaceable construction, thus replacement has required a great number of steps.

For example, if the endoscope shape detecting probe to be replaced is forcibly extracted from the endoscope with a force that destroys this endoscope shape detecting probe, the area from which the endoscope shape detecting probe has been removed is narrowed by other built-in members, and an insertion channel for inserting the new endoscope insertion shape detecting probe has not been secured, the new endoscope insertion shape detecting probe to be inserted strikes the other built-in members which essentially prevent the insertion thereof. Accordingly, the device must be disassembled, or subjected to likewise procedures, in order to insert the endoscope insertion shape detecting probe, requiring a great amount of time and much experience to insert the endoscope insertion shape detecting probe into the endoscope.

The endoscope is comprised of a great variety of members over the entire length thereof, such as the curving portion and so forth. Unless an endoscope shape detecting probe closely matching each endoscope configuration is used, correct shape detection is impossible. The selection of the endoscope shape detecting probe for each examination is also a troublesome issue.

With systems wherein the endoscope shape detecting probe is inserted from the endoscope forceps channel in the same manner as treatment equipment used for endoscope inspection, thereby detecting the shape, the endoscope shape detecting probe protrudes from the forceps channel, thus the connector for the endoscope shape detecting probe hangs loosely. The weight of this connector places mechanical stress on the endoscope shape detecting probe, thereby reducing the life expectancy thereof in some cases.

Conventionally, the array intervals of the magnetism generating elements built into the endoscope or the endoscope shape detecting probe were constant.

Endoscopes, flexible endoscopes in particular, are formed with a hard portion at the very tip of the insertion portion, followed by a curving portion and a flexible portion. While the hard portion at the tip never bends, a technician can operate the endoscope such that the curving portion curves into a tight curve. Although the flexible portion does bend, since it is configured in a flexible manner, the flexible portion does not bend into a tight curve, as with the curving portion.

As described above, conventionally, the array intervals of the magnetism generating elements built into the endoscope or the endoscope shape detecting probe are constant. Narrowing the intervals and increasing the number of magnetism generating elements arrayed in the endoscope allows the shape of the curving portion which curves into a tight curve to be detected with high precision, thereby allowing a high-precision image of the shape of the endoscope to be displayed with displaying means, such as a monitor or the like. However, increasing the number of arrayed magnetism generating elements increases costs.

If the intervals are increased and the number of magnetism generating elements arrayed in the endoscope or endoscope shape detecting probe are reduced in order to cut costs, the shape of the curving portion of the endoscope displayed with the display means will exhibit lower precision, different from the true form of the curving portion, as illustrated in dotted lines.

As noted in Japanese Unexamined Patent Publication No. 8-107875, an endoscope shape detecting probe can be inserted into the forceps channel of the endoscope while performing an endoscopic examination, thereby displaying the shape of the endoscope insertion portion on a monitor, thus permitting a technician to make reference to the shape of the endoscope insertion portion displayed on the monitor and readily perform the operations for inserting the endoscope insertion portion deep into the body cavity.

The nature of the endoscope insertion portion itself is determined by the insertion of the endoscope shape detecting probe into the forceps channel of the endoscope. Thus, a technician may not be able to attains a desired stiffness or resilience, or adjust insertion characteristics. Consequently, the technician many not be able to reduce the pain experienced by a patient, or conduct a smooth endoscopic examination.

If an endoscope shape detecting probe is inserted into the forceps channel of the endoscope, the endoscope shape detecting probe hangs freely at the forceps opening of the endoscope. Thus, if the endoscope operating portion is moved or shaken during the examination, stress is placed upon the flexible endoscope shape detecting probe, which may cause deforming or buckling thereof. Consequently, the endoscope shape detecting probe may not be able to be inserted into the forceps channel of the endoscope, or in the worst case, endoscope shape detection may become impossible.

With conventional endoscope arrangements, the magnetic field detecting means is positioned at an absolute spatial position, for easy reference with respect to an examination table upon which the patient lies. The endoscope provided with the magnetic field generating means is inserted into the body of the patient on the bed. The magnetic field generated by the magnetic. geld generating means is detected by the magnetic field detecting means. If the position of the patient changes at the time of inserting the endoscope, the absolute position within the body of the patient changes, making it difficult to ascertain the relationship between the position of the body of the patient and the obtained endoscope shape.

With conventional endoscope shape detection apparatuses, the positions of the magnetic field generating means and the magnetic field detecting means are not close. Accordingly, detection is not always precise, sometimes causing blurring of the endoscope shape image and so forth.

As described in Japanese Unexamined Patent Publication No. 8-107875 for example, a technician had to observe a monitor to know how far the insertion portion had been inserted. In other words, the technician cannot know how far the tip of the insertion portion has advanced into the patient while watching the patient.

Thus, simply displaying the insertion shape of the endoscope still does not allow the technician to readily know how far the endoscope has been advanced into the body cavity. Accordingly, there has been a need to separately provide dedicated source coils for displaying the reference position.

Also, with conventional endoscope shape detecting apparatuses, a monitor for displaying the endoscope shape image generated by the endoscope shape detecting apparatus is provided separately from the monitor for displaying the endoscope image Thus, the technician must perform the inserting operation while observing two monitors, which is problematic.

In recent years, endoscopes which allow observation of an object within the body cavity or treatment or the like as necessary by inserting treatment equipment through a treatment equipment channel of the endoscope without requiring incision, by means of inserting an insertion portion into the body cavity, have come into widespread use. There are various types of such endoscope apparatuses, such as those which have image-taking means, such as a CCD of the like provided on the tip of the insertion portion. Some endoscopes are configured so as to allow separate image-taking means to be attached to the eyepiece of the endoscope, and so forth. These types of endoscopes having image-taking means are arranged so that the image-taking signals from the image-taking means are converted into image signals with a video processor, and displayed on a monitor.

When using such endoscope apparatuses to examiner a body cavity, e.g., the lower digestive organs, insertion proceeds in a smoother manner during the stage of inserting the insertion portion from the anus to the sigmoidal colon if the insertion portion is softer. However, smooth insertion of the insertion portion is hindered in the stage from passing the sigmoidal colon the deeper areas if the insertion portion is too soft. Accordingly, endoscope apparatus have conventionally been used which have stiffness adjusting means for allowing the stiffness or flexibility of the insertion shape detecting means and the insertion portion to be adjusted.

An example of such an endoscope apparatus having stiffness adjusting means is disclosed in Japanese Examined Patent Publication No. 62-7846. The endoscope apparatus in this example has stiffness adjusting means configured of a coil spring provided within the insertion portion in the longitudinal direction. Pressing the coil spring from the rear side forwardly compresses the coil spring, rendering the insertion portion stiffer.

Another arrangement for stiffness adjusting means disclosed in Japanese Examined Patent Publication No.62-7846 involves a coil spring provided within the insertion portion in the longitudinal direction. Pulling a wire passed through this coil spring backwardly pulls the tip of the coil spring fixed to the tip of the wire backwardly, compressing the coil spring so that the insertion portion becomes stiffer.

In using such endoscope apparatuses having stiffness adjusting means, conventional arrangements for the technician to check the stiffness while using the endoscope involved visually checking marks or the like on the stiffness adjustment operating means, such as a knob operated when adjusting stiffness.

Japanese Unexamined Patent Publication No. 8-107875 describes a plurality of magnetic field generating source coils arrayed in the longitudinal direction of the insertion portion at certain intervals, a plurality of sensing coils for detecting the magnetic field generated from the source coils positioned on an examination table upon which the patient lays, and the insertion shape detecting apparatus, which has obtained signals from these sensing coils. The insertion shape detecting apparatus detects the position of each of the source coils, thereby detecting the insertion shape of the insertion portion, and consequently displaying the insertion shape image indicating the insertion shape of the insertion portion on the monitor.

However, the technician must observe the subject image on the monitor connected to the video processor, observe and confirm the insertion state image on the monitor connected to the insertion shape detecting apparatus, and further confirm the stiffness of the insertion portion from the marks on the stiffness adjustment operating means, requiring much eye movement on the part of the technician, causing difficult operability.

With endoscopes having a plurality of source coils for generating a magnetic field for detecting the insertion of the insertion portion, integrally built in at certain intervals, conventional arrangements involved forming a space within the insertion portion of several millimeters in diameter, and disposing the source coils in this space. However, this causes wasted space at the inner diameter of the source coils, resulting in a greater external diameter for the insertion portion. This also exerts occasional pressure on other built-in members, such as the light guide and the like, consequently reducing the durability thereof.

In Japanese Unexamined Patent Publication No. 8-107875, the shape of the insertion portion displayed on the monitor is a 2-dimensional projection of a 3-dimensional form. Thus the accurate length or curvature of the insertion portion may not be ascertainable from the shape displayed on the screen, consequently reducing operability.

A great number of metal members are generally provided near the tip. Sometimes the magnetic field from the source coil is disturbed due to generation of an eddy current. In such cases, the source coil position analyzed by the insertion shape detecting apparatus is erroneous. Accordingly, the insertion shape image is not correctly displayed on the monitor. Also, the curving portion is generally tightly and frequently curved in order to smoothly insert the insertion portion through the body of the subject. Deterioration easily occurs with the members relating to the magnetic field generating elements, such as the source coils positioned within the curving portion, the wiring for providing electricity to the source coils, members for supporting the source coils, and so forth.

Further, the image of the insertion shape displayed on the monitor is a graphic shape approximating the actual shape of the insertion portion. Sometimes precision of the image of the insertion shape deteriorates at positions removed form the positions where the source coils are provided.

SUMMARY OF THE INVENTION

Accordingly, it is an object of the present invention to provide an endoscope shape detecting apparatus capable of controlling the monitor display and controlling the driving of the magnetic field generating means, according to the connection state of the magnetic field generating means.

Another object of the present invention is to provide an endoscope wherein replacement of endoscope shape detecting probes can be easily performed.

Another object of the present invention is to provide an endoscope shape detecting apparatus wherein, performing shape detection and endoscopic examination at the same time, the trouble and number of procedures necessary to select an endoscope shape detecting probe which appropriately matches the endoscope selected from a wide variety of endoscopes is reduced, thereby facilitating ease of selecting combinations of matching endoscopes and endoscope shape detecting probes.

Another object of the present invention is to provide an endoscope shape detecting apparatus wherein, when inserting an endoscope shape detecting probe from the forceps channel and detecting the shape, the mechanical stress placed on the endoscope shape detecting probe due to the weight of the connector of the endoscope shape detecting probe is reduced, thereby extending the life of the endoscope shape detecting probe.

Another object of the present invention is to provide an endoscope shape detecting probe or endoscope shape detecting apparatus wherein damage of the probe inserted into the endoscope channel near the endoscope forceps opening is reduced, thereby improving durability, and improving endoscopic examination efficiency.

Another object of the present invention is to provide an endoscope shape detecting apparatus whereby the insertion shape of the endoscope can be detected in an inexpensive manner yet with high precision.

Another object of the present invention is to provide an endoscope shape detecting apparatus capable of accommodating preferences in stiffness/resilience of the endoscope insertion portion and the insertion skills of many technicians, thereby preventing deterioration in the insertability into a body cavity, and consequently improving the efficiency of endoscopic examination.

Another object of the present invention is to provide an endoscope shape detecting apparatus capable of ascertaining with high precision the position of the body of the patient and the insertion shape of the endoscope, regardless of the bodily position of the patient at the point of insertion.

Another object of the present invention is to provide an endoscope shape detecting apparatus whereby a technician can appreciate how far the tip of the insertion portion of the endoscope has been inserted while watching the patient.

Another object of the present invention is to provide an endoscope shape detecting apparatus wherein a reference position can be displayed, without necessitating extra dedicated source coils for display of the reference position.

Another object of the present invention is to provide an endoscope shape detecting apparatus facilitating ease of viewing of an endoscopic image and endoscope shape image, thereby improving the operability of the insertion portion.

Another object of the present invention is to provide an endoscope shape detecting apparatus capable of reducing the amount of eye movement of a technician using an endoscope apparatus having stiffness adjusting means and insertion form detecting means, thereby improving operability.

Another object of the present invention is to provide an endoscope shape detecting apparatus having and endoscope with source coils arrayed within the insertion portion, while preventing increase in the diameter of the insertion portion.

Another object of the present invention is to provide an endoscope shape detecting apparatus whereby the operability of the endoscope system can be improved by quantitatively [knowing] understanding the insertion shape of the insertion portion.

Another object of the present invention is to provide an endoscope shape detecting apparatus having magnetic field generating elements whereby disturbance of magnetic fields due to metal members of the insertion portion can be reduced, and deterioration of the curving portion of the insertion portion can be prevented.

Another object of the present invention is to provide an endoscope shape detecting apparatus whereby the arrayed position of source coils in the insertion portion can be ascertained.

The endoscope shape detecting apparatus according to the present invention comprises:

an endoscope for observing a subject image by inserting an insertion portion into the body of a subject, such as into a body cavity;

a magnetic signal generating means for generating a magnetic field by supplying driving signals; a magnetic field detecting means for detecting the magnetic field generated by the magnetic field generating means; and a control means, the control means comprising:

a driving means for generating the driving signals;

a computing means for computing the shape of the inserted portion of the endoscope, from relative positional information between the magnetic field generating means and the magnetic field detecting means, based on detection signals detected by the magnetic field detecting means with one or the other of the magnetic field generating means and the magnetic field detecting means;

a display control means for displaying the endoscope shape obtained from the computation results based on the computing means on a display means; and a connection state detecting means for detecting the connection state of the magnetic field generating means;

wherein the control means controls at least one of the driving means, the computing means, and the display control means, based on the detection results of the connection state;

thereby controlling the display on the monitor and controlling the driving of the magnetic field generating means, according to the connection state of the magnetic field generating means.

Other features and advantages of the present invention will become sufficiently clear from the following description.

BRIEF DESCRIPTION OF THE DRAWINGS

This invention is described below with reference to the following figures, throughout which similar reference characters denote corresponding features consistently, wherein:

FIGS. 1A through 6 relate to a first embodiment of the present invention, wherein FIG. 1A is a diagrammatic view of an endoscope system constructed according to principles of the invention;

FIG. 1B is a partial diagrammatic view, drawn to an enlarged scale, of the area circumscribed by line 1b in FIG. 1A;

FIG. 1C is a partial diagrammatic view, drawn to an enlarged scale, of the area circumscribed by line 1c in FIG. 1A;

FIG. 1D is a partial diagrammatic view, drawn to an enlarged scale, of the area circumscribed by line 1d in FIG. 1A;

FIG. 2 is a schematic view of the function of the endoscope shape detecting apparatus shown in FIG. 1A;

FIG. 3 is a configuration diagram illustrating the configuration of the endoscope shape detecting apparatus shown in FIG. 2;

FIG. 4 is a schematic view of the configuration of the source coil driving circuit and marker coil driving circuit shown in FIG. 3;

FIG. 5 is a display view of the endoscope shape displayed by the endoscope shape detecting apparatus shown in FIG. 3;

FIG. 6 is a flowchart illustrating the operation of the endoscope shape detecting apparatus shown in FIG. 3;

FIGS. 7 through 10 relate to a second embodiment of the present invention, wherein FIG. 7 is a perspective view of the external configuration of a video endoscope constructed according to principles of the invention;

FIG. 8 is a transverse cross-sectional detail view of the insertion portion of the embodiment shown in FIG. 7;

FIG. 9 is transverse a cross-sectional detail view of the universal cord of the embodiment shown in FIG. 7;

FIG. 10 is a transverse cross-sectional detail view of the tube portion of the embodiment shown in FIG. 1;

FIGS. 11 through 14 relate to a third embodiment of the present invention, wherein FIG. 11 is a perspective view of the external configuration of a video endoscope constructed according to principles of the invention;

FIG. 12 is a partial perspective view of the relay connector of the embodiment shown in FIG. 11;

FIG. 13 is a second partial perspective view of the relay connector of the embodiment shown in FIG. 11;

FIG. 14 is a transverse cross-sectional detail view of insertion means at the insertion portion of a variation of the video endoscope shown in FIG. 11;

FIGS. 15 through 17 relate to a fourth embodiment of the present invention, wherein FIG. 15 is a perspective view of a video endoscope and probe constructed according to principles of the invention;

FIG. 16 is a perspective view of a first variation of the video endoscope and probe shown in FIG. 15;

FIG. 17 is a perspective view of a second variation of the video endoscope and probe shown in FIG. 15;

FIGS. 19 through 21 relate to a sixth embodiment of the present invention, wherein FIG. 19 is a perspective view of the endoscope proper of a video endoscope wherein a probe is inserted through the forceps channel;

FIG. 20 is a perspective view of the elastic member shown in FIG. 19;

FIG. 21 is a perspective view of the probe proper wherein an elastic member 102 is provided integrally with the relay connector shown in FIG. 19;

FIGS. 22 and 23 relate to a seventh embodiment of the present invention, wherein FIG. 22 is a perspective view of the endoscope proper of a video endoscope wherein a probe is inserted through the forceps channel;

FIG. 23 is a partial perspective view, drawn to an enlarged scale of the relay connector portion and waterproof cap connected by the chain shown in FIG. 21;

FIGS. 24–25B relate to an eighth embodiment of the present invention, wherein FIG. 24 is a side elevational view of the insertion portion of a video endoscope through which a probe is inserted;

FIG. 25A is a side elevational view of the probe shown in FIG. 24;

FIG. 25B is a display view of the probe of FIG. 25A;

FIGS. 27 through 31 relate to a tenth embodiment of the present invention, wherein FIG. 27 is a longitudinal cross-sectional detail view of a video endoscope;

FIG. 28 is a side elevational view, partially in cross-section, of a first probe inserted through the forceps channel of the video endoscope shown in FIG. 27 and used for insertion shape detection;

FIG. 29 is a side elevational view of a second probe inserted through the forceps channel of the video endoscope shown in FIG. 27 and used for insertion shape detection;

FIG. 30 is a side elevational view of a third probe inserted through the forceps channel of the video endoscope shown in FIG. 27 and used for insertion shape detection;

FIG. 31 is a diagrammatic view of the video endoscope shown in FIG. 27 inserted into the large intestine;

FIGS. 33 and 34 relate to a twelfth embodiment of the present invention, wherein FIG. 33 is a side elevational view of a first probe inserted through the forceps channel of a video endoscope and used for insertion shape detection;

FIG. 34 is a side elevational view of a second probe used with the first probe;

FIGS. 35 and 36 relate to a thirteenth embodiment of the present invention, wherein FIG. 35 is a longitudinal cross-sectional detail view of an endoscope with a probe inserted through the forceps channel of the video endoscope;

FIG. 36 is a cross-sectional detail view of the inside of a coil comprising the stiffness adjusting mechanism in a variation of the probe shown in FIG. 35;

FIGS. 37 and 38 relate to a fourteenth embodiment of the present invention, wherein FIG. 37 is a side elevational view of a connector of a universal cord;

FIG. 38 is an end view in the direction of the arrow A in FIG. 37;

FIGS. 39 through 44 relate to a fifteenth embodiment of the present invention, wherein FIG. 39 is a diagrammatic view of an endoscope system constructed according to principles of the invention;

FIG. 40 is a diagrammatic view of the array of source coils built into the insertion portion of the video endoscope shown in FIG. 39;

FIG. 41 is a transverse cross-sectional detail view drawn along lines A—A and B—B of the insertion portion of the video endoscope shown in FIG. 40, wherein solid lines represent the structure along lines A—A and broken lines represent the structure along lines B—B;

FIG. 42 is a side elevational view of a variation of the array of source coils built into the insertion portion of the video endoscope shown in FIG. 39;

FIG. 43 is a diagrammatic view of the coil unit shown in FIG. 39;

FIG. 44 is a longitudinal cross-sectional detail view of a sensing coil unit of the coil unit shown in FIG. 43;

FIGS. 45 and 46 relate to a sixteenth embodiment of present invention, wherein FIG. 45 is diagrammatic view of the belt-shaped coil unit mounted on a patient;

FIG. 46 is a perspective view of the coil unit shown in FIG. 45;

FIGS. 47 through 51 relate to a seventeenth embodiment of the present invention, wherein FIG. 47 is a diagrammatic view of an endoscope shape detecting system constructed according to principles of the invention;

FIG. 48 is a schematic view of the endoscope shape detecting unit shown in FIG. 47;

FIG. 49 is perspective view of the coil unit prior to engaging with the magnetic field detecting generating unit shown in FIG. 47;

FIG. 50 is a first longitudinal cross-sectional detail view of the coil unit engaging with the magnetic field detecting/ generating unit shown in FIG. 47;

FIG. 51 is a second cross-sectional detail view of the coil unit engaging with the magnetic field detecting/generating unit shown in FIG. 47;

FIGS. 52 through 58 relate to an eighteenth embodiment of the present invention, wherein FIG. 52 is a diagrammatic view of a shape detecting apparatus;

FIG. 53 is a perspective view of the coil unit prior to engaging with the magnetic field detecting/generating coil unit shown in FIG. 52;

FIG. 54 is a schematic view of the endoscope shape detecting apparatus shown in FIG. 52;

FIG. 55 is a first cross-sectional detail view of a first variation of the coil unit engaging with the magnetic field detecting/generating coil unit shown in FIG. 53;

FIG. 56 is a second cross-sectional detail view of a first variation of the coil unit engaging with the magnetic field detecting/generating coil unit shown in FIG. 53;

FIG. 57 is a perspective view engaging with a second variation of the coil unit engaging with the magnetic field detecting/generating coil unit shown in FIG. 53;

FIG. 58 is a perspective view of the coil member shown in FIG. 57;

FIGS. 59 through 64 relate to a nineteenth embodiment of the present invention, wherein FIG. 59 is a diagrammatic view of an endoscope shape detecting system configured according to principles of the invention;

FIG. 60 is a diagrammatic view of the position detecting mechanism in a first variation of FIG. 59;

FIG. 61 is a diagrammatic view of the position detecting mechanism in a second variation of FIG. 59;

FIG. 62 is a perspective view of the position detecting mechanism in a third variation of FIG. 59;

FIG. 63 is a perspective view of the position detecting mechanism in a fourth variation of FIG. 59;

FIG. 64 is a perspective view of the position detecting mechanism in a fifth variation of rig. 59;

FIGS. 65 and 66 relate to a twentieth embodiment of the present invention, wherein FIG. 65 is a diagrammatic view of an endoscope shape detecting system configured according to principles of the invention;

FIG. 66 is a perspective view of the knob operation amount detecting means shown in FIG. 65;

FIGS. 67 through 69H relate to a twenty-first embodiment of the present invention, wherein FIG. 67 is a schematic view of an endoscope shape detecting system configured according to principles of the invention;

FIG. 68A is a first graphical view of the timing of signals when performing display control of the endoscopic image and endoscope shape image using the controller shown in FIG. 67;

FIG. 68B is a second graphical view of the timing of signals when performing display control of the endoscopic image and endoscope shape image using the controller shown in FIG. 67;

FIG. 69A is a first graphical view of the timing of signals in a variation of performing display control of the endoscopic image and endoscope shape image using the controller shown in FIG. 67;

FIG. 69B is a second graphical view of the timing of signals in a variation of performing display control of the endoscopic image and endoscope shape image using the controller shown in FIG. 67;

FIG. 69C is a third graphical view of the timing of signals in a variation of performing display control of the endoscopic image and endoscope shape image using the controller shown in FIG. 67;

FIG. 69D is a fourth graphical view of the timing of signals in a variation of performing display control of the endoscopic image and endoscope shape image using the controller shown in FIG. 67;

FIG. 69E is a fifth graphical view of the timing of signals in a variation of performing display control of the endoscopic image and endoscope shape image using the controller shown in FIG. 67;

FIG. 69F is a sixth graphical view of the timing of signals in a variation of performing display control of the endoscopic image and endoscope shape image using the controller shown in FIG. 67;

FIG. 69G is a seventh graphical view of the timing of signals in a variation of performing display control of the image and endoscope shape image using the controller shown in FIG. 67;

FIG. 69H is an eighth graphical view of the timing of signals in a variation of performing display control of the endoscopic image and endoscope shape image using the controller shown in FIG. 67;

FIGS. 70 through 75 relate to a twenty-second embodiment of the present invention, wherein FIG. 70 is a schematic view of the function of an endoscope system;

FIG. 71 is a schematic view of the apparatus proper of the video processor and endoscope shape detecting apparatus shown in FIG. 70;

FIG. 72 is a schematic view of the image synthesizing device shown in FIG. 70;

FIG. 73 is a a display view of a monitor according to the image synthesizing device shown in FIG. 72;

FIG. 74 is a display view of a monitor in a first variation according to the image synthesizing device shown in FIG. 72;

FIG. 75 is a display view of a monitor in a second variation according to the image synthesizing device shown in FIG. 72;

FIGS. 76 through 80 relate to a twenty-third embodiment of the present invention, wherein FIG. 76 is a schematic view of an endoscope system;

FIG. 77 is a schematic view of the image synthesizing device shown in FIG. 76;

FIG. 78 are display views displayed with a monitor according to the image synthesizing device shown in FIG. 77 with a switch-over switch in a first state;

FIG. 79 are display views displayed with a monitor according to the image synthesizing device shown in FIG. 77 with a switch-over switch in a second state;

FIG. 80 are display views of a synthesized image displayed with a monitor according to the image synthesizing device shown in FIG. 77;

FIGS. 81 through 83 relate to a twenty-fourth embodiment of the present invention, wherein FIG. 81 is a schematic view of an endoscope system;

FIG. 82 are display views of a synthesized image displayed with a monitor according to the endoscope system shown in FIG. 81;

FIG. 83 is a schematic diagram of a variation of the endoscope system shown in FIG. 81;

FIGS. 84 through 88 relate to a twenty-fifth embodiment of the present invention, wherein FIG. 84 is a side elevational view of a video endoscope for generating an endoscope shape image wherein the curving portion is identifiable;

FIG. 85 is a display view of an endoscope shape image wherein the curving portion is identifiable with the video endoscope shown in FIG. 84;

FIG. 86 is a display view of a first variation of an endoscope shape image wherein the curving portion is identifiable with the video endoscope shown in FIG. 84;

FIG. 87 is a display view of a second variation of an endoscope shape image wherein the curving portion is identifiable with the video endoscope shown in FIG. 84;

FIG. 88 is a display view of a third variation of an endoscope shape image wherein the curving portion is identifiable with the video endoscope shown in FIG. 84;

FIGS. 89 and 90 relate to a twenty-sixth embodiment of the present invention, wherein FIG. 89 is a diagrammatic view of a sensing coil unit capable of removing the effects of metal members;

FIG. 90 is a diagrammatic view of a variation of the positioning of a sensing coil unit shown in FIG. 89, capable of removing the effects of metal members;

FIGS. 91A through 97 relate to a twenty-seventh embodiment of the present invention, wherein FIG. 91A is diagrammatic view of an endoscope apparatus;

FIG. 91B is a partial diagrammatic view, drawn to an enlarged scale, of the area circumscribed by line 91b in FIG. 91A;

FIG. 91C is a partial diagrammatic view, drawn to an enlarged scale, of the area circumscribed by line 91c in FIG. 91A;

FIG. 91D is a partial diagrammatic view, drawn to an enlarged scale, of the area circumscribed by line 91d in FIG. 91A;

FIG. 92 is side elevational view, partially in cross section, of stiffness adjusting means;

FIG. 93 is a perspective view of a photo-reflector;

FIG. 94 is a diagrammatic view of a rotary encoder;

FIG. 95 is a schematic view of the electrical system;

FIG. 96 is a display view displayed on the monitor when not performing image synthesizing;

FIG. 97 is a display view displayed on the monitor when performing image synthesizing;

FIGS. 98 through 100 relate to a twenty-eighth embodiment of the present invention, wherein FIG. 98 is a diagrammatic view of an endoscope with a source coil provided within the insertion portion;

FIG. 99 is a cross-sectional detail view, drawn along line A—A in FIG. 98, of the insertion portion;

FIG. 100 is a cross-sectional detail view, drawn along line A—A in FIG. 98, of another configuration of the insertion portion;

FIGS. 101 through 103 relate to a twenty-ninth embodiment of the present invention, wherein FIG. 101 is a schematic view of the insertion shape detecting apparatus;

FIG. 102 is a schematic view of the marked image generating unit;

FIG. 103 is a display view of the insertion shape image;

FIG. 104 is a display view of another configuration of the insertion shape image;

Figure 105:
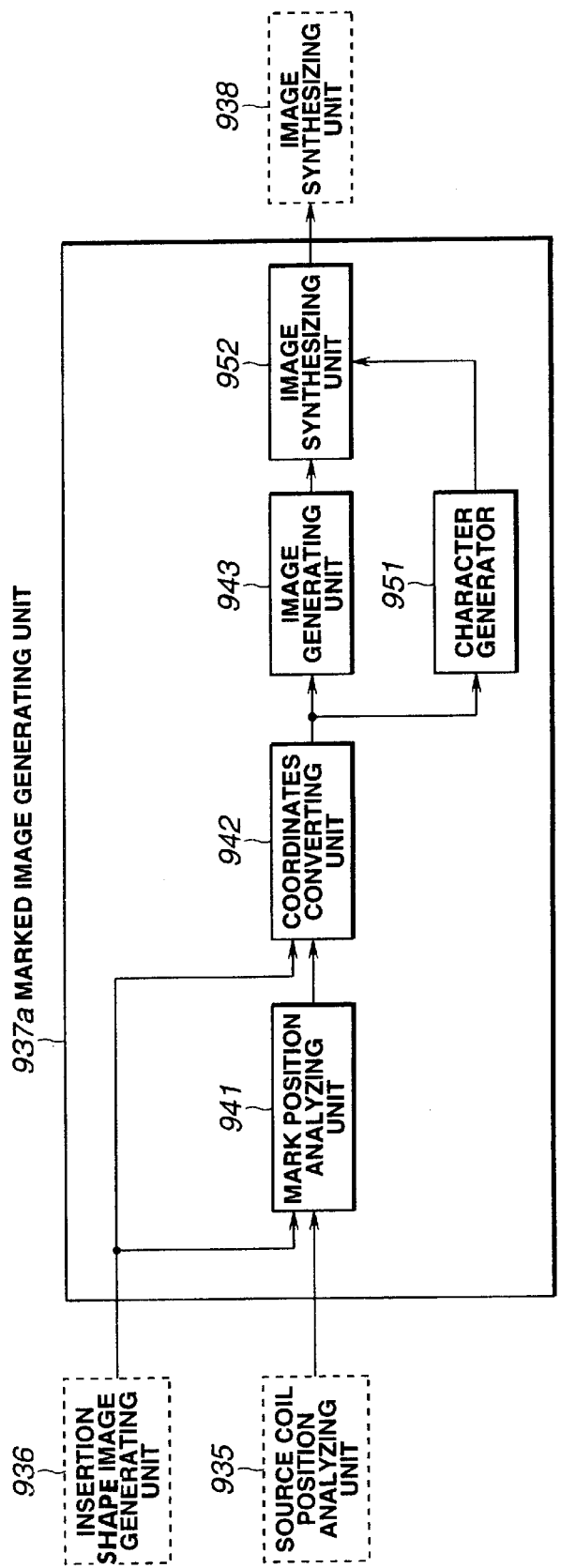
Figure 106:
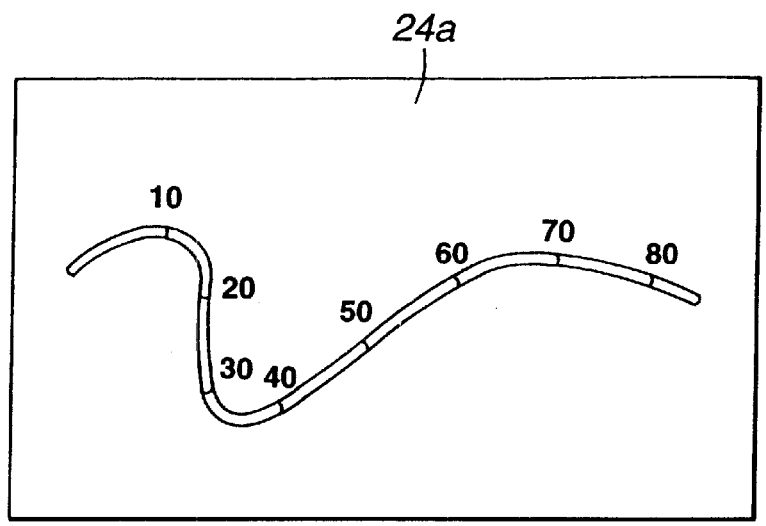
Figure 108:
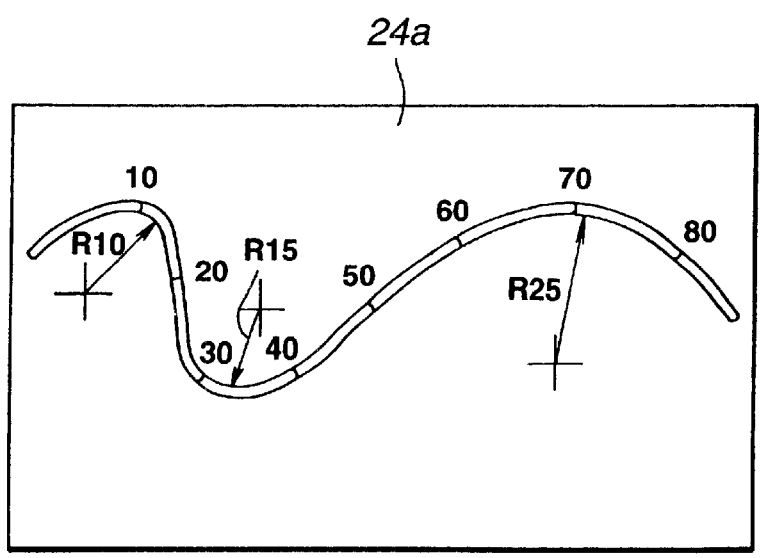
Figure 107:
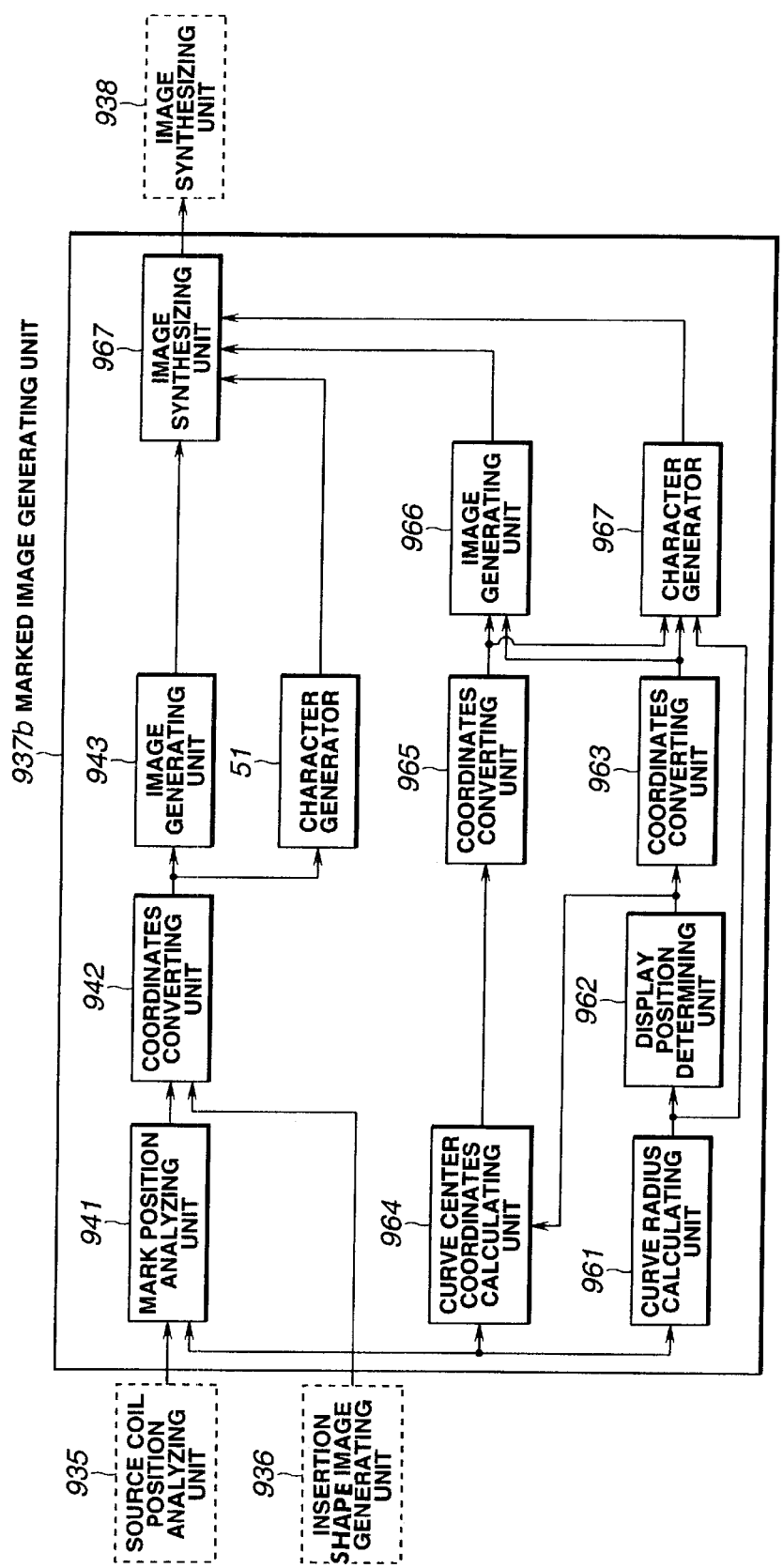
Figure 109:
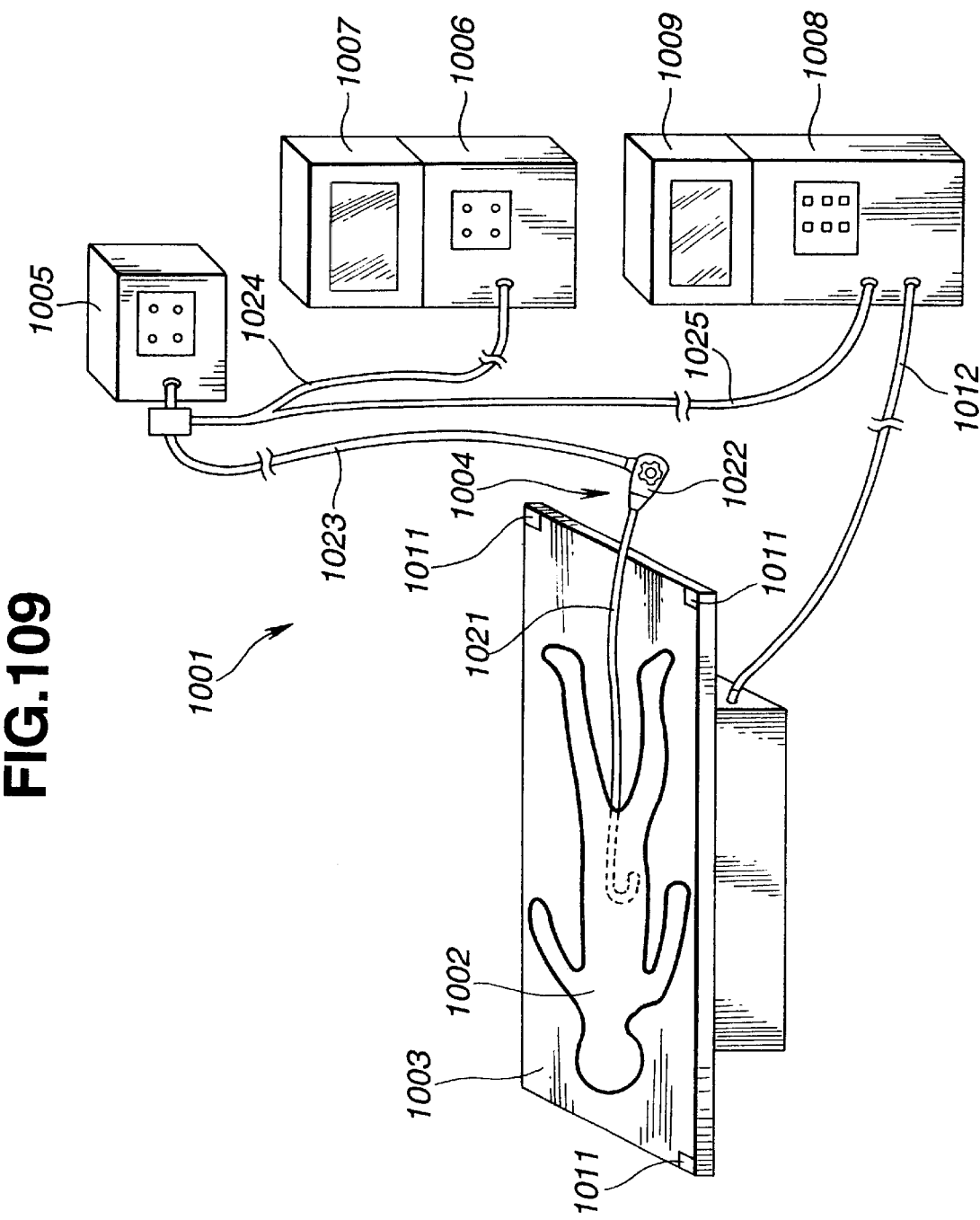
Figure 110:
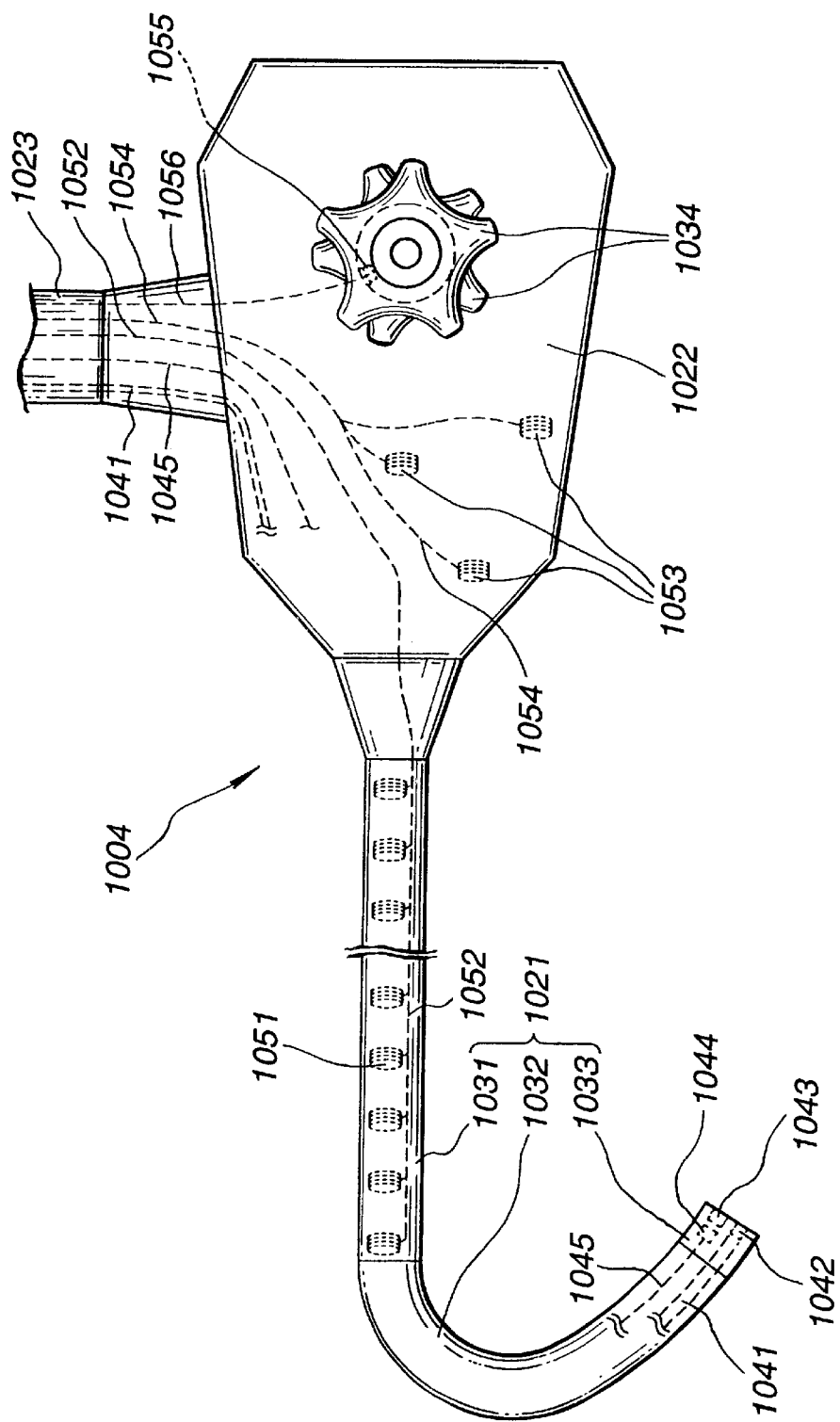
Figure 111:
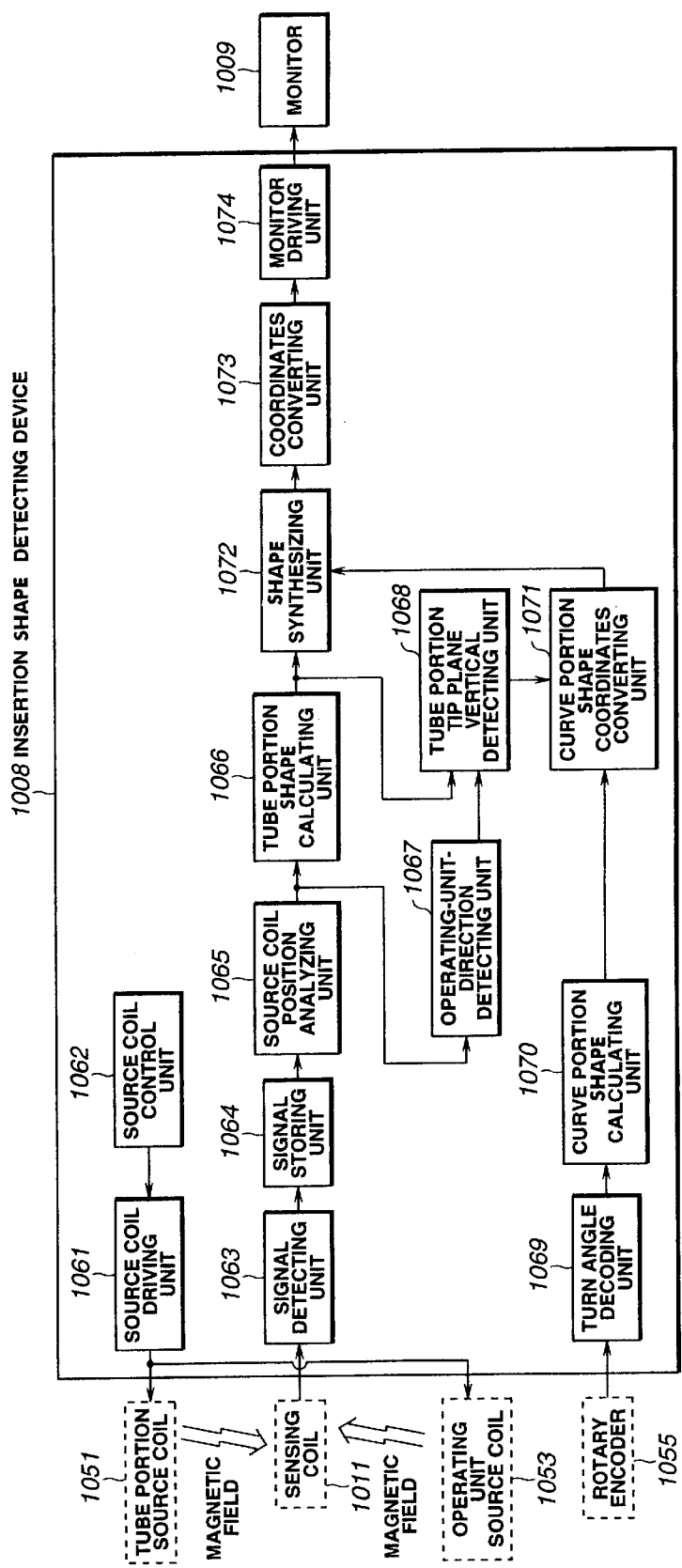
Figure 112:
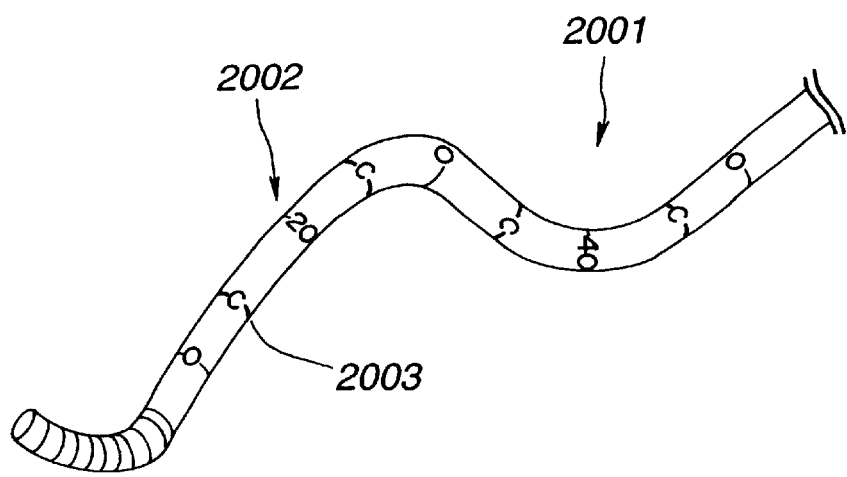
Figure 113:
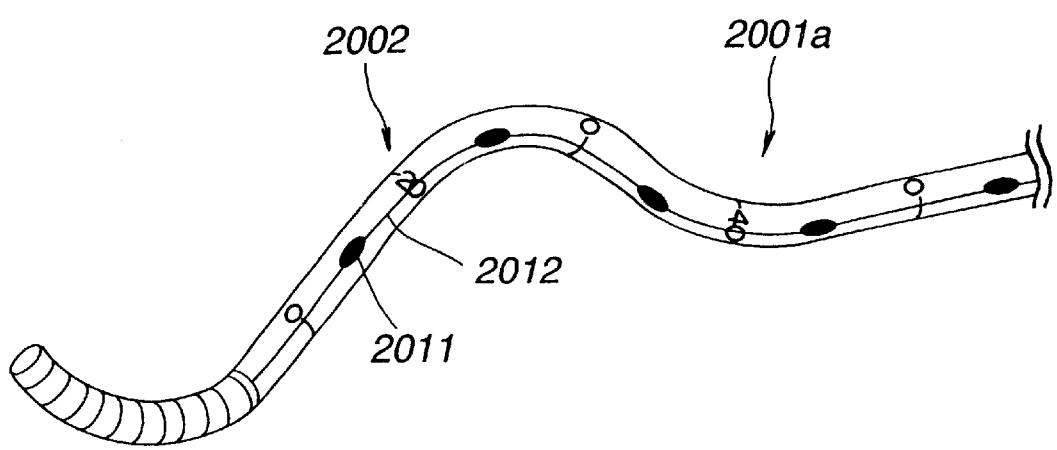

FIGS. 105 and 106 relate to a thirtieth embodiment of the present invention, wherein FIG. 105 is a schematic view of the marked image generating unit;

FIG. 106 is a display view of the insertion shape image;

FIGS. 107 and 108 relate to a thirty-first embodiment of the present invention, wherein FIG. 107 is a schematic view of the marked image generating unit;

FIG. 108 is a display view of the insertion shape image;

FIGS. 109 through 111 relate to a thirty-second embodiment of the present invention, wherein FIG. 109 is a diagrammatic view of an endoscope system;

FIG. 110 is a side elevational view of the endoscope shown in FIG. 109;

FIG. 111 is a schematic view of the insertion shape detecting apparatus shown in FIG. 109;

FIGS. 112 and 113 relate to a thirty-third embodiment of the present invention, wherein FIG. 112 is a perspective view of an insertion portion providing ease of recognition of the arrayed position of the source coils; and FIG. 113 is a perspective view of another insertion portion providing ease of recognition of the arrayed position of the source coils.

DESCRIPTION OF THE PREFERRED EMBODIMENTS

As shown in FIG. 1, the endoscope system 1 according to the present embodiment has an endoscope device 2 for performing endoscopic examination, and an endoscope shape detecting apparatus 3 used for facilitating endoscopic examinations. This endoscope shape detecting apparatus 3 is used as an insertion helping means for inserting the insertion portion 7 of a video endoscope 6 into the body cavity of a patient 5 lying on an examination table 4, and performing endoscopic examination.

The video endoscope 6 has an operating unit 8 comprising an curve operating knob provided at the rear end of the flexible insertion portion 7. A universal cord 9 extends from this operating unit 8, and is connected to a video imaging system (or a video processor) 10.

A light guide for transmitting illumination light from a light source unit within the video processor 10 passes through this video endoscope 6, so as to emit light from an illumination window at the tip of the insertion portions, thereby illuminating the patient. The image object, such as the illuminated affected portion or the like, is imaged onto an image-taking element provided at an image-forming position, by means of an object lens attached to an observation window next to the illumination window, and is subjected to photo-electrical conversion by this image-taking element.

The signals subjected to photo-electrical conversion are processed by an image signal processing unit within the video processor 10 so as to generate standard picture signals, which are displayed on a monitor 11 connected to the video processor 10.

A forceps channel 12 is provided to the video endoscope 6. Through the insertion opening 12a of this forceps channel 12 is inserted a probe 14 having, e.g., twelve magnetic field generating elements 13a, 13b, . . . , 13l, thereby positioning the source coil 13g within the insertion portion 7.

The source cable 15 which extends from the rear end of the probe 14 is detachably connected to the apparatus proper 16 of the endoscope shape detecting apparatus 3 with the connector at the rear end thereof. The source coil 13g radiates electromagnetic waves accompanied bye magnetic field by means of applying high-frequency signals or driving signals from the apparatus proper 16 to the source coil 13g serving as the magnetic field generating means, via the source cable 15 serving as high-frequency signal transmitting means.

While the present embodiment involves placing the source coil 13g within the insertion portion 7 of the electron endoscope 6 by means of inserting and fixing a probe 14 haying the source coiling attached thereto through the forceps channel 12 of the video endoscope 6, the source coil 13g may be directly assembled within the insertion portion 7 of the video endoscope 6.

Four markers 17a, 17b, 17c, and 1id, are provided for positioning on the surface of the body of the patient 5 (hereafter represented by 17a). Each marker 17a has one magnetism generating element or marker coil 18a. The marker cable 19 which extends from a portion of the marker 17a is detachably connected to the apparatus proper 16 of the endoscope shape detecting apparatus 3 at the connector at the rear end thereof, as with the source coil lag. The marker coil 18a also radiates electromagnetic waves accompanied by a magnetic field by means of applying high-frequency signals,or driving signals, from the apparatus proper 16 to the marker coil 18a serving as the magnetic field generating means, via the marker cable 19 serving as high frequency signal transmitting means.

Positioned within the coil unit 20 and placed at a certain position relative to the examination table 4 by a post 20a is a plurality of sensing coils. The sensing coils are comprised of single-core coils, as shown in FIG. 2, e.g., 16 sensing coils 21a, 21b, . . . , 21p (hereafter represented by 21j).

Returning to FIG. 1, the sensing coil 21j within the coil unit 20 is connected to the apparatus proper 16 via a sensing cable 22 serving as detecting signal transmitting means. An operating panel 23 or a keyboard or the like is provided to the apparatus proper 16 for a user to operate the apparatus. A monitor 24 is connected to the apparatus proper 16 for displaying the endoscope shape.

Further description will be made regarding the detailed configuration of the endoscope shape detecting apparatus 3.

As shown in FIG. 2, the endoscope shape detecting apparatus 3 is configured of a driving block 25 for driving the source coil 13g and marker coil 18a, a detecting block 26 for detecting signals received by the sensing coil 21j, and a host processor 27 for processing the signals detected by the detecting block 26.

Figure 3:
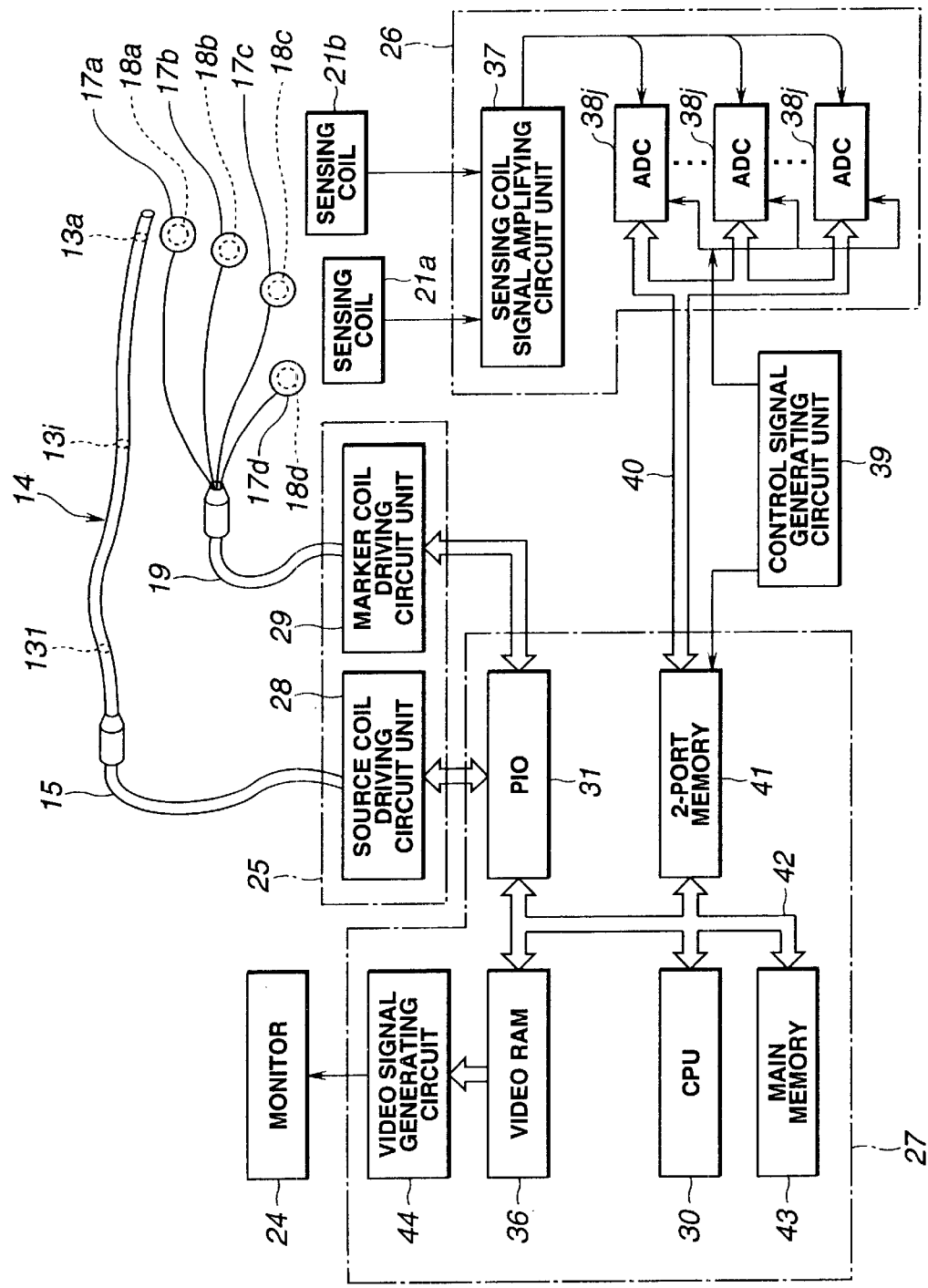

As shown in FIG. 3, twelve source coils 13g for generating magnetic fields are arrayed at certain intervals within the probe 14 positioned within the insertion portion 7 of the video microscope 6, as described above. These source coils 13g are connected to a source coil driving circuit unit 28 for generating distinct high-frequency driving signals, comprising the driving block 25.

The marker coils 18a are connected to a marker coil driving circuit unit 29 for generating distinct high-frequency driving signals, different from the above source coil driving signals, comprising the driving block 25.

The source coil driving circuit unit 28 and marker coil driving circuit unit 29 respectively drive the source coils 13g and marker coils 18a with sine wave driving signal currents having distinct frequencies corresponding to driving frequency setting data or driving frequency datastored in driving frequency setting data storage means or driving frequency setting data storing means (not shown) within the source coil driving circuit unit 28 and marker coil driving circuit unit 29. This driving frequency data is stored in the driving frequency data storage means (not shown) within the source coil driving circuit unit 28 and marker coil driving circuit unit 29 via a PIO (parallel input/output circuit) 31 by the CPU (central processing unit) 30 which performs calculation processing and so forth of the endoscope shape, within the host processor 27.

Figure 4:
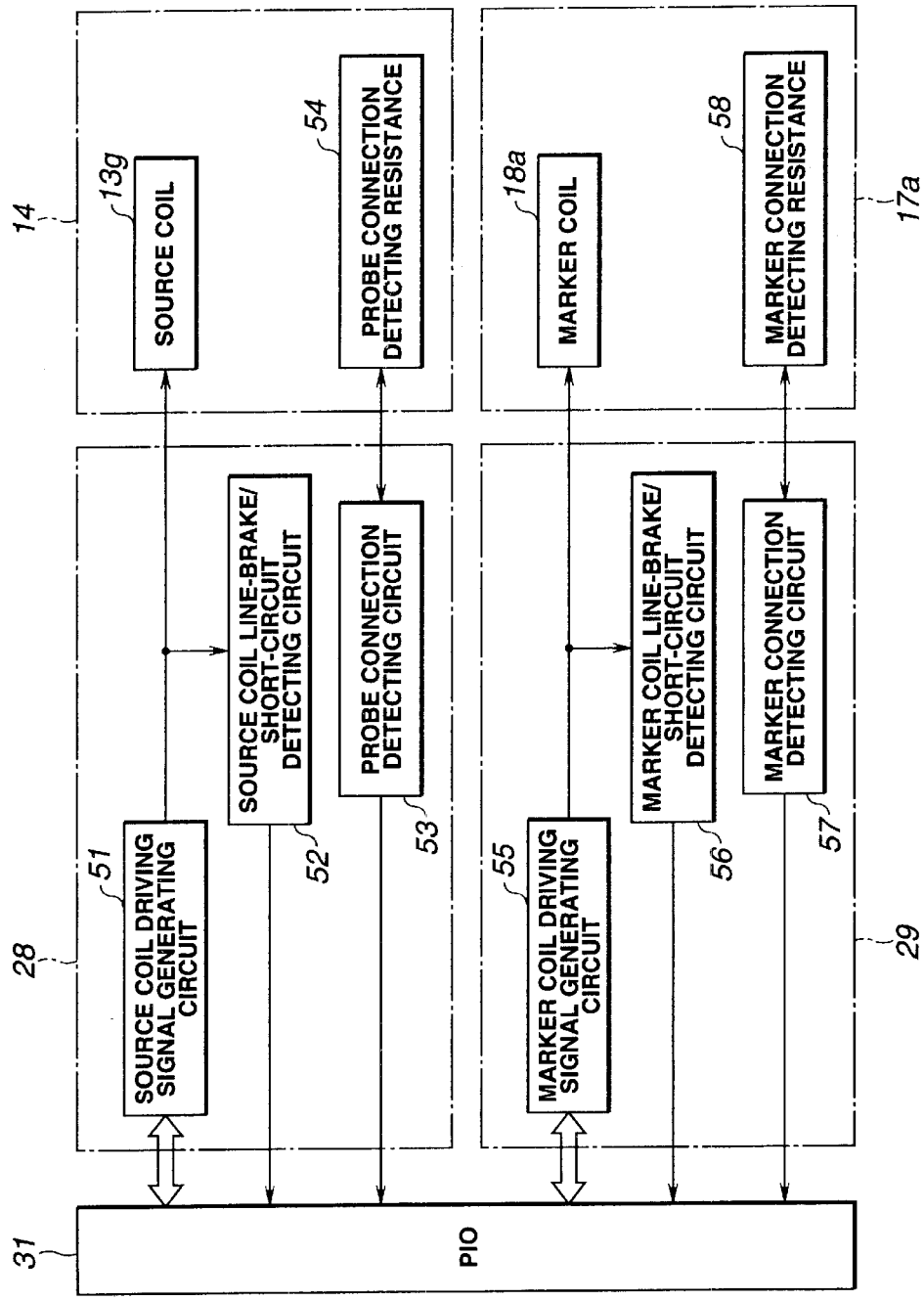

As shown in FIG. 4, the source coil driving circuit unit 28 is provided with a source coil driving signal generating circuit 51, a source coil line-break/short-circuit detecting circuit 52, and a probe connection detecting circuit 53.

The source coil driving signal generating circuit 51 generates sine wave driving signal current for driving the source coils 13g under the control of the CPU 30 via the PIO 31. The source coil line-break/short-circuit detecting circuit 52 detects line-break/short-circuit states in the source coils 13g by measuring the current flowing through each of the source coils 13g. The probe connection detecting circuit 53 detects whether there is connection with the probe 14, by measuring the current flowing through a probe connection detecting resistor 54 within the connector connecting the source cable 15 extending from the probe 14 to the apparatus proper 16. The detection results of the source coil line-break/short-circuit detecting circuit 52 and probe connection detecting circuit 53 are output as source coil line-break/short-circuit detecting signals and probe connection detecting signals, to the PIO 31.

Similarly, the marker coil driving circuit unit 29 is provided with a marker coil driving signal generating circuit 55, a marker coil line-break/short-circuit detecting circuit 56, and a marker connection detecting circuit 57.

The marker coil driving signal generating circuit 55 generates sine wave driving signal current for driving the marker coils 18 a under the control of the CPU 30 via the PIO 31. The marker coil line-break/short-circuit detecting circuit 56 detects line-break/short-circuit states in the marker coils 18a by measuring the current flowing through each of the marker coils 18a. The marker connection detecting circuit 57 detects whether there is connection with the markers 17a by measuring the current flowing through a marker connection detecting resistor 58 within the connector connecting the marker cable 19 to the apparatus proper 16. The detection results of the marker coil line-break/short-circuit detecting circuit 56 and marker connection detecting circuit 57 are output as marker coil line-break/short-circuit detecting signals and marker connection detecting signals to the PIO 31.

The source coil line-break/short-circuit detecting signals and probe connection detecting signals, and the marker coil line-break/short-circuit detecting signals and marker connection detecting signals are output to the video RAM 36 via the CPU 30, thereby controlling the display of the endoscope shape.

Returning to FIG. 3, the sensing coil 21j are connected to a sensing coil signal amplifying circuit unit 37 comprising the detecting block 26.

As shown in FIG. 3, the sensing coil 26 is configured of the sensing coil signal amplifying circuit unit 37 and an ADC (analog/digital converter) 38j, so that minute signals detected by the sensing coil 21j are amplified at the sensing coil signal amplifying circuit unit 37, and then converted by the ADC 38j into digital data which the host processor 27 can read. The digital data are written to the 2-port memory 41 via the local data bus 40 by means of control signals from the control signal generating circuit unit 39.

The CPU 30 reads the digital data written to the 2-port memory 41 by means of control signals from the control signal generating circuit unit 39, via the internal bus 42. The CPU 30 performs frequency extraction processing (Fast Fourier Transform, FFT) on the digital data using the main memory 43. The CPU 30 separates and extracts magnetic field detecting information from the frequency components corresponding to the driving frequency of the source coils 13g and the marker coils 18a. The CPU 30 calculates the spatial position coordinates of the source coils 13g and the marker coils 18a within the insertion portion 7 of the video endoscope 6, from the digital data in the separated magnetic field detecting information.

The insertion shape of the insertion portion 7 of the video endoscope 6 is estimated from the calculated positional coordinates data of the source coils lag. Display data for forming an endoscope shape image are generated and output to the video RAM 36. Display data of the marker coils 18a are generated from calculated positional coordinates data of the marker coils 18a and output to the video RAM 36.

Figure 5:
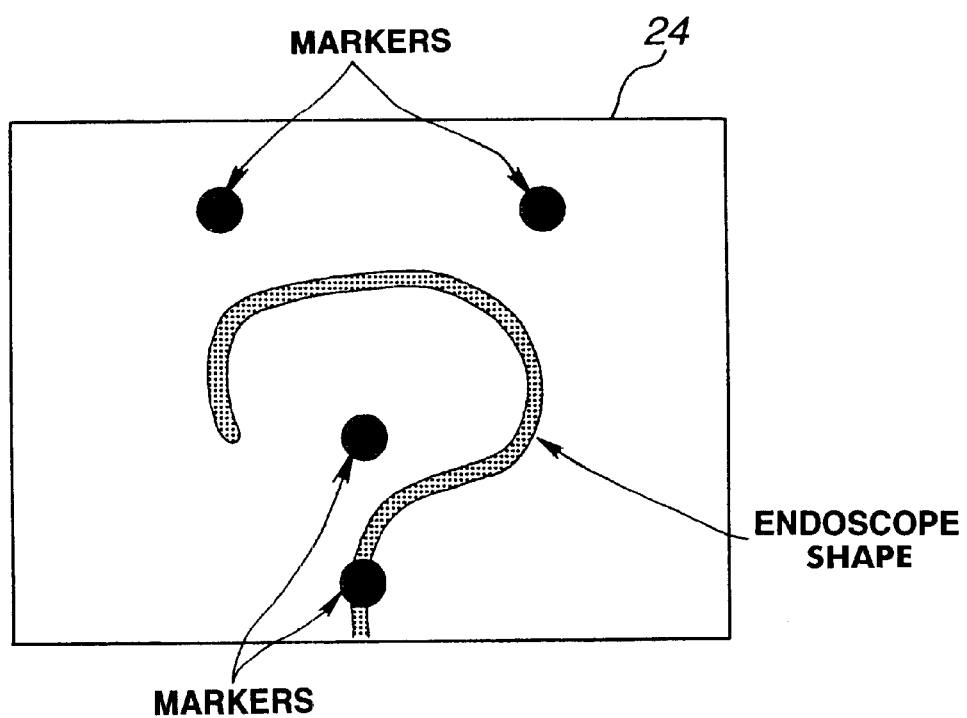

The data written to The video RAM 36 are read by a video signal generating circuit 44 and converted into analog video signals and output to the monitor 24. Inputting of the analog video signals displays the insertion shape of the insertion portion 7 of the video endoscope 6 and the marker positions on the display screen of the monitor 24, as shown in FIG. 5.

Next, the method by which the connection state of the probe 14 and markers 17a is detected by the detecting means, the source coil line-break/short-circuit detecting circuit 52 and probe connection detecting circuit 53, and marker coil line break/short-circuit detecting circuit 56 and marker connection detecting circuit 57 of FIG. 4, provided within the driving block 26, and by which display of the endoscope shape image is controlled, will be described.

Figure 6:
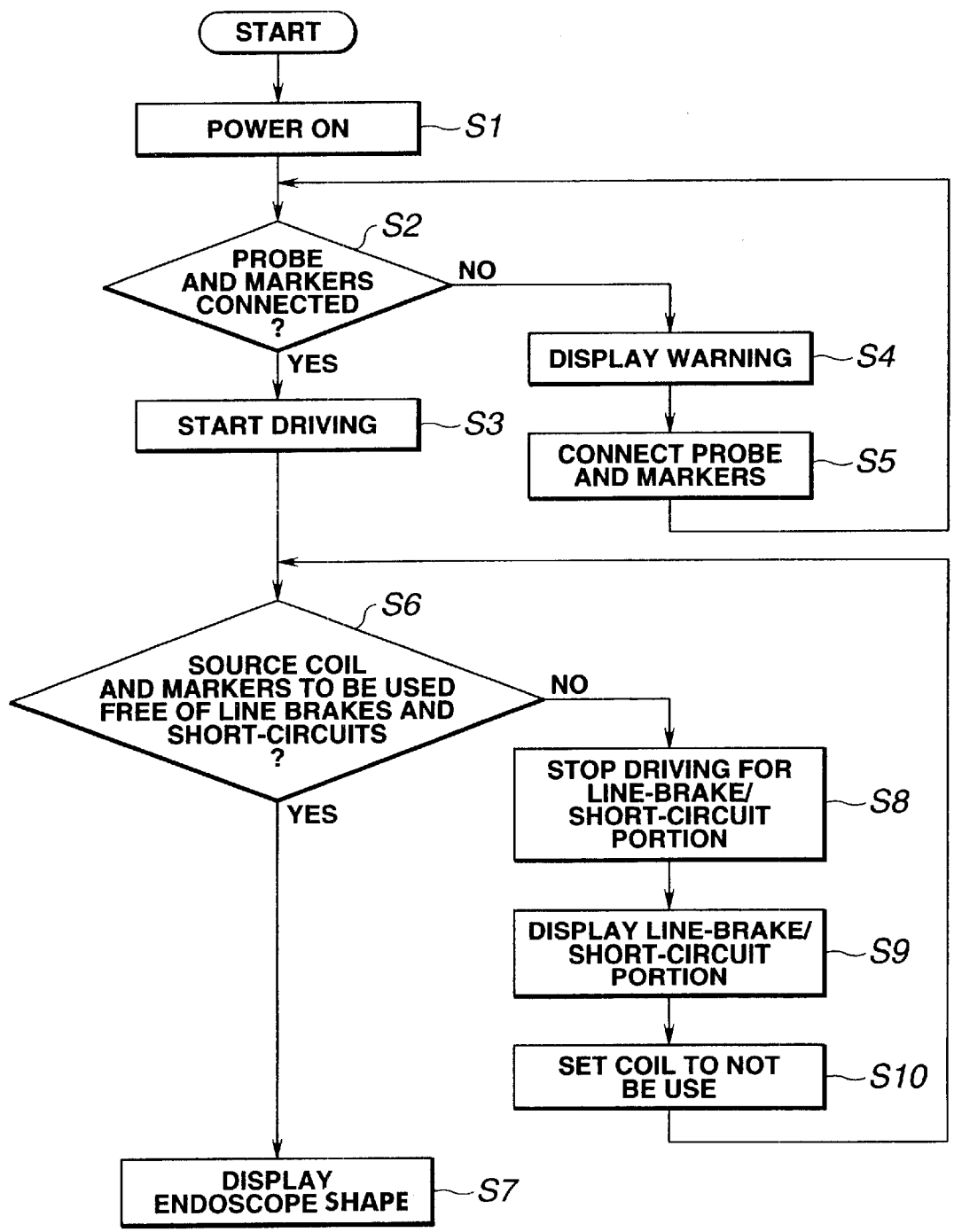

As shown in FIG. 6, once the power is turned on in step S1, first, in step S2, whether the probe 14 and markers 17a are connected to the apparatus proper 16 is detected by the probe connection detecting circuit 53 and marker connection detecting circuit 57. This detection is performed by measuring the current flowing through the probe connection detecting resistor 54 within the connector connecting the source cable 15 to the apparatus proper 16, with respect to the probe connection detecting circuit 53. Similarly, the detection is performed by measuring the current flowing through the probe connection detecting resistor 58 within the connector connecting the marker cable 19 to the apparatus proper 16, with respect to the marker connection detecting circuit 57.

If the probe 14 and markers 17a are connected to the apparatus proper 16, the control passes to step S3. At step S3, the source coil 13g and marker coil 18a begin driving, by means of the source coil driving signal generating circuit 51 and marker coil driving signal generating circuit 55.

If the probe 14 and markers 17a are not connected to the apparatus proper 16, the control passes to step S4. At step S4 a warning display is displayed on the monitor 24 to the effect that the probe 14 or markers 17a are not connected. The warning need not be restricted to a display on a monitor, and may involve a warning sound being emitted.

Following the warning, control pauses at step S5 for the technician to connect the probe 14 or markers 17a, then returns to step S2. At this time, stopping the source coil driving signal generating circuit 51 and marker coil driving signal generating circuit 55 serves to conserve electricity.

Once the source coil 13g and marker coil 18a begin to be driven in step S3, at step S6, detection of line-breaks and short-circuits of the source coils 13g and marker coils 18a is performed by the source coil line-break/short-circuit detecting circuit 52 and marker coil line-break/short-circuit detecting circuit 56. This detection is performed by measuring current flowing through the source coils 13g and marker coils 18a.

If the source coils 13g and marker coils 18a are free of line-breaks and short-circuits, control passes to step S7. At step S7, the endoscope shape image and marker image are displayed on the screen of the monitor 24 (see FIG. 5).

If there are any line-breaks or short circuits in the source coils 13g or marker coils 18a at step S6, control passes to step S8. At step S8 the driving of the coil with a line-break or short-circuit is terminated, and the coil that has a line-break or short-circuit is displayed on the screen of the monitor 24 in step S9. Subsequently, the coil(s) that are not to be used is/are set in the preset screen in step S10. The processing is changed such that a coil that is not to be used is ignored. The flow control then returns to step S6 again. At step S7 the endoscope shape image and marker image are displayed on the screen of the monitor 24.

According to the present embodiment, whether the probe 14 and markers 17a are connected to the apparatus proper 16 is detected by the probe connection detecting circuit 53 and marker connection detecting circuit 57 at the time of turning on the power. Thus, a state wherein the probe 14 and markers 17a are not connected to the apparatus proper 16 can be avoided, thereby preventing detecting environment noise instead, when the probe 14 and markers 17a are not connected to the apparatus proper 16, consequently displaying an unintended random image on the monitor 24.

Only the driving of the malfunctioning portion is stopped, thus, if one of the source coils within the probe 14 or a source coil in the markers 17a malfunctions during examination, the examination can be continued without replacing the probe 14 or marker 17a. If the malfunction is a short-circuit, excessive current that can damage the endoscope shape detecting apparatus proper can be prevented since the driving is stopped.

Detection of connection, line-breaks and short circuits need not only be performed at the time of turning on the power. Detection of connection, line-breaks and short-circuits may be performed while in use as well. The detection of connection, line-breaks and short-circuits may be manually initiated or timed such that detection of connection, line-breaks and short-circuits is performed regularly and automatically. Even if the probe 14 or marker 17a come loose or malfunction during use, a warning is automatically displayed on the monitor so the issue can be dealt with speedily.

While the present embodiment involves inserting a probe 14 having the source coils 13g attached thereto through the forceps channel 12 of the video endoscope 6, the present embodiment is not restricted to such an arrangement. The present embodiment can be applied in the same manner to an endoscope having source coils 13g directly built in to the insertion portion 7. In this case, the endoscope shape detecting apparatus proper to which the probe 14 is connected and the endoscope device proper for connecting the endoscope having source coils built therein are not separate, but the same and connectable to either. Detection may be made regarding which is connected: the probe or the endoscope having source coils built therein. The result of the detection is then displayed on the display screen.

The second embodiment is almost the same as the first embodiment. Description of the second embodiment will be made regarding only the differing points. Similar configurations with the previous embodiment will be denoted with the same reference characters with the description thereof omitted.

It is an object of the second embodiment to provide a video endoscope wherein replacement of the probe 14 is simple.

The first embodiment involved a probe 14 being inserted through the insertion opening 12a of the forceps channel 12. The present embodiment provides a dedicated guide channel for passing the probe 14 through the video endoscope, in order to allow biopsies to be performed by extending treatment equipment through the insertion opening 12a of the forceps channel 12 and out of a tip opening.

Figure 7:
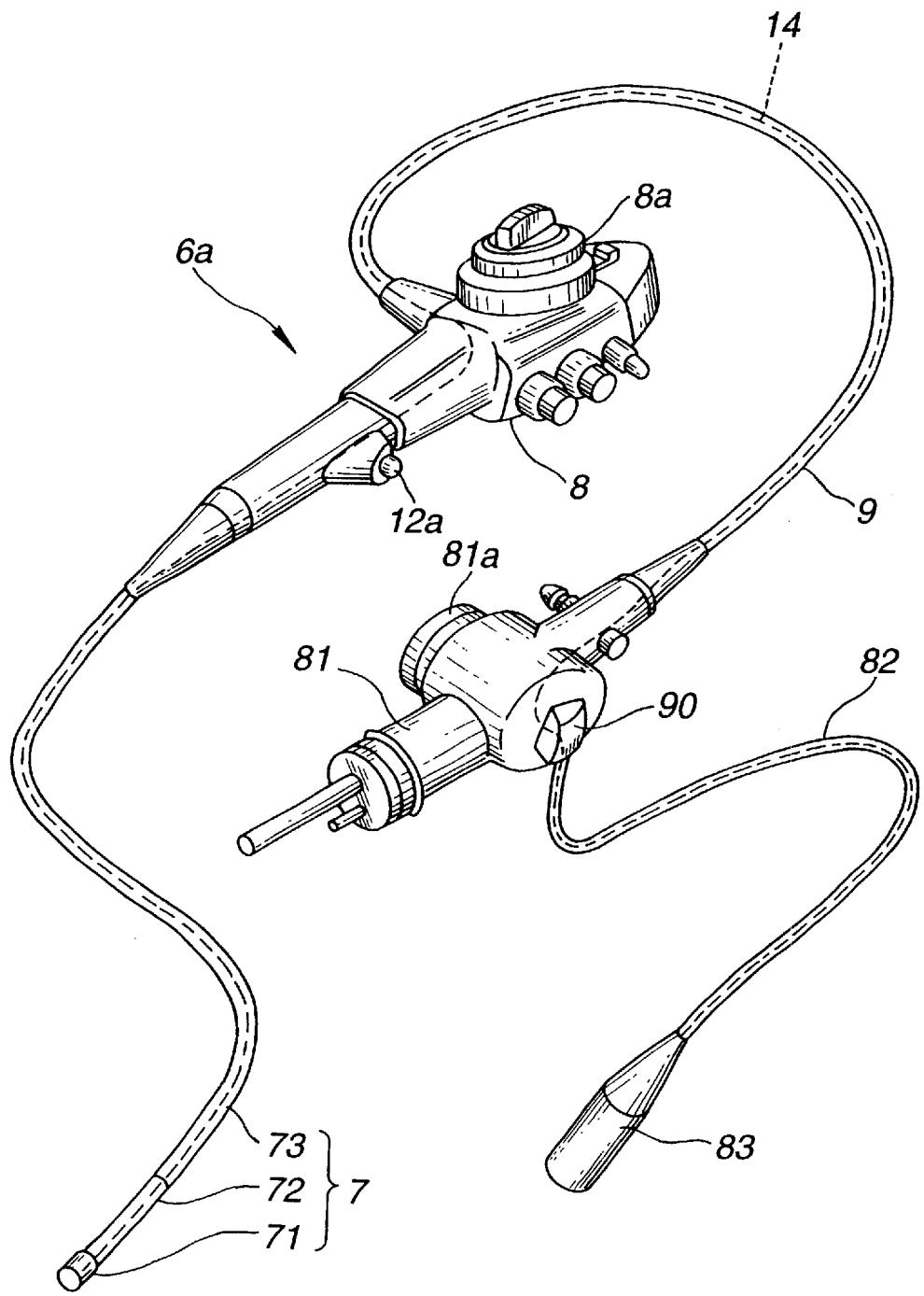

As shown in FIG. 7, the insertion portion 7 of the video endoscope 6a according to the present embodiment is comprised of a tip portion 71, a curvable curving portion 72, and a flexible flexible portion 73.

The universal connector 81 at the end portion of the universal cord 9 is detachable from the video processor 10. Light is provided by the base of the light guide protruding from the front end of the universal connector 81 which is connected to the light source unit of the video processor 10. The video processor 10 obtains image signals via an electric connector 81a of the universal connector 81.

An insertion opening 12a for inserting treatment equipment is provided near the front end of the operating unit 8. Treatment equipment, such as biopsy forceps or the like (not shown) can be inserted from this insertion opening 12a. Treatment equipment inserted from this insertion opening 12a protrudes from the tip opening via the forceps channel 12 within the insertion opening 12a such that biopsies and the like can be performed. The forceps channel insertion opening 12a connects to the forceps channel 12 and a suction channel (not shown) extending toward the operating unit 8.

The probe 14 is inserted in a tube portion 82 connected to the universal connector 81. The probe 14 is inserted into the video microscope 6a through the tube portion 82 and the universal connector 81. A probe connector 83, provided to the rear end of this tube portion 82, is detachably connected to the apparatus proper 16 of the endoscope shape detecting apparatus 3.

The probe connector 83 and tube portion 82 are arranged to be detachably connectable.

With the video microscope 6a according to the present embodiment, a hollow tube 84 forming a dedicated insertion channel through which the probe 14 is inserted, passes through the insertion portion, shown in FIG. 8, the universal cord 9, shown in FIG. 9, and the tube portion 82, shown in FIG. 10. The tip of the tube 84 is fixed by being press-fit or the like to the tip portion 71 of the insertion portion 7.

The tube portion 82 is formed of a tube with a greater internal diameter than the outer diameter of the tube 84, for example, so that the tube portion 82 is inserted through the tube 84. The tube portion 82 has an internal diameter that is somewhat larger than the outer diameter of the tube 84, so that, not only is extracting the probe 14 from this tube 84 through which it has been passed relatively easy, but inserting a new probe 14 is also relatively easy.

In other words, with the video microscope 6a according to the present embodiment, a dedicated insertion or guide channel for inserting the probe 14 through a tube 84 is provided, thereby configuring an a video microscope 6a through which a probe 14 can be passed and permitting detecting the insertion shape.

The present embodiment is characterized by the cross-sectional form of the hollow portion of the tube 84 being similar to the cross-sectional form of the probe 14 but greater in size, thereby forming an inserting/extracting mechanism or mounting/detaching mechanism, which allows easy insertion and removal, or mounting and removal, of the probe 14.

It is preferable that this tube 84 have thin walls and flexibility to maintain the insertion portion 7 which is flexible. Preferably, the tube 84 should be formed of a material having elasticity which returns the shape of the wall to a circular cross-section form so that the insertion channel, which facilitates ease of insertion of the probe 14 at the time of replacing probes 14, is secured. The tube 84 also may be constructed from a material with a certain degree of stiffness so as to maintain the circular cross-section.

If the tube 84 is formed of a synthetic resin or the like, and the elasticity is insufficient from forming the walls too thinly, a fine metal coil may be embedded within the thin walls of the tube 84 in order to increase the resilience for returning the shape of the walls to the circular cross-section. Other such steps may be taken.

As shown in FIGS. 8 and 9, in addition to the probe 14 inserted through the tube 84, other members pass through the universal cord 9 of the insertion portion 7. One member is a forceps channel 12 or suction channel 85 for inserting treatment equipment, such as biopsy forceps and the like. Another member is a cable 86 connected to an image-taking element provided within the tip portion 71. Another member is a light guide 87 for transmitting light from the light source unit of the video processor 10.

A plurality of source coils 13g (not shown) is provided, each source coil 13g being at certain intervals along the insertion portion 7 of the probe 14 to be inserted into the body cavity. Each source coil 13g is connected to a plurality of signal lines extending to a probe connector 83.

The front, top portion of the tube portion 82 is fixed to the universal connector 81 in a watertight manner by means of a fixing cover 90 (see FIG. 7) at the side of the universal connector 81. Other configurations of this embodiment are the same as those in the first embodiment.

The operation of the present embodiment will be described. The probe 14 is provided to the video endoscope 6a so that when the insertion portion 7 is inserted into a body cavity of a patient, the insertion shape of the insertion portion 7 can be displayed on the monitor 24 by position detection of the source coils 13g within the probe 14, in the same manner as with the first embodiment.

This allows the insertion portion 7 to be smoothly inserted into the body cavity by the technician making reference to the insertion shape display displayed on the monitor 24. If replacement of the probe 14 becomes necessary due to repeated usage, the probe connector 83 is removed from the tube portion 82, or the fixing cover 90 fixed with screws or the like, is removed and the probe 14 is extracted, thereby allowing the probe 14 to be pulled out through the tube 84.

Conversely, to repair or install a new probe 14 within the video endoscope 6a, the probe 14 is inserted into the tube portion 82 from the tip, and pushed into the tube 84 of the tube portion 82, until the tip of the probe 14 reaches the endoscope tip portion 71.

The probe 14 can be smoothly inserted through the universal cord 9, the operating unit 8, and even the insertion portion 7, by passing through the inner hollow portion of the tube 84, having a hollow cross-section which is greater than the cross-section of the probe 14, the tube 84 serving as a guide.

When removing an old probe 14, the cross sectional shape of the inner hollow of the tube 84 within the video endoscope 6a may be deformed into an oval shape or narrowed from the round cross-sectional shape, of the probe 14, due to pressure imparted by other built-in members. However, the tube 84 regains its circular cross-sectional shape due to the elasticity thereof upon being spread open by the tip of the probe 14 being inserted through the inside thereof, hence facilitating smooth passage of the probe 14.

When, the tip of the probe 14 reaches the tip plane of the tip portion 71, the fixing cover 90 is the fixed, and the tube portion 82 and probe connector 83 are connected, thus completing the replacement.

The present embodiment has the following advantages.

First, the number of procedures necessary for replacing the probe 14 can be greatly reduced. Accordingly, the amount of time required for repair can be reduced. Finally, reducing the number of procedures facilitates the ease of work, which also reduces repair costs.

As shown in FIG. 10, a tube 84 may be inserted through the tube portion 82. However, a variation may be made wherein only the front tip of the tube portion 82 comes into contact with the tube 84. In this case, if the probe 14 must be replaced, the old probe 14 is extracted, following which a new probe 14 is passed through the tube portion 82 and further inserted into the endoscope from the tube 84 facing the tip thereof, thereby exhibiting advantages similar to the present embodiment.

The third embodiment is almost the same as the second embodiment. Only the differing points will be described. Similar configurations with the earlier embodiments will be denoted with the same reference characters with description thereof omitted.

The objects of the present invention are the same as those in the second embodiment.

Figure 11:
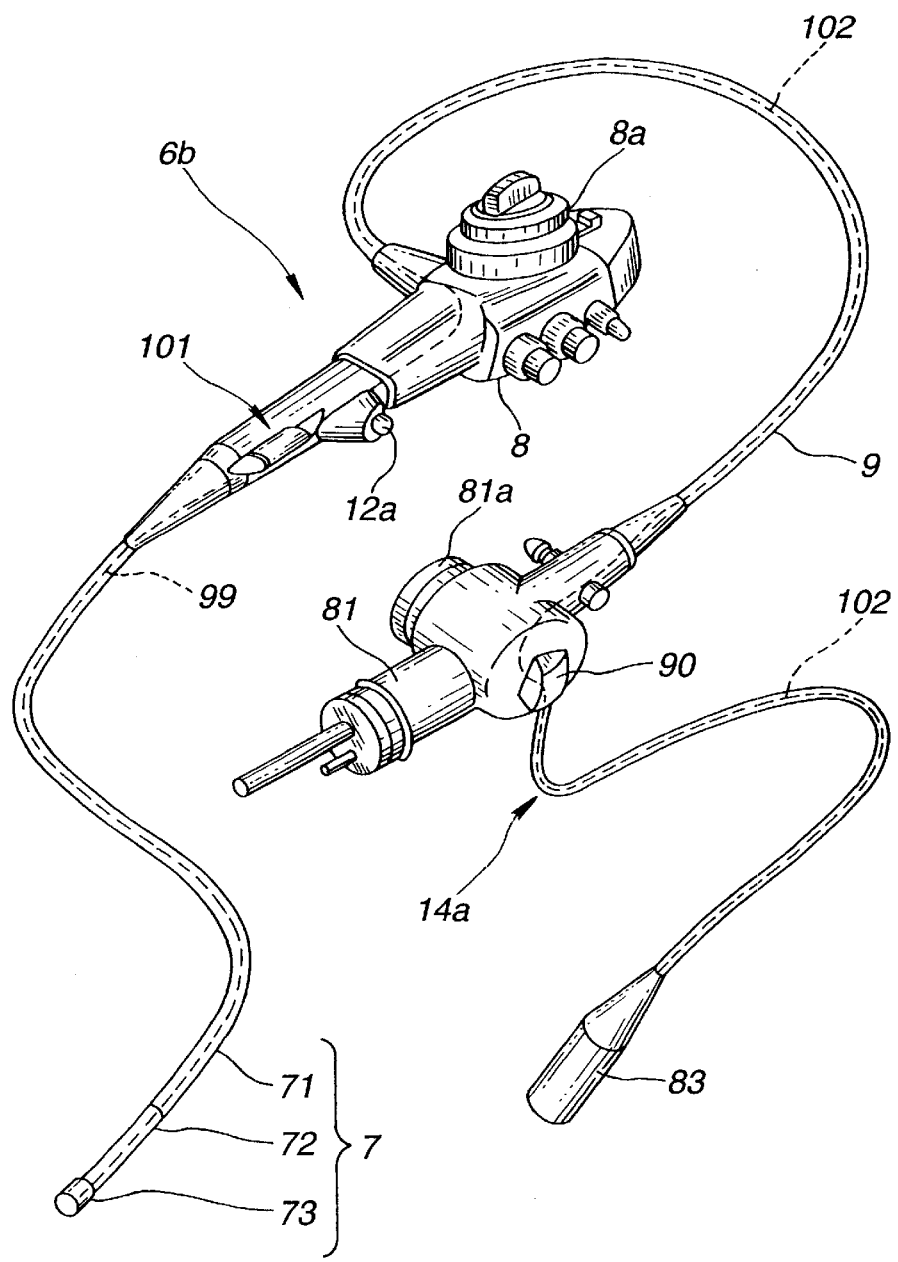

As shown in FIG. 11, the video endoscope 6b employs a probe 14a which allows the probe main unit 99 portion within the insertion portion 7 to be easily replaced, unlike the video endoscope 6a according to the second embodiment.

According to this video endoscope 6b,a relay connector potion 101 is provided to the side of the front end of the operating portion neighboring the buckling prevention member at the rear end or base of the insertion portion 7 which is inserted into the body cavity of the patient. The rear end of the probe main unit 99 inserted within the insertion portion 7 is detachably connected to one end of a relay cable 102 at the relay connector portion 101.

The relay cable 102 passes through an operating portion 8 and the universal cord 9, and extends from the universal connector 81, with the probe connector 83 at the other end being detachably connected to the apparatus proper 16 of the endoscope shape detecting apparatus 3.

In other words, with this video endoscope 6b, the probe 14a is comprised of a probe main unit 99 inserted through the insertion portion 7; and a relay cable 102 detachably connected to the probe main unit 99 at the relay connector portion 101, with a portion thereof being passed within the operating unit 8 and universal cord 9 and externally extended from the universal connector 81; wherein the rear end of this relay cable 102 is attached to probe connector 83 which can be attached and removed.

Figure 12:
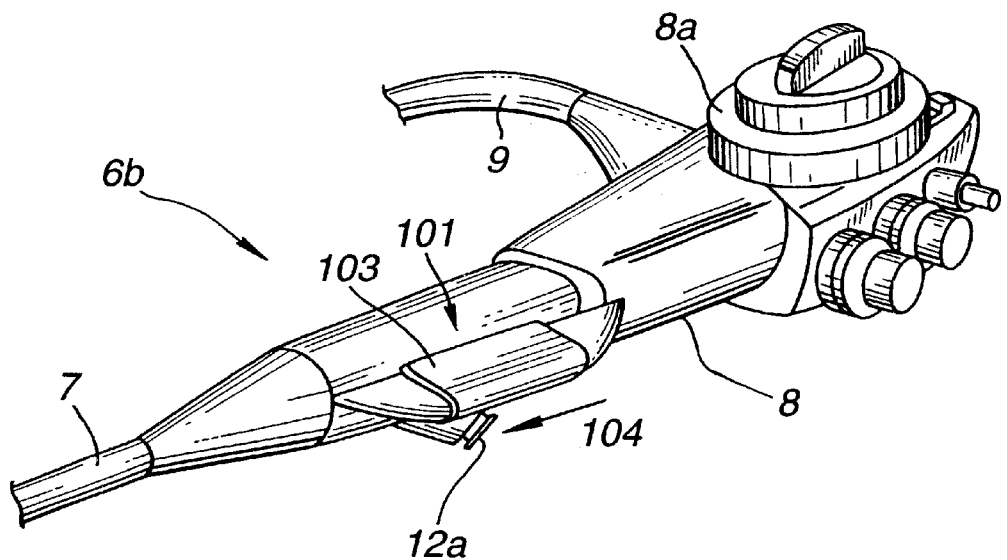
Figure 13:
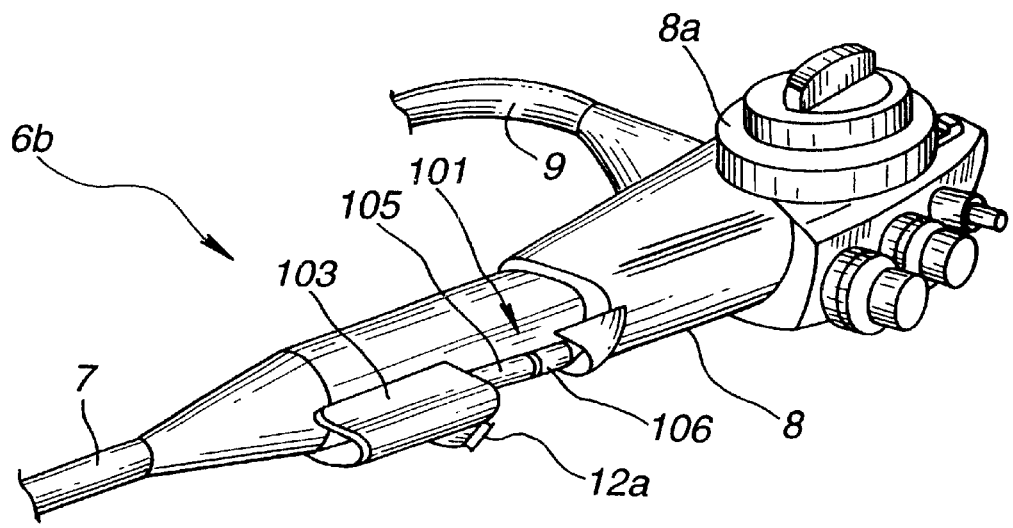

FIGS. 12 and 13 illustrate the detailed construction of a relay connector portion 51.

As shown in FIG. 12, the relay connector portion 101 is covered with a waterproof cover 103. The waterproof cover 103 slides in the direction 104. As shown in FIG. 13, a connector 105, at the rear end of the probe main unit 99, and a connector 106, at the front end of the relay cable 102, detachably connected to the connector 105, within the waterproof cover 103.

As shown in FIG. 12, a watertight seal member is attached to the inner side of the waterproof cover 103, for example, so that the inner perimeter portion comes into tight contact when the waterproof cover 103 covers the connectors 105 and 106, thereby maintaining the inside of the waterproof cover 103 in a watertight state.

Although not shown in FIGS. 11 through 13, a tube 84, such as described in the second embodiment, passes through the insertion portion 7 (see FIG. 8). The rear end of this tube 84 is exposed at the inner side of the waterproof cover 103 near the front end of the operating unit 8.

This facilitates replacing the probe main unit 99. The relay cable 102 side may also pass through the tube 84. Or, the arrangement may be such that the relay cable 102 side does not pass through the tube 84, since the relay cable 102 side can be used for a long time before necessitating replacement.

The operation of the present embodiment will be described.

The insertion shape of the endoscope can be displayed with this video endoscope 6b according to the present embodiment, as with the first embodiment. Replacement of the portion of the probe 14a inserted in the insertion portion 7, i.e., the portion belonging to the probe main unit 99, is occasionally necessitated, due to repeated insertion and removal of the insertion portion 7 to and from a tortuous body cavity.

To do so, the waterproof cover 103 of the relay connector portion 101 is opened, as shown in FIG. 13, exposing the relay connectors 105 and 106, which are removed one from another. Then, the relay connector 105 portion of the probe main unit 99 is pulled and removed from the insertion portion 7.

The probe main unit 99 is inserted through the tube 84 which has a hollow portion with a cross sectional shape that is larger than the cross-sectional shape of the probe main unit 99, and thus can be easily extracted.

Inserting, or pushing in, the new replacement probe 14a from the end portion of the tube 84 exposed within the waterproof cover 103 from the relay connector 101 applies force for spreading the tube 84 serving as a guide. The tube 84, returning to the same circular cross-sectional shape, which is the same cross-sectional shape as that of the probe main unit 99, due to the elasticity or reverting force thereof, allows the probe main unit 99 to be easily inserted within the insertion portion 7.

Following insertion of the tip of the probe main unit 99 to the tip of the video endoscope 6b, the connectors 105 and 106 are connected. Closing the waterproof covering completes the connection.

According to the present invention, advantages of enabling the probe 14a to be replaced easily and in a short time can be obtained, similar to the second embodiment.

With the present embodiment, the probe main unit 99 passing through the insertion portion 7, which necessitates replacement at a relatively high frequency, can be replaced independently, further reducing the number of procedures necessary for replacement. Only one part of the overall probe is replaced, further reducing costs.

Figure 14:
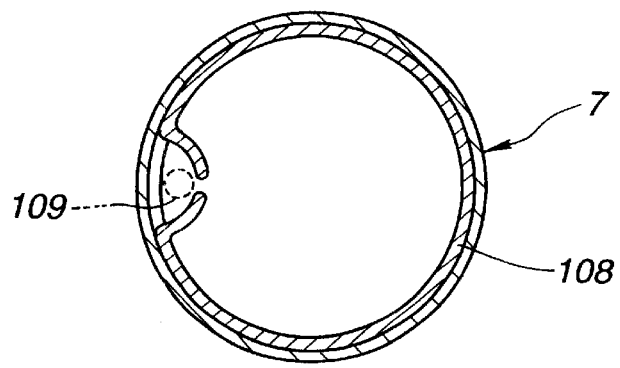

As with the second embodiment, the present embodiment has a tube 84 for easy mounting and removal of the probe 14a, or probe main unit 99 provided, within the insertion portion 7a variation thereof provides a coil, for example, or a probe insertion channel 109 formed using a structure 108 within the insertion portion 7, as shown in FIG. 14.

A probe insertion channel 109 may be formed by raising flaps or the like inwardly within the insertion portion 7, as shown by dotted lines, for example.

Other various arrangements may be made so long as securing a path for the probe 14a is realized. This embodiment is not restricted to the tube 84. Rather, coils or other members may be used. The structure 108 within the insertion portion 7 shown in FIG. 14 can be used effectively.

A variation of the tube 84 forming an insertion channel for the probe 14 or probe 14a, or probe main unit 99, in the second and third embodiments, provide a coil-shaped member formed of a shape memory alloy, for example, embedded within the walls of a flexible tube, such that both ends are exposed in the universal connector 81 or the waterproof cover 103.

When replacing the probe 14 or the probe main unit 99, an electric current may be applied to both ends so as to apply heat, transforming the coil-shaped shape memory alloy to the high-temperature phase, so as to restore the circular cross-section shape of the memory alloy in that phase.

Instead of applying an electrical current to apply heat and cause a phase transformation, a chamber heated to a temperature or higher for enabling phase transformation may be used so that the tube is restored to the circular cross-section shape.

The tube may be restored to the circular cross-section shape by setting the shape at the low-temperature phase, instead of restoring the tube to the circular cross-section shape found at the high-temperature phase.

The fourth embodiment is similar to the first embodiment. Only the differing points from the earlier embodiments will be described. Similar configurations will be denoted with the same reference characters and the description thereof omitted.

The fourth embodiment of the present invention is described with reference to FIGS. 15 through 17. It is an object of the present invention to provide an endoscope shape detecting apparatus wherein a proper combination of video endoscope and probe can be used.

Figure 15:
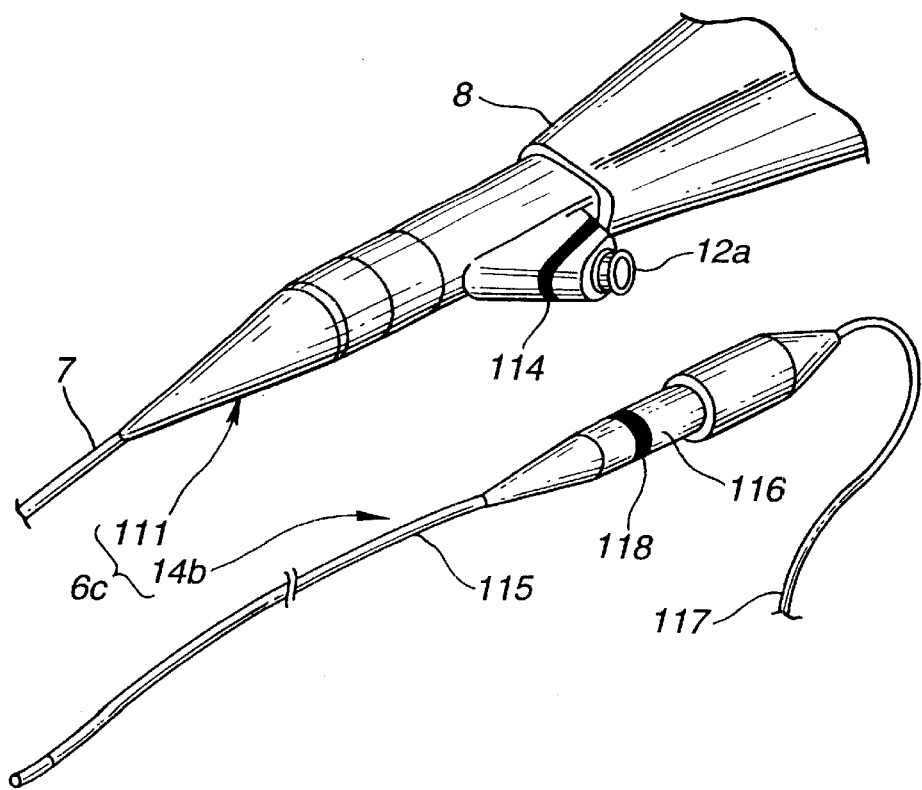
Figure 16:
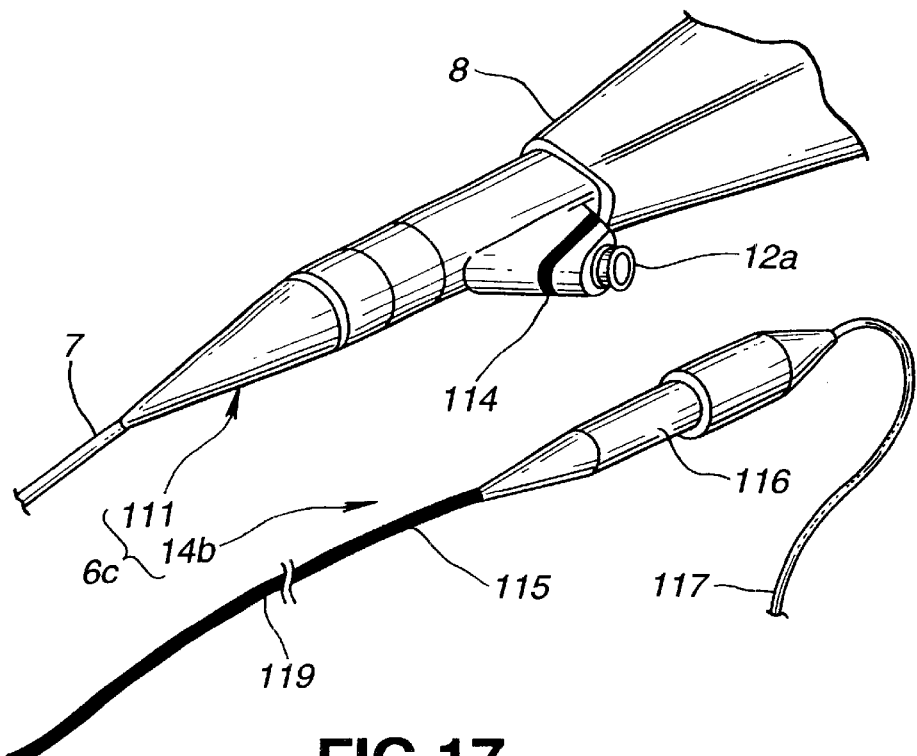

FIG. 15 illustrates an endoscope main unit 111 and video endoscope 6c for which endoscope insertion shape detecting is performed by inserting a probe 14b into the forceps channel insertion opening 12a of the endoscope main unit 111.

With the present embodiment, marking 114 is provided to the forceps channel insertion opening 12a, for example, the color of the marking 114 being clearly distinguished from the color of the operating unit 8.

The probe 14b to be inserted through the forceps channel insertion opening 12a is comprised of a probe main unit 115, a relay connector portion 116 at the rear end of the probe main unit 115, and a relay cable 117 connected to the relay connector portion 116. The probe 14b to be inserted through the forceps channel insertion opening 12a is provided with the same marking 118 as the marking 114 provided to the relay connector portion 116, for example.

When the technician inserts the probe 14b through the forceps channel insertion opening 12a of the endoscope main unit 111 so as to use the probe 14b, the technician may select the probe 14b with the same marking 118 provided as the marking 114, without error.

Thus, the endoscope main unit 111 and the probe 14b which can be used in combination therewith are provided with identifying markings 114 and 118 which differ from the marking on probes which cannot be used in combination therewith.

A probe connector (not shown) is provided to the rear end of the relay cable 117, and is detachably connected to the apparatus proper 16 of the endoscope shape detecting apparatus 3.

In FIG. 15, the endoscope main unit 111 and the probe 14b are identifiable as a pair, by the same color line markings. The present embodiment is not restricted to such identification. Rather, as shown in FIG. 16, the color of the marking 114 provided to the endoscope main unit 111 and the color 119 of the probe main unit 115, for example of the probe 14*b* may be matched.

Figure 17:
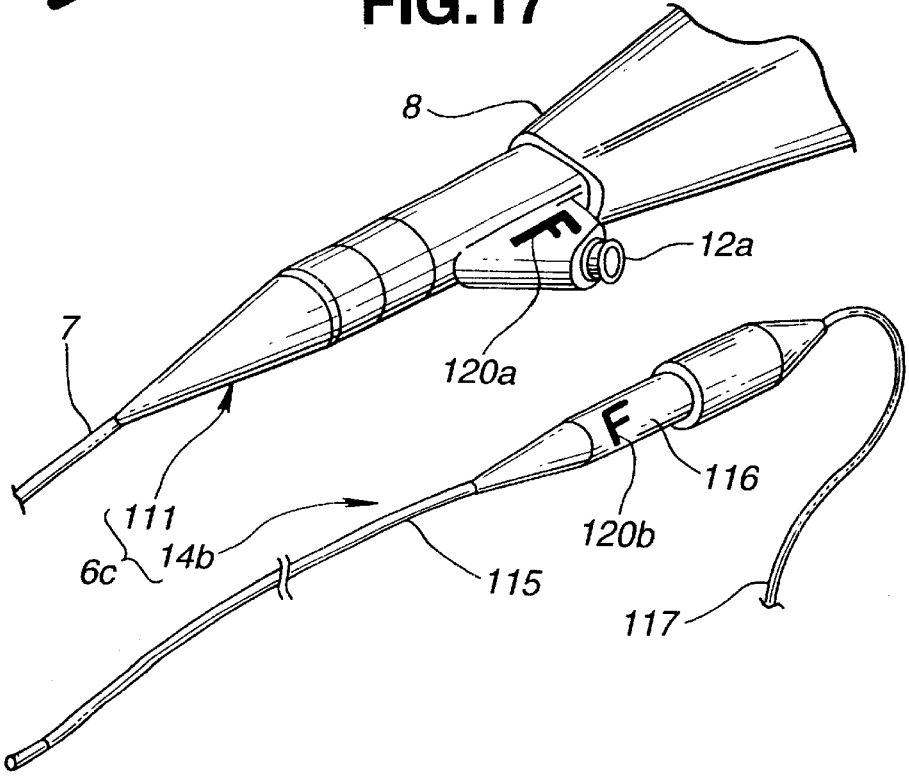

As shown in FIG. 17, markings 120*a* and 120*b*, which display the same characters, may be used, or the same numerals, protrusions or recessions of the same shape, etc., may be used.

The operation of the present embodiment will be described.

When preparing a probe to perform insertion shape detection, confirming whether the identification information, such as the marking 114, on the endoscope main unit 111 and the identification, information such as the marking 118 on the probe 14*b*, are the same allows the user to easily tell whether the probe 14*b* can be used with the endoscope main unit 111.

The present embodiment has the following advantages.

First, erroneously selecting a probe 14*b* to use in combination with the endoscope main unit 111 for endoscope inspection are reduced, thereby improving inspection efficiency.

Second, once the probe 14*b* is inserted into the forceps channel 12, conventional arrangements did not provide for ascertaining whether the length thereof matches the insertion portion 7 of the endoscope main unit 111. According to the present embodiment, whether the combination is correct can be confirmed according to the marking 118 and so forth, thereby providing for accurate insertion shape detection without mistakes.

The fifth embodiment is similar to the first embodiment. Only the differing points from the first embodiment will be described. Similar configurations will be denoted with the same reference characters and the description thereof omitted. The object of the present embodiment is similar to that of the fourth embodiment.

Figure 18:
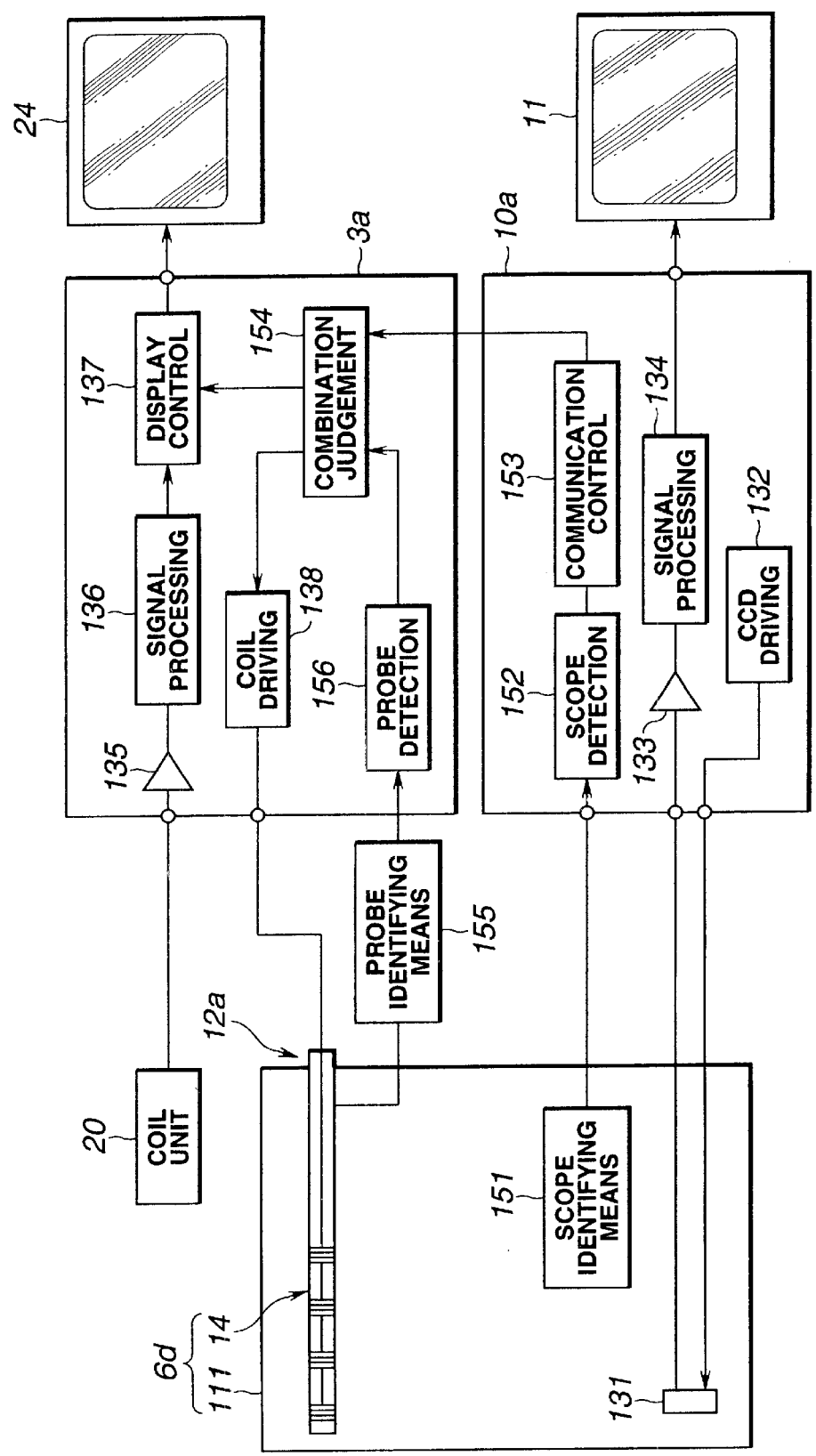
FIG. 18 is a schematic view of an endoscope system relating to the fifth embodiment of the present invention.

FIG. 18 shows the connection relationship between the video endoscope 6*d*, video processor 10*a*, and endoscope shape detecting apparatus 3*a*, according to the present embodiment.

As shown in FIG. 18, the video endoscope 6*d* performs detection display with the probe 14 inserted through the forceps channel 12 of the endoscope main unit 111.

The video processor 10*a* includes a CCD driving circuit 132 for driving a CCD 131, which is an image-taking element provided within the tip portion of the insertion portion 7 of the video endoscope 6*d*, an amplifying circuit 133 for amplifying the imaging taking signals from the CCD 131, and a signal processing circuit 134 for processing the imaging taking signals which have passed through the amplifying circuit 133, and displaying an endoscopic image on a monitor 11.

The endoscope shape detecting apparatus 3*a* includes an amplifying circuit 135, comprising a detecting block 26 and host processor 27 (see FIG. 2), a signal processing circuit 136 and display control circuit 137, and a coil driving circuit 138, comprising a driving block 25 (see FIG. 2).

With the present embodiment, the endoscope main unit 111 of the video endoscope Ed is provided with an endoscope identifying means or scope identifying means 151 for identifying the endoscope main unit 111. The video processor 10*a* is provided with a scope detecting circuit 152 for detecting or identifying the identifying means 151, so that the information identified with the scope detecting circuit 152 is sent to a combination determining circuit 154 within the endoscope shape detecting apparatus 3*a* via the communication control circuit 153.

A probe identifying means 155 is provided to the probe 14 for identifying the probe 14. The probe identifying means 155 is identified by the probe detecting circuit 156 within the endoscope shape detecting apparatus 3*a*. The identification information is sent to the combination determining circuit 154.

The combination determining circuit 154 has therein a combination information storing means including an EEPROM or the like in which is stored correct combination information. The combination determining means 155 determines whether the scope information detected by the scope detecting circuit 152 and the scope information detected by the probe detecting circuit 156 match correct combination information stored in the combination information storing means.

If the combination is appropriate, insertion shape detection is performed normally. If the combination is inappropriate, the display control circuit 137 outputs a signal indicating that the combination is inappropriate and insertion shape detection is not performed. In this case, a message to the effect that the combination is inappropriate is displayed on the observation screen.

The operation of the present embodiment will be described.

In an arrangement wherein the endoscope shape can be displayed along with the endoscope examination, the identifying means 151 and 155 provided to the endoscope main unit 111 and probe 14 are read by detecting circuits 152 and 156 provided to the video processor 10*a* and endoscope shape detecting apparatus 3*a*, and sent to the combination determining circuit 154.

Whether this combination is appropriate is determined by the combination determining circuit 154. If the combination is appropriate, insertion shape detection is performed normally. If the combination is inappropriate, insertion shape detection is not performed, and a message to this effect is displayed on the screen of the monitor 24.

A warning sound may be emitted along with the display of the message indicating that the combination is inappropriate, or a warning sound alone may indicate that the combination is inappropriate.

Known means can be used for identifying the scope, or endoscope main unit 111, or the probe 14. For example, the combination of conducting pins in the plurality of pins provided at the connector portion may be changed according to the type of scope, or endoscope main unit 111, or probe 14, thereby determining whether the scope, or endoscope main unit 111, or the probe 14 is correct by detecting the conducting pins at the time of connecting. ROM alternatively may be provided to the scope, or endoscope main unit 111, or the probe 14 for determining whether the combination of the scope, or endoscope main unit 111, and probe 14 is correct by reading the information at the time of connecting.

The present embodiment has the following advantages.

First, a correct combination of video endoscope and probe is always used at the time of performing insertion shape detecting, ensuing proper insertion shape detecting, thereby improving the precision of displaying the insertion shape, and performing insertion and the like in a smoother manner.

Second, erroneous connections are exposed, thus even if the displayed insertion shape detecting image is abnormal, whether the cause is a malfunction or an erroneous connection can be determined immediately, thereby allowing the examination to proceed smoothly.

The sixth embodiment is similar to the first embodiment. Only the differing points from the first embodiment will be described. Similar configurations will be denoted with the same reference characters and the description thereof omitted.

It is an object of the present embodiment to provide a holding means for holding the connector supplying electrical signals to the endoscope main unit, for a probe inserted into the forceps channel and used for insertion shape detection, thereby preventing buckling of the probe and line breaks in the signal lines.

Figure 19:
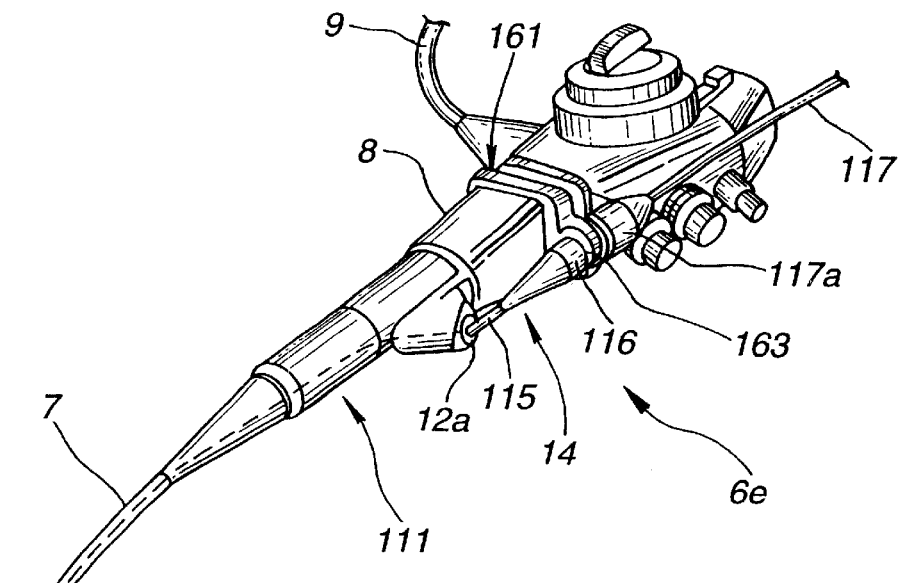

The probe 14 according to the present embodiment is inserted through the insertion opening 12a of the forceps channel 12. As shown in FIG. 19, the probe 14 is comprised of a probe main unit 115, a relay connector portion 116 at the rear end of the probe main unit 115, and a relay cable 117 having a connector 117a connected to the relay connector portion 116. The insertion shape detecting video endoscope 6e according to the present embodiment comprises an elastic member 161 for fixing the relay connector 116 to the endoscope main unit 111.

Figure 20:
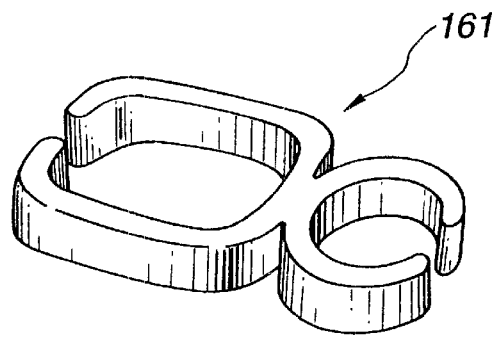

The elastic member 161 has a shape, shown in FIG. 20, that defines two arcs. The elastic member 161 has a side to be received in the ring-shaped joining groove or fitting groove 163 of the relay connector 116, and a side to be received on the operating unit 8 of the endoscope main unit 111,, as shown in FIG. 19.

The relay connector 116 has a ring-shaped joining groove 163 which receives the smeller arc portion. The smaller arc portion of the elastic member 161 can be fixed to the joining groove 163, and also removed, due to the elasticity thereof.

As shown, the two arcs define an H-like shape. Two rings may be connected instead. In this case, mounting of the elastic member 161 is performed from the tip of the probe 14 and the insertion portion 7 of the endoscope main unit 111.

Figure 21:
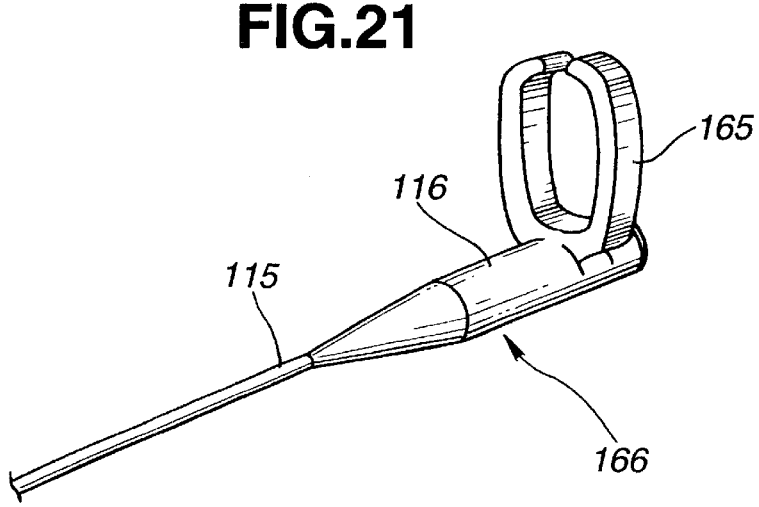

The relay connector 116 and elastic member 161 may be provided integrally. The probe main unit 166, as shown in FIG. 21, may have a detachable scope attaching frame 165 that protrudes from the operating unit 8.

The operation of the present embodiment will be described.

As shown in FIG. 19, attaching an elastic member 161 to both the relay connector portion 116 and the operation unit 8 of the endoscope main unit 111 allows both to be relatively restricted, thereby greatly reducing the mechanical force placed upon the probe 14 for performing insertion shape detecting, due to the weight of the relay connector portion 116.

Alternatively, the elastic member 161 may be attached to the universal cord 9 instead of the operating unit 8.

The present embodiment has the following advantages.

First, the relay connector portion 116 and the operation unit 8 of the endoscope main unit 111 are relatively restricted, thereby reducing the load placed on the probe 14 for performing insertion shape detecting. This extends the life of the probe 14, consequently reducing repair costs. Second, if the relay connector portion 116 and the elastic member 161 are formed integrally, chances of the elastic member 161 being lost are eliminated, thereby preventing needless costs.

The seventh embodiment is similar to the sixth embodiment. Only the differing points from the sixth embodiment will be described. Similar configurations will be denoted with the same reference characters and the description thereof omitted. The object of the present embodiment is similar to that of the sixth embodiment.

Figure 22:
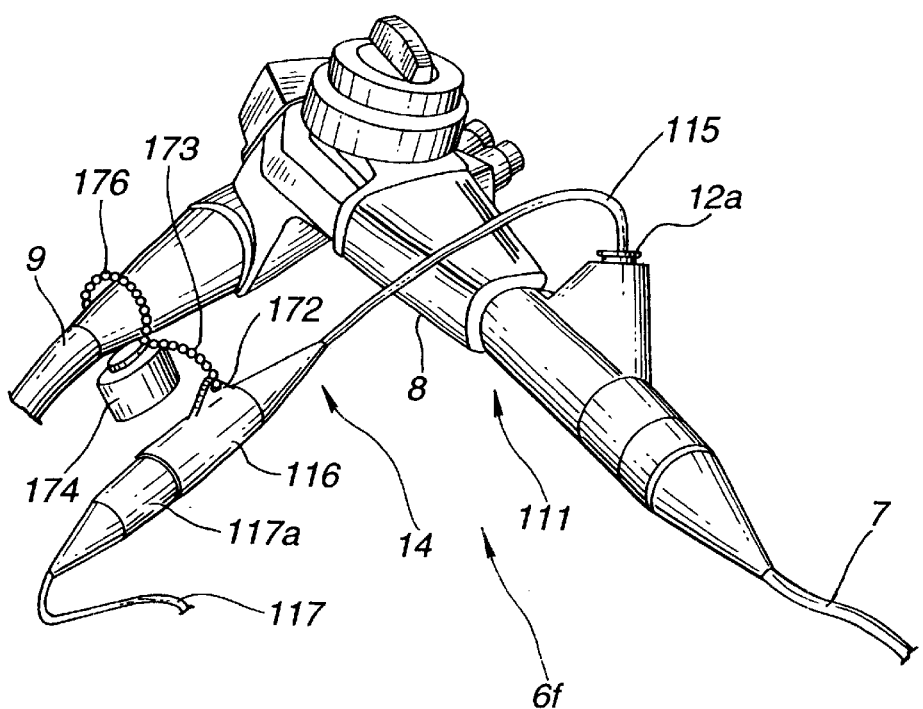

As shown in FIG. 22, the video endoscope 6f according to the seventh embodiment is equivalent to the embodiment of the video endoscope 6e of the sixth embodiment, shown in FIG. 19, provided with means for restricting or holding the portion of the probe 14 extending from the insertion opening 12a of the forceps channel 12, so as to lessen or prevent the effects of the load placed on the probe 14 by the relay connector portion 116.

A flange 172 is provided to the relay connector portion 116 extending from the insertion opening 12a of the forceps channel 12. One end of a chain 173 passes through a hole in the flange 172 and is fixed. A waterproof cap 174 is attached to the other end of the chain 173.

Figure 23:
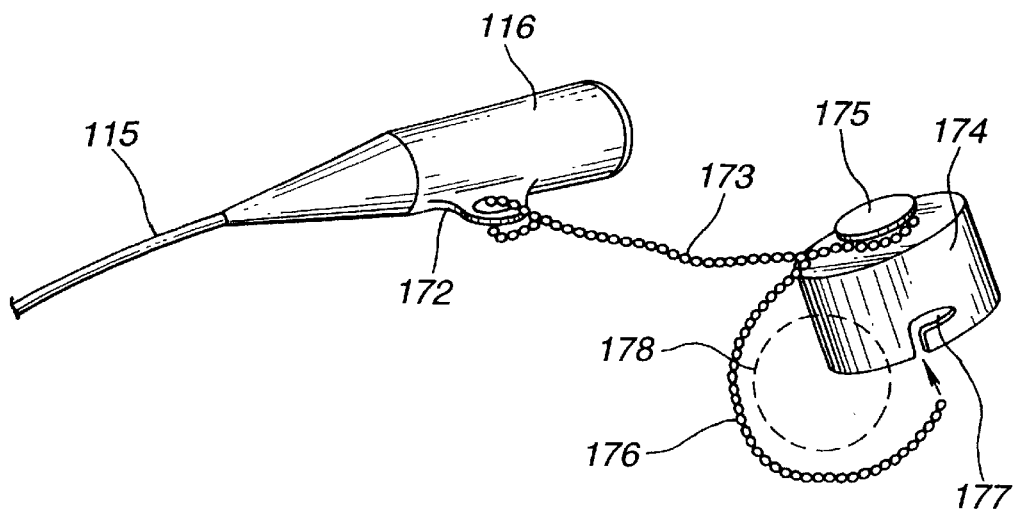

As shown in an enlarged manner in FIG. 23, the other end of the chain 173 and one end of a second chain 176 are attached to a chain attaching portion 175 on the waterproof cap 174. The other end of the chain 176 is attachable to a notch 177 in the waterproof cap 174. The arrangement of the chain 176 attached to the notch 177 generally forms a circle 178.

The size of the circle 178 is greater than the outer diameter of the universal cord 9, with the area near the base of the universal cord 9 passing therethrough, as shown in FIG. 22, so as to hold the relay connector portion 116 and prevent the probe 14 from bending downwardly under the weight of the relay connector portion 116.

Accordingly, the probe 14 can be prevented from bending downwardly under the weight of the relay connector portion 116, and inner line breaks, which easily occur due to bending downwardly under the weight of the relay connector portion 116, can be effectively prevented.

The operation of the present embodiment will be described.

FIG. 22 illustrates an endoscope, wherein the circular portion 178 formed by the chain 173 attached to the notch 177 of the waterproof cap 174 receives the universal cord 9, so that the waterproof cap 174, relay connector portion 116, and connector 117 a are relatively restricted relative to the universal cord 9, by friction and the like between the chain 173 and the universal cord 9.

The present embodiment has the following advantages.

As with the sixth embodiment, the mechanical load placed on the probe 14, which performs the insertion shape detection, is reduced, thereby extending the life of the probe 14. Further, according to the present embodiment, the waterproof cap 174 is restricted to the probe, so loss of the waterproof cap 174 can be eliminated.

The foregoing operation can be obtained by attaching a fixing member to the relay connector portion 116, with a member assembled with the fixing member being attached to the endoscope main unit 111.

The eighth embodiment is similar to the first embodiment. Only the differing points from the first embodiment will be described. Similar configurations will be denoted with the same reference characters and the description thereof omitted.

Figure 24:
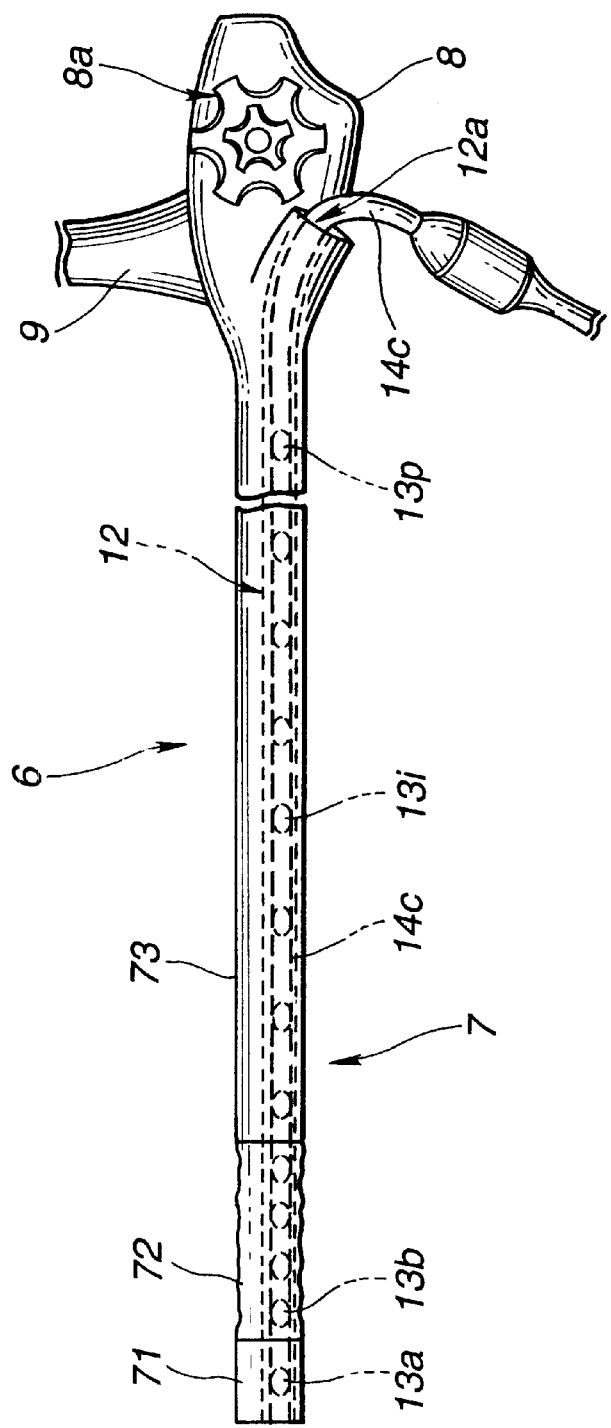

As shown in FIG. 24, the insertion portion 7 of the video endoscope 6 is comprised of a tip portion 71, curved portion 72, and flexible portion 73. An image-taking element, such as an object lens, etc., are assembled in the tip portion 71. Although the tip portion 71 itself does not bend, a technician can bend the curving portion 72 when inserting same into a body cavity by operating a curving operating knob 8 a provided to the operating unit 8. Although the flexible portion 73 bends, it does not bend with an arc as small as the curving portion 72.

The insertion opening 12a of the forceps channel 12 receives a probe 14c having, e.g., 16 magnetic field generating elements or source coils 13a, 13b, . . . , 13p (represented by 13g hereafter), thereby positioning the source coil 13g within the insertion portion 7.

The positioning of the source coils 13g within the probe 14a requires high precision in estimating the position since the curving portion 72 curves with a small arc. A greater number of the source coils 13g are positioned in the curving portion 72 with narrow intervals. The positioning of the source coils 13g does not require as high a precision in estimating the position since, at the flexible portion 73, as with the curving portion 72, the flexible portion 73 does not curve with as small an arc as the curving portion 72, thus a fewer number of the source coils 13g are positioned in the flexible portion 73 with wider intervals.

Figure 25:
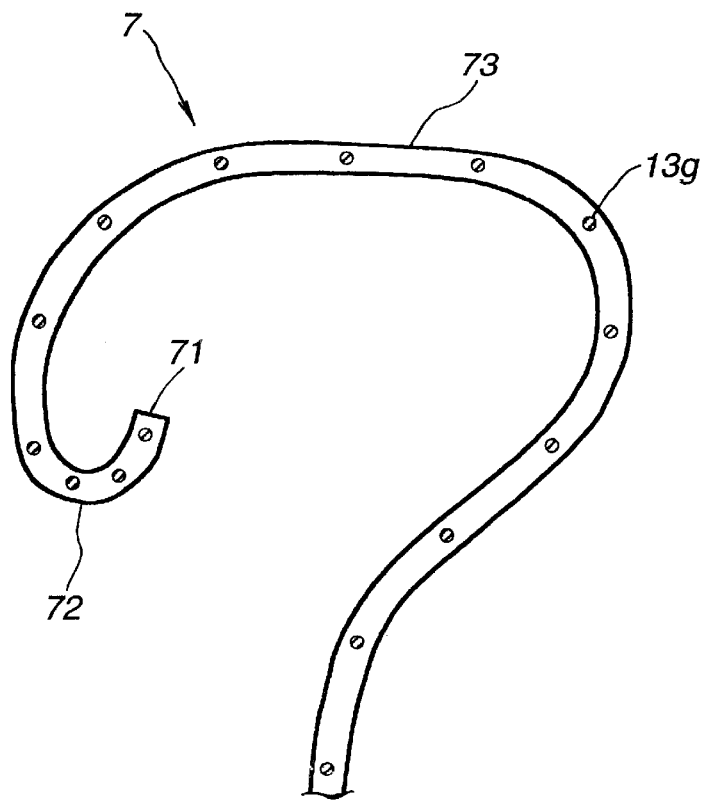
Figure 25:
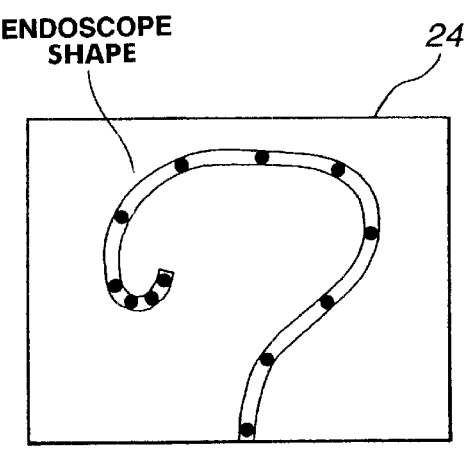

As show in FIG. 25, the probe 14a has a greater number of source coils 13g positioned in the curving portion 72, at narrow intervals, and a fewer number thereof positioned in the flexible portion 73, at wider intervals. By using the probe 14a, the monitor 24 displays the insertion shape of the insertion portion 7 of the video endoscope 6 according to the source coils 13g.

The present embodiment provides a greater number of source coils 13g at the curving portion 72, with narrow intervals, since high precision is required in estimating the position as the curving portion 72 curves with a small arc. The present embodiment provides a fewer number of source coils 13g at the flexible portion 73, with wider intervals. Not as high a precision is required at the flexible portion 73 as compared with the curving portion 72, since the flexible portion 73 does not curve with as small an arc as the curving portion 72. Accordingly, the number and positions of source coils 13g for detecting the shape of the insertion portion 7 of the video endoscope 6 can be optimized, thereby allowing the insertion shape to be detected with good precision while minimizing costs.

Also, the source coils 13g are positioned within the probe 14a, so endoscope shape detection can be performed by combining with an endoscope having an insertion opening 12a of a forceps channel 12.

The above probe 14a be applied to the first embodiment as well as to each of the embodiments of the present invention.

The ninth embodiment is similar to the eighth embodiment. Only the differing points from the eight embodiment will be described. Similar configurations will be denoted with the same reference characters and the description thereof omitted.

Figure 26:
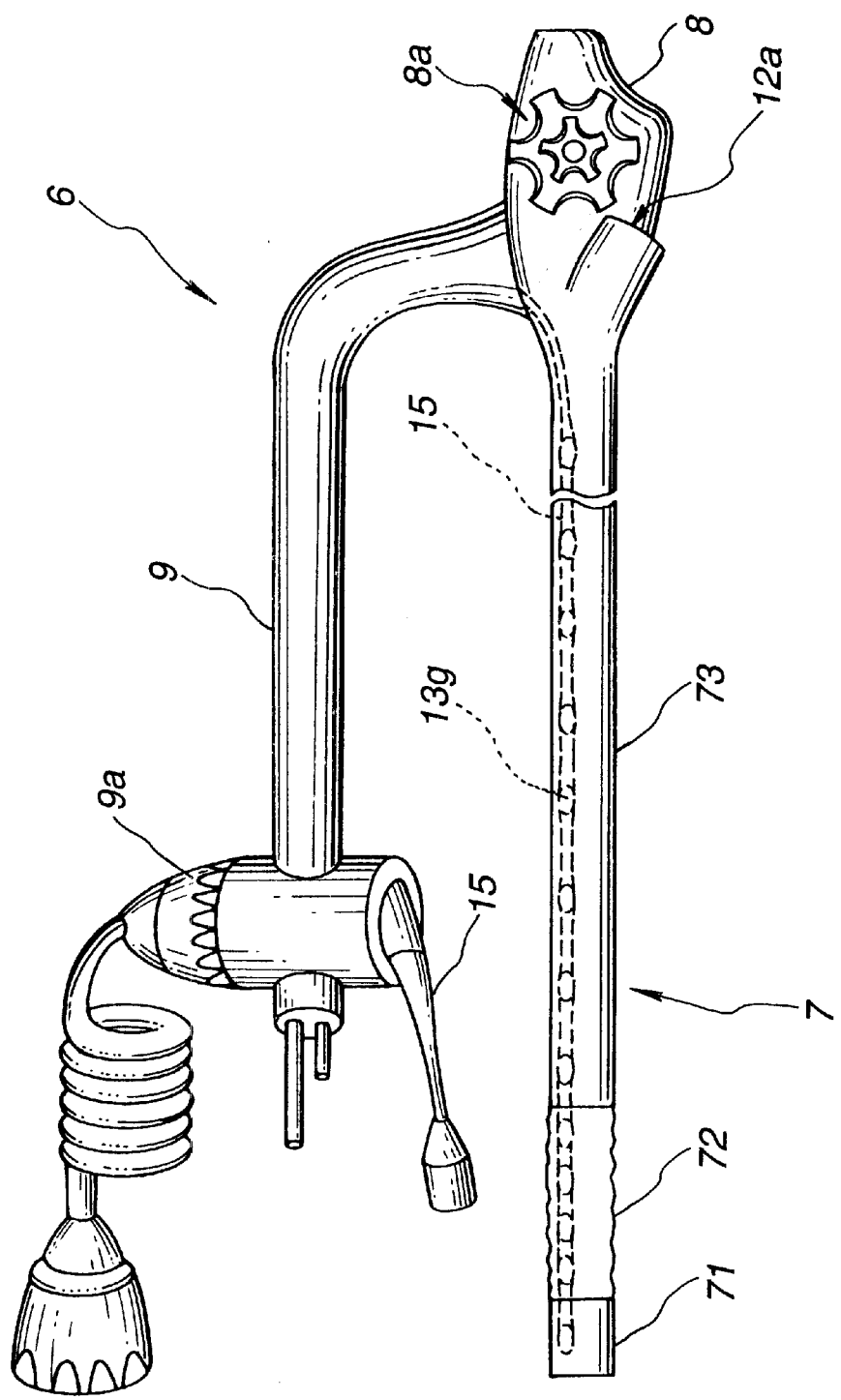
FIG. 26 is a perspective view of a video microscope relating to a ninth embodiment of the present invention.

As shown in FIG. 26, the present embodiment differs from the eighth embodiment in that the source coils 13g are built into the video endoscope 6, instead of into the probe 14c. A greater number of source coils 13g are positioned in the curving portion 72 of the video endoscope 6, at narrow intervals, and a fewer number thereof are positioned in the flexible portion 73 of the video endoscope 6, at wider intervals. The source cable 15 passes through the universal cord 9, extending from a connector 9a connected to the video processor 10, provided at the tip of the universal cord 9.

The source cable 15 may be connected to the operating unit 8 of the video endoscope 6, instead of passing through the universal cord 9.

Accordingly, with the present embodiment, in addition to the advantages of the eighth embodiment, the source coils 13g are built into the video endoscope 6. This permits forceps to be inserted through the insertion opening 12a of the forceps channel 12 and used while performing endoscope shape detection, permitting desired treatment on the part being observed. If the source cable 15 is passed through the universal cord 9, the troublesome source cable 15 is removed form the area of the operating unit 8, thereby improving operability.

The tenth embodiment is similar to the first embodiment, so only the differing points will be described, and the other same configurations will be denoted with the same reference numerals and description thereof will be omitted.

Figure 27:
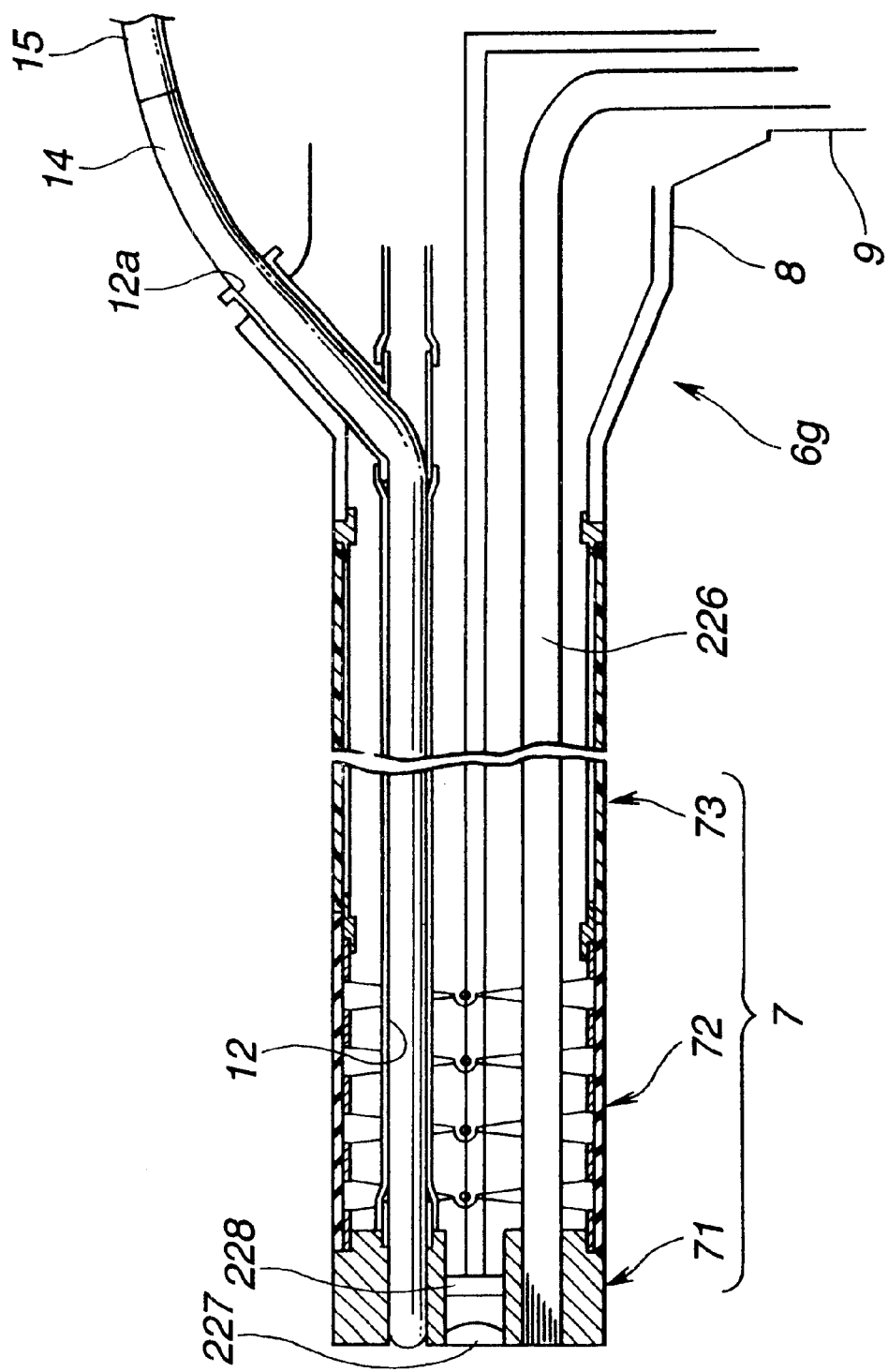

As shown in FIG. 27, the insertion portion 7 of the video endoscope 6g according to the tenth embodiment is comprised of a tip portion 71, curved portion 72, and flexible portion 73, with a light guide 226 being passed through the insertion portion 7. The light guide 226 passes through the universal cord 9 extending from the operating unit 8. Light transmitted by the light guide 226 is emitted from a tip window provided to the illumination window of the tip portion 71 of the insertion portion 7.

The object of imaging, such as the inner wall of a body cavity or an affected portion, illuminated by light emitted from the illumination window, is imaged by a charge coupled device (CCD) 228 serving as a solid imaging device. The CCD 228 is positioned at the focal point of an object lens 227 attached to the observation window formed next to the illumination window at the top portion 71.

Image signals subjected to photo-conversion at the CCD are output as CCD driving signals from a CCD drive circuit within a signal processing unit (not shown) built into the video processor 10 connected to the CCD 228. The output image signals are subjected to image processing at a signal processing circuit within the video processor 10 via a signal line inserted through the insertion portion 7 and the like, thus converting the image signals into standard picture signals. The picture signals are output to the monitor 11, thereby making a color display of the endoscopic image that has been imaged on the photo-electric conversion plane of the CCD 228 with the object lens 227.

An insertion shape detecting probe 14 for detecting the position and shape of the insertion portion 7 inserted into a body cavity may be inserted into the above channel 12, and the tip side of the probe 14 set at a certain position within the channel 12.

As shown in FIGS. 28 through 30, according to the present embodiment, three probes 14A, 14B, and 14C, for example, with differing flexibility are provided as the insertion shape detecting probe 14. A technician can select one of the three probes 14A, 14B, and 14C according to the usage environment (probe 14 in FIG. 27 representing one of the three probes 14A, 14B, and 14C).

With the present embodiment, these probes 14A, 14B, and 14C have the outermost covering tubes 230A, 230B, and 230C, respectively, formed of materials with differing stiffness.

For example, the probe 14A shown in FIG. 28 is formed of a covering tube 230A having insulation and flexibility, but also relatively stiff and having great resilience, i.e., having snap. The material for this covering tube 230A is a material using polyethylene, for example, with increased stiffness and resilience.

As for elements for generating a magnetic field, source coils 13g are attached within the covering tube 230A to a flexible rod-shaped supporting member 232 at certain interval distances d. The supporting member 232 is formed of a material which has no stretching or shrinking in the longitudinal direction, if positioned in the axial direction of the insertion portion 7, so that the intervals between the source coils 13g remain constant even if the covering tube 230A bends.

Each of the source coils 13g are formed of a coil comprised of copper wire 234 wound about a magnetic member 233. One of the copper wires 234 of the two wound terminals is used in common, and extended along the supporting member 232, for example. The copper wires 234 from the other terminal each extend backwardly from the respective source coils lag, and connected to connection points in a connector 217 connected to the shape detecting apparatus proper 16 at the base side of the covering tube 230A.

A through hole is provided in the magnetic member 233 for each source coil 13g. The supporting member 232 passes through the through holes, and is fixed at the certain interval distances a with an insulating adhesive agent 235.

If the walls of the covering tube 230A are thin, the covering tube 230A might be crushed by external force and buckle. A filling material 236, such as silicone or the like, may fill the interior of the covering tube 230A near the source coils 13g to reduce buckling.

A generally half-sphere shaped tip 237 is attached to the tip of the covering tube 230A, thereby improving sliding through the channel 12. The covering tube 230A is connected to the source cable 15. A buckling prevention member 238 is provided between the rear end of the source cable 15 and the connector 217. The source cable 15 also may be formed of the covering tube 230A.

The probe 14B, shown in FIG. 29 has a covering tube 230B having insulation and is sufficiently soft, with little resilience, i.e., having no snap. The material for this covering tube 230B is a material using polyethylene, for example, with lowered stiffness and resilience. The inner structure of this covering tube 230B is the same as that shown in FIG. 28.

The probe 14C, shown in FIG. 30, has a covering tube 230C having insulation, and stiffness and resilience of en intermediate value, between that of the covering tube 230A and the covering tube 230B. The material for this covering tube 230C is a material using polyethylene, for example, with intermediate-value stiffness and resilience. The inner structure of this covering tube 230C is the same as that shown in FIG. 28.

The stiffness of the covering tube 230A shown in FIG. 28, for example, may be increased by providing blades, coils, etc., on the inner side of the covering tube 230B of the same material shown in FIG. 29.

As described above, it is a characteristic of the present embodiment that a plurality of probes 14A, 14B, and 14C with differing stiffness or flexibility and resilience are provided as the insertion shape detecting probe to be inserted through the channel 12. A technician can selectively use the probe 14 with the appropriate flexibility according to the insertion technique and so forth, thus performing endoscopic examination.

The operation of the present embodiment will be described.

During endoscopic examination of the large intestine, simple pressing of the insertion portion 7 of the electron endoscope 6g will not further progression of the tip of the insertion portion 7.

Figure 31:
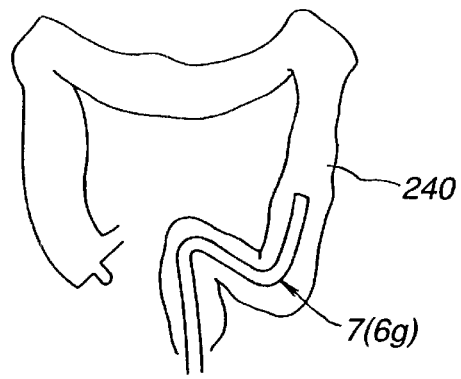

In such cases, it is important to know what shape the insertion portion 7 has assumed within the body of the patient. As shown in FIG. 31, for example, if the insertion portion 7 of the video endoscope 6g inserted into the large intestine 240 has formed a bend or loop, the insertion can be made to smoothly proceed by correcting the bend or loop.

If a loop has formed, the probe 14A shown in FIG. 28 with great stiffness and resilience, i.e., with snap, is inserted into the forceps channel 12 of the endoscope 2, thereby correcting the loop by the stiffness thereof, and changing the nature of the insertion portion 7, following which the insertion portion 7 and the lumen are linearized. Increasing the stiffness and resilience of the insertion portion 7 of the video endoscope 6g prevents looping following linearization of the lumen, thereby facilitating ease of the insertion operation and a smooth endoscopic examination.

Smooth insertion means that the endoscopic examination can be conducted effectively, thereby reducing pain at the time of insertion, reducing pain inflicted upon the patient by reducing the amount of time of the endoscopic examination.

Another method involves the insertion portion 7 being very soft and pressing the insertion portion 7 forwardly following the intestine. In this case as well, confirming the shape of the insertion portion 7 of the video endoscope 6g within the body of the patient during the examination allows the inspection to proceed easier. The probe 14B, as shown in FIG. 29, with little resilience, i.e., having no snap, is inserted into the forceps channel 12 of the video endoscope fig. Then, the examination is performed while confirming the shape of the insertion portion 7 within the body of the patient.

The probe 14B, which is soft end has little resilience, is inserted into the video endoscope 6g, so there is hardly any change in the shape of the insertion portion 7 of the video endoscope 6g. Consequently, a smooth examination can be realized wherein the video endoscope 6g is pressed forwardly while the soft insertion portion 7 follows the intestine as the technician confirms the shape of the insertion portion 7 of the video endoscope 6g.

Examination may be performed by using the foregoing insertion methods at the same time. To do so, the intermediate type probe 14C, shown in FIG. 30, may be used to realize a smooth examination.

Several types of probes 14 may be used to deal with various situations within a single inspection.

According to such a configuration, the preferences of the technician regarding stiffness and resilience, and the characteristics of the insertion method, can be adjusted, thereby realizing a smooth examination.

The present embodiment provides an endoscope shape detecting apparatus capable of accommodating the preferences of many technicians regarding stiffness and resilience, and characteristics of insertion methods, thereby improving the efficiency of endoscopic examinations.

Probes 14 appropriate for the insertion technique preferred by the technician can be used, so the insertion can be performed smoothly and in a short time, thereby reducing the pain inflicted upon the patient.

Although the probes 14A, 14B, and 14C to be inserted through the channel 12 in the present embodiment are described as having different stiffness and resilience, a probe 14 wherein only one of these characteristics is changed may be prepared, or, a great number may be prepared, with each differing only slightly from the next..

Display means may be provided so the technician can visually identify the degree of stiffness and resilience of each probe. For example, the degree of stiffness or resilience may be displayed by a plurality of circular lines on the external Surface of the connector 217, for example. The stiffness may be represented in increments of "1" to "10", the technician identifying the stiffness from the number of lines on the connector 217.

The resilience may be represented by rings of a differing color, for example. Alternatively, a color code may be used, such as used for representing the values of resistors.

Numerical representations may be used as well, such as to represent that the stiffness is "2" and the resilience is "3". The ring or color coding method is advantageous in that the information can be understood regardless of the direction from which the connector 217 is viewed, while numeric displays, such as stiffness of "2" and so forth, can only be identified when viewed from a certain direction.

Although the above description involved placing the source coils 13g which generate magnetic fields within the probe 14, and the sensing coils 21j for detecting magnetic fields at the exterior of the probe, endoscope shape detection and insertion shape display can be performed similarly even if these are switched.

The eleventh embodiment is similar to the tenth embodiment. Only the differing points from the tenth embodiment will be described similar configurations will be denoted with the same reference characters and the description thereof omitted.

Figure 32:
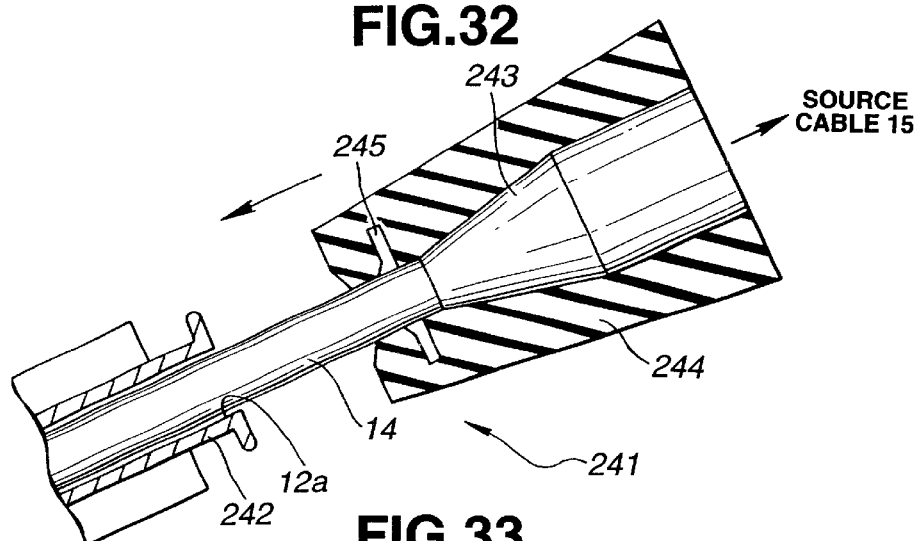
FIG. 32 is a longitudinal cross-sectional detail view of a buckling prevention member near the insertion opening of the forceps channel and so forth, relating to an eleventh embodiment of the present invention.

The eleventh embodiment, according to the present invention, will be described with reference to FIG. 32. As shown in FIG. 32, the probe 14 is fixed to the insertion opening 12a with a fixing mechanism 241 using an elastic member.

A buckling prevention member 244 constructed from an elastic member formed from silicone rubber or the like, which stores the connector 243 at the rear end of the probe 14, is provided to the base 242 comprising the insertion opening 12a.

The buckling prevention member 244 is a hollow cylinder containing the connector 243 therein, with a hollow portion 245 storing the flange portion of the base 242 comprising the insertion opening 12a formed at the lower inner circumference thereof. Pressing the lower side into the base 242 causes elastic deformation of the lower side of the bucking buckling prevention member 244 so as to be stored within the hollow portion 245 of the flange portion, thereby, allowing detachable mounting or connection of the buckling prevention member 244 to the base 242 to be realized. Once mounted, the buckling prevention member 244 is not easily removed from the base 242.

According to the present embodiment, a connector 243 is formed near a position that the probe 14 extends externally from the insertion opening 12a. The connector 243 is detachably connected to the connector provided at the front end of the source cable 15. The rear end of this source cable 15 has a connector 217 detachably connected to the apparatus proper 16, as with the tenth embodiment.

Although the present embodiment has been described as using elasticity for detachably connecting the connector 243 to the base 242, the present invention is not restricted to such. Other structures may be used, such as a slotting groove provided at the lower end side of the buckling prevention member 244, with a tightening ring provided to the perimeter thereof. The base 242 may be detachably fixed by the tightening ring. Alternatively, an inserting member having a screw hole may be provided to the buckling prevention member 244, and a fixing screw provided to the exterior of the buckling prevention member 244 is screwed through the screw hole, thereby fixing the buckling prevention member 244. An adhesive agent also may be used.

The probe 14 in the present embodiment represents the probes 14A, 14B, and 14c shown in FIGS. 28 through 30.

The buckling prevention member 244 can be mounted to the base 242 of the insertion opening 12a with a quick-connector like operation, so the operability thereof is excellent. Deforming or buckling of the probe 14 near the insertion opening 12a can be effectively prevented.

The twelfth embodiment similar to the tenth embodiment. Only the differing points from the tenth embodiment will be described Similar configurations will be denoted with the same reference characters and the description thereof omitted.

The twelfth embodiment according to the present invention will be described with reference to FIGS. 33 and 34. With the present embodiment, a probe constructed so as to be divided into the source cable portion and probe portion, as shown in FIG. 32, for example, is formed with differing stiffness and resilience portions in the longitudinal direction thereof.

Figure 33:
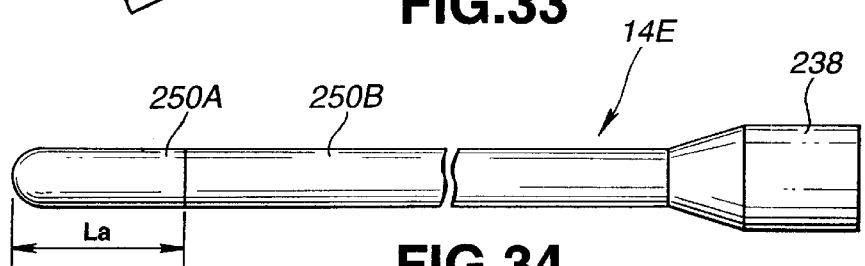

The probe 14E shown in FIG. 33 has a covering tube 250A which is soft, i.e., with low stiffness, and has low resilience for the length La, e.g., 30 cm, from the tip. The probe 14E has a high-resilience covering tube 250B which is stiff from that point on back.

The above construction can be realized by forming the walls of the outermost tube thicker only at the portion closer to the operator, or by using double covering tubes at that portion, etc.

Figure 34:
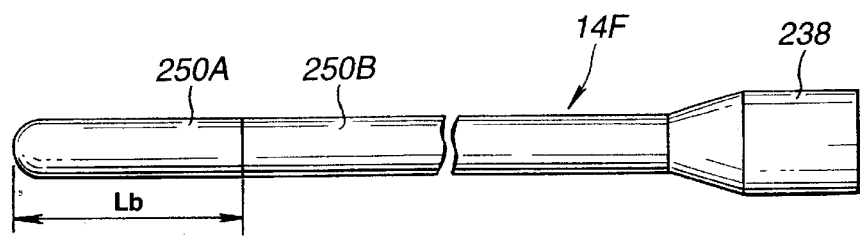

The probe 14F shown in FIG. 34 has of a covering tube 250A which is soft,i.e., with low stiffness, and has low resilience for the length Lb,e.g., 40 cm, from the tip. The probe 14 has a high-resilience covering tube 250B which is stiff from that point on back.

Inserting. a probe 14E or 14F, with a soft and only slightly resilient tip, inside of the forceps channel 12 of the video endoscope 6 g enables adjusting the probe 14 to suit the preferences of technicians regarding stiffness and resilience, hence the characteristics of insertion methods, as with the tenth embodiment, as well as reducing the amount of curving force.

Although the probes 14E and 14F have been shown in FIGS. 33 and 34 to be of a separable structure from the source cable 15, the present embodiment can be applied to an arrangement wherein the probe 14 and source cable 15 are integrally formed.

The present invention is by no means restricted to these embodiments, and may involve a plurality of probes differing only in flexibility or only in resilience.

The thirteenth embodiment is similar to the tenth embodiment. Only the differing points from the tenth embodiment will be described. Similar configurations will be denoted with the same reference character and the description thereof omitted.

The thirteenth embodiment according to the present invention will be described with reference to FIG. 35. In the present embodiment, the teeth embodiment for example has been arranged into [an electron] a video endoscope 6h having a stiffness changing mechanism or stiffness adjusting mechanism for the insertion portion 7, and more particularly, the flexible portion 73 of the insertion portion 7.

Figure 35:
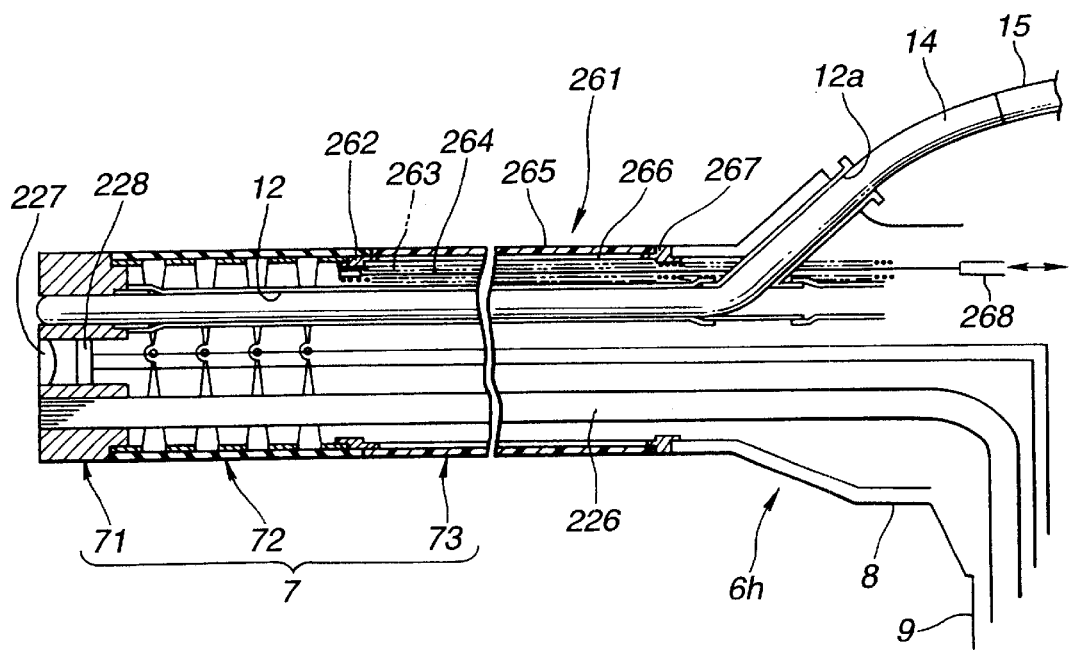

The video endoscope 6h shown in FIG. 35 is configured by providing the video endoscope 6g shown in FIG. 27 with a stiffness changing mechanism 261. For example, the tip of a stiffness adjusting coil 263, which is nearly in a close coil state, and a stiffness adjusting wire 264 inserted through this coil 263, are fixed to the inner wall surface of the connecting base 262 provided at the border between the curving portion 72 and the flexible portion 73 within the insertion portion 7, by means of soldering.

A flexible tube 263, comprising the flexible portion 73, and the coil 263 passed through the spiral tube 266 within the flexible tube 263 are soldered to the inner wall of a connecting tube 267 on the side of the operator near the front end of the operating unit 8 extending from the operating unit 8. The coil 263 is arranged so that there will be no disturbance in positioning, such as the coil entangling other built-in members.

The tip and rear end of the coil 263 are fixed, in a state that there is no force placed on the coil 263 in the longitudinal direction, so that there is sufficient softness or flexibility.

An operating rod 268 is attached to the rear end of the wire 264 protruding from the coil 263.

The operating rod 268 protrudes outwardly from the operating unit 8 at one portion of the operating unit 6, so that the rod can be moved and operated along the wire 264, as shown by the arrow. When the wire 264 is relaxed, the coil 263 has the greatest flexibility. Tensioning the wire 264 with the operating rod 268 places compressive pressure upon the coil 263, thereby adjusting the state wherein bending is suppressed, i.e.,a state wherein the stiffness is greater.

The coil 263 is formed so as to meander somewhat within the flexible tube 265, so that the coil 263 is not tensioned and thereby stiffened if the flexible portion 73 is simply bent.

The present embodiment comprises video endoscope 6h capable of adjusting the stiffness of the flexible portion 73 of the insertion portion 7 in particular. Selective use of appropriate probes 14 with differing stiffness according to the usage environment can be made. The stiffness can be further adjusted from the side of the video endoscope 6h.

Accordingly, the technician is provided with a greater selection regarding stiffness and the like which can be adjusted, thus the video endoscope is even handier to use, and even more readily adjustable to match the usage environment.

Figure 36:
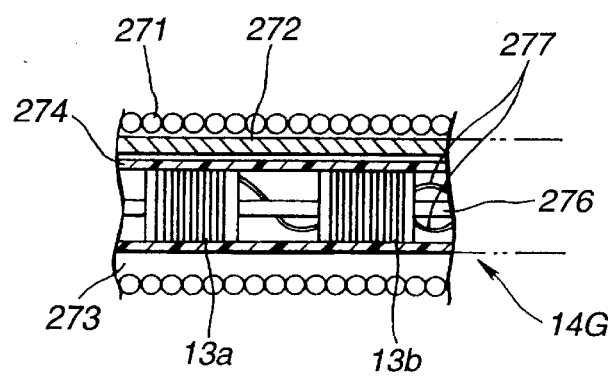

The structure of the video endoscope also may be such as that of the variation shown in FIG. 36.

As shown, the stiffness adjusting coil 271 passes through the adjusting wire 272. The probe 14G passes through the available space 273 remaining in the stiffness adjusting coil 271.

The probe 14G is arranged such that source coils 13a, lab, and so forth for generating a magnetic field are fixed to a flexible supporting member 276 within the covering tube 274. The lead lines 277 connected to the source coils 13a, lab, and so forth passes through the covering tube 274.

This configuration allows effective use of space, consequently realizing reduction in the diameter of the insertion portion of the endoscope.

The fourteenth embodiment is similar to the tenth embodiment. Only the differing points from the tenth embodiment will be described. Similar configurations will be denoted with the same reference characters and the description thereof omitted.

Figure 37:
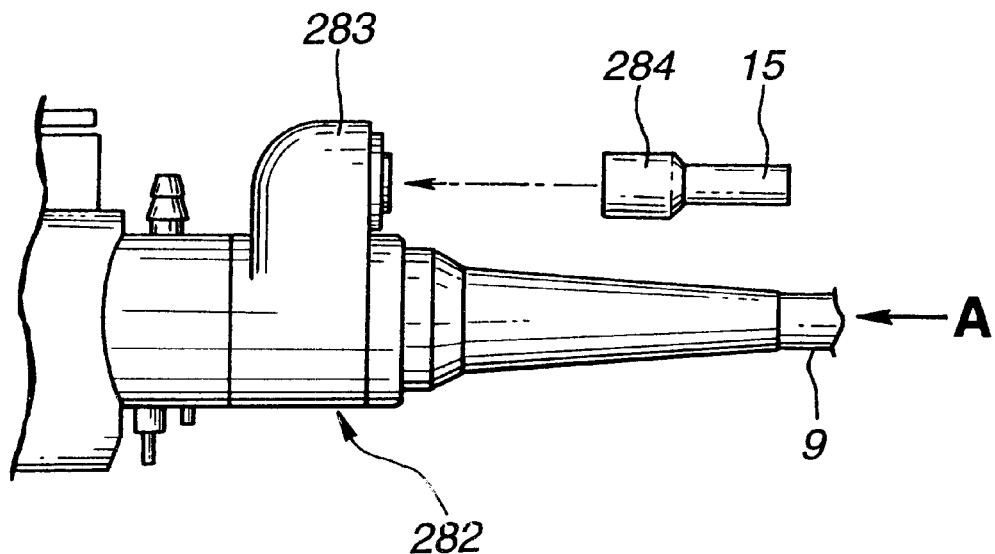
Figure 38:
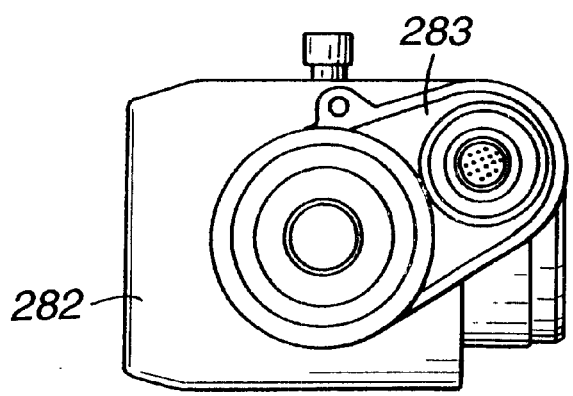

The fourteenth embodiment according to the present invention will now be described with reference to FIGS. 37 and 38. FIG. 37 shows a portion of the connector 282 at the end portion of the universal cord 9. FIG. 38 is an end view from the direction A in FIG. 37.

As shown in FIG. 37, the video endoscope 6 according to the present embodiment has a probe 14 and part of the source cable 15 built in. A connection portion 283 of the probe 14 or source cable 15 is provided to a connector 282 equivalent to the connector at the end of the universal cord 9 connected to the video processor 10. The connecting portion 283 is not outside of the external diameter of the connector 82, as shown in FIG. 38. The connecting.connector 284 of the source cable 15 is detachably connectable to the connecting portion 283.

According to the structure of the present embodiment, the connection portion 283 does not get in the way during examination, nor does the connection portion 283 get in the way when storing the video endoscope 6.

The fifteenth embodiment is similar to the second embodiment. Only the differing points of from the second embodiment will be described. Similar configurations will be denoted with the same reference character and the description thereof omitted.

Figure 39:
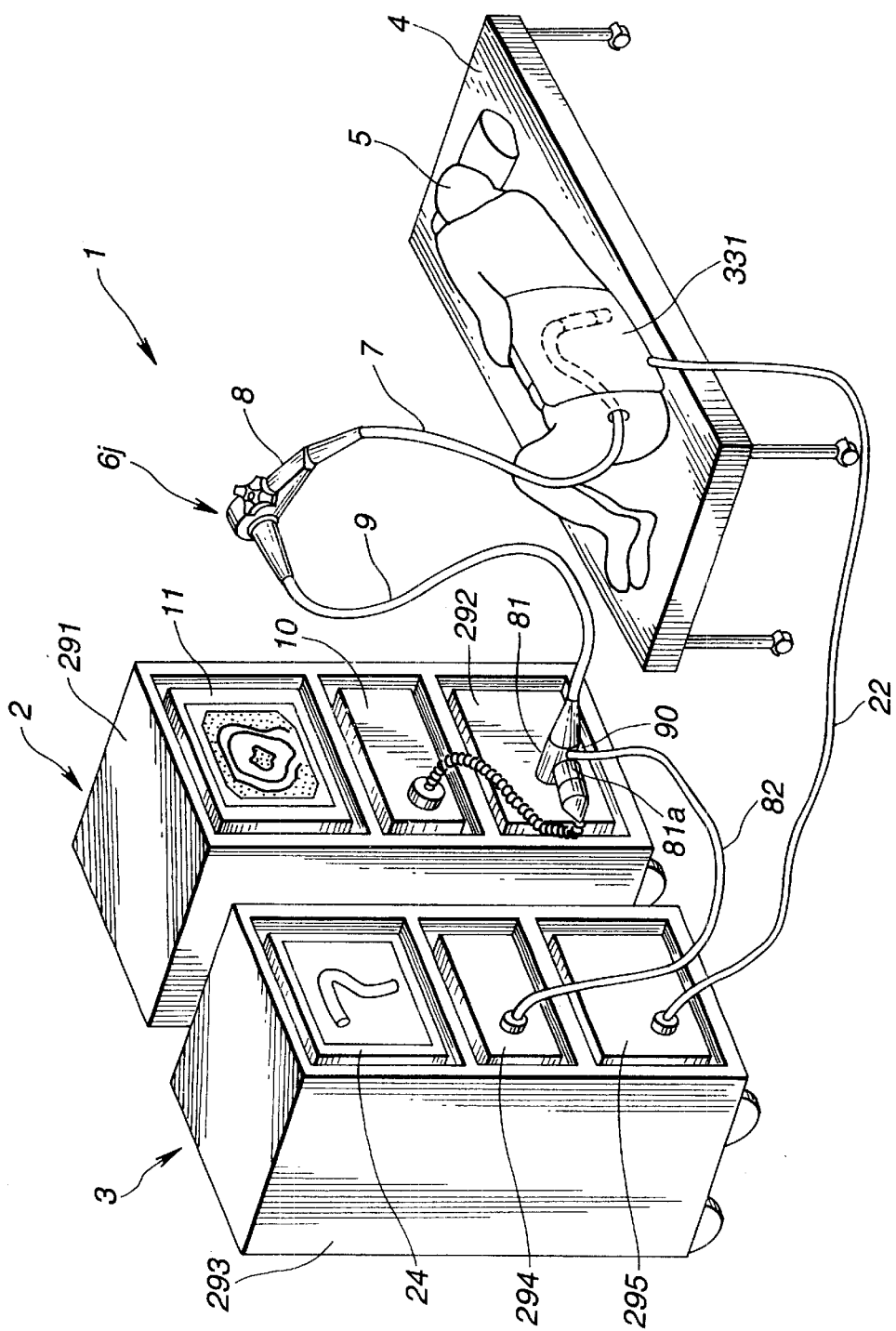

As shown in FIG. 39, with the present embodiment, an endoscope device 2 has a light source, mounted on a cart 291, comprised of a light source device 292 configured separately from video processor 10. An endoscope device 3 includes an apparatus proper 16, mounted on a cart 293, comprised of a magnetic field generating device 294 including a driving block 26 (See FIG. 2), a detecting block 26, and a form calculating device 295 formed of a host processor 27 (See FIG. 2). While the first embodiment has been described with the sensor coil unit 20 being positioned at a certain position on the examination table 4, with the present embodiment, the coil unit 331 is positioned on the body surface of the patient 5.

Figure 40:
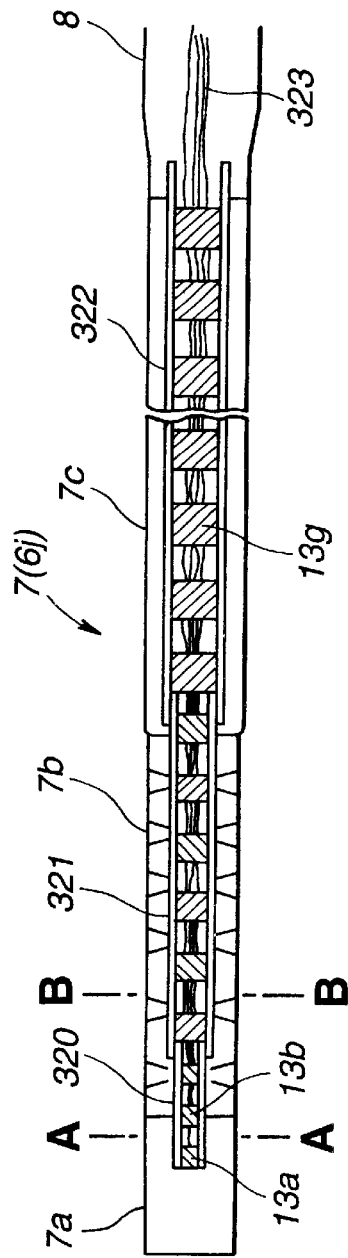
Figure 41:
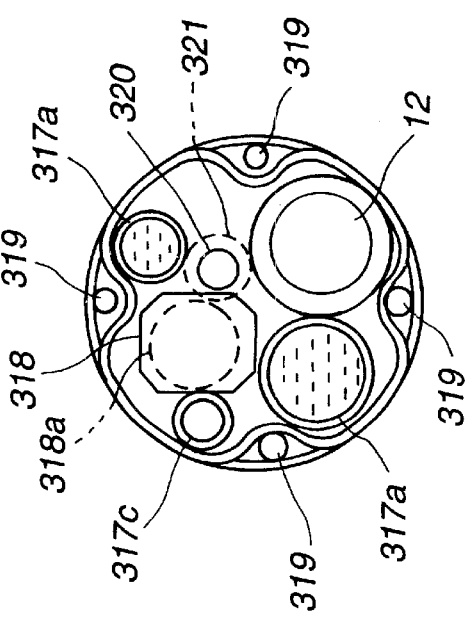

The insertion portion 7 of the video endoscope 6j according to the present embodiment is configured so that the tip portion 7a, curving portion 7b, and flexible tube 7c are sequentially connected from the tip end, as shown in FIG. 40. Built-in members, such as the light guide 317a, forceps channel 12, air/water feeding channel 317c, etc., are provided in the insertion portion 7, as shown in FIG. 41. little open space exists between the built-in members at the tip portion 7a, since this is the portion where the image-taking unit 318 and the tip of the curving wire 319 for curving the curving portion 7b are provided. An image-taking cable 318 a is provided in the curving portion 7b and the flexible tube 7c, however, not requiring as much space as the image-taking unit 318. The thickness of the outer skins of the light guide 317a, forceps channel 12, and air/water feeding channel 317c are thick at the curving portion 7b subjected to curving operation, and relatively thin at the flexible tube 7b. Accordingly, the open space between the built-in members at the curving portion 7b is smaller than the open space between the built-in members at the flexible tube 7b. That is, the open space between the built-in members increases from the tip portion 7a to the flexible tube 7c.

Accordingly, as shown in FIG. 40, the source coils 13g are provided as follows. Source coils 13g are positioned and fixed to the inner side of a first tube 320 of a first diameter at the tip portion 7a. Source coils 13g are positioned and fixed to the inner side of a second tube 321 of a second diameter that is greater than the first diameter at the curving portion 7b. And source coils 13g are positioned and fixed to the inner side of a third tube 322 of a third diameter that is greater than the second diameter at the flexible tube 7c. The first tube 320, second tube 321, and third tube 322 are are connected by an adhesive agent or the like.

The diameters of the source coils 13g can be increased sequentially. Thus, the signal lines 323 to be connected to each of the source coils 13g are inserted through the source coils lag. That is, few signal lines 323 are connected to the source coils 13g in the first tube 320, but the number of signal lines 23 connected to the source coils 13g sequentially increase as passing through the second tube 321 and third tube 322. The diameter of the source coils 13g increases, so the signal lines 323 can be inserted through the source coils lag. Consequently, no space occupied by built-in members is necessary for the signal lines 323 connected to the source coils 13g, therefore the diameter of the insertion portion 7 does not have to be increased.

The source coils 13g may be positioned as shown in FIG. 42. That is, the source coils 13g may be positioned and fixed to the inner side of a fourth tube 324 of a first diameter with a semi-circular cross-sectional shape at the tip portion 7a. Similar coils 13g may be positioned and fixed to the inner side of a fifth tube 325 of a second diameter with a semi-circular cross-sectional shape that is greater than the first diameter at the curving portion 7b. Source coils 13g may be positioned and fixed to the inner side of a sixth tube 326 of a third diameter with a semi-circular cross-sectional shape that is greater than the second diameter up to a certain position of the flexible tube 7c. And source coils 13g may be positioned and fixed to the inner side of a seventh tube 327 of a fourth diameter with a semi-circular cross-sectional shape that is greater then the third diameter from the certain position of the flexible tube 7c. The fourth tube 324, fifth tube 325, sixth tube 326, and seventh tube 327 may be connected by an adhesive agent or the like. The signal lines 323 may be connected to each of the source coils 13g through the source coils lag.

According to the configuration such as shown in FIG. 42, the space occupied by built-in members owing to the source coils 13g in the tip portion 7a and the curving portion 7b can be reduced. The flexible tube 7c provides greater flexibility from a certain position on toward the tip, and less flexibility from the certain position backwards since the sixth tube 326 has more flexibility than the seventh tube 327 as the seventh tube 327 has a greater diameter than the sixth tube 326.

As shown in FIG. 39, a coil unit 331 having a plurality of sensing coils, described below, for detecting electromagnetic waves accompanying the magnetic field generated by the source coils 13g is positioned at the back of the patient.

As shown in FIG. 43, the coil unit 331 is comprised of a sensing coil unit 33a, and a fixing belt 332b for fixing the sensing coil unit 332a to the patient 5. A plurality, of, e.g., six sensing coils 21j formed of single-core cables are provided within the sensing coil unit 332a. Each of the sensing cords 334 are connected to each of the sensing coils 21j via the sensing cable 22.

Figure 44:
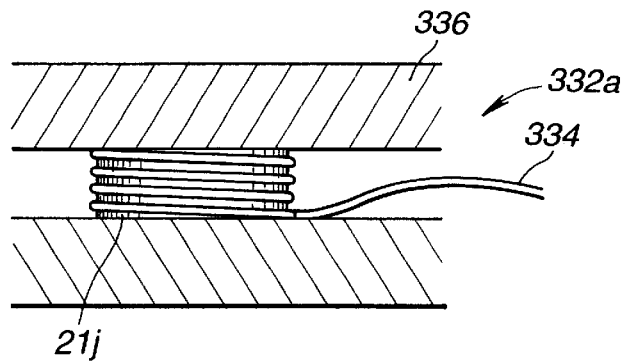

As shown in FIG. 44, the sensing coil unit 332a is configured such that each of the sensing coils 21j are fixed between sheets 336. Thus, when the coil unit 331 is mounted on the back of the patient 5, the position and orientation of each of the sensing coils 21j are maintained at a constant spatial relationship.

Returning to FIG. 39, each of the sensing coils 21j within the coil unit 331 are connected to the shape calculating device 295 of the endoscope shape detecting apparatus 3 via the sensing cable 22 serving as detection signals transmitting means. An operating panel, keyboard, or the like (not shown) is provided for the user to operate the shape calculating device 295. The shape calculating device 295 is connected to a monitor 24 for displaying the endoscope shape detected thereby.

With the present embodiment, the coil unit 331, with the sensing coils 21j built in, is positioned on the back of the patient 5. The coil unit 331 detects the endoscope shape, even in the event that the position of the patient 5 changes at the time of inserting the video endoscope 6j into the body. The relative positional relation between the sensing coils 21j and the source coils 13g inserted into the body of the patient 5 does not change since the coil unit 331 moves with the body position. An endoscope shape image of the shape of the endoscope in the body of the patient 5 can be easily recognized can be displayed. The sensing coils 21j and the source coils 13g can be positioned at close proximity, raising the detection sensitivity of the magnetic field from the source coils lag, so a highly precise endoscope shape image can be displayed.

The sensing coils 21j may be positioned within the insertion portion 7, the source coils 13g positioned within the coil unit 331, and the magnetic field from the source coils 13g within the coil unit 331 are detected by the sensing coils 21j within the insertion portion 7, for calculating the endoscope shape.

The sixteenth embodiment is similar to the fifteenth embodiment. Only the differing points from the fifteenth embodiment will be described. Similar configurations will be denoted with the same reference characters and the description thereof omitted.

Figure 45:
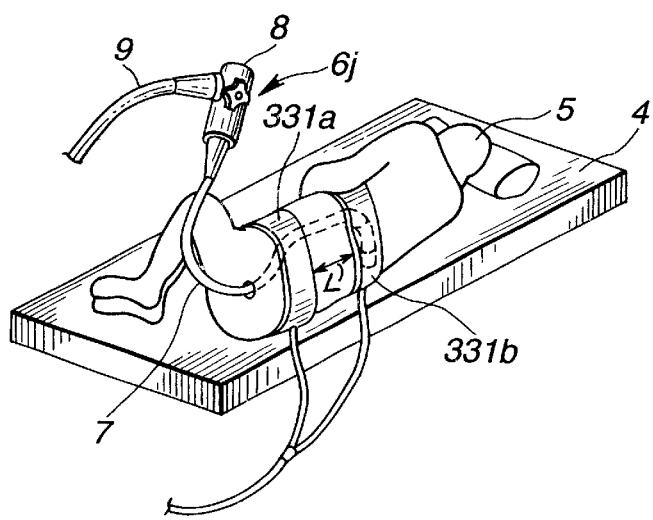

As shown in FIG. 45, the coil unit according to the present embodiment is comprised of two belt-shaped coil units 331a and 331b. The coil units 331a and 331b are separated by a distance L, and thus positioned on the beck of the patient 5.

Figure 46:
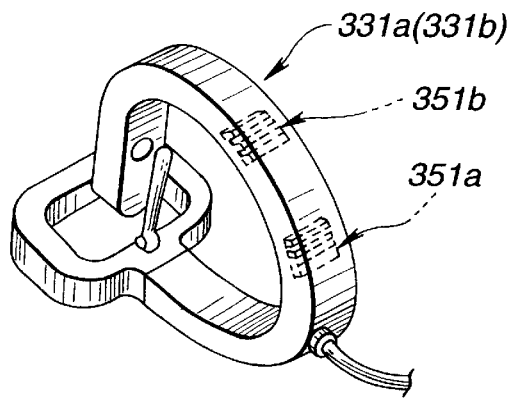

As shown in FIG. 46, the coil units 331a and 331b have two sets of sensing coil groups 351a and 351b each composed of three single-core coils. The patient has a total of 12 single-core coil sensing coils 21j positioned on the back of the patient 5.

According to the present embodiment, in addition to the advantages of the fifteenth embodiment, positioning the two belt-shaped coil units 331a and 331b so as to be separated by distance L positions the coil units 331a and 331b on the hip and back of the patient 5, respectively, thereby expanding the range of detection with the source coils lag.

Figure 47:
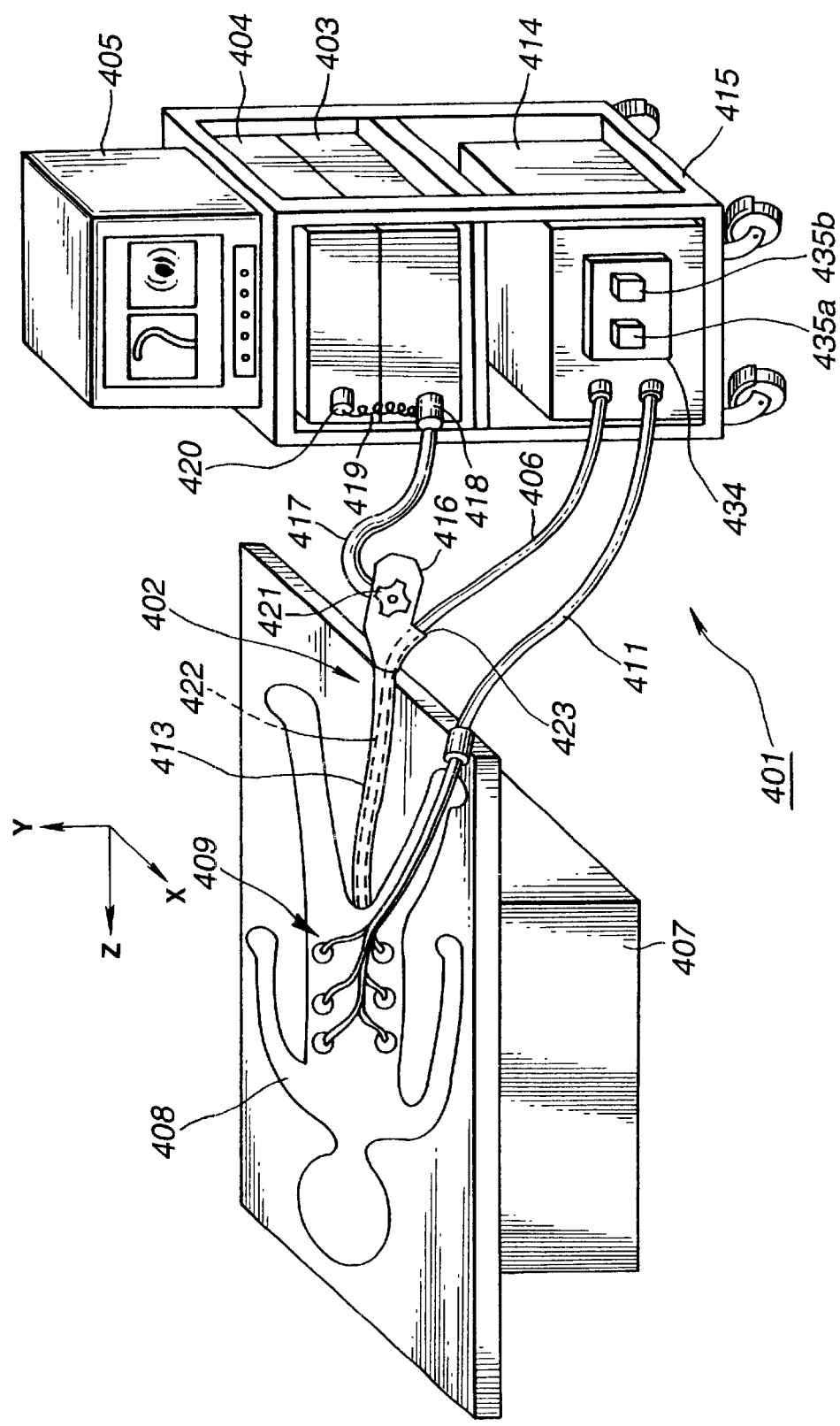

As shown in FIG. 47, the endoscope shape detecting system 401 is comprised of an endoscope 402 for performing endoscopic examination, a light source device 403 for providing light to this endoscope 402, a camera controlling unit (hereinafter "CCU") 404 for performing signal processing for the image-taking means of the endoscope 402, a color monitor 405 for displaying picture signals output from the CCU 404 and a probe 406 provided within the channel of the endoscope 402. A cable 411, to which is provided magnetic field detecting/generating coil units 9, has a display element for displaying the position of the insertion portion 413, as well as allowing selection between magnetic field detecting functions and magnetic field generating functions, positioned on the outer surface of the patient 408 on the endoscopic examination table 407. A shape detecting device 414, wherein the probe 406 and cable 411 are connected, detects the positions of each of the magnetic field generating elements within the probe 406 by generation and detection of magnetic fields. The shape of the insertion portion 413 of the endoscope 402 is estimated based on the detected positions. Picture signals corresponding with the image of the endoscope insertion portion are modeled so as to correspond with the estimated shape are generated and output to the CCU 404, so that the endoscopic image corresponding to the picture signals taken with the image-taking means and the shape image of the insertion form can be superimposed and displayed on the display screen of the monitor 405.

The above light source device 403 CCU 404, monitor 405, and shape detecting device 414 are mounted on a movable cart 415.

The endoscope 402 has an insertion portion 413 which is flexible, a wider operating unit 416 formed behind the insertion portion 413, and a universal cord 417 extending from the side portion of the operating unit 416. The terminal connector 418 of the universal cord 417 is detachably connected to the light source device 403. The connector 420 of the signal cable 419 extending from the connector 418 can be detachably connected to the CCU 404.

A light guide (not shown) is inserted through the insertion portion 413, and further inserted through the operating unit 416 and the universal cord 417, reaching the terminal connector 418. Light from a lamp (not shown) within the light source device 3 is supplied to the end plane of the connector 418, and transmitted by the light guide, so that the transmitted light is emitted from the tip plane fixed to the illumination window of the tip portion of the insertion portion 413.

The object, such as the wall of the body cavity or the affected portion, by the illumination light emitted from the illumination window is imaged on a CCD serving as a solid image-taking element, placed at the focal point of an object lens (not shown) attached to the observation window formed near the illumination window at the tip.

CCD driving signals output from the CCD driving circuit within the signal processing unit (not shown) built into the CCU 404 are applied to the CCD. Photo-electric converted image signals are output, passed through the signal line inserted through the insertion portion 13 and the like, subjected to signal processing at the signal processing unit, thereby converting the color endoscope image imaged on the photo-electric conversion plane of the CCD by the object lens, into standard picture signals, and output to the color monitor 405.

A curving operation knob 421 is provided to the operating unit 416, so that turning the knob 421 allows the curving portion formed near the tip area of the insertion portion 413 to be curved, thereby allowing the tip portion to be curved so as to follow the bent body cavity channel and be smoothly inserted.

A hollow channel 422 is formed within the insertion portion 413 of the endoscope 402. Inserting treatment equipment, such as forceps, through the insertion opening 423 at the base of the channel 422 enables the treatment equipment to protrude from the channel exit at the tip plane of the insertion portion 413, so as to perform biopsy, treatment, etc., on the affected portion.

A probe 406, for detecting the position and shape of insertion portion 413 inserted into the body cavity, is inserted into the channel 422. The tip side of the probe 6 can be set at a certain position within the channel 422.

Figure 48:
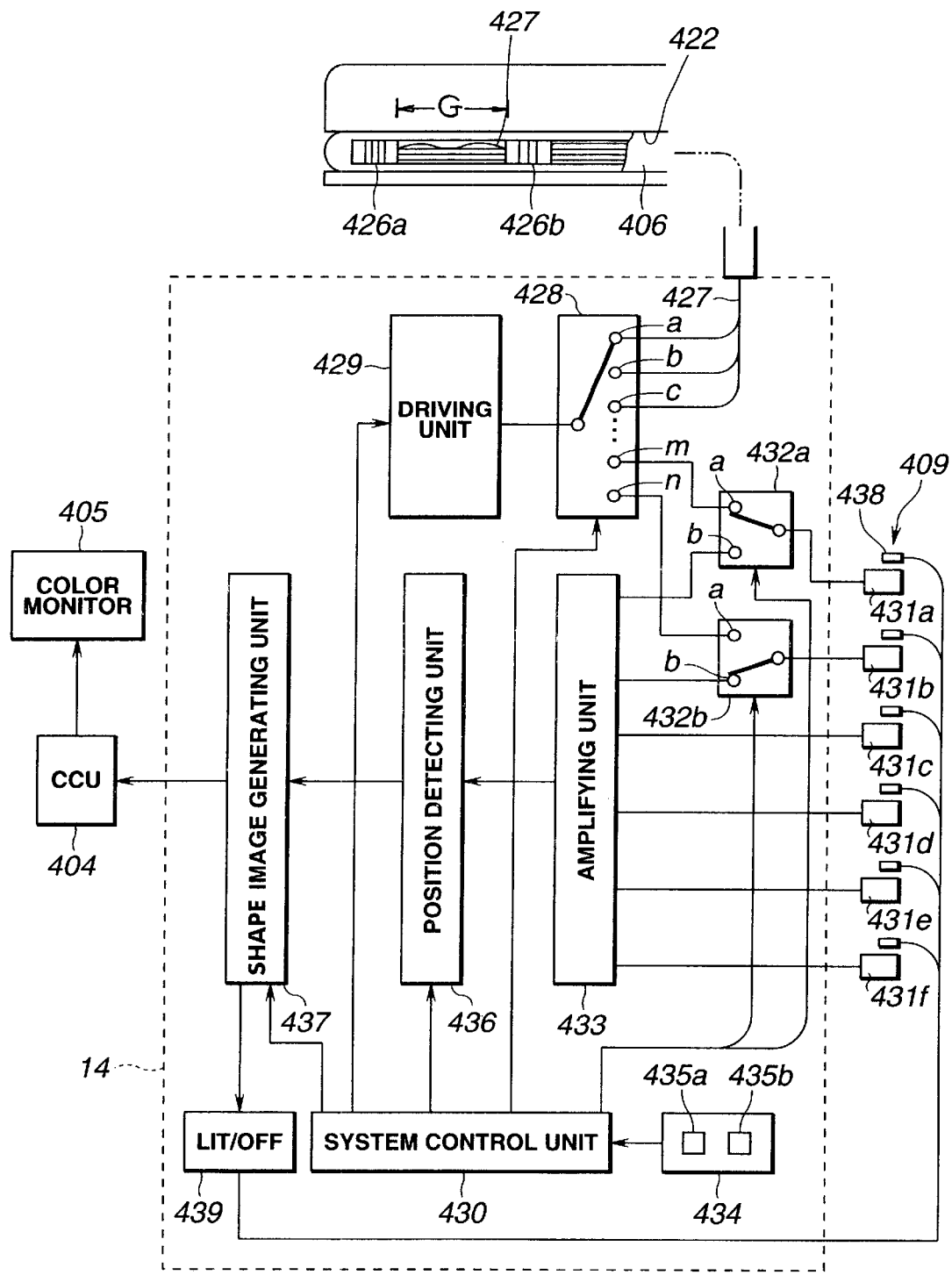

FIG. 48 illustrates an overview of the configuration of the shape detecting unit including the shape detecting device 414.

As shown in FIG. 48, the probe 406 is positioned within the channel 422 of the endoscope 402. A plurality of source coils 426a, 426b, and so forth are magnetic field generating elements fixed at certain intervals within the flexible tube of this probe 406. For example, the source coil 426a is positioned within the tip portion of the insertion portion 413, and the source coil 426b is at a position removed therefrom in the longitudinal direction of the insertion portion 413 by a gap G. Accordingly, detecting each of these positions allows each position from the tip portion of the insertion portion 413 to the rear side to be determined.

The signal lines 427 connected to each of the source coils 426i (wherein I=a, b, and so forth) extend from the rear side of the probe 6, and connect with a source coil driving unit 429 via a multiplexer 428 within the shape detecting device 414. Magnetic fields are generated around the source coils 426i to which the driving signals from the driving unit 429 have been supplied.

This driving unit 429 generates driving signals, for generating the necessary magnetic field, which are applied to the source coils 426i via contact points j (wherein j=a, b, c, and so forth), selected by switching signals from the system controlling unit 30.

The magnetic field detecting/generating coil unit 9 is comprised of, e.g., six coil units 431a, 431b, . . . , 431f. According to the present embodiment, the first coil unit 431a and the second coil unit 431b can each be selectively connected to the multiplexer 428 and amplifying unit 433 by pressing the switching switches 432a and 432b.

The switching switches 432a and 432b connected to the first coil unit 431a and the second coil unit 431b can select between the contact points a and b via the system control unit 430 by selecting switches 435a and 435b of the operating unit 434. If the contact point a is selected, driving signals are applied to a magnetic field generating source coil. If the contact point b is selected, driving signals are applied to a magnetic field detecting sensing coil for detecting the position of the source coils along with the other four coil units 431c through 431f.

For example, as shown in FIG. 48, if the switch 432a is set by the selecting switch 435a such that the contact point a is on, driving signals are applied to the coil unit 431a when the contact point m of the multiplexer 428 is selected, in the same manner as with the source coil 426i. If the switches 432a and 432b are both set such that the contact point a and the contact part b are on, driving signals are applied to the coil units 431a and 431b when the contact points m and n of the multiplexer 428 are selected.

As shown in FIG. 48, if the switch 432b is set by the selecting switch 435b such that the contact point b is on, the coil unit 431b is used as a source coil, along with the other coil units 431c through 431f.

Signals detected by the sensing coils of the magnetic field detecting/generating coil unit 409 are amplified at the amplifying unit 433, then input to a position detecting unit 436. Computation of the position detection of each of the source coils 426i is performed. The data detected, the position estimated, with this position detecting unit 436 is input into the shape image generating unit 37. A three-dimensional image is formed by smoothly connecting the position of data of each of the source coils 426i within the probe 406, thereby generating the insertion shape image of the insertionportion 413. The picture signals of this insertion shape image are output to the color monitor 405 via the superimposing circuit of the CCU 404, so that the insertion shape is displayed as a three dimensional image, along with the endoscopic image.

If the coil units 431a or 431b in the magnetic field detecting/generating coil unit 409 are selected as source coils, the standard position of the source coils are displayed on the insertion shape image on the color monitor 405 as markers.

As described below, the present embodiment has light-emitting diodes 438 serving as display elements for displaying whether there is a certain position of the insertion portion 413, provided to each of the coil units 431k (wherein k=a, b, . . . , f) of the magnetic field detecting/generating coil unit 409. For example, as shown in FIG. 47, if the insertion direction, for inserting the insertion portion 413 with the probe 406 having been inserted therein from the anus of the patient 408, has been set to the Z-axial direction, the LEDs 438 which have reached the value of the Z-coordinate of the tip position of the probe 406, or the tip of the insertion portion 413, are lit, thereby permitting the technician to readily understand the position in the patient 408 the tip of the insertion portion 413.

Signals output from the shape image generating unit 437, or position detecting unit 436, are applied to the LEDs 438 via the lit/off circuit 439, thereby controlling energizing of the LEDs 438. FIG. 48 shows the coil unit 431$k$ to be connected to the multiplexer 428 or amplifying unit 433 in order to simplify the description. However, in reality, the internal coils 446 (see FIGS. 49 through 51) are connected.

Figure 49:
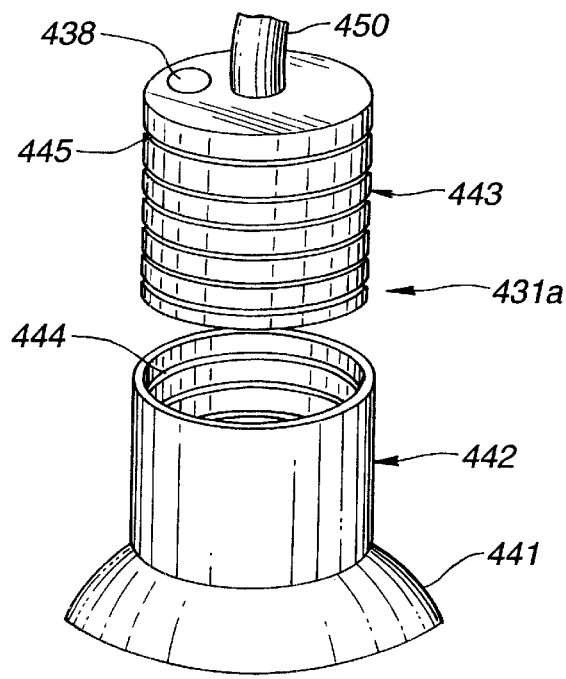

FIG. 49 shows the construction of, e.g., the first coil unit 431$a$ making up the magnetic field detecting/generating coil unit 409. The other coil units 431$b$ through 431$f$ are of the same construction.

This first coil unit 431$a$ is comprised of a fixing member 442 provided with a suction cup 441 which is detachable from the surface of the body of the patient 408 which is the object of inspection, and a coil member 443 which is attached to this fixing member 442 so as to be adjustable height-wise.

The fixing member 442 has a hollow cylinder provided above the suction cup 441. Ring-shaped protrusions 444 provided on the inner circumference of this hollow cylinder at fixed intervals engage with groove portions 445 provided on the outer perimeter of the cylindrical coil member 443.

Figure 50:
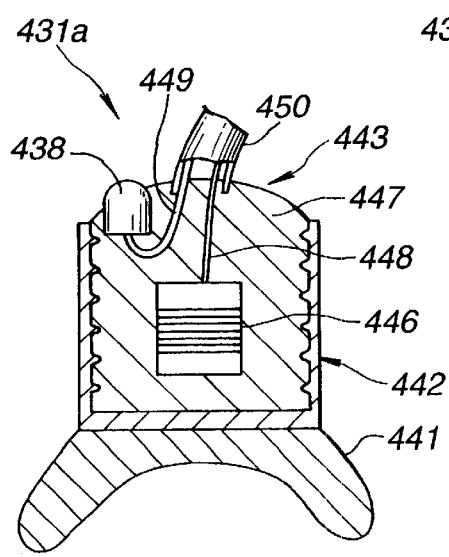
Figure 51:
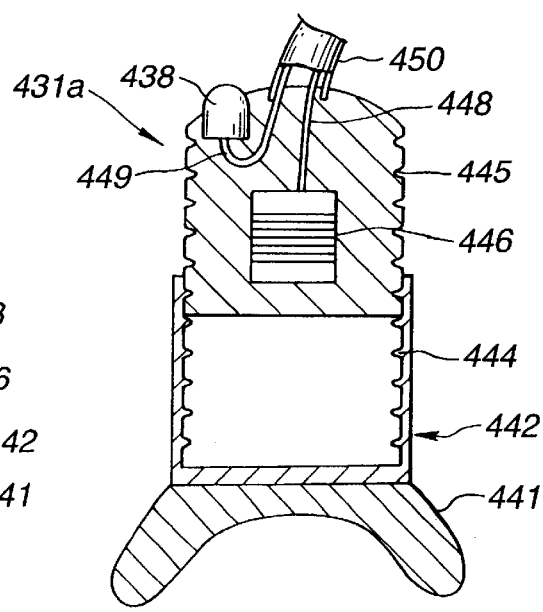

As shown in FIGS. 50 and 51, the coil member 443 is covered with a coil protecting material 447 formed of a resin covering a coil 446 wound onto a magnetic material in the same manner as the source coil 426$i$. An LED 438 is embedded in the coil protecting material 447 near the coil 446 so that the light-emitting portion is exposed.

The signal lines 448 connected to both ends of the coil 446 and the signal line 449 connected to the LED 438 extend from the coil protecting material 447 which is covered by the cable covering 450, with the connector thereof at the side of the operator being detachably connected to the shape detecting device 414.

With the present embodiment, the coil units 431$c$ through 431$f$ can be easily fixed to known X-Z coordinated positions on the patient 408 for example, simply by pressing the suction cups 441 thereon. The known Y coordinate can be achieved by sliding the coil unit 443 and adjusting the height thereof as shown in FIGS. 50 or 51.

A keyboard or the like for inputting three-dimension positional data of at least the four coil units 431$c$ through 431$f$ set at the known positions is provided to the operating unit 434.

The operation of the present embodiment will be described.

As shown in FIG. 47, the endoscope 402 is connected to the light source device 403 and the CCU 404. The probe 406 is inserted through the channel 422 from the insertion opening 423, so that the tip plane of the probe 406 is positioned at the tip position of the exit of the channel 422, for example.

According to such a setting, as shown in FIG. 48, the positions of each of the source coils 426$i$ for generating magnetic fields within the probe 406 are determined within the insertion portion 413, in the longitudinal direction from the tip of the insertion portion 413, for example. Accordingly, detecting the position of each of the source coils 426$i$ allows for detection of each position of the insertion portion 413.

The connector of the probe 406 is closer to the technician, connected to the shape detecting device 414. The coil units 431$a$ through 431$f$ making up the magnetic field detecting/generating coil unit 409 are fixed to the surface of the patient 408, with the suction cups 441 serving as the attaching means thereof.

At least the four coil units 431$c$ through 431$f$ in the magnetic field detecting/generating coil unit 409 are positioned and fixed, defining known positions. The two coil units 431$a$ and 431$b$ can be selectively used for magnetic field detection or magnetic field generation, i.e., display of a reference position, by selection of the technician.

For example, as shown in FIG. 48, if the coil unit 431$a$ alone is used for display of the reference position, the coil unit 431$a$ is fixed with the suction cup 441 to the reference position to be displayed. The coil unit 431$b$ is set to a known position in the same manner as the four coil units 431$c$ through 431$f$ to be used for magnetic field detection. The coil units also may be set at an arbitrary position, then measured with a scale or the like, so that the positions thereof are known.

If the set position, the position on the X-Z plane shown in FIG. 47, is obtained relatively easily, but there is a greater chance that error in the height direction position is great, the height adjusting means may be used to array the height positions or set the positions so as to be easily obtainable.

To reflect the selection of the technician in the system 401 setting state, the selection switch 435$a$ is pressed to set the coil unit 431$a$ to reference position detecting, via the system control unit 430. The selection switch 435$b$ is not pressed, and is used for magnetic field detection in the same manner as the other coil units 431$c$ through 431$f$.

The three-dimensional positions of the coil units 431$b$ through 431$f$ used for magnetic field detection of the magnetic field detecting/generating coil unit 409 are input from the keyboard or the like (not shown). Then, based on these positions, positional detection of the source coils 426$i$ within the probe 406 and positional detection of the coil unit 431$a$ used as a marker coil can be performed.

Having enabled shape detection, the insertion portion 413 of the endoscope 402 is inserted into the patient 408 from the anus, for example. When each of the power sources of the system 401 are on, the light of the light source device 403 is emitted from the tip plane the endoscope 402 via the light guide thereof, thereby illuminating the interior of the body cavity, so the state of the body cavity thus illuminated is imaged by the COD, and displayed as an endoscopic image on the color monitor 405, having been subjected to signal processing by the CCU 404.

Under control of the system control unit 430 within the shape detecting device 414, the driving signals generated at the driving unit 429 are sequentially applied to the source coils 426$i$ within the probe 406, via the contact point j selected at the multiplexer 428. For example, event if the contact point a has been selected at the multiplexer 428, driving signals are applied to the source coil 426$a$, thereby generating a magnetic field in the surrounding area thereof.

The magnetic field induces voltage in each of the coils in the coil units 431$b$ through 431$f$ serving as sensing coils at known positions, this voltage being proportionate to the intensity of the magnetic field at that position. Each of the voltages are amplified at the amplifying unit 433, input to the position detecting unit 436, subjected to orthogonal detection and the like, and the position detecting data of the source coil 426a is stored in the internal memory. When storage of this position detecting data is complete, the system control unit 430 switches the multiplexer 428 to the contact point b, whereby processing the same as that performed regarding the source coil 426a is performed for the source coil 426b.

When the same processing is completed for the last source coil within the probe, 426d, in this example, the contact point m of the multiplexer 428 is selected, and the same processing performed for the source coil 426i is performed for the coil 446 of the coil unit 431a.

Following this processing, the multiplexer 428 has the first contact point a thereof selected, and the same processing is repeated.

The position detecting data stored in the position detecting unit 436 is subjected to processing for detecting the position of the source coils 426i from the position detecting data, with the known positions of the coil units 431b through 431f as references. The calculated positional data for the source coils 426i is sent to the shape image generating unit 437.

The position detecting data regarding the coil unit 431a stored in the memory of the position detecting unit 436 is subjected to processing for detecting or estimating the position thereof with the known positions of the coil units 431b through 431f as references. The calculated positional data for the coil unit 431a is also sent to the shape image generating unit 437.

Picture signals of an image representing the insertion portion shape in a three-dimensional manner are formed by smoothly connecting the position data of the source coils 426a, 426b, 426c, and 426d calculated by the shape image generating unit 437. The picture signals are output to the superimposing circuit of the CCU 404. A marker point indicating the position of the coil unit 431a is superimposed over the picture signals.

Accordingly, an endoscopic image is displayed on the color monitor 405, and a three-dimensional image of the insertion shape is also displayed next to the endoscopic image. A reference position where the coil unit 431a is positioned is also displayed as a marker.

Accordingly, the technician can ascertain easily the position in the body cavity of the patient 408 the insertion portion 413 has assumed, owing to the insertion position shape display and the marker display indicating the reference position of the patient 408. Thus, insertion of the insertion portion 413 can be smoothly conducted, which means that the pain inflicted upon the patient 408 is reduced due to the smooth insertion.

With the present embodiment, LEDs 438 are provided for each coil unit 431k. For example, the Z coordinate values of the position data of the source coil 426a of the position detecting unit 436 or the shape image generating unit 437, and the Z coordinate values of the position data of the coil units 431a through 431f, are output to the lit/off circuit 39, the lit/off circuit 39 compares the value of the Z coordinate value of the source coil 426a with the Z coordinate value of the coil units 431a through 431f, and, if the value of the Z coordinate values of the source coil 426a is greater than the Z coordinate value of the coil units 431a through 431f for the coil unit 431k, the LED 438 of the coil unit 431k is lit.

Accordingly, the technician can easily confirm the position in the body cavity of the patient 408 of the tip of the inserted insertion portion 413 even when looking at the patient 408, owing to the lit LEDS 438 in the coil units 431a through 431f positioned on the surface of the body of the patient 408.

According to the present embodiment, sensing coils normally set at known positions on the outside of the body of the patient 408 are selectively used as sensing coils and marker coils for detecting reference positions in order to detect the position of the source coils 426i provided within the probe 406 for detecting each position of the probe 406 or the insertion portion 413. Display of reference position can be made without providing new markers.

LEDS 438 are provided as display means to the coil units 431a through 431f positioned on the surface of the body of the patient 408. The LEDs 438 are arranged so that the LED 438 of the position to which the tip position of the probe 406 or the insertion portion 413 has reached is lit, so the technician can ascertain readily how far the tip of the insertion portion 413 has been inserted.

The eighteenth embodiment is similar to the seventeenth embodiment. Only the differing points from the seventeenth embodiment will be described. Similar configurations will be denoted with the same reference characters and the description thereof omitted.

The seventeenth embodiment has been described as being configured such that two of the coil units 431a and 431b of the magnetic field detecting/generating coil unit 409 can be used for either magnetic field detecting or magnetic field generating. The present embodiment provides a configuration such that all of the coil units 431a through 431f of the magnetic field detecting/generating coil unit 409 can be used for either magnetic field detecting or magnetic field generating.

Figure 52:
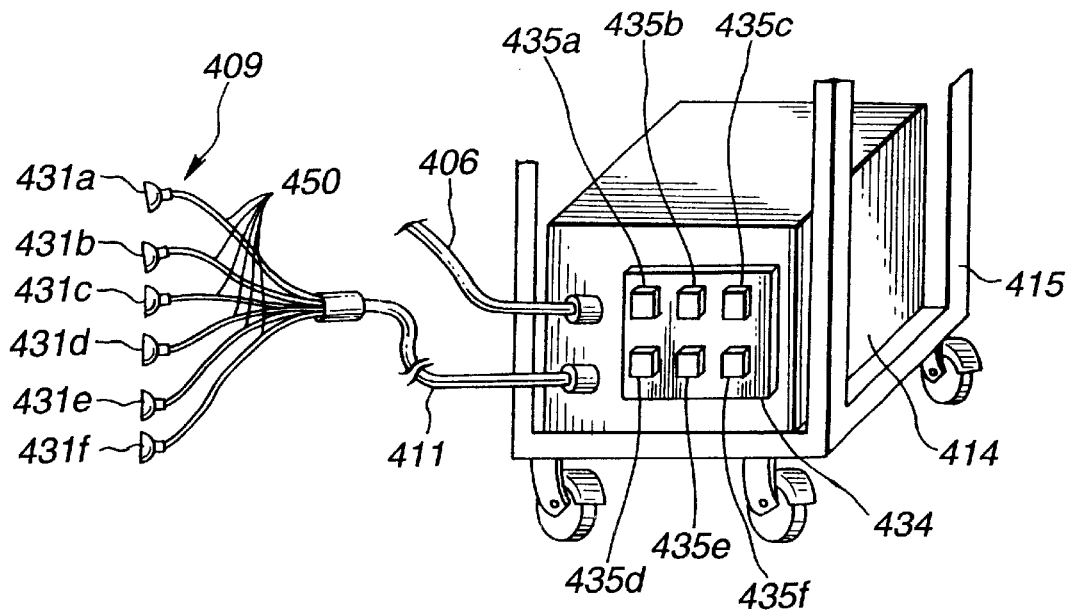

Accordingly, while the operating panel 434 of the shape detecting device 414, shown in FIG. 47, only had two selecting switches 435a and 435b, with the present embodiment, six selecting switches 435a through 435f are provided, as shown in FIG. 52.

Figure 53:
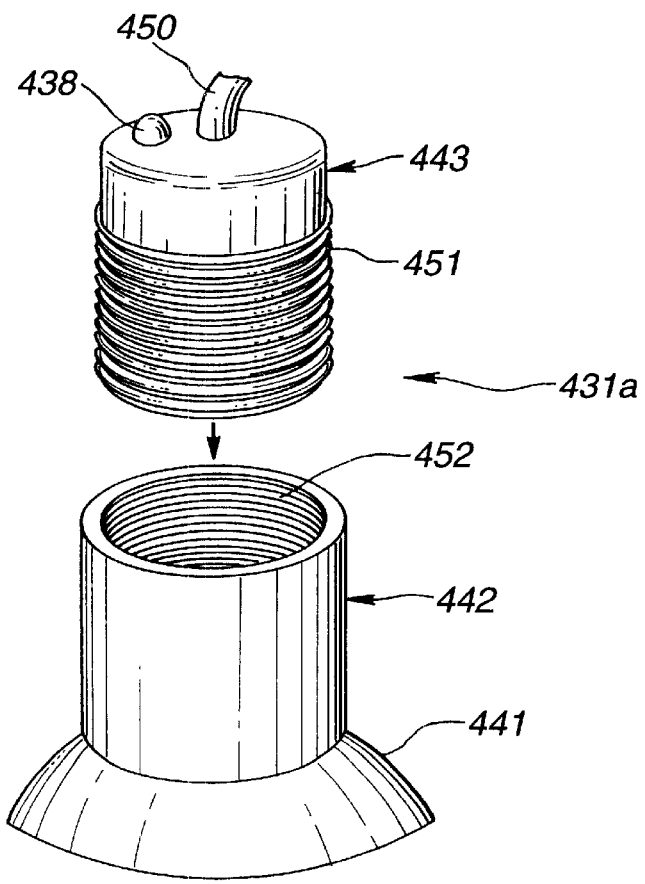

The present embodiment also provides the height adjusting mechanism of the magnetic field detecting/generating coil unit 409 different from that in the seventeenth embodiment. As shown in FIG. 53, a male thread 451 is provided to the outer perimeter of the side of the coil member 443 comprising the first coil unit 431a. A female thread 452, for engaging this male thread 451, is provided to the inner circumference of the fixing member 442.

Other configurations are the same as those shown in FIG. 49. The other coil units 431b through 431f are of like configuration.

Threadingly adjusting the male thread 451 and the female thread 452 enables the height position of the first coil unit 431a to be changed and set.

Figure 54:
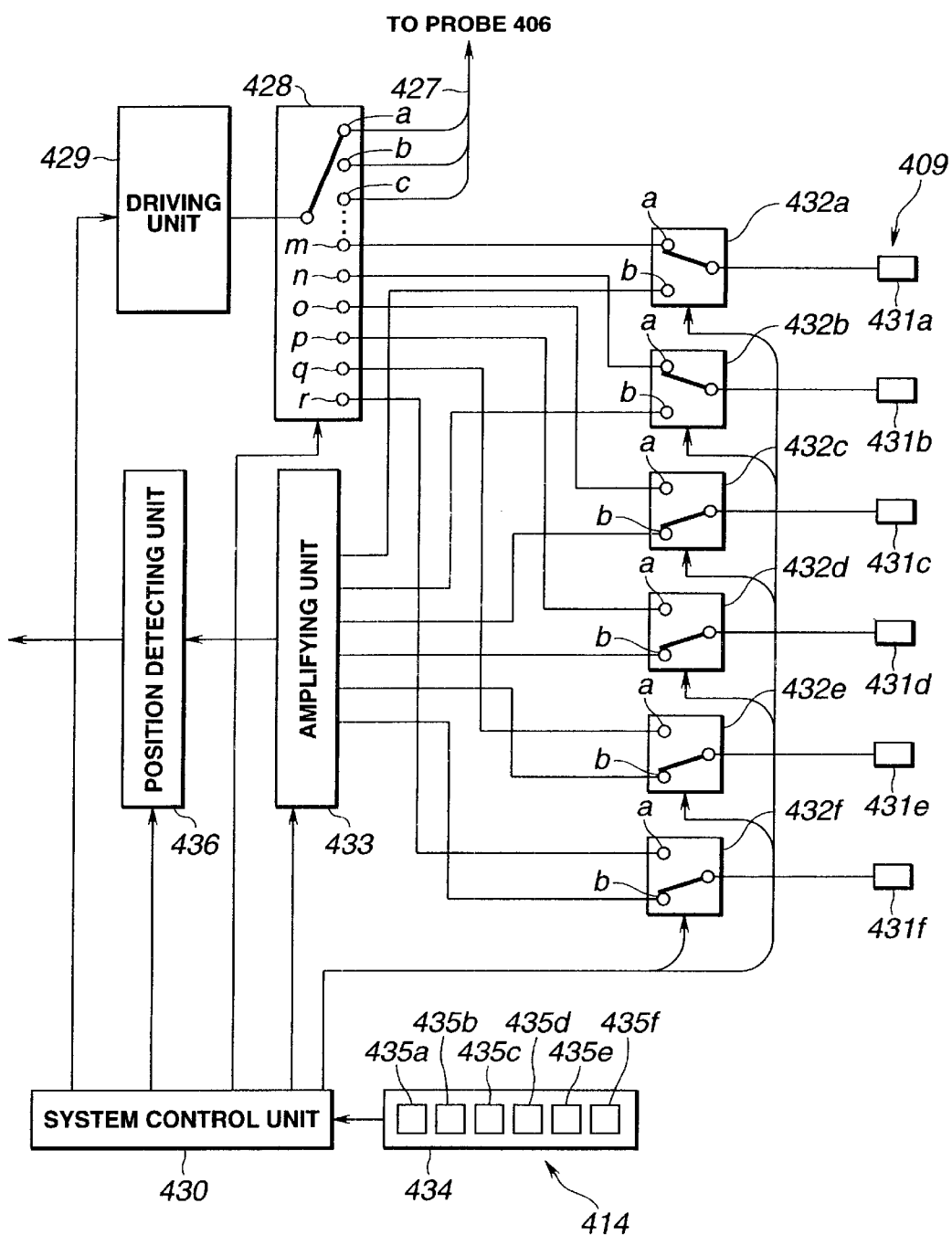

The configuration of the principal members of the shape detecting device 414 according to the present embodiment are as shown in FIG. 54. That is, in FIG. 48, the two switching switches 432a and 432b are replaced with six switching switches 432a through 432f. The contact point a of the switching switches 432a through 432f connect to six contact points m through r, with the contact points m and n of the multiplexer 428 shown in FIG. 48 being increased. The contact point b is connected to the input terminal of the amplifying unit 433.

Other configurations are the same as those in the first embodiment.

According to the present invention, all of the coil units 431a through 431f of the magnetic field detecting/generating coil unit 409 can be selectively used for either magnetic field detecting or reference position display, instead of the two coil units 431a and 431b in the seventeenth embodiment. Other operations and advantages are almost the same as those of the seventeenth embodiment.

With the present embodiment, although all of the coil units 431a through 431f of the magnetic field detecting/generating coil unit 409 can be selectively used for either magnetic field detecting or reference position display, at least two or more need to be set for magnetic field detecting. The reason is because, if all are set to magnetic field generating source coils, none remain to detect the positions thereof. While position detecting can be made, in principle, with one sensing coil, at least two or more should be used for position detecting in order to improve detecting precision.

Figure 55:
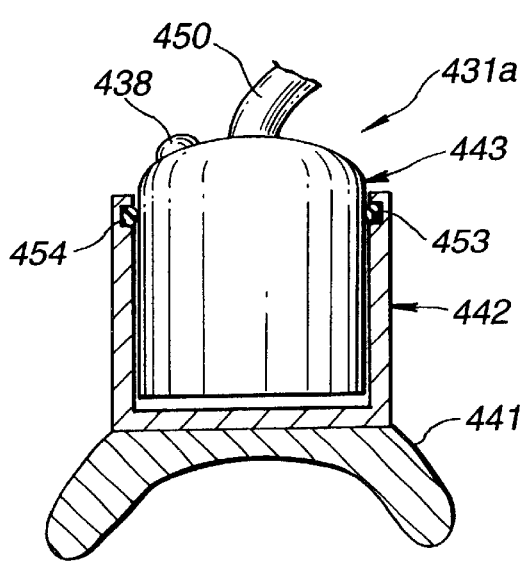
Figure 56:
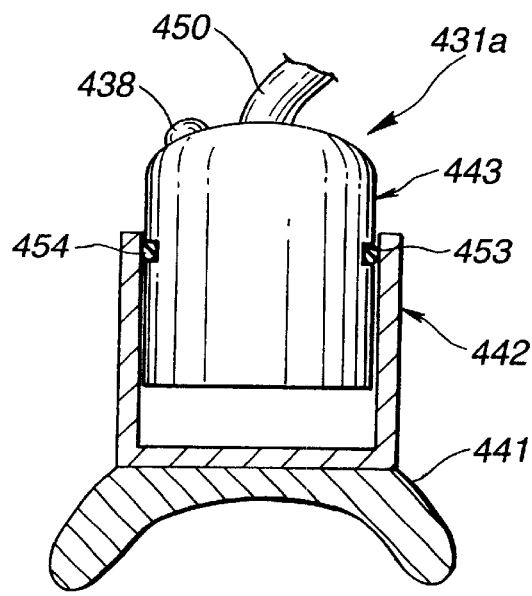

FIGS. 55 and 56 illustrate the configuration of a first coil unit 431a, for example, in a first variation, with a different height adjustment mechanism, as shown in FIG. 53. As shown in FIG. 55, the outer perimeter of the side of the coil member 443 of the first coil unit 431a has a cylindrical shape. A ring-shaped groove 453 is provided to the inner perimeter of the fixing unit 442. An o-ring 454 is introduced therebetween.

Following sliding the coil member 443 along the fixing unit 442, the coil member 443 is fixed at the position to which it has been moved, due to the friction with the o-ring 454.

Although an o-ring 454 has been provided in the groove 453 to the side of the fixing unit 442 in FIG. 55, the same advantages can be obtained by providing the o-ring 454 in a groove 453 to the side of the coil member 443, as shown in FIG. 56.

Figure 57:
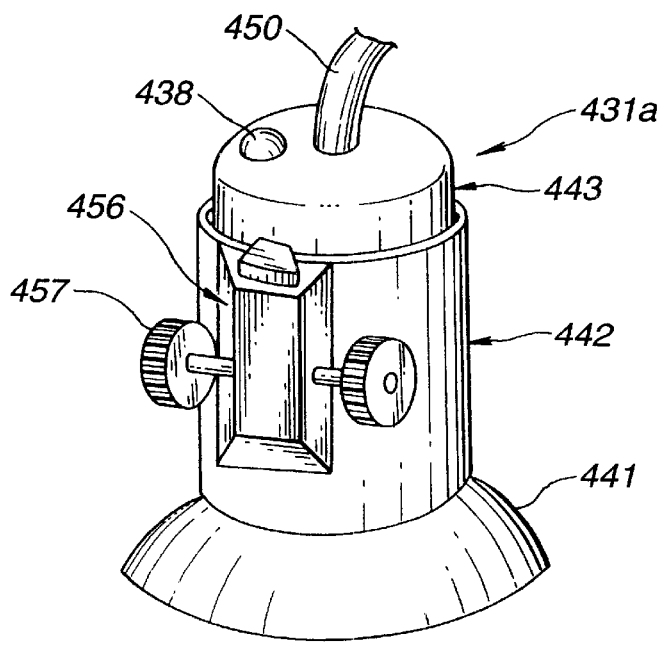
Figure 58:
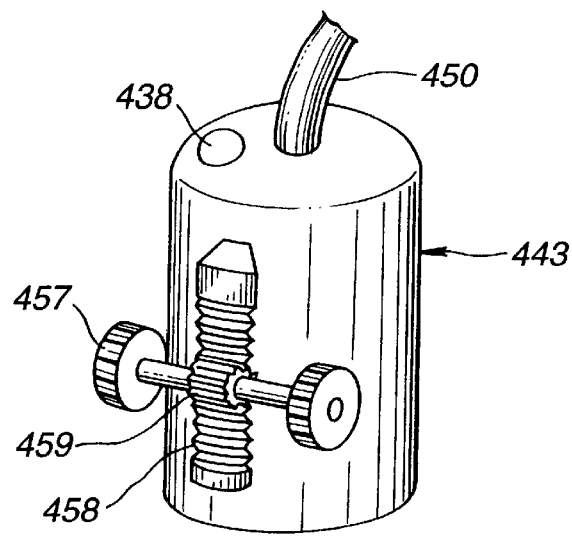

FIGS. 57 and 58 illustrate the configuration of a first coil unit 431a, for example, in a second example, with a different height adjustment mechanism than that shown in FIG. 53. As shown in FIG. 57, a rack-and-pinion 456 height adjustment mechanism is provided for the first coil unit 431a, for example. The height of the coil member 443 can be changed and set relative to the fixing unit 442 by turning a knob 457.

The stator side of the rack-and-pinion 456 is provided to the fixing unit 442 side, and the rack 458 is provided in the height direction on the outer perimeter of the fixing unit 442, as shown in FIG. 58. The rack 458 engages with the pinion 459 attached to the shaft of the knob 457.

Arrangements using the foregoing examples are capable of setting height position in almost the same manner.

The nineteenth embodiment is similar to the seventeenth embodiment. Only the differing points from the seventeenth embodiment will be described. Similar configurations will be denoted with the same reference characters and the description thereof omitted.

The endoscope shape measuring system 401 according to the seventeenth embodiment, shown in FIG. 47, has position detecting means for the magnetic field detecting/generating coil unit 409.

The endoscope shape measuring system 401, shown in FIG. 47, includes a stand 462 connected to the examining table 407. A television camera 464 is attached to the arm 463 of the stand 462, as shown in FIG. 59. The television camera 464 can be used to take images of the magnetic field detecting/generating coils 409 positioned around the abdomen of the patient 408, from an overhead position toward the abdomen of the patient 408, for example.

The image-taking element within the television camera 464 is input to the shape detecting device 414 via a cable 465. The two-dimensional coordinate positions on the X-Z plane of the magnetic field detecting/generating coils 409 positioned on the abdomen of the patient 408, can be detected by a position detecting circuit (not shown) provided within the shape detecting device 414. Thus, the height position can also be detected, although at a slightly lower precision. In order to improve the precision of the height position setting, the height may be set to a known value using the height adjusting mechanism provided to each coil unit 431k.

According to the present embodiment, the task of inputting the positional data for at least four coil units 431c through 431f used for magnetic field detecting in the magnetic field detecting/generating coilunit 409 can be reduced or eliminated, as compared with the seventeenth embodiment. The other advantages are the same as those of the seventeenth embodiment.

Although with the present embodiment, inputting the positional data for at least four coil units 431c through 431f, or further coil units 431a and 431b by selection, used for magnetic field detecting in the magnetic field detecting/generating coil unit 409 can be reduced or lightened by using the output signals of the television camera 464, the television camera 464 may be used alongside to improve position detection precision. The television camera 464 also may not be used but employed for position detection and setting.

Figure 60:
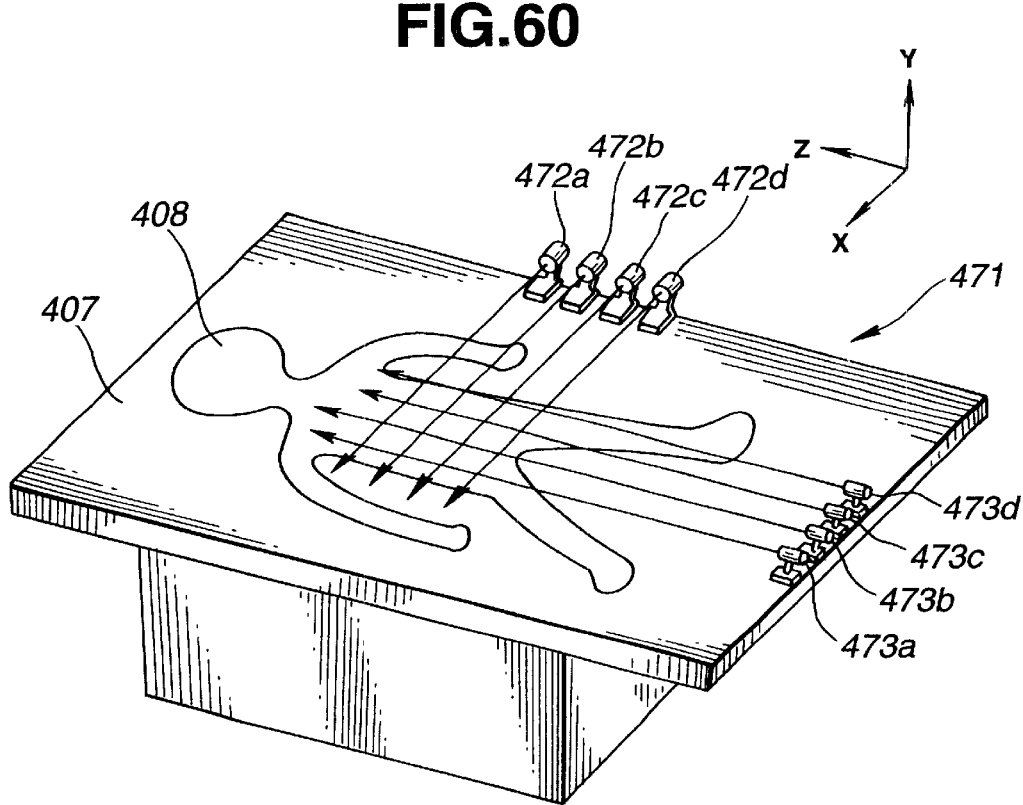

FIG. 60 illustrates a position detecting mechanism 471 according to a first example. Laser beam emitting units 472a through 472d and 473a through 473d are provided around the examining table 407d nd emit laser beams in the X direction and Z direction, setting mesh-like marker positions or reference positions on the patient 408.

Setting the mesh-like marker positions in this way allows the technician to set the coil units 431k used for detection of the magnetic field detecting/generating coil unit 409 on the surface of the body of the patient 408 with good precision on the X-Z plane, by setting each coil unit 409 on the mesh-like marker positions.

When detecting with a television camera 464, inputting the marker position information beforehand allows position detection to be performed with good precision.

Figure 61:
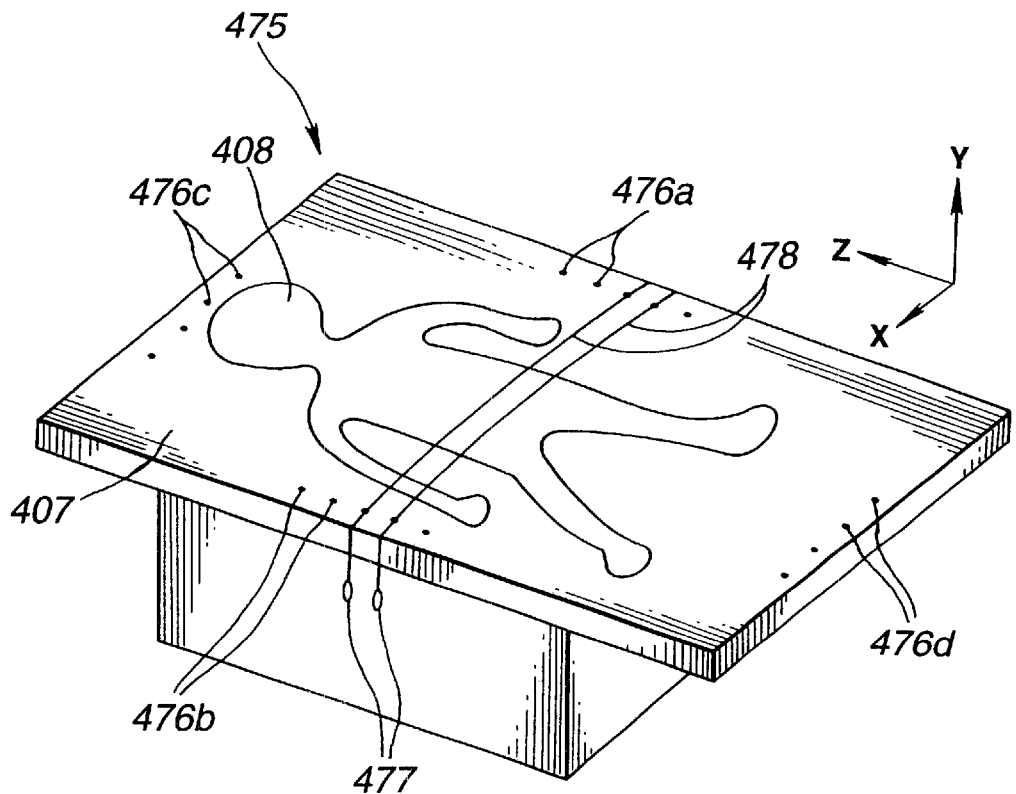

FIG. 61 illustrates a position detecting mechanism 471 according to a second example. Markers 476a, 476b, 476c, and 476d are provided on reference positions on the examination table 407.

Alternatively, a thread or cord 478 with a weight 477 attached on the end thereof may be drawn along the markers 476a and 476b. The operation advantages thereof are almost the same as those of the first example.

Figure 62:
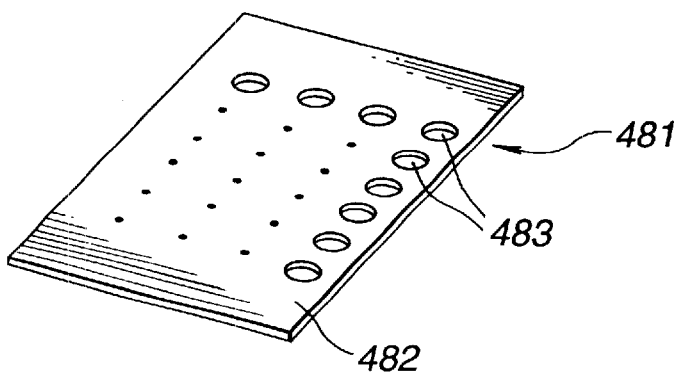

FIG. 62 illustrates a position detecting mechanism 481 according to a third example. This position detecting mechanism 481 has holes 483 for each set position of a lattice-like structure of a plate 482, for example. By positioning the first through sixth coils of the magnetic field detecting/generating coil unit 409 at an arbitrary hole 483, the position of the unit 409 may be known.

In FIG. 62, a great number of holes 483 are shown in a lattice-like structure. However six of the holes 483, the same as the number of coil units in the magnetic field detecting/generating coil unit 409, may be provided thereto.

Figure 63:
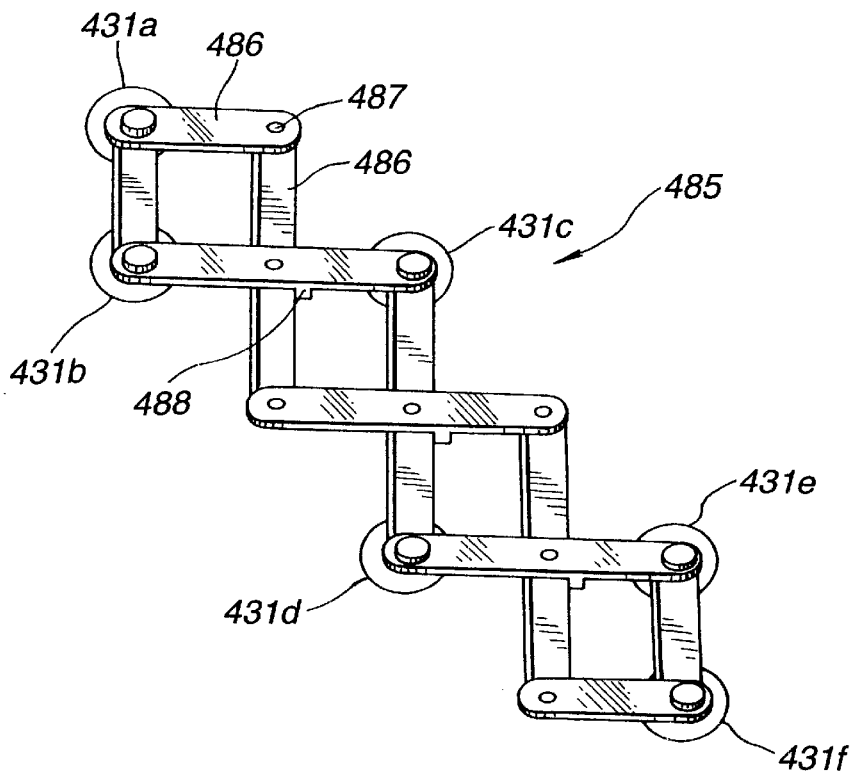

FIG. 63 illustrates a position detecting mechanism 485 according to a fourth example. This position detecting mechanism 485 has a plurality of arms 486 that are rotatably linked with rotating axes 487 at a certain position so as link with rhomboid shapes following the diagonal lines thereof.

Coil units 431a through 431f making up the magnetic field detecting/generating coils 409 are attached to certain positions on the arms 486.

The arms 486 are provided with stoppers 488, preventing excessive deformation. According to this example, the position of the coil units 431a through 431f can be determined even if the positions of all of the coil units 431a through 431f are not known. The attachment position thereof can be changed by turning it with the rotating axes 487.

Figure 64:
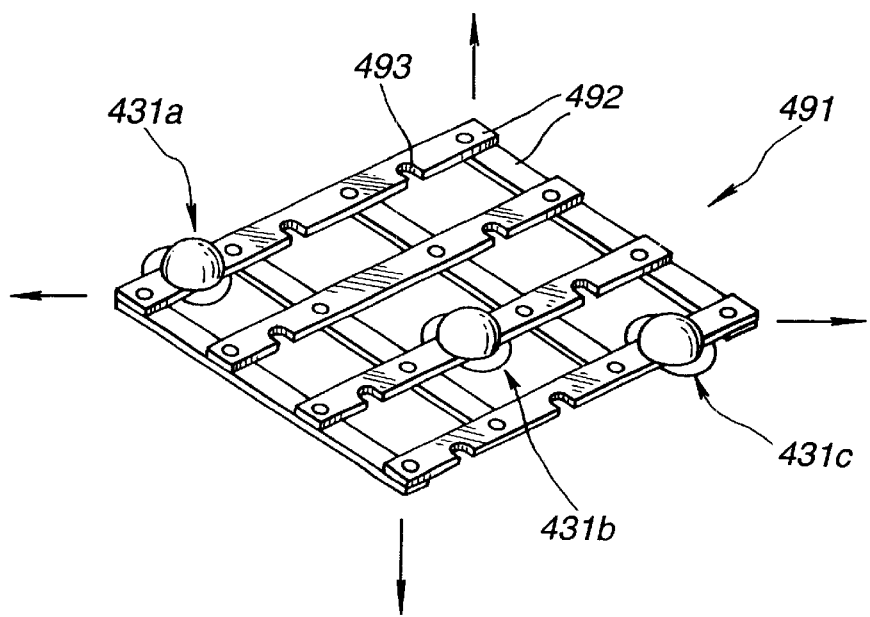

FIG. 64 illustrates a position detecting mechanism 491 according toe fifth example. This position detecting mechanism 491 has a plurality of arms 492 arrayed so as to intersect in a parallel manner, rotatably connected at the intersecting positions, so as to be deformed in the diagonal direction as shown in FIG. 64.

Grooves 493 are provided at certain positions, to which the coils 431a, 431b, 431c, etc., comprising the magnetic field detecting/generating coil unit 409 are attached. The present example has almost the same operations and advantages as that of the fourth example.

The twentieth embodiment is similar to the nineteenth embodiment. Only the differing points from the nineteenth embodiment will be described. Similar configurations will be denoted with the same reference characters and the description thereof omitted.

Figure 65:
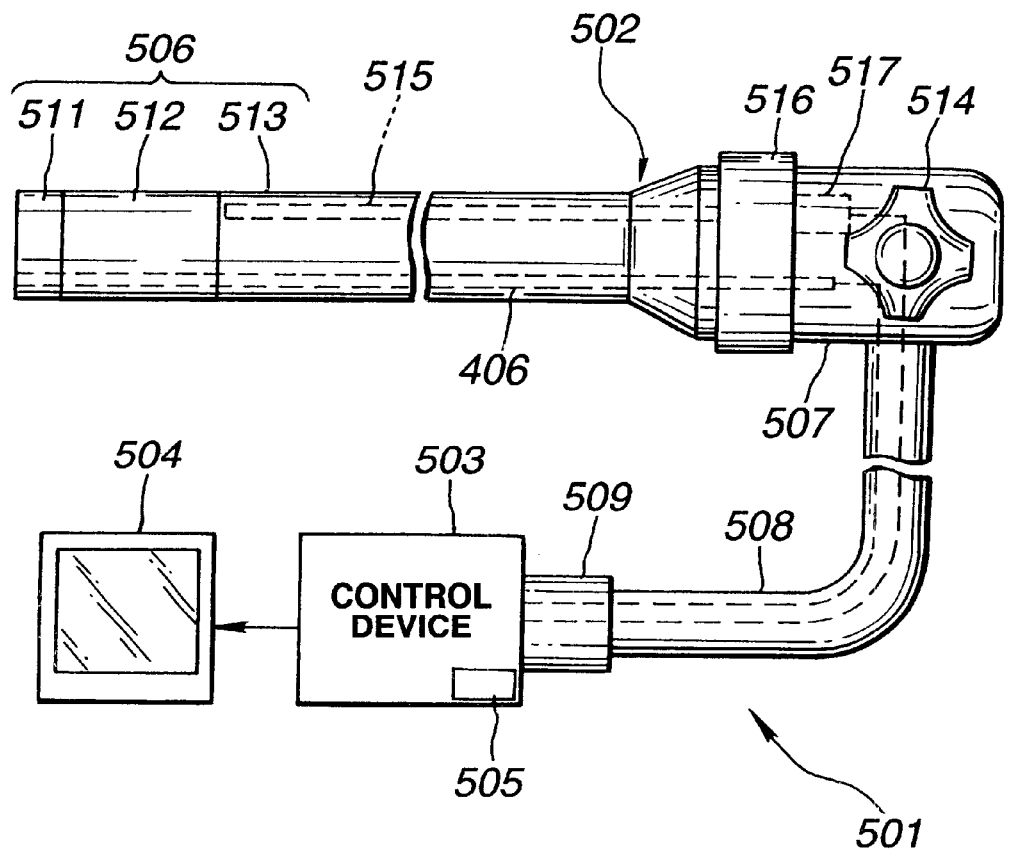

As shown in FIG. 65, according to the present embodiment, an endoscope 502 with a built-in probe 406 mounted in the channel 422 of the endoscope 402, shown in FIG. 47, the light source device 403, shown in FIG. 47, a control device 503 wherein the CCU 404 and shape detecting device 414 have been integrated, a monitor 504 for displaying picture signals output from the control device 503, and a magnetic field detecting coil unit (not shown) are provided, with a recording device 505 being provided to the control device 503.

The endoscope 502 is comprised of an insertion portion 506 having flexibility, and operating unit 507, and a universal cable 508. The connector 509 at the end portion of the universal cable 508 is detachably connected to the control device 503.

The insertion portion 506 is formed of a tip portion 511, a curving portion 512, and a flexible portion 513. The curving portion 512 can be curved by operating the curving operation knob 514 provided to the operating unit 507.

The probe 406 built into the insertion portion 506 is connected to a shape detecting device (not shown) within the control device 503. The detecting device also is connected to a magnetic field detecting coil unit, thereby allowing shape detection. Image data of the shape detection is recorded in the recording device 505.

A stiffness changing means or flexibility changing means 515 is provided within the insertion portion 506. The stiffness changing means 515 is formed of a coil and a wire inserted through the coil, for example. The tip thereof is fixed to the tip of the flexible portion 513. The rear end of the coil is fixed and to front end of the operating unit 507. The wire extending from the coil is connected to a stiffness adjusting knob 516 via a wire pulling mechanism.

Turning the stiffness adjusting knob 516 places compressive force on the coil via the wire pulling mechanism, thereby adjusting the flexibility or stiffness of the insertion portion 506, the flexible portion 513 in the present embodiment, at the portion where the stiffness changing means 515 is provided.

The amount of knob operation of this stiffness adjusting knob 516 is detected by a knob operation amount detecting means or stiffness detecting means 517.

Figure 66:
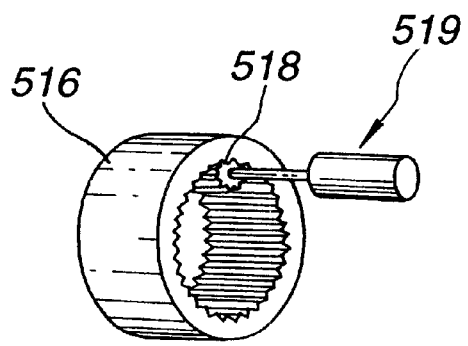

As shown in FIG. 66, the knob operation amount detecting means 517 includes a gear 518 engaging with a threaded hole in the inner circumference of the stiffness adjusting knob 516 which is attached to the rotating shaft of a potentiometer 519. The resistance value of the potentiometer 519 changes in accordance with the rotating of the stiffness adjusting knob 516. This resistance value is input to the control device 503.

A recording button (not shown) is operated, thereby starting the recording operation of the control device 503. The recording device 505 records the knob operation amount data from the knob operation amount detecting means 517 in a manner synchronous with the insertion shape data of the probe 406.

The data recorded in the recording device may be reproduced. Thus, according to the present embodiment, if a technician capable of adjusting the stiffness while making reference to the insertion shape so as to perform an extremely smooth insertion has inserted the insertion portion 506, recording the data in the recording device 105 would allow a less skilled technician to make reference to the recorded data and learn the technique for performing the smooth insertion recorded in the data.

The twenty-first embodiment is similar to the nineteenth embodiment. Only the differing points from the twenty first embodiment will be described. Similar configurations will be denoted with the same reference characters and the description thereof omitted.

FIG. 67 illustrates the overall configuration of the endoscope shape detecting system 521 according to the twenty-first embodiment of the present invention.

With this system 521, the operation of the endoscope device portion 522 and the operation of the shape detecting unit 523 are controlled by the controller 524.

The endoscope device portion 522 is comprised of a COD 525 provided to the endoscope, a CCU 526 for generating image-taking signals corresponding to the endoscopic image by subjecting the picture signals taken by the CCD 525 to signal processing, and memory 527 for temporarily storing the digital picture signals at the CCU 526. The CCU 526 alternately outputs picture signals subjected to real-time processing and picture signals temporarily stored in the memory 527 onto the monitor 528.

The shape detecting unit 523 has the probe 406 and magnetic field detecting coil unit (not shown) connected to a shape detecting device 531. The shape detecting device 531 detects the position of source coils by applying driving signals to the source coils for generating magnetic fields within the probe 406 and detecting the magnetic fields generated around the source coils driving signals applied thereto with the sensor coils of the magnetic field detecting coil unit. The shape detecting unit 523 also generates the insertion shape image of the insertion portion of the endoscope where the probe is passed through, based on positional detection. The shape detecting unit 523 is capable of temporarily storing the digital picture signals of the insertion shape image in memory 532 and outputting the picture signals to the monitor 528.

The real-time picture signals from the shape detecting device and the picture signals output from the memory 532 are alternately output to the monitor 528.

With the present embodiment, memory 527 and 532 are provided respectively to the endoscope device 522 and the form detecting unit 523, so that the real-time endoscopic image and an endoscopic image from a previous field/frame can be simultaneously displayed on the monitor 528 with flexibility in timing such that there are no undesirable effects on the operation of the endoscope device 522 and the form detecting unit 523.

If neither device has memory, as with conventional arrangements, there are great restrictions in the operating timing of each of the devices. That is, shifting timing is difficult for the devices that do not have memory. For example, if driving action timing is shifted, the timing for the display must also be shifted accordingly. However, with the present embodiment, memory is provided for each device, so the driving operation timing can be easily shifted.

That is, temporarily storing in memory the data or image data obtained by shifting the driving operating timing does away with the need to synchronize the display timing with the driving operation timing, processing timing changes can be performed with flexibility.

Systems without memory exhibit a display gap or cycle that becomes great,causing moving objects to appear unstable. The present invention includes memory so that smooth movement can be reproduced. Conversion to standard picture signals for viewing on a normal monitor can also be realized.

For example, control can be performed with the controller 524 so that the endoscopic image and shape image are displayed, as shown in FIGS. 68A and 68B.

In FIG. 68A, the period for directly outputting the endoscopic image from the CCU 526 to the monitor 528 is represented by ON. The period wherein the endoscopic image from one frame period or.one field period before temporarily stored in the memory 527 is output to the monitor 528 is represented by OFF.

In FIG. 68B, the period for directly outputting the shape image from the shape detecting device 531 to the monitor 528 is represented by ON. The period wherein the shape image from one frame period or one field period before temporarily stored in the memory 532 is output to the monitor 528 is represented by OFF.

In the operation example shown in FIGS. 68A and 68B, the shape detecting unit 523 outputs the shape image temporarily stored in the memory 532 to the monitor 528 during the time (Ta, Tb, Tc, Td, etc.). The realtime endoscopic image from the CCU 526 is output to the monitor 528. The endoscopic image and the shape image from a previous frame/field are simultaneously displayed.

While outputting the endoscopic image stored in the memory 527 to the monitor 528, the shape detecting unit 523 outputs the shape image according to the shape detecting device 531 to the monitor 528 and displays the shape image synchronously with the endoscopic image from the previous frame/field.

As the result of performing such image display, the gaps between displays are not too long, moving images can be smoothly displayed for both of the endoscopic image and the shape image, and display can be made with little effect therebetween.

The present invention is not restricted to such timing control. Timing may be used wherein there is little interference between the image-taking operation and the operation of shape detection. FIGS. 69A through 69H illustrate and example of this timing control.

In this case, in FIG. 67, image-taking signals or signals carrying the taken image from photo-electrical conversion at the photo-receptor photosensitive member of the CCD 525 are accumulated, and output through the transfer unit by means of application of driving signals are subjected to A/D conversion, and temporarily stored in the memory 527. The output signals of the sensing coils, if source coils are driven to generate a magnetic field for detecting the shape, are subjected to A/D conversion, and temporarily stored in memory 532.

Timing is controlled by the controller 524 such that the period of output of the picture signals and the period of output of output signals from the sensing coils, if the source coils are driven, do not overlap. In other words, the periods for CCD driving and coil driving or magnetic field generation/detection do not overlap, this being described with reference to FIGS. 69A through 69H.

In FIG. 69A, transfer signals are applied to the CCD 525 upon completion of each frame period from the CCD driver within the CCU 526. One frame worth of signal charges accumulated in the photo-receptor or photosensitive member of the CCD 525 are transferred to the transfer unit. The signal charge transferred to the transfer unit is further subjected to application of vertical and horizontal transfer signals shown in FIG. 69B, CCD driving signals in this case. The picture signals are output from the transfer portion of the CCD 525 to the CCU 52 6, and then temporarily stored in the memory 527. That is, the memory storage is as shown in FIG. 69C. Transfer of the above transfer signals starts a new image-taking or accumulation of signal charge for the photo-receptor.

The output period of the above CCD drive signals is at least shorter than one frame period, e.g., a period somewhat less than half of one field period (T1 in the Figure. The picture signals taken within the one frame at the photo receptor of the CCD 525 is stored in the memory 527 following the output period T1.

The picture signals stored in the memory 527 are subjected to picture signal processing within the CCU 526. One frame worth is output over a one frame cycle of normal picture signals, during the next frame period for example, and displayed on the monitor 528 as standard picture signals along with synchronous signals. This is represented in FIG. 69D as picture signals or as field-cycle interlaced-display picture signals.

The shape detecting portion 523 applies driving signals for driving the probe, or more particularly, the source coils within the probe, to the source coils when the above transfer signals and CCD driving signals are not being output. During the period T2, shown in FIG. 69E, described as coil driving, the magnetic field generated around the source coils is detected with the sensing coils. The detection signals are passed through the shape detecting device 531 and subjected to A/D conversion, and then stored in the memory 532. The B1 is controlled by the controller 524 so that the sequence is performed for all source coils over the duration of the period T2.

That is, during the period T2, the magnetic field generated around the source coils to which driving signals are applied is detected with the magnetic field detecting coils, and the position detection data is stored in the memory 532. Then, the magnetic field detection data for position detection regarding all source coils for which position detecting is necessary is stored in the memory 532.

The memory storage shown in FIG. 69F is completed within the period T2. Once this is completed, the next transfer signal is applied to the COD 525, so that the above operation is repeated.

The magnetic field detecting data stored in the memory 532 has position data generated at the position detecting unit within the shape detecting device 531. A shape image is generated during the next one frame at the shape image generating unit. This is simply described as signal processing on FIG. 69G. Then, for example, the picture signals of the shape image generated in the next frame period as shown in FIG. 69H are displayed on the monitor 528.

As a result of such an operation, source coil driving signals with a greet amplitude are not applied to the source coils for magnetic field generation during the time T1 for outputting the signals taken by the CCD 525 to the CCU 526 side. This avoids mixing the source coil driving signals into the weak CCD output signals as noise.

CCD driving signals also are not output to the CCD 525 during the period T2 wherein source coil driving signals are applied to the source coils and the magnetic field generated around the source coils is detected with the sensing coils. Thus, if magnetic fields are generated due to the CCD driving signals in the surrounding transporting lines and the like, the magnetic field generated by the source coils are not affected and can be detected with high precision.

Thus, when the image-taking functions of the endoscope and the form detecting functions lower the S/N ratio, noise can be avoided, and each of the functions can be sufficiently exhibited.

In the above embodiments, description has been made regarding an arrangement wherein source coils to which signals for generating magnetic fields are applied are used for detecting the position of the probe 406 and sensing coils for detecting the magnetic fields generated by the source coils are provided at known positions at the exterior of the endoscope. The present invention is not restricted to such; rather the two may be inverted.

For example, applying this to the seventeenth "embodiment the source coils 426i identical within the probe 406i n FIG. 48 function as sensing coils 426i. Each of the sensing coils 426i are connected to the amplifying units 433. The coil units 431a and 431b are the same, but the coils 446 of the other coil units 431c through 431f function as source coils connected to, e.g., the connection points a, b, c, and d of the multiplexer 428.

Driving signals applied to the coil unit 431c of a known position, for example, from the driving unit 429, generate a magnetic field in the area. The magnetic field is detected with the sensing coils 426i within the probe 406. Each detection output is sent to the position detection unit 436 via the amplifying unit 433.

The contact point of the multiplexer 428 is switched over, and driving signals are applied from the driving unit 429 to the coil unit 431d of a known position, so as to generate a magnetic field in the area. The magnetic field is detected with the sensing coils 426i within the probe 406, and each detection output is sent to the position detection unit 436 via the amplifying unit 433, and so on for all of the coil units 431c through 431f, until position detecting data is obtained for the driving of all.

The coil units 431a and 431b are selectively operated. Thus, the position of the sensing coils 462i within the probe 406 can also be detected from position detecting data obtained in this way.

The twenty-second embodiment is similar to the first embodiment. Only the differing points from the first embodiment will be described. Similar configurations will be denoted with the same reference characters and the description thereof omitted.

Figure 70:
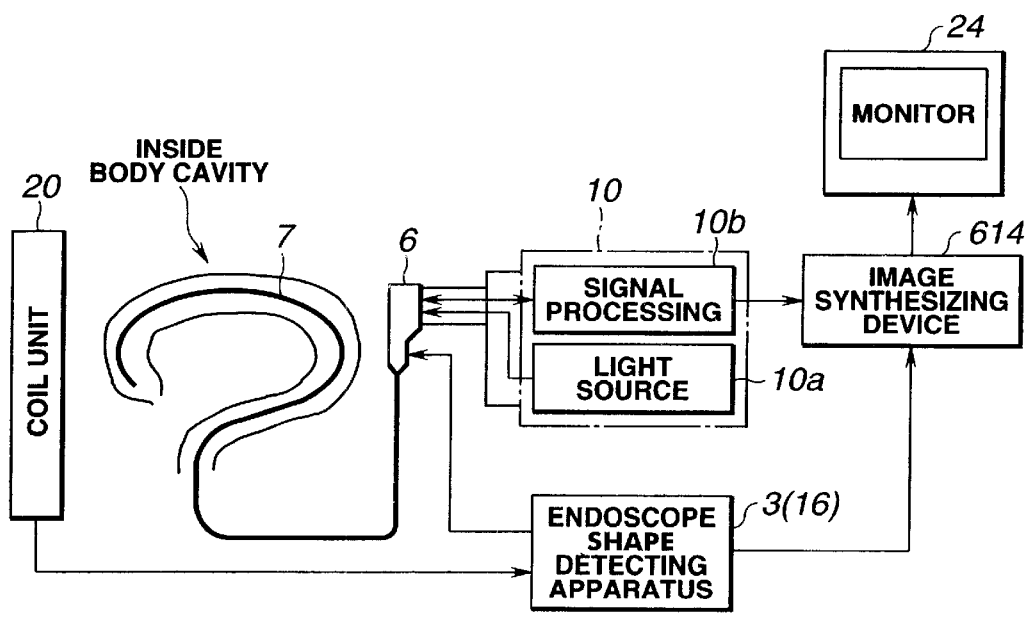
Figure 71:
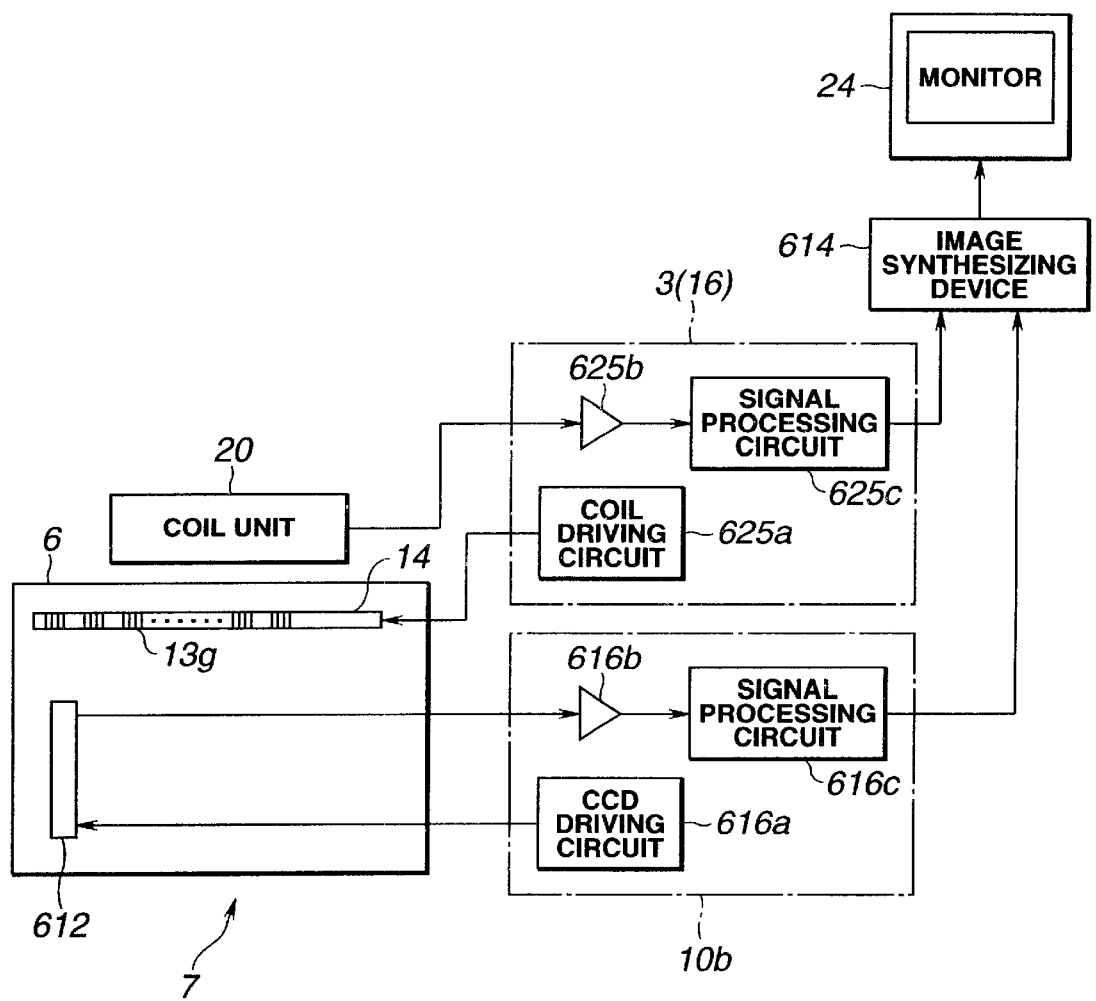

As shown in FIG. 70 and FIG. 71, the video endoscope 6 transmits light from alight source unit 10a within the video processor 10 through which a light guide has been passed. The transmitted light is cast out from the illumination window provided at the tip of the insertion portion 7, thereby illuminating an affected portion or the like(see FIG. 70). The object consisting of the illuminated affected portion or the like is imaged on the CCD 612. The CCD 612 is an image-taking element provided at the imaging position of an object lens attached to the observation window provided next to the illumination window which performs photo-electric conversion(See FIG. 71).

The photo-electrically converted signals are subjected to signal processing by the signal processing unit lob within the video processor 10, thereby generating standard image signals. The endoscope image is output to an image synthesizing device 614 connected to the video processor 10 (See FIG. 70).

More specifically, as shown in FIG. 71, the CCD 612 of the video endoscope 6 is driven by the CCD driving circuit 616 a within the signal processing unit 10b. Following amplifying of the picture signals from the CCD 612 with a preamplifier 616b, the signals are subjected to various types of processing at the signal processing circuit 616c, such as sampling processing, A/D conversion, white balancing processing, outline highlighting processing, gamma correction, etc., then subjected to D/A conversion and output to the image synthesizing device 614.

The sensing coil 21j is connected to the apparatus proper 16 vie s sensing cable 22 serving as detecting signal transmitting means from the connector of the coil unit 20 where the sensing coil 21j is stored. The image synthesizing device 614 for inputting the detected endoscope shape image is connected to the apparatus proper 16.

More specifically, as shown in FIG. 71, at the apparatus proper 16 of the endoscope shape detecting apparatus 3, the source coils 13g are driven by the coil driving circuit 625a. The coil during circuit 625a includes the driving block 25, shown in FIG. 2. The magnetic field from the source coil 13g is detected with the sensing coil 21j within the coil unit 20. The detection signals are amplified at the preamplifier 625b, then subjected to A/D conversion at the signal processing circuit 625c comprising the detection block 26 and host processor 27, shown in FIG. 2. Following which, the position and orientation of the source coil 13g is estimated and the endoscope shape is calculated. The endoscopic image is subjected to D/A conversion and output to the image synthesizing device 614.

At the image synthesizing device 614, the endoscopic image from the video processor 10 and the endoscope shape image from the apparatus proper 16 of the endoscope shape detecting apparatus 3 are synthesized. The synthesized image is displayed on the monitor 24.

Figure 72:
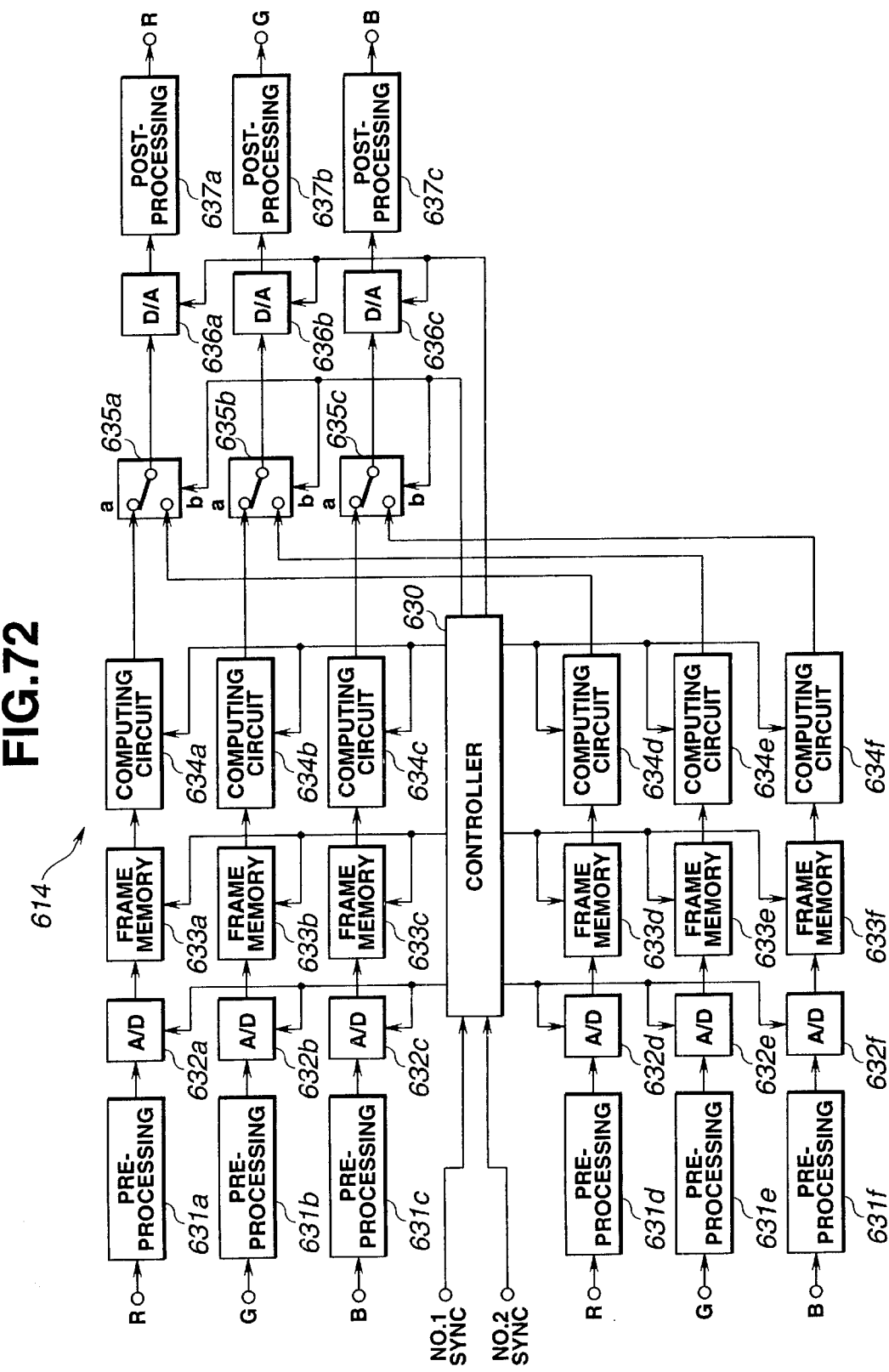

More specifically, as shown in FIG. 72, the image synthesizing device 614 has preprocessing circuits 631a, 631b, and 631c for performing gain adjustment and the like for the R. G. and B endoscopic image signals from the video processor. Preprocessing circuits 631d, 631e, and 631f adjust the gain and the like for the R, G, and B endoscope shape image signals from the apparatus proper 16 of the endoscope shape detecting apparatus 3. A controller 630 inputs the respective synchronous signals from the video processor 10 and apparatus proper 16 (hereafter, the synchronous signal from the video processor 10 will be referred to as first SYNC, and the synchronous signal from the apparatus proper 16 will be referred to as second SYNC), and generates the various control signals.

On the endoscopic image signal side, signals passing through the preprocessing circuits 631a, 631b, and 631c are converted in the A/D converters 632a, 632b, and 632c, by control signals from the controller 630 based on the first SYNC. The signals are stored in the frame memory 633a, 633b, and 633c, by control signals from the controller 630 also based on the first SYNC. Then, the R, G, and B endoscopic image signals read from the frame memory 633a, 633b, and 633c, by control signals from the controller 630 based on the first SYNC, are subjected to certain enlarging/reduction processing by the computing circuits 634a, 634b, and 634 c, and output to the a side of switches 635a, 635b, and 635c of the input terminal.

In the same manner, on the endoscope shape image signal side, signals passing through the preprocessing circuits 631d, 631e, and 631f are converted in the A/D converters 632d, 632e, and 632f, by control signals from the controller 630 based on the second SYNC. The signals are stored in the frame memory 633d, 633e, and 633f, by control signals from the controller 630 also based on the second SYNC. Then, the R, G, and B endoscope shape image signals read from the frame memory 633d, 633e, and 633f, by control signals from the controller 630 based on the second SYNC, are subjected to certain enlarging/reduction processing by the computing circuits 634d, 634e, and 634f, and output to the b side of switches 635a, 635b, and 635c of the input terminal.

At the switches 635a, 635b, and 635c, the signals from the input terminal a side and the signals from the input terminal b side are switched over at a certain timing by a control signal from the controller 630 and output to the D/A converters 636a, 636b, and 636c. The signals are subjected to D/A conversion by the D/A converters 636a, 636b, and 636c and converted into standard TV signals by post-processing circuits 637a, 637b, and 637c, then output to the monitor 24.

The other configurations thereof are the same as those of the first embodiment.

As shown in FIG. 72, the image synthesizing device 614, according to the present embodiment, switches the output of the switches 635a, 635b, and 635c by control signals from the controller 630 and displays a synthesized image, as shown in FIG. 5, on the monitor 24.

Figure 73:
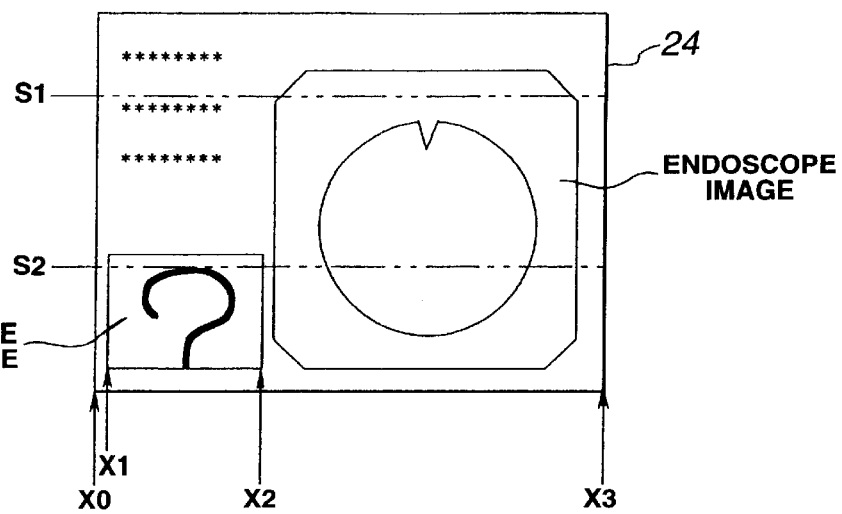

That is, as shown in FIG. 73, if the scan line is S1, the output of the switches 635a, 635b, and 635c is switched over to the endoscopic image, from the input terminal a side. If the scan line is S2, the output of the switches 635a, 635b, and 635c is switched as follows:

| Scan area | Selected input terminal |
|---|---|
| X0 → X1 | a |
| X1 → X2 | b |
| X2 → X3 | a |

The computing circuits 634d, 634e, and 634f output the endoscope shape image signals reduced by a certain first reduction rate to the input terminal b of the switches 635a, 635b, and 635c. The computing circuits 634a, 634b, and 634c output the endoscopic image signals reduced by a certain second reduction rate to the input terminal b of the switches 635a, 635b, and 635c. Thus, a synthesized image with the endoscopic image serving as the main screen, and the endoscope shape image serving as a smaller sub-screen, is displayed on the monitor 24.

Although the computing circuits 634a, 634b, and 634c are described as outputting the endoscopic image signals reduced by a certain second reduction rate, there is no absolute need to reduce the signals. Signal processing may be performed so that a synthesized image such as shown in FIG. 73 is displayed.

Figure 74:
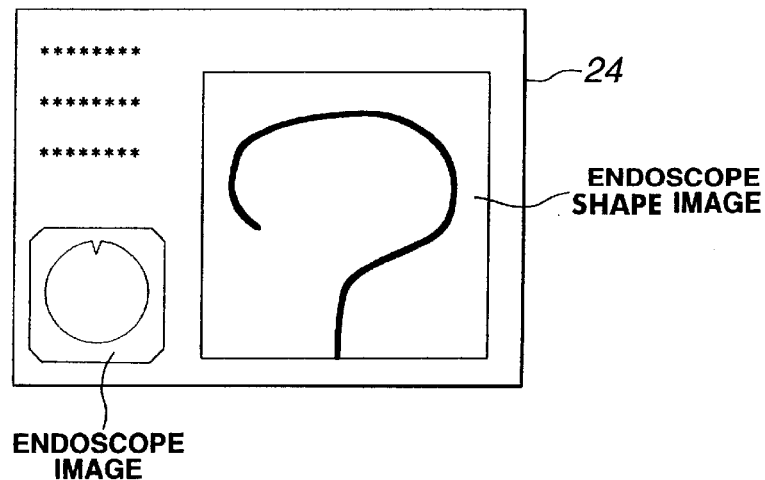
Figure 75:
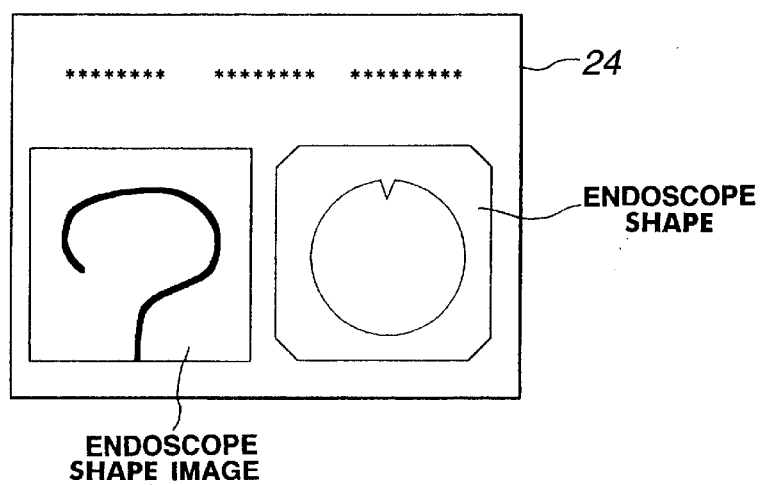

The synthesized image is not restricted to that shown in FIG. 73. The computing circuits 634a, 634b, and 634c, and the computing circuits 634d, 634e, and 634f may be used to perform reduction and enlarging, and the switches 635a, 635b, and 635c used for switching control, to yield a synthesized image wherein the endoscope shape image serves as the main screen and the endoscopic image serves as a smaller cub-screen (FIG. 74). The synthesized image may include the endoscope shape image and the endoscopic image displayed at the same general size (FIG. 75).

According to the present embodiment, a synthesized image of the endoscope shape image and the endoscopic image is displayed on the monitor 24 by switching the output for the switches 635a, 635b, and 635c, based on control signals from the controller 630 in the image synthesizing device 614. Thus, a technician may observe the current insertion shape of the insertion portion along with the endoscopic image, facilitating insertion of the insertion portion in a simpler and easier manner.

The image synthesizing device 614 may be built into the video processor 10 or the apparatus proper 16 of the endoscope shape detecting apparatus 3.

The twenty-third embodiment is similar to the twenty-second embodiment. Only the differing points from the twenty second embodiment will be described. Similar configurations will be denoted with the same reference characters and the description thereof omitted.

Figure 76:
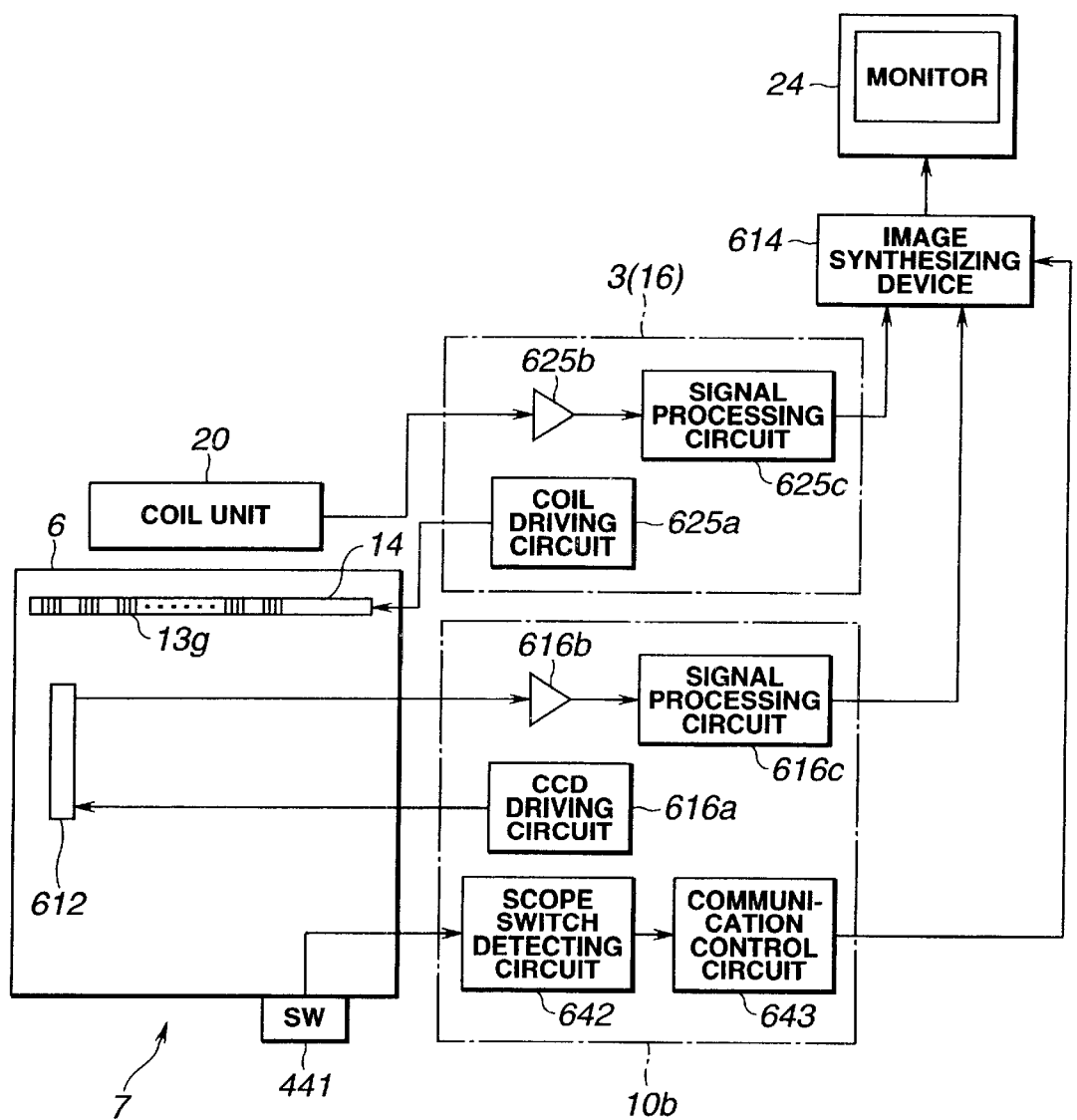

As shown in FIG. 76, according to the present embodiment, a switch-over switch 641 is provided to the video endoscope 6. The signal processing unit has a scope switch detecting circuit 642 for detecting the state of this switch-over switch 641, and a communication control circuit 643 for outputting switching signals to the image synthesizing device 614f from detection signals detected by the scope switch detecting circuit 642.

Figure 77:
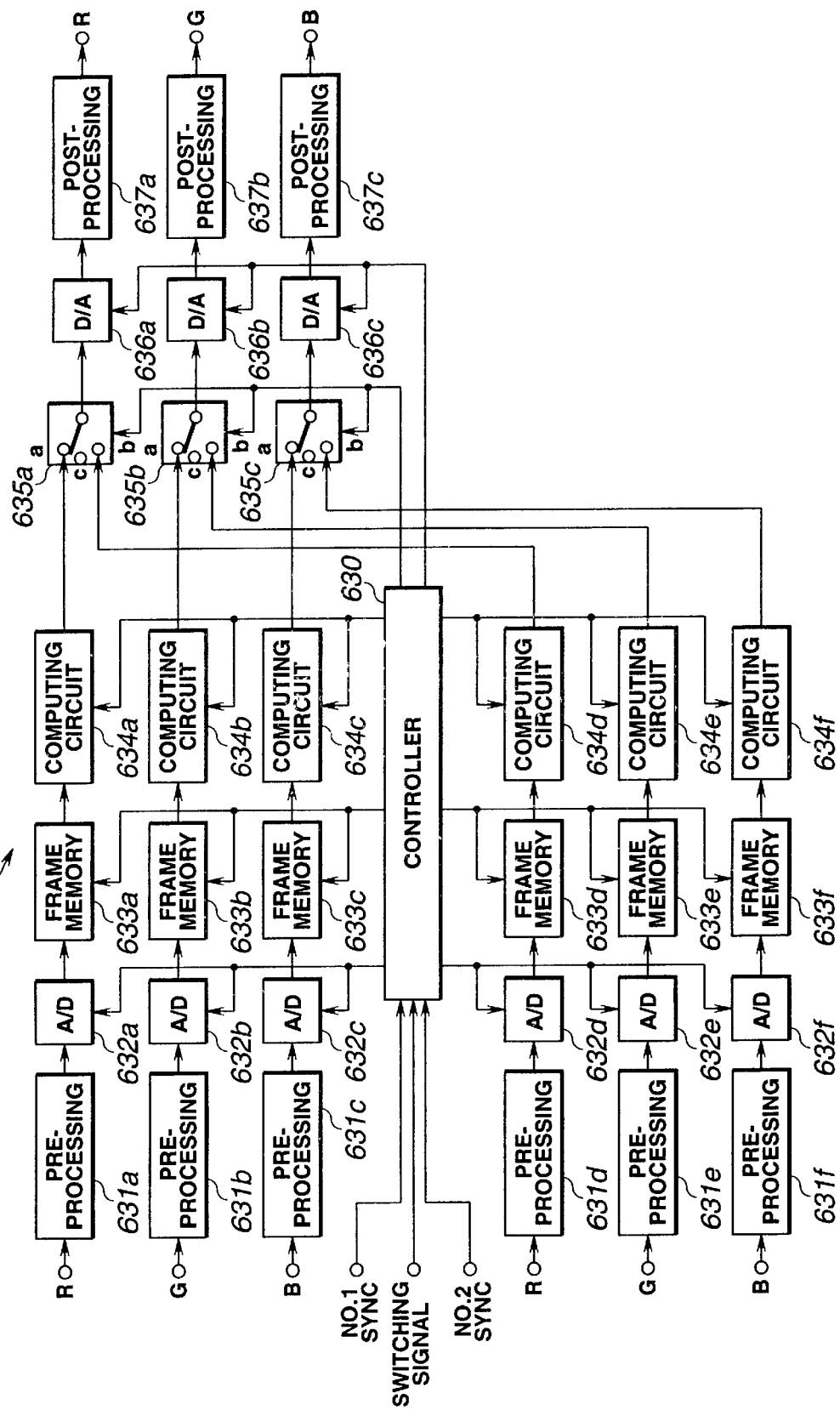

As shown in FIG. 77, at the image synthesizing device 614, switching signals from the communication control circuit 643 are input to the controller 630. The controller 630 outputs control signals to the computing circuits 634a, 634b, and 634c, the computing circuits 634d, 634e, and 634f, and the switches 635a, 635b, and 635c, based on the switching signals.

The switches 635a, 635b, and 635c, according to the present embodiment, are different from those in the twenty-second embodiment in that an unconnected input terminal c is provided in addition to the input terminal a for input of endoscope image signals and the input terminal b for input of endoscope shape image signals. The switches 635a, 635b, and 635c perform switching control of the input terminal a, input terminal b, and input terminal c, based on control signals from the controller 630.

The other configurations are the same as those of the twenty-second embodiment.

Figure 78:
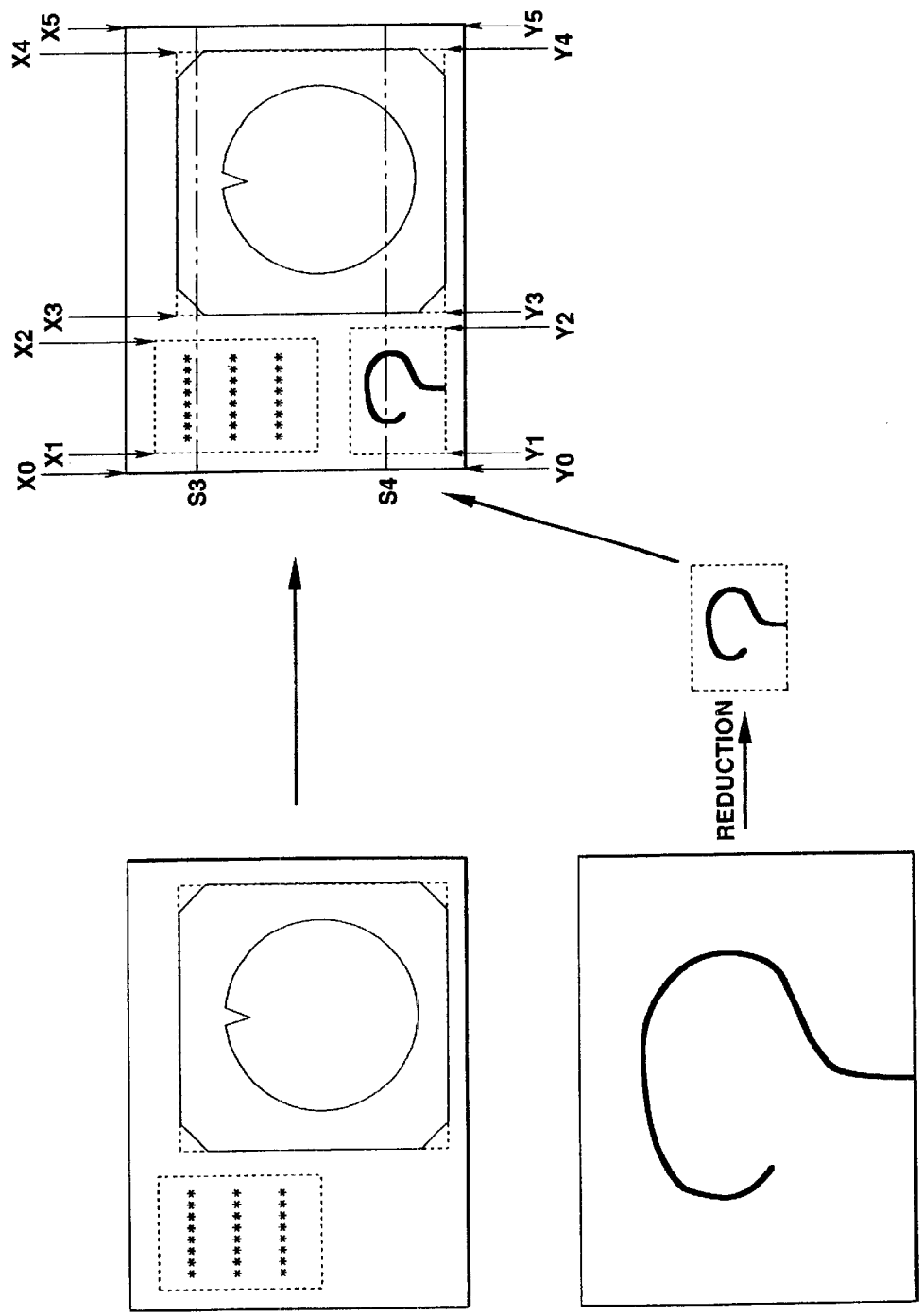

As shown in FIG. 77, with the present embodiment, the image synthesizing device 614 switches the output of the switches 635a, 635b, and 635c, based on control signals from the controller 630, for displaying a synthesized image, such as shown in FIG. 78, on the monitor 24.

That is, as shown in FIG. 78, if the switch 641 of the video endoscope 6 is in the first state, first, controlling signals from the controller 630 cause the endoscopic image to be processed in the computing circuits 634a, 634b, and 634c. The character image portion and the body cavity image portion are cropped out. The endoscope shape image is reduced by a certain reduction rate by the computing circuits 634d, 634e, and 634f.

If the scan line is S3, for example, from the control signals from the controller 630, in order to display the character image portion end body cavity image portion on the monitor 24, the input terminals of the switches 635a, 635b, and 635c are switched as follows:

| Scan area | Selected input terminal | Displayed image |
|---|---|---|
| X0 → X1 | c | No image |
| X1 → X2 | a | Character image portion |
| X2 → X3 | c | No image |
| X3 → X4 | a | Body cavity image portion |
| X4 → X5 | c | No image |

If the scan line is S4, for example, in order to display the reduced endoscope shape image and body cavity image portion on the monitor 24, the input terminals of the switches 635a, 635b, and 635c are switched as follows:

| Scan area | Selected input terminal | Displayed image |
|---|---|---|
| Y0 → Y1 | c | No image |
| Y1 → Y2 | b | Endoscope shape image |
| Y2 → Y3 | c | No image |
| Y3 → Y4 | a | Body cavity image portion |
| Y4 → Y5 | c | No image |

Accordingly, a synthesized image with the body cavity portion as the main screen and the smaller endoscope shape image as the sub-screen is displayed on the monitor 24.

As shown in FIG. 79, if the switch 641 of the video endoscope 6 is in the second state, controlling signals from the controller 630 cause the endoscopic image to be processed in the computing circuits 634a, 634b, and 634c such that the character image portion and the body cavity image portion are cropped out. The body cavity image portion is reduced by a certain first reduction rate, and the endoscope shape image is reduced by a certain second reduction rate by the computing circuits 634d, 634e, and 634f. The body cavity image portion reduced by the certain first reduction rate is smaller than the endoscope shape image reduced by the certain second reduction rate.

If the scan line is S5, for example, from the control signals from the controller 630, in order to display the character image portion end the endoscope shape image reduced by the certain second reduction rate on the monitor 24, the input terminals of the switches 635a, 635b, and 635c are switched as follows:

| Scan area | Selected input terminal | Displayed image |
|---|---|---|
| X0 → X1 | c | No image |
| X1 → X2 | a | Character image portion |
| X2 → X3 | c | No image |
| X3 → X4 | b | Endoscope shape image |
| X4 → X5 | c | No image |

If the scan line is S6, for example, in order to display the body cavity image portion reduced by the certain first reduction rate and the endoscope shape image reduced by the certain second reduction rate on the monitor 24, the input terminals of the switches 635a, 635b, and 635c are switched as follows:

| Scan area | Selected input terminal | Displayed image |
|---|---|---|
| Y0 → X1 | c | No image |
| Y1 → X2 | a | Body cavity image portion |
| Y2 → X3 | c | No image |
| Y3 → X4 | b | Endoscope shape image |
| Y4 → X5 | c | No image |

Accordingly, a synthesized image with the endoscope shape image as the main screen and the smeller body cavity image portion as the sub-screen is displayed on the monitor 26.

The synthesized images shown in FIGS. 78 and 79 are sequentially switched over according to the state of the switch 641 of the video endoscope 6.

Figure 80:
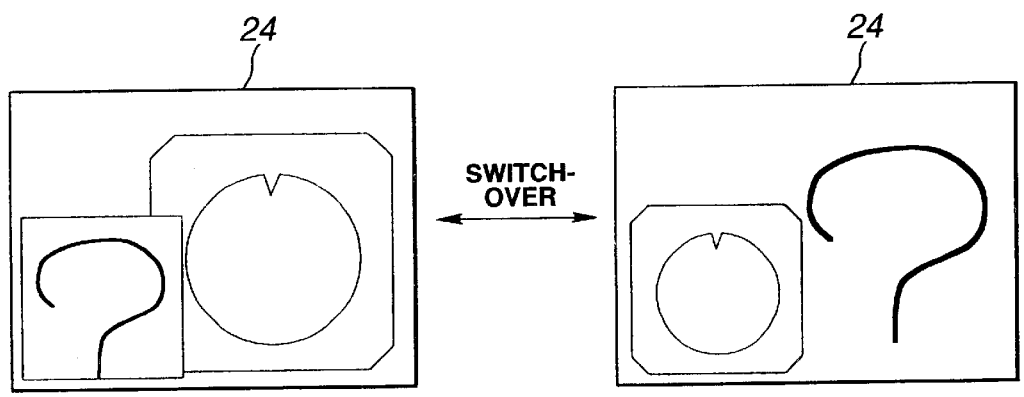

Not only is this restricted to FIGS. 78 and 79, but as shown in FIG. 80, a first superimposed synthesized image may be formed wherein the sub-screen endoscope shape image is superimposed over the main screen body cavity image portion and a second superimposed synthesized image wherein the sub-screen body cavity image portion is superimposed over the main screen endoscope shape image. Switching between images may be sequentially performed according to the state of the switch 641 of the video endoscope 6.

According to the present embodiment, in addition to the advantages of the twenty-second embodiment, the synthesized image can be switched over by the switch 641, so the operability can be further improved by switching the synthesized image according to the insertion operation.

The image synthesizing device 614 may be built into the video processor 10 or the apparatus proper 16 of the endoscope shape detecting apparatus 3. The synthesized image may be switched according to insertion operations performed from an operating panel 23 provided on the apparatus proper 16 instead of the switch 641.

The twenty-fourth embodiment is similar to the twenty-third embodiment. Only the differing points from twenty-third embodiment will be described. Similar configurations will be denoted with the same reference characters and the description thereof omitted.

Figure 81:
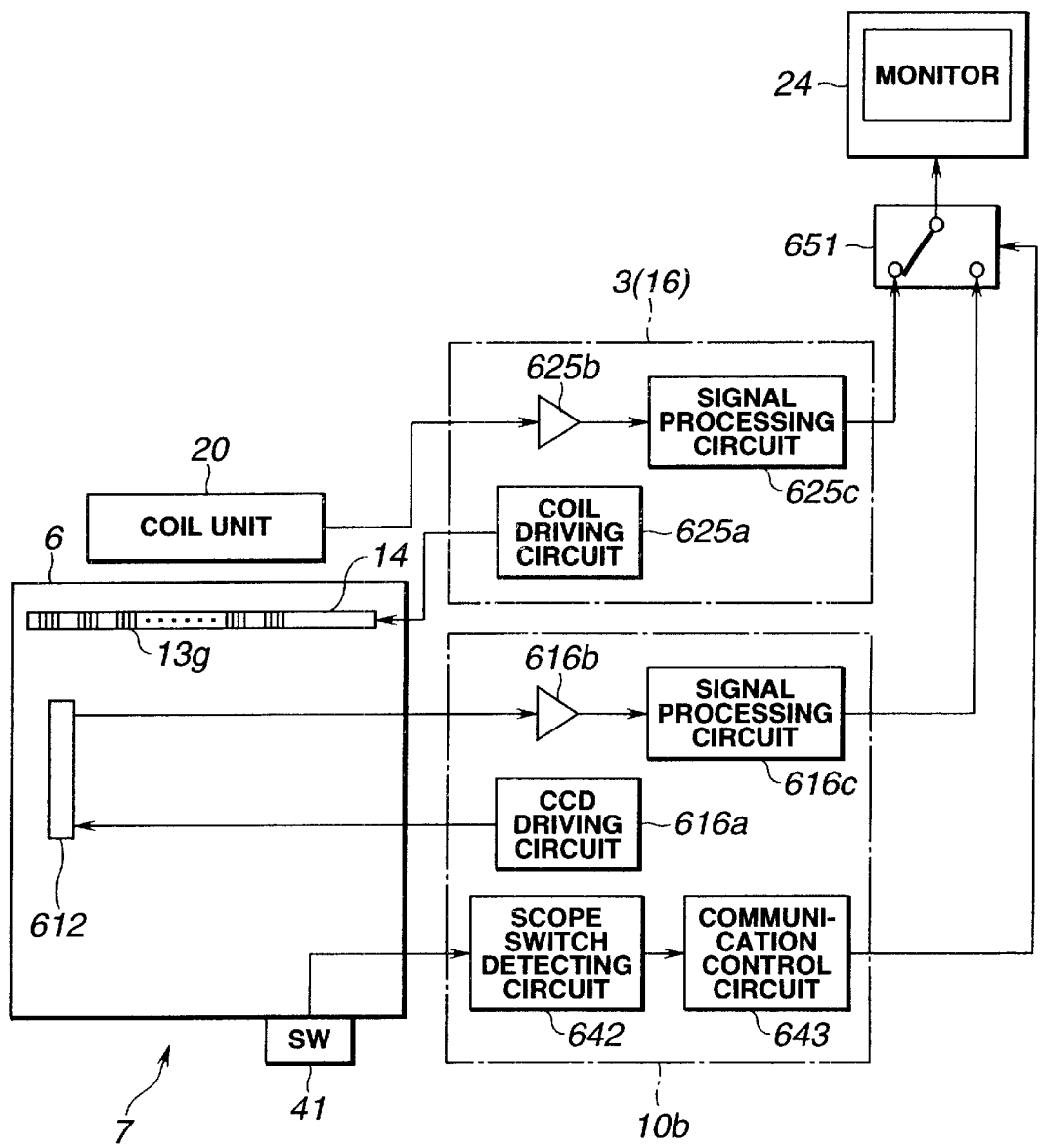

As shown in FIG. 81, instead of the image synthesizing device according to the twenty-second embodiment, a switching device 651 is provided, which switches between the endoscopic image from the video processor 10, and the endoscope shape image from the apparatus proper 16 of the endoscope shape detecting apparatus 3, according to switching signals from the communication control circuit 643 of the video processor 10. The switched image signals are output to the monitor 24.

Other configurations are the same as those in the twenty-third embodiment.

Figure 82:
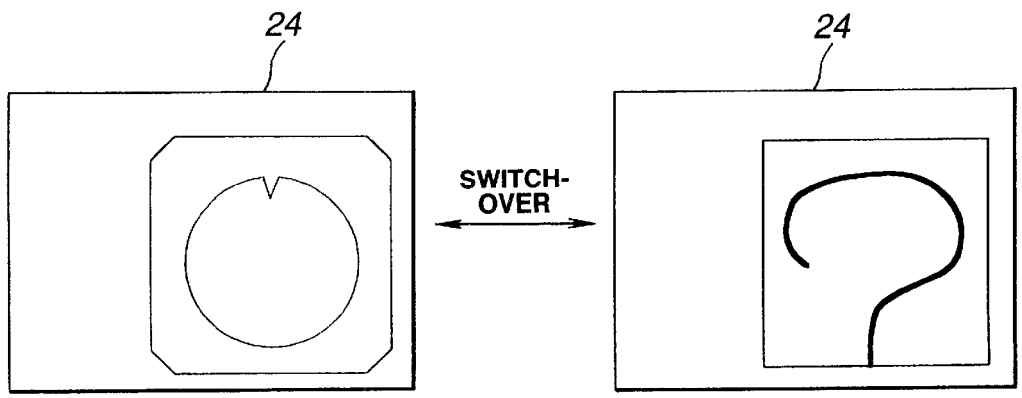

As shown in FIG. 82, with the present embodiment, if the switch 641 of the video endoscope 6 is in the first state, the switching device 651 selects the endoscopic image from the video processor 10 according to the switching signals from the communication control circuit 643 of the video processor 10. The endoscopic image is output to the monitor 24. If the switch 641 of the video endoscope 6 is in the second state, the switching device 651 selects the endoscope shape image from the apparatus proper 16 of the endoscope shape detecting apparatus 3 according to the switching signals from the communication control circuit 643 of the video processor 10. The endoscope shape image is output to the monitor 24. The endoscopic image and the endoscope shape image are sequentially switched according to the state of the switch 641 of the video endoscope 6.

According to the present embodiment, the endoscopic image or the endoscope shape image is output to the monitor 24 by the switching device 651. Thus, the device can be comprised in a less costly manner, yet provide the same advantages as those of the twenty-second embodiment.

Figure 83:
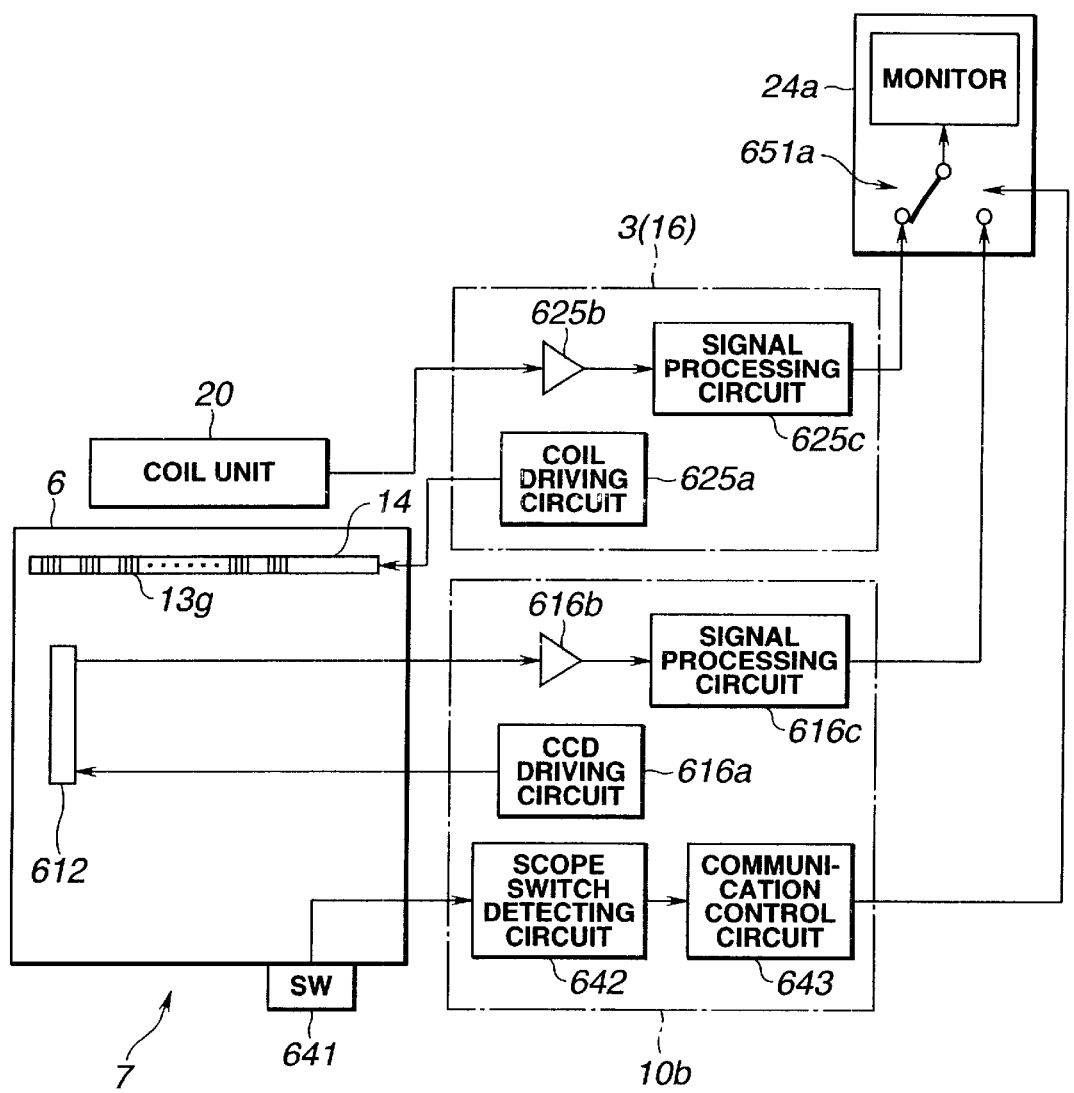

As shown in FIG. 83, if a monitor 24a with two switchable line inputs is used, the two lines may be arranged to receive input of the endoscopic image from the video processor 10 and the endoscope shape image from the apparatus proper 16 of the endoscopic shape detecting apparatus 3. Switching signals are output from the communication control circuit 643 of the video processor 10 to the switching unit 651a provided within the monitor 24a which performs switching of the two lines. This provides selective display of the endoscopic image from the video processor 10 and the endoscope shape image from the apparatus proper 16 of the endoscope shape detecting apparatus 3. This provides the same operations and advantages as the twenty-fourth embodiment.

The twenty-fifth embodiment is similar to the first embodiment. Only the differing points from the first embodiment will tee described. Similar configurations will be denoted with the same reference characters and the description thereof omitted.

Figure 84:
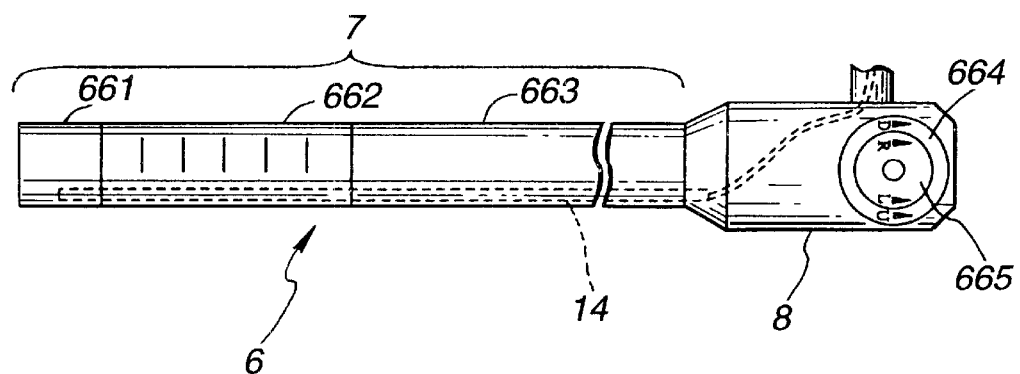

When positioning the probe 14 within the video endoscope 6, it is preferable that the probe 14 be embedded in the insertion portion 7, as shown in FIG. 84. No positional offsetting exists between the source coils 13g and the insertion portion 7.

Embedding the probe 14 in the insertion portion 7 in such a manner secures the absolute position of the source coils 13g to the insertion portion 7.

The insertion portion 7 of the video endoscope 6is comprised of a tip stiff portion 661, a curving portion 662, and a soft portion 663. A vertical curving operating knob 664 and a horizontal curving operating knob 665 are provided to the operating unit 8 connected to the base of the soft portion 663. A technician can operate the curving operating knobs 664 and 665 so as to curve the curving portion 662 in the desired direction while inserting the insertion portion 7 into the body cavity.

Figure 85:
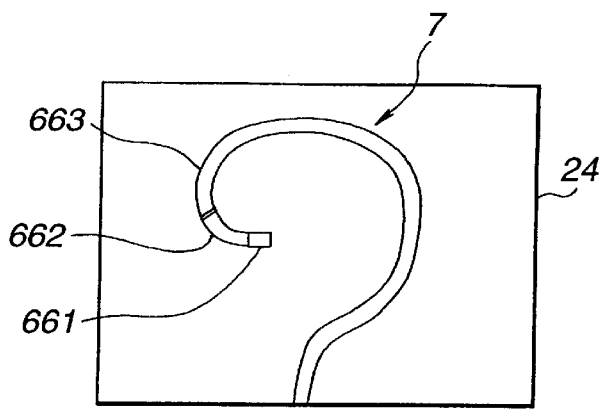
Figure 86:
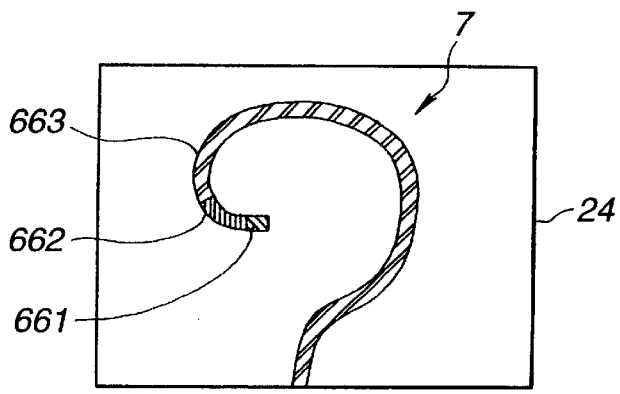

Embedding the probe 14 into the insertion portion 7, as described above, determines the absolute position of the source coils 13g as to the insertion portion 7. The endoscope shape detecting apparatus 3 can generate an endoscope shape image wherein the borders between the tip stiff portion 661, curving portion 662, and soft portion 663 are marked as border lines, as shown in FIG. 85. Accordingly, the curving portion 662 can be recognized on the endoscope shape image, thereby improving the operability of the insertion of the insertion portion 7 into the body cavity.

Figure 87:
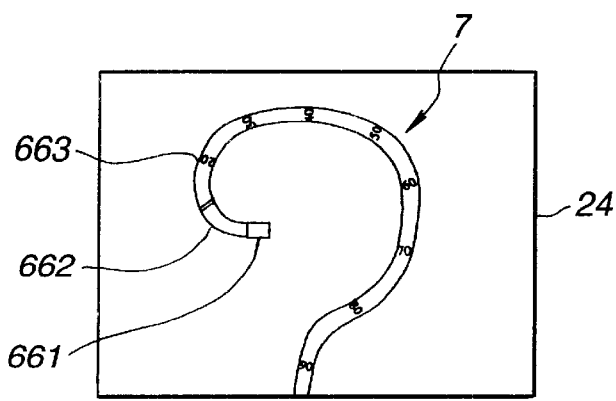
Figure 88:
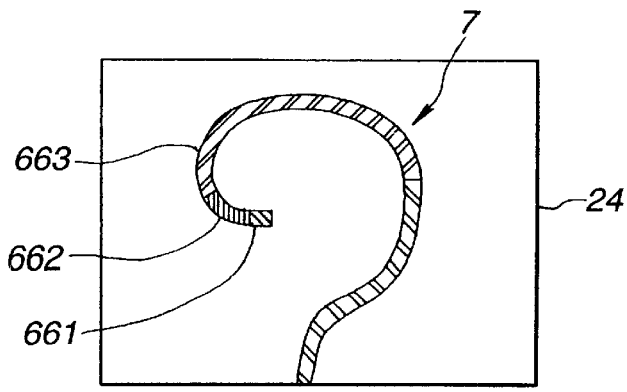

Instead of marking borderlines between the tip stiff portion 661, curving portion 662, and soft portion 663, the distance from the tip portion may be displayed in the endoscope shape image as shown in rig. 86. The tip stiff portion 661, curving portion 662, and soft portion 663 also may be color-coded, as shown in FIG. 87. Color-coding the tip side and operator side of the soft portion 663, as shown in FIG. 88 also may be done.

The twenty-sixth embodiment is similar to the first embodiment. Only the differing points from the first embodiment will be described. Similar configurations will be denoted with the same reference characters and the description thereof omitted.

In the above embodiments, the coil unit 20 has been described as being provided to a post 20a (see FIG. 1). However, forming the post 20a of metal may have adverse effects on the detection signals of the sensing coils 21j.

Figure 89:
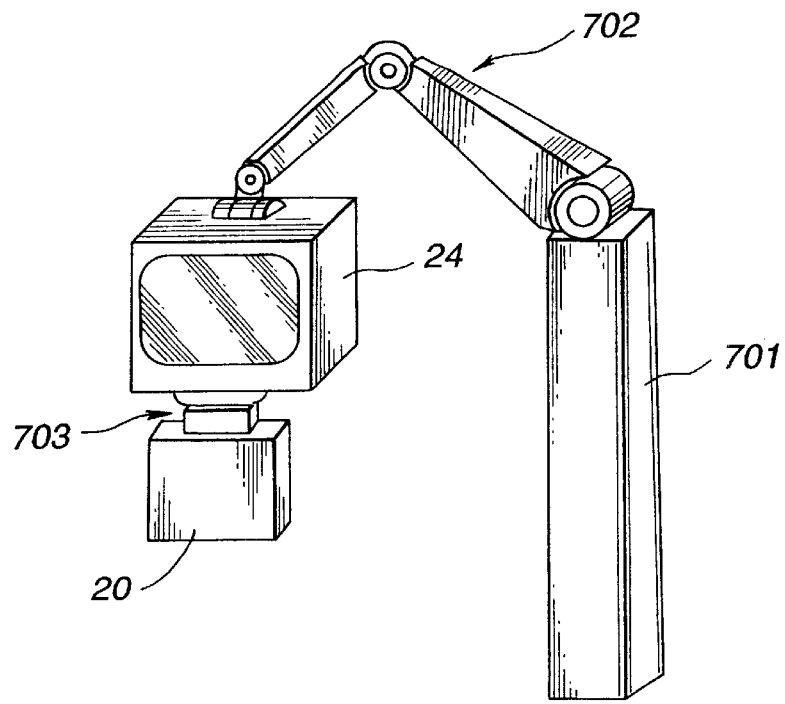

Accordingly, as shown in FIG. 89, amonitorarm 702 capable of moving the monitor 24 to a desired position is provided on the top of the post 701. The coil unit 20 is attached to the base of the monitor 24 attached to the monitor arm 702 via a sensing coil unit arm 703. The coil unit 20 is positioned at a position that is not affected by the noise from the monitor 24.

If the position of the monitor 26is raised by the monitor arm 702, the coil unit 20 follows and is distanced from the examining table 4. The sensor coil unit arm 703 is extended so as to position the sensor coil unit 28 beside the examining table 4.

If the coil unit 20 is not being used, the sensor coil unit arm 703 may be folded away or stored. In this case, the sensor coil unit arm 703 does not lock unless positioned where it should be during usage. Thus, a display to the effect that the sensor coil unit arm 703 is in an unlocked state may be made, or a display to the effect that there is the possibility that effects of metal may occur during the endoscope inspection may be displayed on the endoscope shape display and also the monitor 26. Alternatively, the endoscope shape display itself may be stopped.

The position of the coil unit 20 may be measured by detecting the angles between the joints of the monitor arm 702 and the state of the sensor coil unit arm 703. If the coil unit 20 nears the post 701, a display to the effect that there is the possibility that effects of metal may occur during the endoscopic examination may be displayed on the endoscope shape display on the monitor 24, or the endoscope shape display itself may be stopped.

Figure 90:
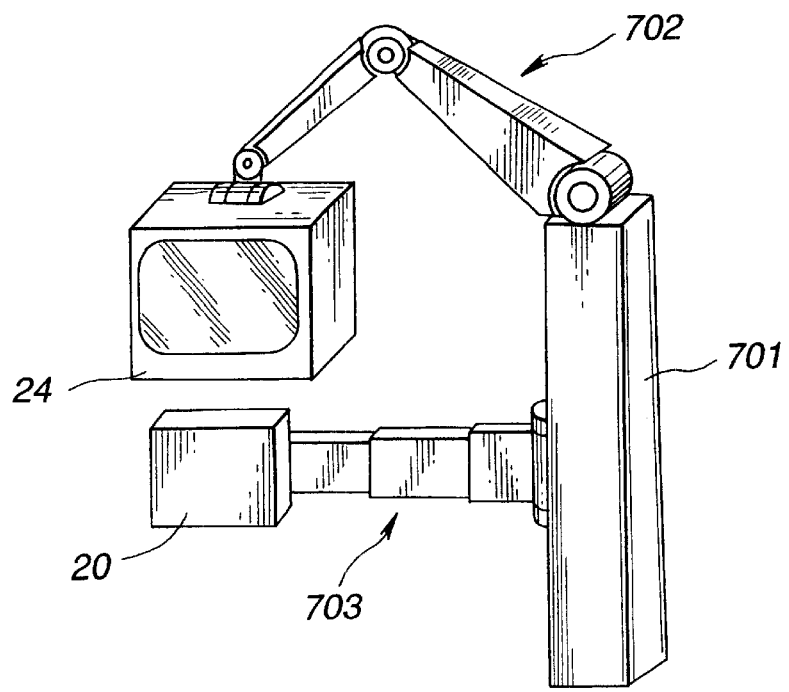

The sensor coil unit arm 703 also may not be provided on the base of the monitor 24, rather provided to the post 701 with the coil unit 20 positioned on the tip thereof, as shown in FIG. 90. In this case, the coil unit 20 is positioned at a place which is not affected by the metal of the post 701. The coil unit 20 is raised or lowered by the sensor coil unit arm 703 according to the height of the examining table 4.

By providing the coil unit 20 such as shown in FIGS. 89 and 90, the monitor 24 is positioned at a desired position, and the coil unit 20 is positioned where there are no effects of the monitor 24 and the metal of the post 701, promoting accurate endoscope shape displays on the monitor 24.

Figure 91:
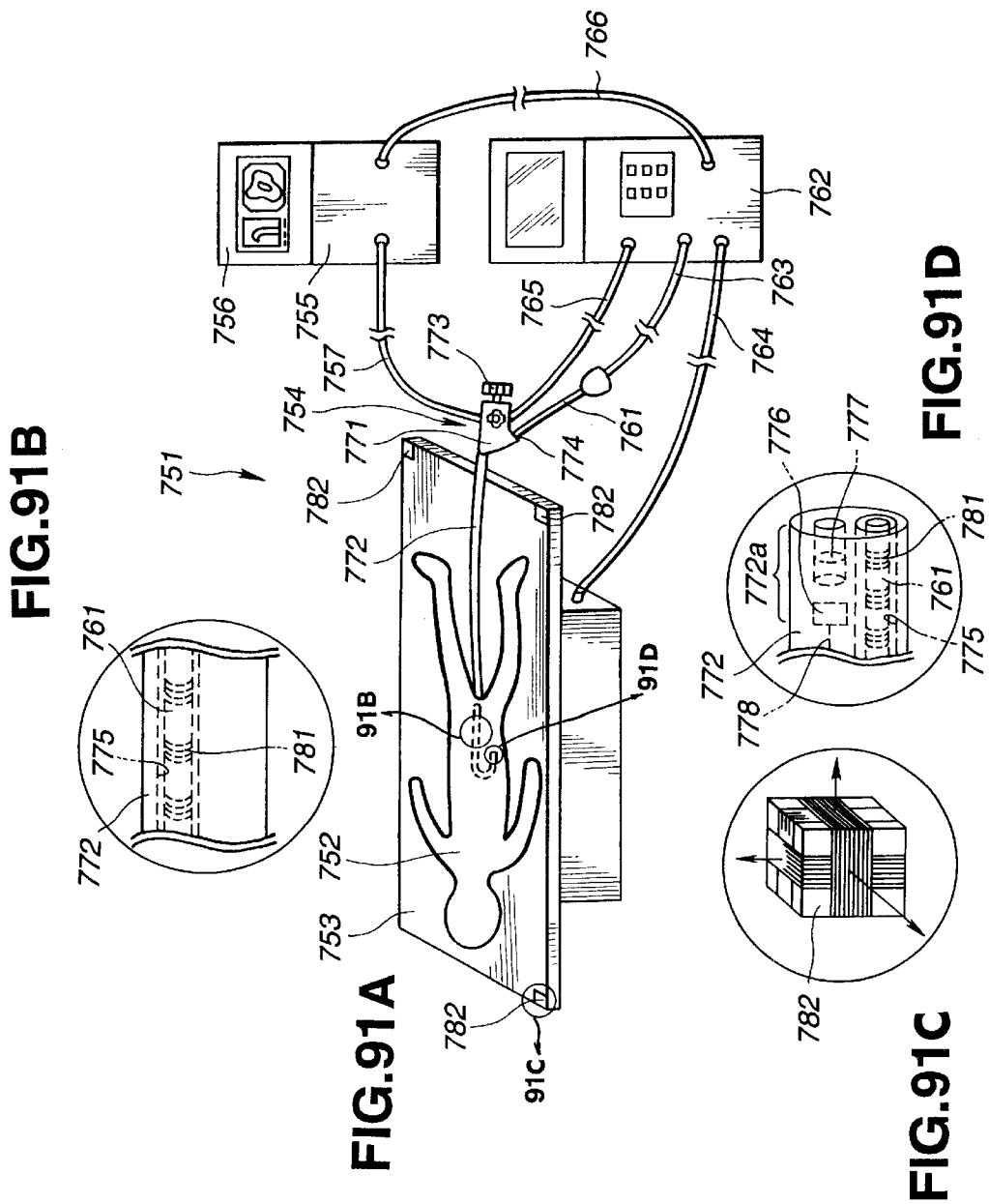

As shown in FIG. 91, the endoscope apparatus 751 according to the present embodiment is comprised of an examination table 753 for placing the patient 752 upon, an endoscope 754 for inserting into the body cavity of the patient 752 so as to obtain image-taking signals corresponding to the object such as the body cavity, a video processor 755 for obtaining picture signals from the image-taking signals obtained by the endoscope 754 which can be displayed on a monitor, a monitor for displaying picture signals obtained by the video processor 755, an image-faking signal cable 757 for transmitting the image-taking signals from at least the endoscope 754 to the video processor 755, an insertion shape detecting probe 761 for inserting into the endoscope 754 and generating a magnetic field used when obtaining the insertion form of the endoscope 754 into the body cavity, an insertion shape detecting device 762 for detecting the insertion shape of the endoscope 754, a cable 763 for electrically connecting this insertion shape detecting device 762 with the above insertion shape detecting probe 761, a cable 764 for electrically connecting the insertion shape detecting device 762 and the above examination table 753, a cable 765 for electrically connecting the insertion shape detecting device 762 and the above endoscope 754, and a cable 766 for electrically connecting the insertion detecting device 762 and the above video processor 755.

The endoscope 754 is formed of an operating unit 771 for grasping and operating the endoscope 754, and an insertion portion 772 extending from the tip side of the operating unit 771 for insertion into the body cavity. The operating unit 771 has a stiffness adjusting knob 773 serving as stiffness adjusting operating means for adjusting the stiffness of the insertion portion 772, and a probe insertion opening 774 into which the above insertion form detecting probe 761 can be inserted.

A probe channel 775, through which the insertion shape detecting probe 761 inserted from the probe inserting opening 774 can be guided, is provided within the operation unit 771 and the insertion portion 772.

Provided to the tip portion 772a and positioned at the tip of the insertion portion 772 are an object optical system 777 for imaging object images, and a CCD 776 serving as an image-taking means for taking images of the object image imaged by the object optical system 777. A signal line 778 for transmitting image-taking signals obtained by the CCD 776 extends from the CCD 776. The signal line 778 is electrically connected to the video processor 755 via the insertion portion 772, operating unit 771, and the image-taking signal cable 757.

A plurality of source coils 781 for generating magnetic fields is provided to the insertion shape detecting probe 761, spaced at certain intervals. The source coils 781 are arranged to be driven by driving signals provided from the insertion shape detecting device 762 via the cable 763.

A plurality of sensing coils 782 is positioned on the examining table 753, for three-dimensional detection of the direction of the magnetic fields generated from the source coils 781. The signals from the sensing coils 782 are provided to the insertion shape detecting device 762 via the cable 764.

Figure 92:
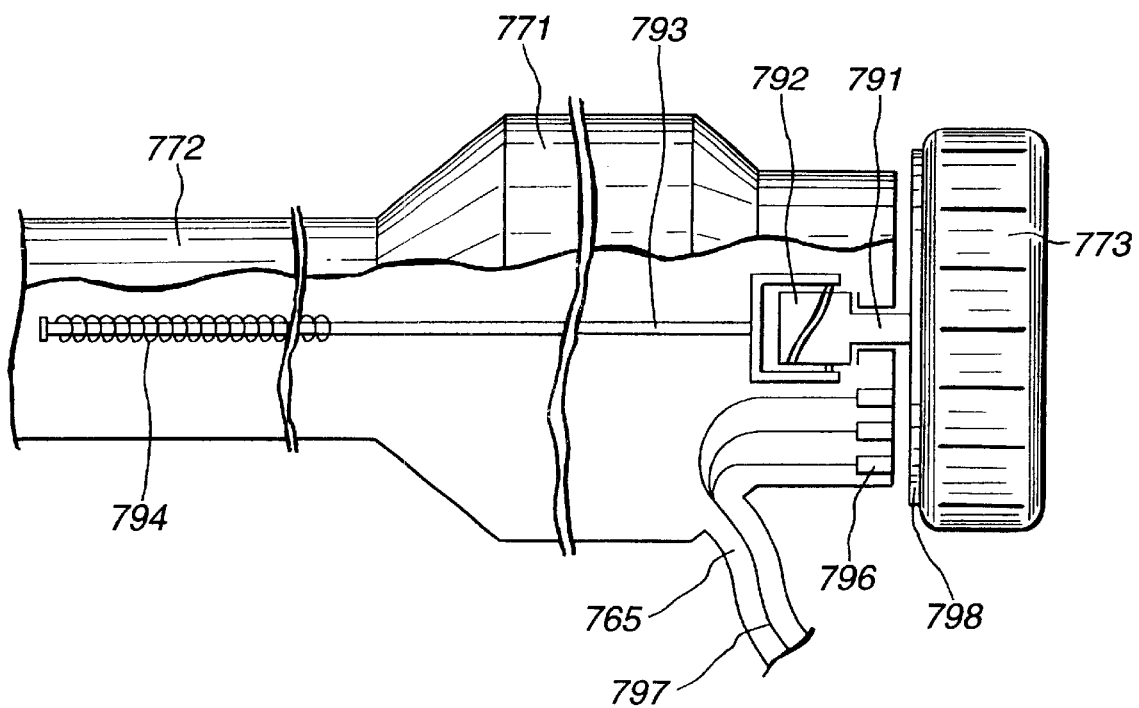

As shown in FIG. 92, the operating unit 771 has a turning axis 791 of the stiffness adjusting knob 773, a cam mechanism 792 for converting the turning motion of the turning shaft 791 into linear motion in the longitudinal direction of the insertion portion 772, and a stiffness adjusting wire 793 pulled in the longitudinal direction of the insertion portion 772 by this cam mechanism 792. This stiffness adjusting wire 793 extends to a certain position near the tip of the insertion portion 772. The stiffness adjusting wire 793 passes through a stiffness adjusting coil spring 794 provided within the insertion portion 772. If the stiffness adjusting wire 793 is pulled toward the operator in the longitudinal direction, the stiffness adjusting coil spring 794, which has the tip thereof fixed to the tip of the stiffness adjusting wire 793, is compressed, and consequently the stiffness of the insertion portion 772 increases.

Accordingly, turning the stiffness adjusting knob 773 adjusts the stiffness of the insertion portion 772. That is, the stiffness adjusting wire 793, stiffless adjusting coil spring 794, stiffness adjusting knob 773, turning shaft 791, and cam mechanism 792 comprise a stiffness adjusting means for adjusting the stiffness of the insertion portion 772.

Figure 93:
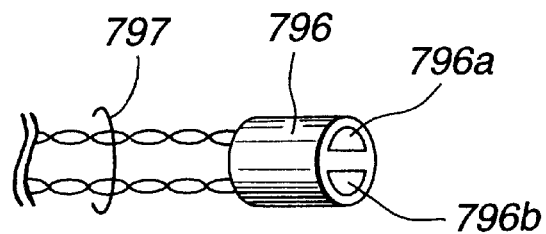

Also, at the position of the operating unit 771 facing the rear side of the stiffness adjusting knob 773 is a plurality of photo-reflectors 796. Three photo-reflectors 796 are arrayed radially, with each being arrayed toward the rear side of the stiffness adjusting knob 773. The photo-reflectors 796 have light-emitting elements 796a and photo-receptors 796b, as shown in FIG. 93. Light from the light-emitting element 796a reflected and cast into the photo-receptor 796b is detected. The photo-receptor 796b transmits a detection signal by the signal line 797. A disk 798 for reflecting the light from the photo-reflectors 796 according to the position of the stiffness adjusting knob 773, is attached to the rear of the stiffness adjusting knob 773.

Figure 94:
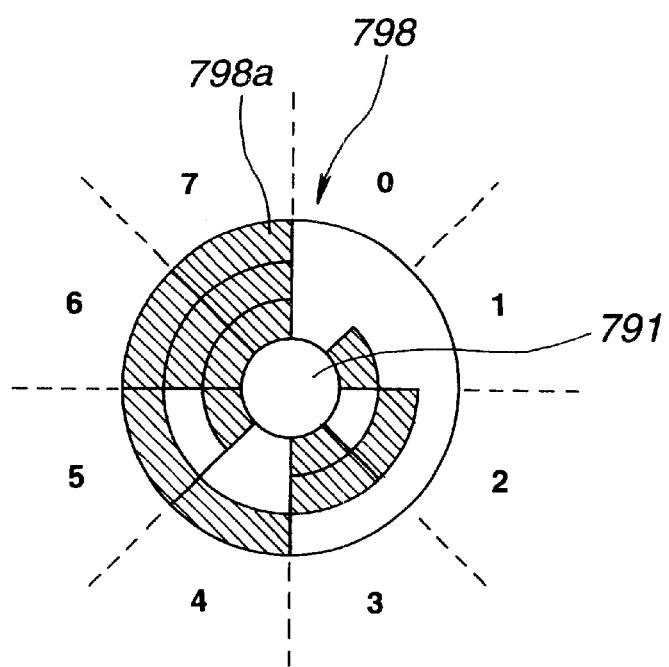

A light-reflecting plate 798a, shown in FIG. 94, is attached to the disk 798. The light-reflecting plate 798a is arranged such that there are eight combinations of light received or not received from the three photo-reflectors 796, according to the rotational positions of the stiffness adjusting knob 773.

That is, the photo-reflectors 796 and disc 798 define a rotary encoder serving as a position detecting means which detects the position of the stiffness adjusting knob 773 in eight increments.

The position of the stiffness adjusting knob 773 corresponds with the stiffness level of the insertion portion 772 owing to the stiffness adjusting means. The signals output from the rotary encoder via the signal line 797 correspond with the stiffness of the insertion portion 772.

Figure 95:
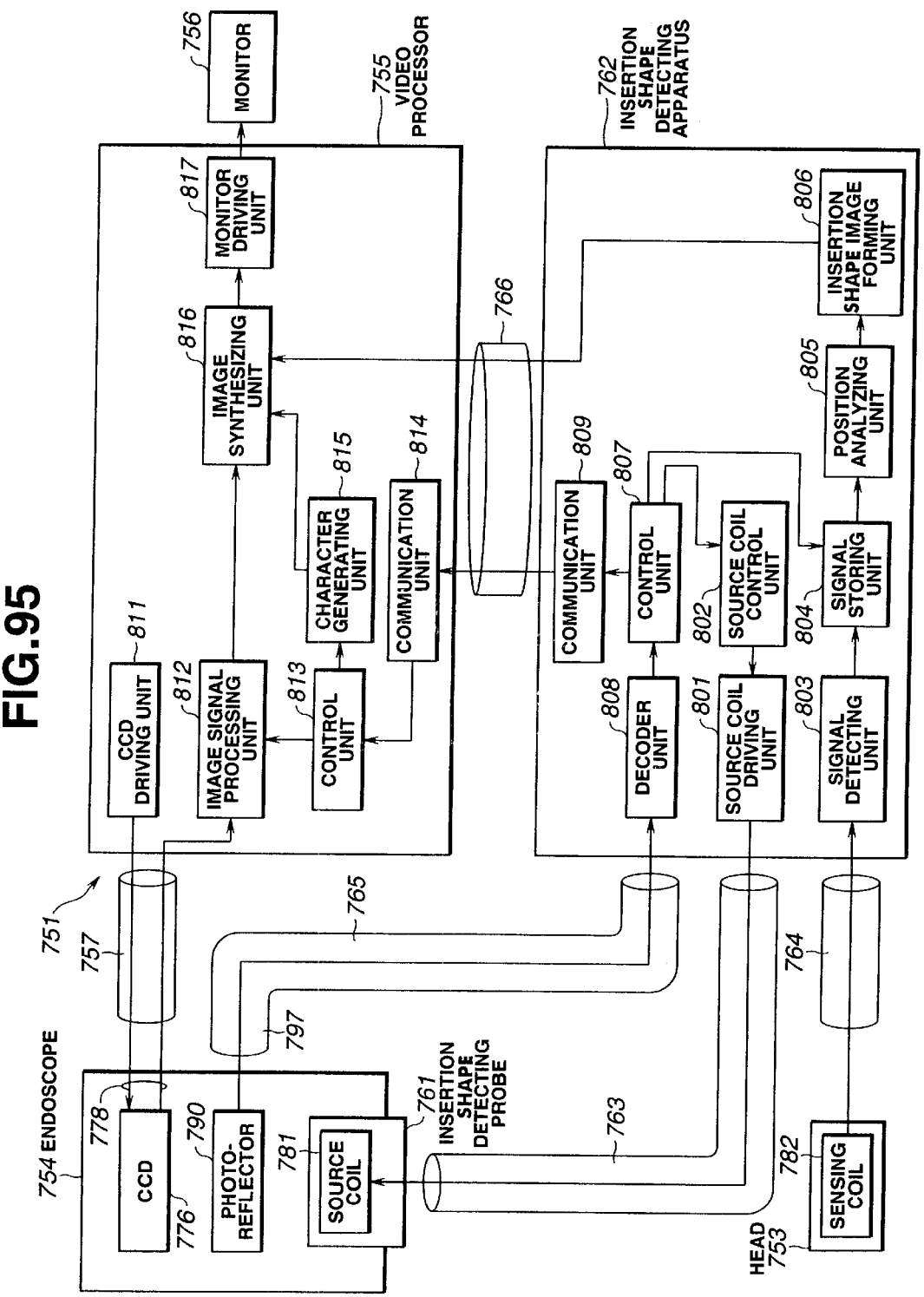

As shown in FIG. 95, the insertion shape detecting device 762 is comprised of a source coil driving unit 801 for driving the source coils 781, a source coil controlling unit 802 for controlling the magnetic field generated by the source coils 781, a signal detecting unit 803 for detecting signals from the sensing coils 782 for detecting magnetic fields generated by the source coils 781, a signal storing unit 804 for temporarily storing output signals from the signal detecting unit 803, a position analyzing unit 805 for analyzing the coordinates position of the source coils 781 by reading the signal information stored in the signal storing unit 804, an insertion shape image generating unit 806 for outputting an insertion shape image which is the insertion shape of the insertion portion 772 formed into an image based on coordinate position information of the source coils 781 obtained at the position analyzing unit 805, in the form of picture signals, a control unit 807 for controlling the various portions of the insertion shape detecting device 762 such as the source coil controlling unit 802 and the signal storing unit 804, a decoding unit 808 for receiving input of the signals from the photo-reflectors 796 and obtaining a stiffness level for the insertion portion 772 represented in increments from level 0 to level 7, and a communication unit 809 which is controlled by the control unit 807 and transfers the stiffness level information obtained at the decoding unit 808 to the video processor.

The picture signals obtained from the insertion shape image generating unit 806 and the stiffness level information output from the communication unit 809 are provided to the video processor 755 via the cable 766.

The video processor 755 is comprised of a CCD driving unit 811 for generating driving signals for driving the CCD 776, a picture signal processing unit 812 which obtains picture signals including endoscope images from the image-taking signals obtained from the CCD 776, a control unit 813 for controlling the various parts of the picture signal processing unit 812 and the video processor 755, a communication unit 814 for communicating with the communication unit 809 of the insertion shape detecting device 762 and receiving stiffness level information, a character generating unit 815 which is controlled by the control unit 813 so as to obtained picture signals including character information representing the stiffness level, an image synthesizing unit 816 for performing image synthesizing of first picture signals from the picture signal processing unit 812, second picture signals from the insertion shape image generating unit 806, and third picture signals from the character generating unit 815, and a monitor driving unit 817 capable of converting picture signals from the image synthesizing unit 816 into picture signals which can be output to a monitor 756.

The operation of the present embodiment will be described.

The insertion shape detecting probe 761 is inserted into the probe channel 775 of the endoscope 754 from the insertion opening 774. Then, the tip position of the insertion shape detecting probe 761 is set to match the tip position of the insertion portion 772. Matching the tip positions means that the insertion shape of the insertion shape detecting probe 761 and the insertion shape of the insertion portion 772 correspond.

Next, the insertion portion 772 of the endoscope 754 is inserted into the body cavity of the patient 752 on the examination table 753.

An object image is imaged on the photo-reception surface of the CCD 776, owing to the object optical system 777 at the tip portion 772a of the insertion portion 772. The CCD 776 is driven by driving signals from the CCD driving unit 811 of the video processor 755. Image-taking signals corresponding to the object image are output to the signal line 778. The image-taking signals output to the signal line 778 are provided to the picture signal processing unit 812 of the video processor 755, haying passed through the insertion portion 772, operating unit 771, and image-taking signal cable 757, in that order.

The picture signal processing unit 812 extracts picture signal components of the image-faking signals, subjects the picture signals to picture signal processing, such as adjusting color and balance and the like, and outputting to the image synthesizing unit 816. If the picture signals from the character generating unit 815 or insertion shape image generating unit 806 are not to be synthesized, the image synthesizing unit 816 provides only the picture signals from the picture signal processing unit 812 to the monitor driving unit 817. This monitor driving unit 817 drives the monitor 756, and an endoscopic image 821, such as that shown in FIG. 96 taken by the COD 776, is displayed on the screen of the monitor 756.

The source coils 781 provided at certain intervals in the insertion shape detecting probe 761 inserted through the insertion portion 772 are supplied with an AC driving current from the source coil driving unit 801 of the insertion shape detecting device 762. The source coils 781 generate magnetic fields. The source coils 781 are each controlled to generate magnetic fields at different timings or with different frequencies, by the source coil controlling unit 801. The source coil controlling unit 801 provides driving current to the source coils 781 with differing timings via the source coil driving unit 801. The unit 801 also may provide driving current to each of the source coils 781 with differing frequencies.

The magnetic fields generated from the source coils 781 are transmitted through the insertion portion 772 and the patient 752. The magnetic fields are detected by the plurality of sensing coils 782 placed on the examination table 753. The sensing coils output signals for detecting the source of the magnetic field, i.e., the source coils 781, in a three-dimensional manner. The plurality of arrayed sensing coils 782 means that signals for detecting the source coils 781 in a three-dimensional manner are output via the cable 764. The plurality of source coils 781 emit magnetic fields with differing timings of frequencies. Thus, signals obtained with the sensing coils 782 allows the position of each of the source coils 781 to be detected.

The signals transmitted from the sensing coils 782 via the cable 764 are provided to the signal detecting unit 53 of the insertion shape detecting device 762. The signal detecting unit 803 increases the signal level of the signals from the sensing coils 782, or performs conversion into digital signals, if necessary. The output signals from the signal detecting unit 53 temporarily are stored in the signal storing unit 804. The signals stored in the signal storing unit 804 are read out by the position analyzing unit 805. The position analyzing unit 805 analyzes the three-dimensional position coordinates of each of the source coils 781. The three-dimensional position coordinates are provided to the insertion shape image generating unit 806. The insertion shape image generating unit 806 analyzes the insertion state of the insertion shape detecting probe 761, i.e., the insertion shape of the insertion portion 772, and creates an image thereof, based on the three-dimensional information from the source coils 781. The unit 806 also provides the insertion shape image as picture signals to the image synthesizing unit 816 of the video processor 755. signals from the photo-reflectors 796 of the rotary encoder provided near the stiffness adjusting knob 773 are provided to the decoding unit 808 of the insertion shape detecting device 762, via the signal line 797. This decoding unit 808 obtains numerical information regarding the range corresponding to the rotational position of the stiffness adjusting knob 773, e.g., from 0 to 7. The stiffness adjusting knob 773 corresponds with the stiffness level of the insertion portion 772. Thus, the numerical information regarding the range, e.g., from 0 to 7, obtained by the decoding unit 808, is stiffness information representing the stiffness level. This stiffness level information is transmitted from the communication unit 809 controlled by the controlling unit 807 to the communication unit 813 of the video processor 755, and provided to the character generating unit 815 via the communication unit 813 of the video processor 755. This character generating unit 815 forms picture signals of character information including the stiffness level information, and provides this to the image synthesizing unit 816.

To adjust the stiffness of the insertion portion 772, the stiffness adjusting knob 773 is turned.

Figure 97:
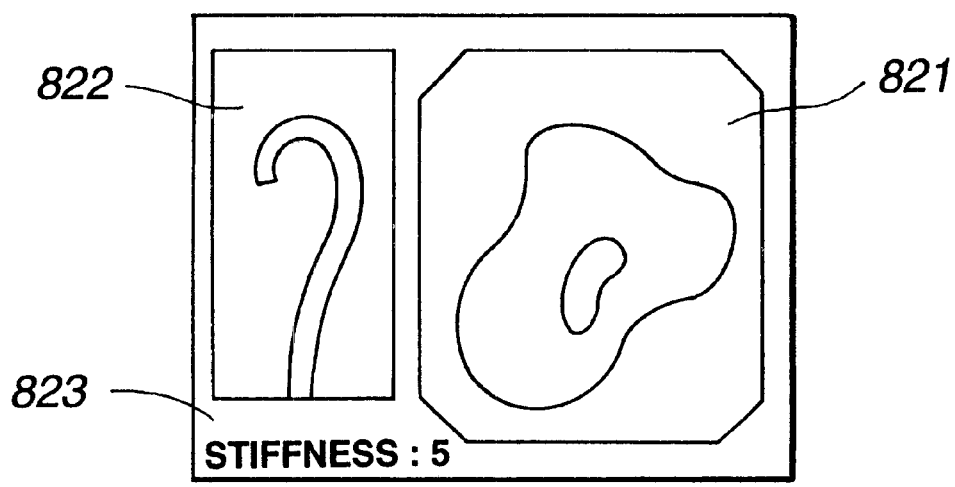

Accordingly, the image synthesizing unit 816 synthesizes the first picture signals from the picture signal processing unit 812, the second picture signals from the insertion shape image generating unit 806, and the third picture signals from the character generating unit 815. As shown in FIG. 97, an image according to the first picture signals, i.e., an endoscopic image 821, an image according to the second picture signals, i.e., an insertion shape image 822, and a display according to the third picture signals, i.e., the stiffness level information display 823, are synthesized on the monitor 756.

The endoscopic image 821, insertion shape image 822, and stiffness level information display 823 are all displayed on a single monitor 756. Thus, a technician needs little eye movement, resulting in good operability, and allowing the insertion shape and stiffness level to be confirmed along with the endoscopic image.

Figure 96:
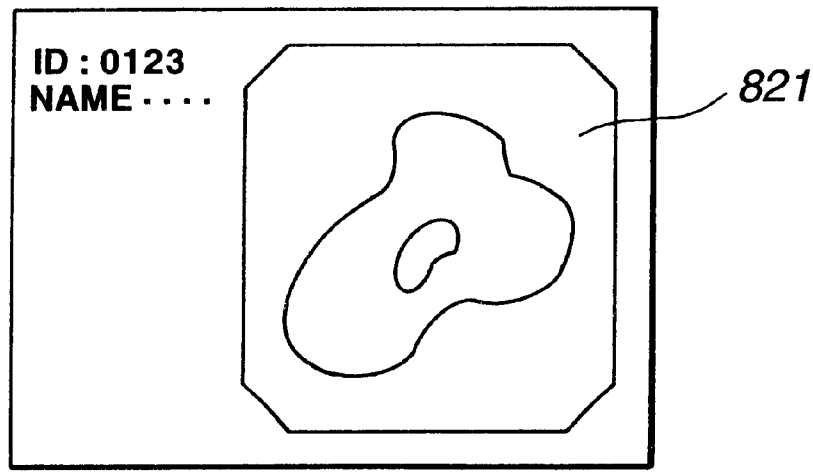

Once the certain time period for the display of the synthesized image shown in FIG. 97 on the monitor 756 elapses, the image displayed on the monitor 756 reverts to the image shown in FIG. 96.

According to the present embodiment as described above, the endoscopic image, insertion shape image, and stiffness level information are all displayed on a single monitor 756. Thus a technician needs little eye movement, thereby reducing the eye movement of the technician using an endoscope device 751 having stiffness adjusting means and insertion shape detecting means, thereby improving operability.

Synthesizing image signals by the image synthesizing unit 816 is not restricted to cases wherein the stiffness adjusting knob 773 is turned. Synthesizing image signals by the image synthesizing unit 816 may be performed at all times. A technician may selectively switch between the endoscopic image alone and the synthesized image.

The probe channel 775 is not restricted to being dedicated for passage of the insertion shape detecting probe 761. The channel may be used for other purposes as well, such as inserting treatment equipment, such as forceps or the like.

Source coils 781 may be provided in the insertion portion of the endoscope 754 itself, instead of providing an insertion shape detecting probe 761.

A probe having stiffness adjusting means may be provided instead of integrally providing stiffness adjusting means, so that this stiffness adjusting probe is inserted into the probe channel in the endoscope 754.

The synthesized image displayed on the monitor 756 is not restricted to an image synthesized of three picture signals, i.e., a first picture signal, second picture signal, and third picture signal. Only two of these picture signals may be synthesized. Such configuration reduces the amount of eye movement of the technician in comparison with conventional arrangements, thereby improving operability.

As shown in FIG. 96, the endoscopic image is not restricted to object images taken with the image-taking means. Rather images with character information representing patient information, for example, may be synthesized therewith.

The endoscope 754 is not restricted to a video endoscope with image-taking means at the tip of the insertion portion 772. The invention may be applied to an optical endoscope wherein the object image obtained at the tip of the insertion portion is optically transmitted to the eyepiece of the operating unit. In this case, image-taking means are attached to the eyepiece, so that image-taking signals from the image-taking means are provided to the video processor 755.

With the present embodiment, the configuration of an endoscope wherein source coils are provided in the insertion portion while preventing increase in the diameter of the insertion portion will be described with reference to FIGS. 98 and 99.

Figure 98:
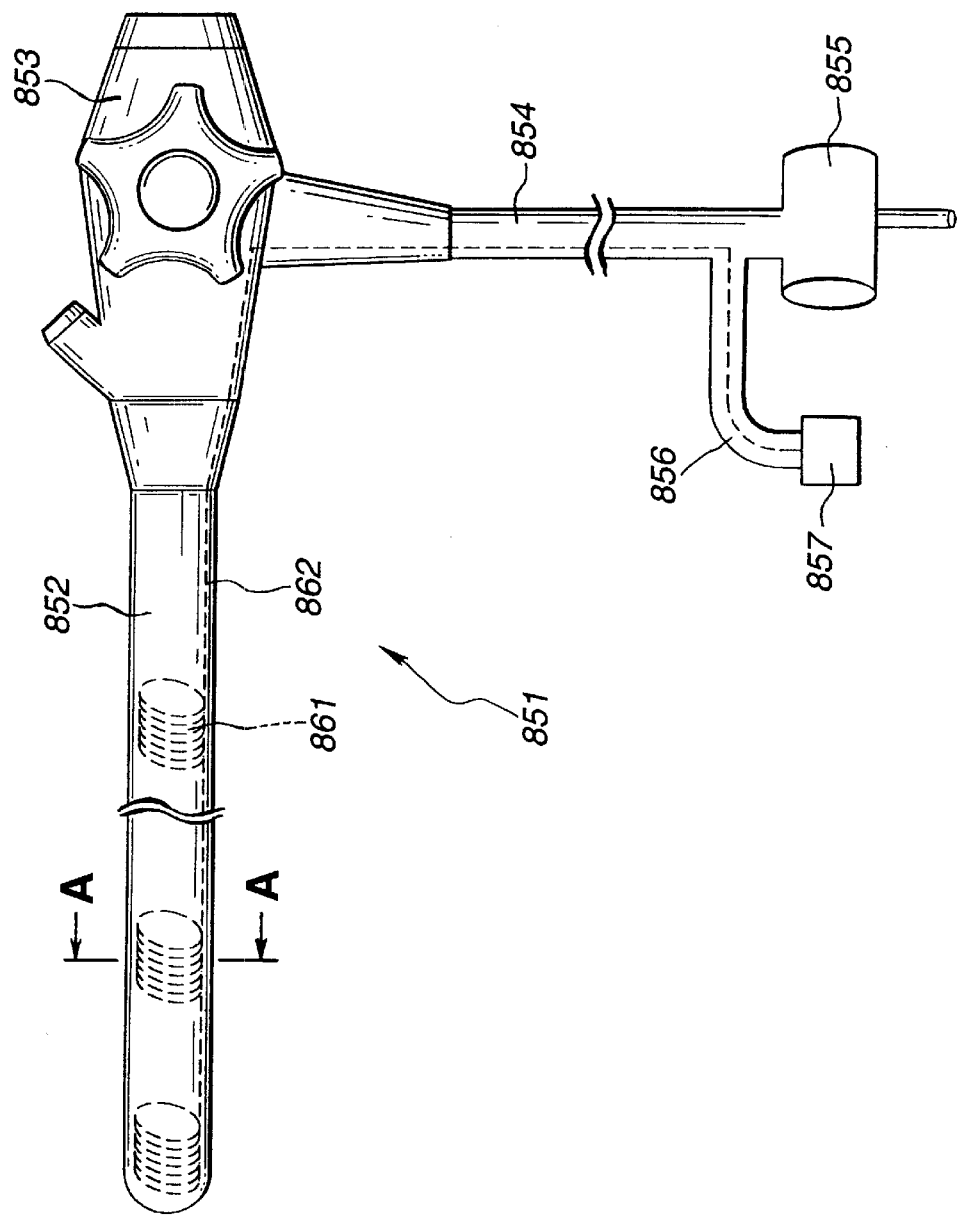

As shown in FIG. 98, the endoscope 851 is comprised of an insertion portion 852 for inserting into a body cavity, an operating unit 853 formed from the base end of the insertion portion 852 for holding and operating the endoscope 851, a universal cord 854 extending from the side of this operating unit 853, a light guide connector 855 provided to the end of the universal cord 854 for connecting to the light source device (not shown) which is an external device, and a cable 856 which splits from the universal cord 854 and has a connector 857 at the end thereof for connecting to the insertion detecting device (not shown) which is an external device.

A plurality of source coils 861 is formed at the outer covering of the insertion portion 852 as described below, at certain intervals. These source coils 861 are provided with driving current from the insertion shape detecting device, via a signal line 862 passing through the connector 857, cable 856, universal cord 854, operating unit. 853, and insertion portion 852. Each of the source coils 861 generates a magnetic field.

Figure 99:
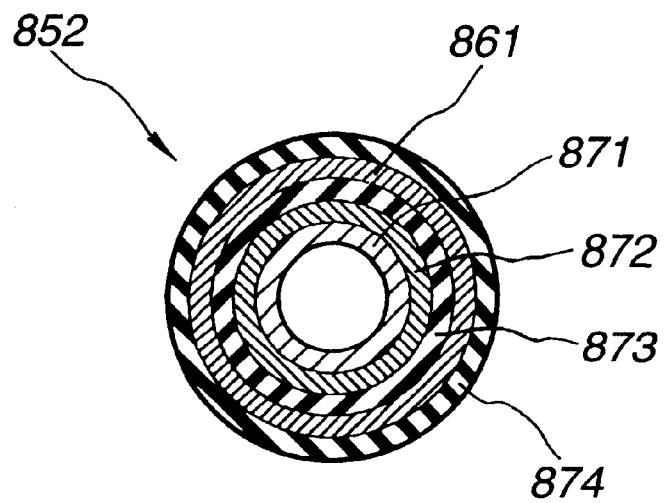

As shown in FIG. 99, the outer covering of the insertion portion 852 is a layered structure of a spiral tube 871, a metal net-like tube 872, insulating tape 873, source coils 861, and resin 874, in that order from the inner layer outwards. That is, the endoscope 851 is formed so that no space is wasted in the inner diameter of the source coil 861.

According to the endoscope 851 described above, there is no wasted space in the inner diameter of the source coil 861. so increase in diameter of the insertion portion 852 can be prevented. Source coils 861 can be provided on the insertion portion 852. This means that space for the built-in members of the insertion portion 852 can be secured. Thus, durability of the built-in members such as the light guide or the like can be improved.

Figure 100:
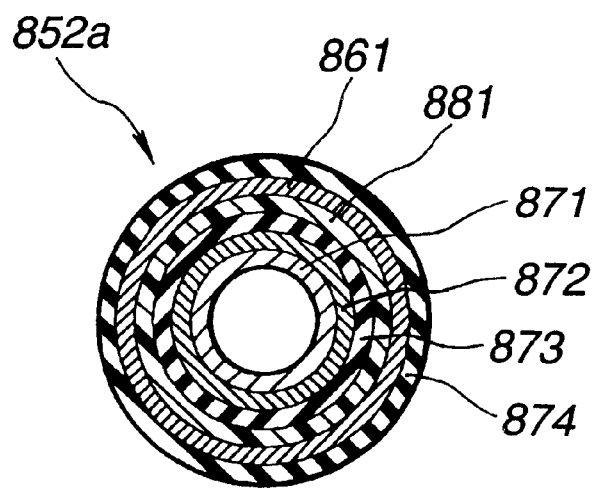

The endoscope 851 may be configured with an insertion portion 852a such as shown in FIG. 100, instead of the insertion portion 852 of the configuration shown in FIG. 99.

As shown in FIG. 100, the outer covering of the insertion portion 852a is a layered structure of a spiral tube 871, a metal net-like tube 872, insulating tape 873, amorphous tape 881, source coils 861, and resin 874, in that order from the inner layer outwards. The insertion portion 852a shown in FIG. 100 differs from the arrangement of the insertion portion 852 shown in FIG. 99, in that it has source coils 861 wrapped around the outer perimeter of amorphous tape 881.

While the insertion portion 852 shown in FIG. 99 has a hollow core for the source coils 861, the insertion portion 852a shown in FIG. 100 has a core formed of amorphous tape 881 for the source coils 861. The magnetic output of the source coils 861 increases due to this amorphous tape 881. Accordingly, the source coils 861 are not wrapped as much as compared with the configuration of the insertion portion 852 shown in FIG. 99. A permalloy may be used instead of the amorphous tape 881.

According to the endoscope 851 having the insertion portion 852a shown in FIG. 100, the number of winds of the source coils 861 can be reduced as compared with the endoscope 851 having the insertion portion 852 shown in FIG. 99, thus the diameter of the insertion portion can be reduced.

The twenty-ninth embodiment is similar to the first embodiment. Only the differing points from the first embodiment will be described similar configurations will be denoted with the same reference characters and the description thereof omitted.

Figure 101:
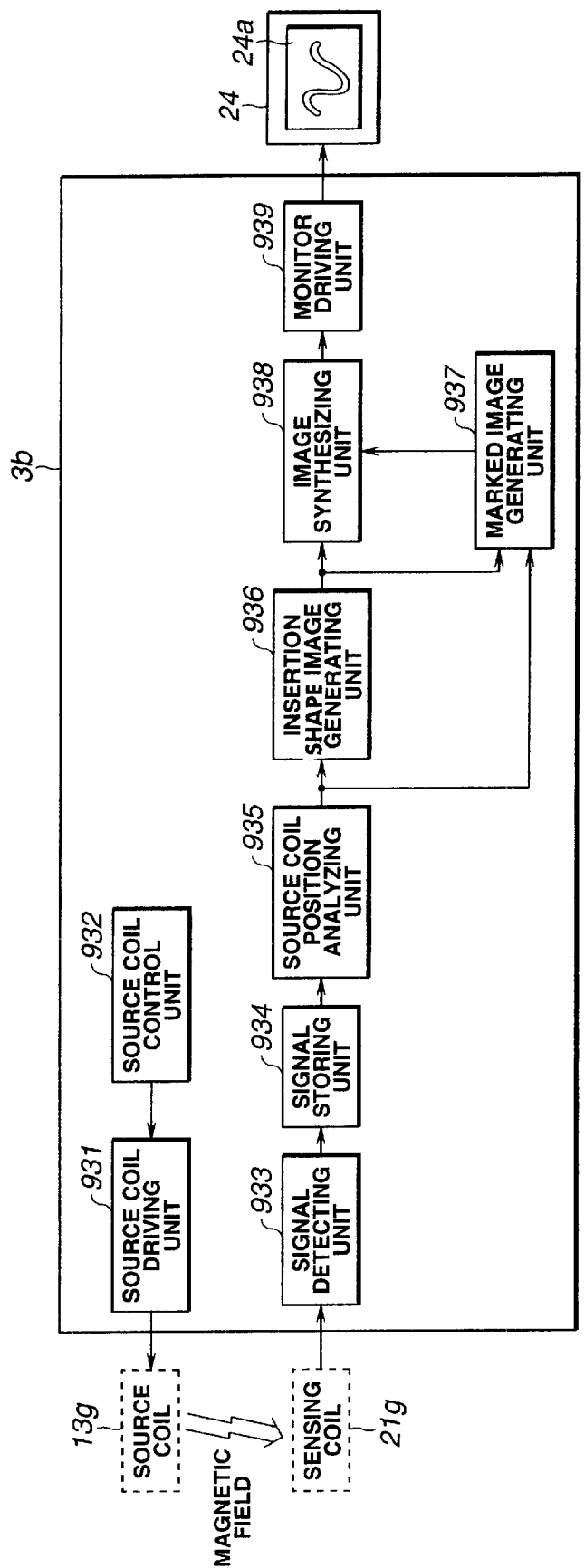

As shown in FIG. 101, the endoscope shape detecting apparatus 3b according to the present embodiment is configured of: a source coil driving unit 931 for driving source coils lag; a source coil control unit 932 for controlling the magnetic field generating timing, frequencies, etc., of the source coils lag, via the source coil driving unit 931; a signal detecting unit 933 for detecting signals obtained with the sensing coils 21j and changing these to a level which can be subjected to signal processing; a signal storing unit 934 for sequentially temporarily storing signals obtained by the signal detecting unit 933, a source coil position analyzing unit 935 for reading the signal data from the signal storing unit 934 and analyzing the three-dimensional position coordinates of the source coils 13g; an insertion shape image generating unit 936 which calculates the three-dimensional shape of the insertion portion 7 from the three-dimensional position coordinates of the source coils 13g obtained from the source coil position analyzing unit 935, andconverting into two-dimensional coordinates for monitor display, forming an image; a marking image generating unit 937 for calculating the three-dimensional position of markings to be superimposed on the insertion shape image, from the insertion shape information obtained from the insertion shape image generating unit 936, and converting into two-dimensional coordinates for monitor display, forming an image; an image synthesizing unit 938 for synthesizing the insertion shape images output from the insertion shape image generating unit 936 and the marking image picture signals output from the marking image generating unit 937; and a monitor driving unit 939 for receiving the picture signals synthesized at the image synthesizing unit 938 and driving the motor 24.

The insertion shape image representing the shape of the insertion portion 7 is displayed upon the monitor screen 24a of the monitor 24 driven with the endoscope shape detecting apparatus 3b.

Figure 102:
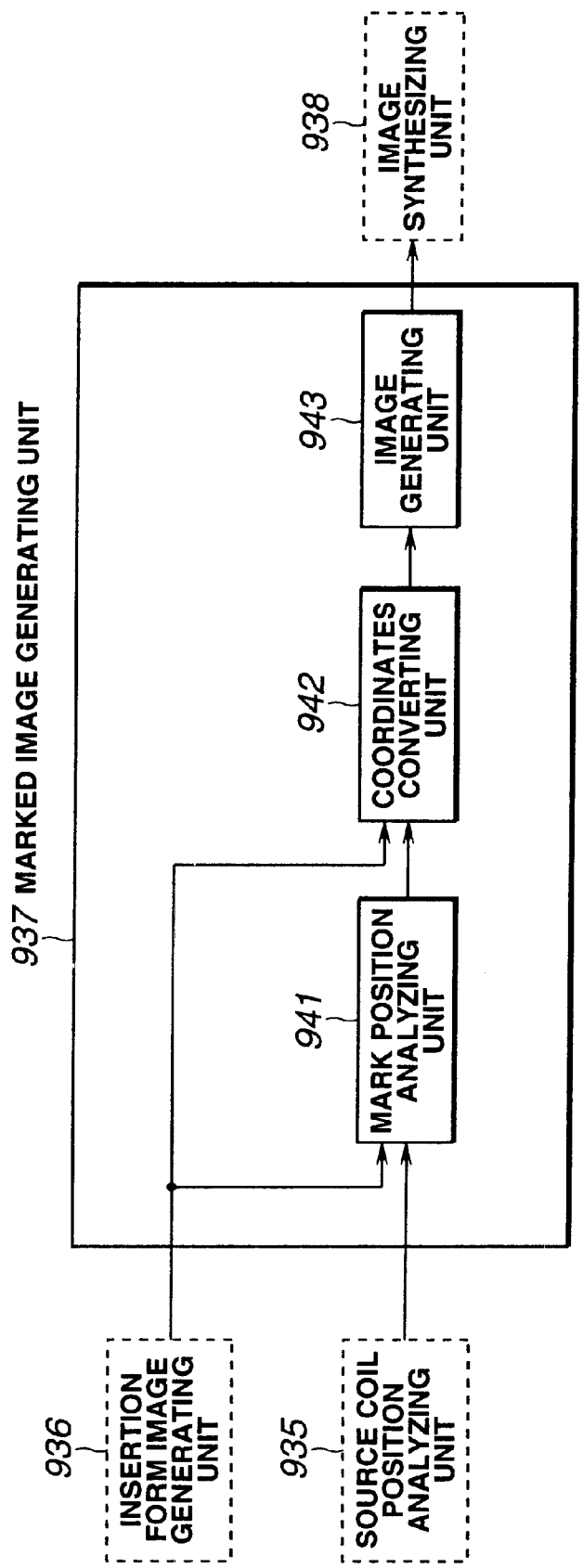

As shown in FIG. 102, the marking image generating unit 937 is comprised of a marking position analyzing unit 941 for calculating the three-dimensional position of markings to be superimposed on the insertion shape image, from the insertion shape information obtained from the insertion shape image generating unit 936; a coordinates converting unit 942 for converting the three-dimensional coordinates obtained by the marking position analyzing unit 941 into two dimensional coordinates for monitor display, in the same manner as that performed with the insertion shape image generating unit 936; and an image generating unit 943 for generating a marking image on the two dimensional coordinates position obtained by the coordinates converting unit 942.

The operation of the present embodiment will be described.

First, the insertion shape detecting probe 14 is inserted into the video endoscope 6 from the insertion opening 12a. The universal cord 9 of the video endoscope 6is connected to the video processor 10. The source cable 15 and sensing cable 22 of the probe 14 are connected to the endoscope shape detecting apparatus 3b. The insertion portion 7 of the video endoscope 6 is inserted into the body cavity or the like of the patient 5.

The object image of the body cavity or the like is imaged by the CCD at the tip of the insertion portion 7. The image-taking signals obtained by this CCD are converted into picture signals which can be displayed on a monitor by the video processor 10. The object image is displayed on the monitor 11.

The source coil controlling unit 932 of the endoscope shape detecting apparatus 3b controls the magnetic fields output from multiple source coils lag, via the source coil driving unit 931. Magnetic fields are generated from the multiple source coils lag, at differing timings. The magnetic fields of the multiple source coils 13g are detected by sensing coils 21j. The detecting signals obtained by the sensing coils 21j are subjected to amplifying and detection at the signal detecting unit of the endoscope shape detecting apparatus 3b. The signals sequentially are stored in the signal storing unit 934. Information may be stored in the signal storing unit 934 identifying which source coil 13g was being driven at the time of obtaining the signal, along with the signals detected by the sensing coil 21j.

The source coil position analyzing unit 935 reads signal information from the signal storing unit 934, and analyzes the three-dimensional position coordinates of each source coil 13g.

The insertion shape image generating unit 936 calculates the three-dimensional shape of the insertion portion 7 from the three-dimensional position coordinates of each of the source coils 13g obtained at the source coil position analyzing unit 935. The shape is converted into two dimensional coordinates for monitor display, formed into an image and output to the image synthesizing unit 938 as picture signals.

The marking position analyzing unit 941 of the marking image generating unit 937 analyzes the position to display marks onto the insertion shape, from the three-dimensional insertion form information obtained by the insertion shape image generating unit 936. When displaying marks at 10 cm intervals, for example, within the insertion shape image, the marking position analyzing unit 941 follows the shape of the insertion portion 7 from the tip side thereof, in the provided insertion portion 7 shape information provided. The unit 941 positions at 10 cm intervals on the path thereof markings.

The mark position information of the three dimensional coordinates obtained by the marking position analyzing unit 941 are converted into two dimensional coordinates for monitor display by the coordinates converting unit 942. The coordinates conversion by the coordinates converting unit 942 is performed in the same manner as the coordinates conversion performed by the insertion shape image generating unit 936.

The mark position information obtained from the coordinates converting unit 942 is provided to the image generating unit 943. The image generating unit 943 provides the image synthesizing unit 938 with picture signals consisting of marking images shown on mark positions.

Figure 103:
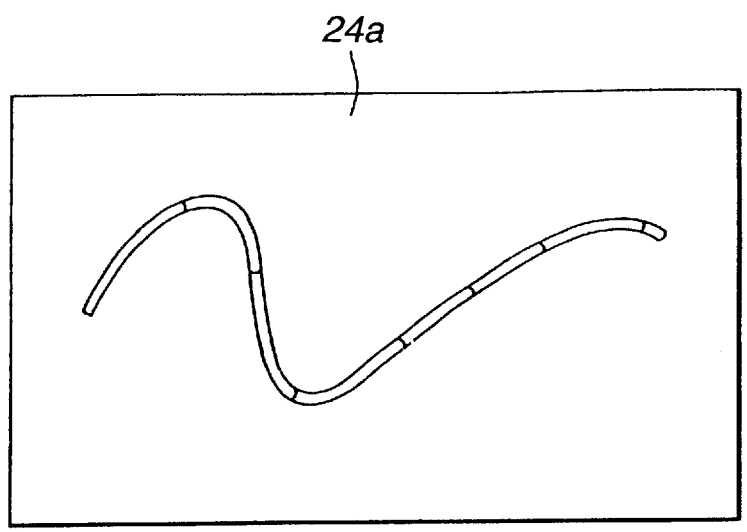

The image synthesizing unit 938 synthesizes the picture signals obtained from the insertion shape image generating unit 936 and the picture signals obtained with the marking image generating unit 937. An insertion shape image, such as shown in FIG. 103 is displayed on the monitor 24a. As shown, line-shaped marks are shown at certain intervals in the insertion shape image, e.g., every 10 cm.

Figure 104:
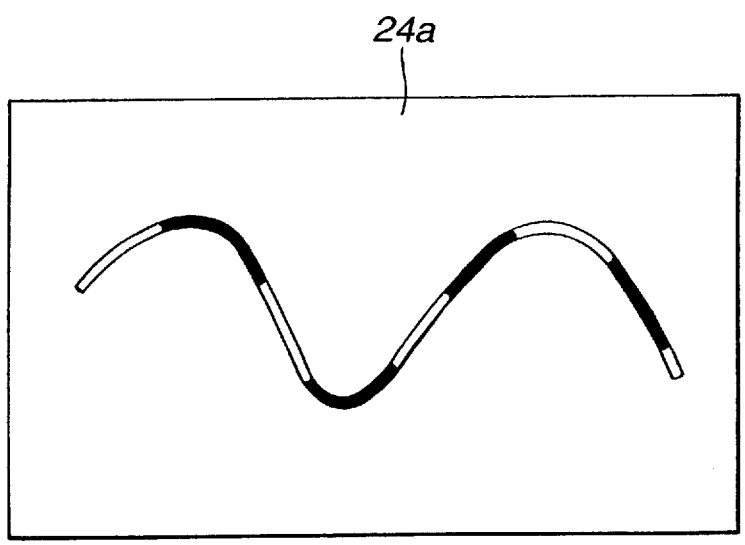

The insertion shape image shown in FIG. 104 may be displayed instead of the insertion shape image shown in FIG. 103. As shown, the color is changed at certain intervals in the insertion shape image, e.g., every 10 cm.

Marks are shown at certain intervals in the insertion shape image displayed on the monitor 24.

According to the present embodiment described above, marks are shown at certain intervals in the insertion shape image of the insertion portion 7 displayed on the monitor 24. The insertion shape of the insertion portion 7 can be understood quantitatively. Thus, the technician can accurately understand the insertion shape of the insertion portion 7 within the body cavity, thereby improving the operability of the endoscope system.

The thirtieth embodiment is similar to the twenty-ninth embodiment. Only the differing points from the twenty seventh embodiment will be described. Similar configurations will be denoted with the same reference characters and the description thereof omitted.

As shown in FIG. 105, the marking image generating unit 937a is comprised of a marking position analyzing unit 941 of the same configuration as that in the twenty-ninth embodiment; a coordinates converting unit 942 of the same configuration as that in the twenty-ninth embodiment; an image generating unit 943 of the same configuration as that in the twenty-ninth embodiment; a character generator 951 for generating image signals for marking values and the display positions indicated in the mark display position information obtained by the coordinates converting unit 942;

and an image synthesizing unit 952 for synthesizing picture signals representing mark graphics obtained by the image generating unit 943 and the information representing mark values obtained by the character generator 951.

The operation of the present embodiment will be described.

As described with the twenty-ninth embodiment, the coordinates converting unit 942 outputs two-dimensional coordinates information representing mark display positions. The image generating unit 943 generates picture signals representing the mark graphics at the mark display positions. The picture signals representing the mark graphics are provided to the image synthesizing unit 952.

The mark display position information obtained from the coordinates converting unit 942 is also provided to the character generator 951. Accordingly, the character generator 951 generates picture signals representing mark values near the mark graphics. The picture signals are provided to the image synthesizing unit 952. Mark values are numerical information indicating the distance from the tip of the insertion portion 7, for example.

Upon receiving the picture signals, the image synthesizing unit 952 generates picture signals of a synthesized image of the picture signals obtained from the image generating unit 943 and the picture signals obtained from the character generator 951, which is output to the image synthesizing unit 938.

As shown in FIG. 106, marks such as "10", "20", "30" and so forth are displayed near each of the line-shaped marks at the certain intervals in the insertion form graphic, on the monitor screen 24a. In this example, the mark values such as "10", "20", "30" and so forth represent the distance from the tip of the insertion portion 7 in centimeters.

According to the embodiment described above, advantages the same as those of the first embodiment can be obtained.

Also, mark values representing the distance from the tip of the insertion portion 7 are additionally displayed near the marks displayed at certain intervals from the tip of the insertion portion 7 within the insertion form image. A technician can ascertain the shape of the insertion portion 7 in a more quantitative manner than from the twenty-ninth embodiment, thereby improving the operability of the endoscope system.

The thirty-first embodiment is similar to the twenty-ninth embodiment except for the configuration of the marking image generating unit. Description thereof will be omitted. The members that are the same as those in the twenty-ninth embodiment and thirtieth embodiment will be denoted with the same reference characters and the description thereof omitted.

As shown in FIG. 107, the marking image generating unit 937b is comprised of a marking position analyzing unit 941 of the same.configuration as that in the twenty-ninth embodiment; a coordinates converting unit 942 of the same configuration as that in the twenty-ninth embodiment; an image generating unit 943 of the same configuration as that in the twenty-ninth embodiment; a character generator 951 of the same configuration as that in the thirtieth embodiment; a curvature radius calculating unit 961 for obtaining three-dimensional inserting shape graphic information from the insertion form generating unit and calculating the curvature radius at each position at certain intervals along the shape of the insertion portion 7 from the tip side thereof; a display position determining unit 962 for obtaining the curvature radius from the curvature radius calculating unit 961 and determining the position at which to draw the curvature radius; a coordinates converting unit 963 for converting the coordinates of the curvature radius calculating unit obtained by the display position determining unit 962 from three-dimensional coordinates to two-dimensional coordinates for monitor display; a curvature center coordinates calculating unit 964 for calculating the curvature center coordinates of the insertion portion 7 within the curvature radius information display position obtained by the display position determining unit 962; a curvature center coordinates calculating unit 964 for converting the curvature center coordinates obtained by the display position determining unit 962 from three-dimensional coordinates to two-dimensional coordinates for monitor display; an image generating unit 966 for taking the two-dimensional coordinates of the curvature radius information display position obtained from the coordinates converting unit 963 and the two-dimensional coordinates of the curvature center coordinates obtained from the coordinates converting unit 965, thereby generating picture signals for displaying graphics indicating the display position of the curvature radius and graphics indicating the curvature center position; a character generator 967 for generating picture signals for displaying character information representing the curvature radius near the graphic representation generated by the image generating unit 966; and an image generating unit 968 for synthesizing the picture signals from the image generating unit 943, character generator 951, image generating unit 966, and character generator 967, and outputting the picture signals.

The operation of the present embodiment will be described.

As described in the twenty-ninth embodiment, the image generating unit 943 generates picture signals representing marking graphics to be displayed in the insertion shape graphics. Also as described in the thirtieth embodiment, the character generator 951 generates picture signals representing marking values to be displayed near the marks. Then, the picture signals from the image generating unit 943 and the character generator 951 are both provided to the image synthesizing unit 968.

The curvature radius calculating unit 961 obtains insertion shape information from the insertion shape image generating unit 936, and calculates the curvature radius at each position at certain intervals along the shape of the insertion portion 7 from the tip side thereof. The curvature radius information corresponding to each portion is provided to the display position determining unit 962. This display position determining unit 962 displays positions at which this curvature radius value is greater than a certain value for example, and provides this position information to the coordinates conversing unit 963 and the curvature center coordinates calculating unit 964. The coordinates converting unit 63 converts the curvature radius display position coordinates from three-dimensional coordinates to two-dimensional coordinates for monitor display.

The curvature center coordinates calculating unit 964 obtains display position coordinates information for the curvature radius from the display position determining unit 962 and insertion shape information from the insertion shape image generating unit 936, calculates the curvature center coordinates at the curvature radius display position, and provides the results to the coordinates converting unit 965. The curvature center coordinates may be calculated by calculating tangents for two points on either side of the curvature radius display position on en arc as to the arc respectively in the insertion shape graphic, calculating perpendicular lines to the two tangent lines, and calculating the intersecting coordinates of the two tangent lines. The coordinates converting unit 965 converts the curvature center coordinates from three-dimensional coordinates to two-dimension coordinates for monitor display.

The image generating unit 966 obtains curvature radius display position coordinates information from the coordinates converting unit 963 end curvature center coordinates information from the coordinates converting unit 965, and generates picture signals for displaying graphics representing the curvature center portions and graphics representing the curvature radius display position. The character generator 967 obtains curvature radius display position coordinates information from the coordinates conversing unit 963 and curvature center coordinates information from the coordinates converting unit 965, and generates picture signals for displaying characters indicating the values of the curvature radius near the curvature radius display position.

Image synthesizing unit 968 receives and synthesizes the picture signals from the image generating unit 43, character generator 951, image generating unit 966, and character generator 967, and outputs the picture signals.

As shown in FIG. 108, the monitor 24a displays the insertion shape graphics, marking graphics, and marking values. The monitor 24A displays graphics indicating the curvature radius display position for each place wherein the curvature radius of the insertion portion 7 is under a certain value, such as 25 cm for example, and also characters indicating the curvature radius near the graphic representation, and graphics indicating the curvature center position. As shown, the graphics form a cross-shape meeting at the curvature center position, for example. The graphics indicating the curvature radius display position is in the form of an arrow connecting the curvature radius display position coordinates from the curvature center position coordinates. The character string representing the curvature radius is configured such as "R10", "R15", "R25", and so forth, wherein a value such as in the increments of centimeters is placed after the letter "R", indicating that this represents the curvature radius.

According to the present embodiment described above, the same advantages as those of the thirtieth embodiment can be obtained.

Also, information relating to the curvature radius of the insertion portion 7 is displayed in the insertion shape screen. A technician can easily ascertain the excessively bent portions of the insertion portion 7, thereby improving the operability of the endoscope system.

The marking position analyzing unit 941 may store the actual distance information from the tip of the insertion portion 7 to each of the source coils 13g in the insertion portion 7 to calculate the actual distance information for the source coil positions within the insertion shape graphics based on the actual distance information of the source coil 13g and the source coil position information obtained from the source coil position analyzing unit 935 and supplement the distance information for tracing the insertion shape graphics from the tip.

If the source coils 13g are provided to the insertion portion 7 beforehand at certain intervals, e.g., 10 cm intervals, the actual distance of the source coils 13g from the tip of the insertion portion 7 may be stored in the marking position analyzing unit 941 beforehand. The marking position analyzing unit 941 can calculate the actual distance information for the source coil positions within the insertion shape graphics based on the actual distance information of the source coil 13g and the source coil position information obtained from the source coil position analyzing unit 935, thereby having the source coil positions within the insertion shape graphics as the marking positions.

The mark drawing intervals for the marking position analyzing unit 941 need not be 10 cm, but rather any distance.

The present embodiment has been described with reference to the video endoscope 6, but is not restricted to such. The endoscope may be an optical endoscope.

With the present embodiment, an example of an endoscope system wherein disturbance of magnetic fields owing to the metal member configuring the insertion portion can be reduced. The system has magnetic field generating elements capable of preventing deterioration owing to the curving of the insertion portion, as described with reference to FIGS. 109 through 111.

The endoscope system 1001 shown in FIG. 109 is comprised of an insertion shape detecting table 1003 upon which the subject 1002 is placed, and endoscope 1004 to be inserted into the body cavity of the subject 1002 so as to observe portions within the body cavity and the like, a light source device 1005 for generating light to be supplied to this endoscope 1004, a video processor 1006 for obtaining picture signals which can be displayed on a monitor, from image-taking signals obtained from the observation portion with the endoscope 1004, a monitor 1007 for displaying the picture signals from the video processor 1006, an insertion shape detecting device 1008 for detecting the insertion shape of the endoscope 1004 inserted into the body cavity or the like and displaying an insertion shape image, and a monitor 1009 for obtaining the picture signals from the insertion shape detecting device 1008 and displaying an insertion shape image.

The insertion shape detecting table 1003 is comprised of a plurality of sensing coils 1011 for detecting the magnetic field, and cables 1012 for transmitting the signals from the sensing coils 1011 to the insertion shape detecting device.

The endoscope 1004 is comprised of an insertion portion 1021 to be inserted into the body cavity of the subject 1002, an operating unit 1022 formed from the base end of the insertion portion 1021 for holding and operating the endoscope 1004, and a universal cord 1023 extending from the side of this operating unit 1022. A connector for optically connecting to the light source device 1005 is provided to the other end of the universal cord 1023. From this connector extends a cable 1024 for electrically connecting to the video processor 1006 and a cable 1025 for electrically connecting to the insertion shape detecting device 1008.

As shown in FIG. 110, the insertion portion 1021 of the endoscope 1004 is comprised of a flexible tube portion 1031 from the operating unit 1022, a curving portion 1032 which can be curved by remote control, and a tip portion 1033 formed at the tip wherein the framing is formed of metal.

The tip portion 1033 includes a light emitting end portion for the light guide 1041 with the light input side connected to the light source device 1005, a light distribution optical system 1042 for distributing the light emitted from the light emitting end of the light guide 1041 towards the object, an object optical system for imaging the object image, a CCD 1044 serving as image-taking means for obtaining the image of the object which has been imaged by the object optical system 1043, and the tip of a signal line 1045 electrically connected to the CCD 1044 and the video processor. The light guide 1041 has been inserted through the insertion portion 1021, the operating unit 1022, universal cord 1023, and cable 1024, and extends to the connector that is connected to the light source device 1005. The signal line 1045 is electrically connected to the video processor 1006, via the insertion portion 1021, operating unit 1022, universal cord 1023, and cable 1024.

A plurality of tube portion source coils 1051 are provided at certain intervals to the tube portion 1031. The signal line 1052 for supplying driving current to each of the tube portion source coils 1051 is electrically connected to the insertion shape detecting device 1008, via the tube portion 1031, operating portion 1022, universal cord 1023, and cable 1025.

The operating unit 1022 is comprised of two curving operating knobs 1034 for vertical and horizontal operating of the curving portion 1032 for example, rotary encoders 1055 for detecting the turning position of the two curving operating knobs 1034, and e.g., three operating portion source coils 1053 for generating magnetic fields. The rotary encoder 1055 has a signal line 1056 for transmitting signals corresponding to the rotational position of the curving operating knobs 1034 detected by the rotary encoder 1055. The signal line 1056 is electrically connected to the insertion shape detecting device 1008, via the operating portion 1022, universal cord 1023, and cable 1025. Extending from the operating portion source coils 1053 is a signal line 1054 for supplying driving current to the operating portion source coils 1053. The signal line 1054 is electrically connected to the insertion shape detecting device 1008, via the operating portion 1022, universal cord 1023, and cable 1025.

As shown in FIG. 111, the insertion shape detecting device 1008 is comprised of a source coil driving unit 1061 for driving the tube portion source coils 1051 and operating portion source coils 1053; a source coil control unit 1062 for controlling the timing for generating magnetic fields and frequency of the tube portion source coils 1051 and operating portion source coils 1053 via the source coil driving unit 1061; a signal detecting unit 1063 for detecting the signals obtained by the sensing coils 1011 and changing these signals to a level appropriate for signal processing; a signal storage unit 1064 for sequentially temporarily storing the signal data obtained from the signal detecting unit 1063; a source coil position analyzing portion 1065 for reading the signal data from the signal storage unit 1064 and analyzing the three-dimensional position coordinates of the tube portion source coils 1051 and the operating portion source coils 1053; a tube portion shape calculating unit 1066 for calculating the three-dimensional shape of the tube portion 1031 based on the three-dimensional position coordinates information of the tube portion source coils 1051 obtained from the source coil position analyzing portion 1065; an operating direction detecting unit 1067 for calculating the direction of the operating unit 1022, such as the vertical direction, from three-dimensional position coordinates information of the operating portion source coils 1053 obtained from the source coil position analyzing portion 1065; a tube portion tip plane vertical direction detecting unit 1068 for following the tube portion shape information obtained from the tube portion shape calculating unit 1066 in the vertical direction from the base thereof, thereby detecting the vertical direction of the tip of the tube portion 1033, i.e., at the base of the curving portion 1032; a decoding unit 1069 for decoding signals from the rotary encoder 1055 and thereby obtaining position information for the curving operating knobs 1034; a curving portion shape calculating unit 1070 containing information [obtained beforehand] indicating the relationship between the position of the curving operating knob 1034, the curving portion 1032, and the tip portion 1033 for calculating the shape of the curving portion 1032 and the tip portion 1033 from the position information obtained from the decoding unit 1069; a curving portion shape coordinates converting unit 1071 for performing three-dimensional coordinates conversion wherein the orientation of the shape of the curved portion 1032 and tip portion 1033 obtained at the curving portion shape calculating unit 1070, based on the vertical direction information of the tip plane of the tube portion 1031, i.e., the vertical direction of the base end of the curving portion 1032, obtained at the tube portion tip plane vertical direction detecting unit 1068, thereby obtaining the actual shape of the curving portion 1032 attached to the tip of the tube portion 1031 and also the tip portion 1033; a shape synthesizing unit 1072 for synthesizing the shape information of the tube portion 1031 obtained at the tube portion 1033 shape calculating unit 1066 and the shape information of the curving portion 1032 and tip portion 1033 obtained from the curving portion shape coordinates converting unit 1071, and obtaining the shape information of the insertion portion 1021; a coordinates converting unit 1073 for converting the shape information obtained from the shape synthesizing unit 1072 from three-dimensional coordinates to two-dimensional coordinates which can be displayed on a monitor, and outputting the converted picture signals; and a monitor driving unit 1074 for displaying the picture signals from the coordinates converting unit 1073 by driving the monitor 1009.

Thus, according to the endoscope system described with reference to FIGS. 109 through 111, if source coils 1051 are not positioned in the curving portion 1032 and tip portion 1033, an insertion shape image of the insertion portion 1021, including the curving portion 1032 and the tip portion 1033 can be displayed.

The source coils 1051, having many metal members, are not provided near the tip portion 1033. Disturbance in the magnetic fields from the source coils 1051 can be reduced. Accordingly, the detection processing of the information shape of the insertion portion 1021 improves, and the operability of the endoscope system 1001 improves.

The source coils 1051 are not provided to the curving portion 1032 which bends tightly and frequently. Thus, deterioration of the magnetic field generating elements, such as the source coils 1051, signal line 1052, a member for supporting the source coils (not shown) is avoided. Accordingly, the life of the members related to the magnetic field generating elements increases, and maintenance costs are reduced.

The rotary encoder 1055 is not restricted to that shown. Any item capable of converting angular position information into electrical signals can be used, such as a coil configuration for example.

The source coils 1051 may be integrally attached to the endoscope 1004. The source coils 1051 also may be separately and detachably mounted on the endoscope 1004.

FIG. 112 shows an insertion portion whereby the positions of the source coils can be understood.

Marks 2002 are provided on the outer surface of the endoscope insertion portion 2001, shown in FIG. 112, at certain intervals from a certain position, e.g., at 10 cm intervals. The marks 203 are provided at the positions where source coils are provided.

These marks 2003 allow the operator to easily ascertain the arrayed position of the source coils on the endoscope insertion portion 2001.

FIG. 113 shows another configuration. Marks 2002 are provided on the outer surface of the endoscope insertion portion 2001*a* of the endoscope shown in FIG. 113 at certain intervals from a certain position, e.g., at 10 cm intervals. The marks 2011 are provided at the positions where source coils are provided. Linear marks 2012 connecting the marks 2011 are provided.

The marks 2012 provided on the endoscope insertion portion 2001a allow the marks 2011 to be observed more easily. Throughout the description of the above embodiment, the source coils for generating magnetic fields within the body cavity, and the sensing coils for detecting the magnetic fields outside of the body. However these may be inverted still provide endoscope shape detection and insertion shape display in almost the same manner.

It is clearly understood that a wide range of differing embodiments may be made based on the present embodiment, without departing from the spirit or scope thereof. The present invention is not restricted in any way by any particular embodiments thereof, except for as restricted by the appended claims.

What is claimed is:

1. An endoscope shape detecting apparatus, comprising:
   an endoscope for observing a subject image by inserting an insertion portion into the body of a subject, such as a body cavity;
   a magnetic field generating means for generating a magnetic field by supplying driving signals;
   a magnetic field detecting means for detecting the magnetic field generated by said magnetic field generating means; and
   a control means comprising:
      a driving means for generating said driving signals;
      a computing means for computing a shape of the inserted portion of said endoscope, from relative positional information between said magnetic field generating means and said magnetic field detecting means, based on detection signals detected by said magnetic field detecting means with one or the other of said magnetic field generating means and said magnetic field detecting means
      a display control means for displaying the endoscope shape obtained from computation results from said computing means on a display means; and
      a connection state detecting means for detecting a connection state of said magnetic field generating means;
   wherein said control means controls at least one of said driving means, said computing means, and said display control means, based on said connection state.

2. An endoscope shape detecting apparatus according to claim 1, wherein said connection state detecting means detects the connection state of said magnetic field generating means while said magnetic field generating means is being driven.

3. An endoscope shape detecting apparatus according to claim 1, further comprising:
   a dedicated introduction channel for introducing an endoscope insertion shape detecting probe, having one or the other of said magnetic field generating means and said magnetic field detecting means, into the insertion portion of said endoscope; and
   a detaching and mounting mechanism for detaching and mounting said endoscope insertion shape detecting probe, said mechanism being provided in said introduction channel and having a cross-sectional shape which is similar to the cross-sectional shape of said endoscope insertion shape detecting probe but with a greater cross-sectional area, and being formed of a tube which elastically returns to said cross-sectional shape.

4. An endoscope shape detecting apparatus according to claim 3, wherein said endoscope insertion shape detecting probe has a relay connector and is dividable before and behind said relay connector.

5. An endoscope shape detecting apparatus according to claim 4, wherein said relay connector is detachable from outside of said endoscope.

6. An endoscope shape detecting apparatus according to claim 4, wherein said relay connector has a waterproof cover.

7. An endoscope shape detecting apparatus according to claim 1, further comprising:
   an endoscope insertion shape detecting probe having one or the other of said magnetic field generating means and said magnetic field detecting means; and
   an introduction channel for introducing said endoscope insertion shape detecting probe into said endoscope;
   wherein said introduction channel has a cross-section of a size and shape which allows said endoscope insertion shape detecting probe to be detachable.

8. An endoscope shape detecting apparatus according to claim 7, wherein said introduction channel for introducing said endoscope insertion shape detecting probe into said endoscope is formed of a hollow tube.

9. An endoscope shape detecting apparatus according to claim 1, comprising an endoscope insertion shape detecting probe having one or the other of said magnetic field generating means and said magnetic field detecting means;
   wherein said endoscope insertion shape detecting probe has a relay connector which is detachable from outside of the operating unit of said endoscope.

10. An endoscope shape detecting apparatus according to claim 9, wherein said relay connector has a waterproof cover.

11. An endoscope shape detecting apparatus according to claim 1, comprising an endoscope insertion shape detecting probe having one or the other of said magnetic field generating means and said magnetic field detecting means;
    wherein said endoscope and said endoscope insertion shape detecting probe are provided with identifying means relying on sight or touch;
    and wherein said identifying means has a certain uniformity with said endoscope and said endoscope insertion shape detecting probe.

12. An endoscope shape detecting apparatus according to claim 1, comprising:
    an endoscope insertion shape detecting probe having one or the other of said magnetic field generating means and said magnetic field detecting means;
    endoscope identifying means for identifying a type of endoscope; and
    endoscope insertion shape detecting probe identifying means for identifying a type of endoscope insertion shape detecting probe.

13. An endoscope shape detecting apparatus according to claim 12, comprising notifying means for collating identification results of said endoscope identifying means and identification results of said probe identifying means, and making notification of the collation results.

14. An endoscope shape detecting apparatus according to claim 1, comprising:
    an endoscope insertion shape detecting probe having one or the other of said magnetic field generating means and said magnetic field detecting means; and
    a holding member for integrally connecting said endoscope insertion shape detecting probe and said endoscope.

15. An endoscope shape detecting apparatus according to claim 1, said magnetic field generating means or said magnetic field detecting means to be inserted in the body of said subject comprising:
- a first coil group wherein a plurality of coils are arrayed at a certain first interval within a flexible tube portion of said endoscope; and
- a second coil group wherein a plurality of coils are arrayed at a certain second interval which is narrower than said first interval, within a curving portion of said endoscope.

16. An endoscope shape detecting apparatus according to claim 1, one or the other of said magnetic field generating means and said magnetic field detecting means to be inserted in the body of said subject comprising:
- a first coil group wherein a plurality of coils are arrayed at a certain first interval, within a curving portion of said endoscope, based on a maximum curvature of said curving portion; and
- a second coil group wherein a plurality of coils are arrayed at a certain second interval, which is wider than said first interval, within a flexible tube portion of said endoscope.

17. An endoscope shape detecting apparatus according to claim 1, comprising a plurality of endoscope insertion shape detecting probes, having one or the other of said magnetic field generating means and said magnetic field detecting means, each with at least one of the flexibility and resilience of the portion inserted in the channel of said endoscope differing with respect to the remainder of said plurality and endoscope insertion shape detecting probes.

18. An endoscope shape detecting apparatus according to claim 17, wherein at least one of said flexibility and said resilience differs between a rear end side and a tip side of said plurality of endoscope insertion shape detecting probes in the longitudinal direction.

19. An endoscope shape detecting apparatus according to claim 17, wherein at least one of said flexibility and said resilience of said plurality of endoscope insertion shape detecting probes is variable at a rear end side and a tip side, by changing an insertion diameter in the longitudinal direction.

20. An endoscope shape detecting apparatus according to claim 17, wherein said plurality of endoscope insertion shape detecting probes have a display unit for identifying the degree of at least one of said flexibility and said resilience.

21. An endoscope shape detecting apparatus according to claim 17, further comprising stiffness changing means for changing the stiffness of the insertion portion.

22. An endoscope shape detecting apparatus according to claim 1, comprising:
- an endoscope insertion shape detecting probe having one or the other of said magnetic field generating means and said magnetic field detecting means; and
- a buckling prevention member formed of an elastic member, detachable from a forceps opening of said endoscope at a connector toward the handling side of said endoscope insertion shape detecting probe.

23. An endoscope shape detecting apparatus according to claim 1, comprising a position fixing means for positioning and fixing the one of said magnetic field generating means or said magnetic field detecting means not inserted into the body of said subject, against the surface of the body of said subject.

24. An endoscope shape detecting apparatus according to claim 1, comprising:
- an attaching means for attaching the one of said magnetic field generating means or said magnetic field detecting means not inserted into the body of said subject, onto the surface of the body of said subject; and
- a display means provided to said magnetic field detecting unit for displaying whether there is a certain position for said insertion portion.

25. An endoscope shape detecting apparatus according to claim 1, comprising:
- an attaching means for attaching the one of said magnetic field generating means or said magnetic field detecting means not inserted into the body of said subject, onto the surface of the body of said subject; and
- a selecting means for enabling at least one of a plurality of coils making up said magnetic field generating means or said magnetic field detecting means attached onto the surface of the body of said subject with said attaching means to be selectively set to either of magnetic field generating or magnetic field detecting.

26. An endoscope shape detecting apparatus according to claim 1, comprising:
- an endoscope device for outputting an endoscope image within the body of said subject from said endoscope; and
- an image synthesizing means for synthesizing said endoscope image from said endoscope device with an endoscope shape image from said display control means, for display on a single display means.

27. An endoscope shape detecting apparatus according to claim 1, comprising:
- an endoscope device for outputting an endoscope image within the body of said subject from said endoscope; and
- an image switching means for switching between said endoscope image from said endoscope device and an endoscope shape image from said display control means, for display on a single display means.

28. An endoscope shape detecting apparatus according to claim 1, wherein said display control means generates said shape image such that parts of said insertion portion with differing bending properties can be identified.

29. An endoscope shape detecting apparatus according to claim 1, wherein said magnetic field generating means or said magnetic field detecting means not inserted into the body of said subject is movable in relation to said display means.

30. An endoscope shape detecting apparatus according to claim 1, wherein said magnetic field generating means or said magnetic field detecting means to be inserted into the body of said subject further comprises stiffness changing means for changing the stiffness at the insertion portion.

31. An endoscope shape detecting apparatus according to claim 1, wherein said magnetic field generating means or said magnetic field detecting means to be inserted into the body of said subject is layered and positioned within exterior material of the insertion portion of said endoscope.

32. An endoscope shape detecting apparatus according to claim 1, comprising:
- an image-taking means for obtaining images of the object observed with said endoscope, said image-taking means being constructed either within said endoscope or constructed separately from said endoscope;
- a means for obtaining a first image signal from image signals obtained by said image-taking means;
- a stiffness adjusting means for adjusting the stiffness of said insertion portion;

a means for obtaining a second image signal by forming an image of information such as numerical values indicating the stiffness set at said stiffness adjusting means;

a synthesizing means for inputting said first image signal, said second image signal, and an endoscope shape image from said display control means, as a third image signal, and synthesizing at least two types of image signals from the group comprised of said first image signal, said second-image signal, and said third image signal; and a display means for displaying the image signals synthesized by said synthesizing means.

33. An endoscope shape detecting apparatus according to claim 32, wherein said stiffness adjusting means comprises:

a knob for setting stiffness; and a detecting means for detecting the position of said knob; said detecting means comprising:

a light reflecting means provided to said knob; and a light detecting means for detecting reflected light from said light reflecting means.

34. An endoscope shape detecting apparatus according to claim 1, comprising:

a means for obtaining shape information representing said insertion shape; and a means for obtaining image signals for overlapping and displaying said shape information over a graphic image of said insertion shape.

35. An endoscope shape detecting apparatus according to claim 34, wherein said shape information includes graphic marks displayed over said graphic image of said insertion shape.

36. An endoscope shape detecting apparatus according to claim 34, wherein said shape information includes numerical information, displayed near a position on said graphic image of said insertion shape corresponding with certain distance interval positions of said endoscope insertion portion, and representing the distance from a certain position of said endoscope insertion portion.

37. An endoscope shape detecting apparatus according to claim 34, wherein said shape information includes numerical information or character information indicating the curvature radius of said endoscope insertion portion at said certain position, displayed near the position on said graphic image of said insertion shape corresponding with the certain position of said endoscope insertion portion.

38. An endoscope shape detecting apparatus according to claim 37, wherein said certain position is where the curvature radius of said endoscope insertion portion is smaller than a certain value.

39. An endoscope shape detecting apparatus according to claim 1, wherein the insertion portion of said endoscope has at least a soft tube portion and a curvable curving portion extending from the tip side of said tube portion;

wherein said endoscope comprises at least curve operating means for operating said curving portion; and wherein said magnetic field generating means or said magnetic field detecting means to be inserted into the body of said subject is positioned in said tube portion;

said endoscope shape detecting apparatus further comprising:

a curving operation position detecting means for detecting an operating position of said curve operating means;

a curving portion shape detecting means for detecting a shape of said curving portion from information of the operating position of said curve operating means obtained by said curving operation position detecting means; and a means for obtaining image signals for synthesizing the shape of said tube portion obtained by said computing means and the shape of said curving portion obtained by said curving shape detecting means, and displaying the graphic image of said insertion shape.

40. An endoscope shape detecting apparatus, comprising:

an endoscope for observing a subject image by inserting an insertion portion into the body of a subject, such as a body cavity;

a magnetic field generating means for generating a magnetic field by supplying driving signals;

a magnetic field detecting means for detecting the magnetic field generated by said magnetic field generating means;

a driving means for generating said driving signals;

a computing means for computing a shape of the inserted portion of said endoscope, from relative positional information between said magnetic field generating means and said magnetic field detecting means, based on detection signals detected by said magnetic field detecting means with one or the other of said magnetic field generating means and said magnetic field detecting means;

a display control means for displaying the endoscope shape obtained from computation results from said computing means on a display means;

a connection state detecting means for detecting connection state of said magnetic field generating means; and a control means for controlling said display control means, based on said connection state.

41. An endoscope shape detecting apparatus, comprising:

an endoscope for observing a subject image by inserting an insertion portion into the body of a subject, such as a body cavity;

a magnetic field generating means for generating a magnetic field by supplying driving signals;

a magnetic field detecting means for detecting the magnetic field generated by said magnetic field generating means;

a driving means for generating said driving signals;

a computing means for computing a shape of the inserted portion of said endoscope, from relative positional information between said magnetic field generating means and said magnetic field detecting means, based on detection signals detected by said magnetic field detecting means with one or the other of said magnetic field generating means and said magnetic field detecting means;

a display control means for displaying the endoscope shape obtained from computation results from said computing means on a display means;

a connection state detecting means for detecting a connection state of said magnetic field generating means; and a control means for controlling said computing means, based on said connection state.

42. An endoscope shape detecting apparatus, comprising:

an endoscope for observing a subject image by inserting an insertion portion into the body of a subject, such as a body cavity;

a magnetic field generating means for generating a magnetic field by supplying driving signals;

a magnetic field detecting means for detecting the magnetic field generated by said magnetic field generating means;

a driving means for generating said driving signals;

a computing means for computing a shape of the inserted portion of said endoscope, from relative positional information between said magnetic field generating means and said magnetic field detecting means, based on detection signals detected by said magnetic field detecting means with one or the other of said magnetic field generating means and said magnetic field detecting means;

a display control means for displaying the endoscope shape obtained from computation results from said computing means on a display means;

a connection state detecting means for detecting a connection state of said magnetic field generating means; and a control means for controlling said driving means, based on said connection state.

* * * * *